US012624123B2

(12) United States Patent
Balthasar et al.

(10) Patent No.: US 12,624,123 B2
(45) Date of Patent: May 12, 2026

(54) COMPOSITIONS AND METHODS FOR REDUCING OFF-TARGET TOXICITY OF ANTIBODY DRUG CONJUGATES

(71) Applicant: The Research Foundation for The State University of New York, Amherst, NY (US)

(72) Inventors: Joseph P. Balthasar, Lancaster, NY (US); Brandon M. Bordeau, Amherst, NY (US); Toan Duc Nguyen, Amherst, NY (US); Joseph Ryan Polli, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 740 days.

(21) Appl. No.: 17/782,549

(22) PCT Filed: Dec. 4, 2020

(86) PCT No.: PCT/US2020/063453
§ 371 (c)(1),
(2) Date: Jun. 3, 2022

(87) PCT Pub. No.: WO2021/113740
PCT Pub. Date: Jun. 10, 2021

(65) Prior Publication Data
US 2023/0071019 A1        Mar. 9, 2023

Related U.S. Application Data

(60) Provisional application No. 62/943,358, filed on Dec. 4, 2019.

(51) Int. Cl.
*C07K 16/32* (2006.01)
*A61K 47/68* (2017.01)
*A61P 35/00* (2006.01)

(52) U.S. Cl.
CPC .......... *C07K 16/32* (2013.01); *A61K 47/6803* (2017.08); *A61K 47/68031* (2023.08); *A61K 47/68033* (2023.08); *A61K 47/68037* (2023.08); *A61K 47/6805* (2017.08); *A61K 47/6817* (2017.08); *A61K 47/6851* (2017.08); *A61K 47/6889* (2017.08); *A61P 35/00* (2018.01)

(58) Field of Classification Search
CPC .................................................... C07K 16/44
See application file for complete search history.

(56) References Cited

U.S. PATENT DOCUMENTS

| | | | | |
|---|---|---|---|---|
| 5,562,907 A | * | 10/1996 | Arnon | C07K 16/1282 |
| | | | | 424/236.1 |
| 6,827,935 B2 | * | 12/2004 | Frank | C07K 14/21 |
| | | | | 424/139.1 |
| 7,312,243 B1 | * | 12/2007 | Pravda | A61K 31/12 |
| | | | | 424/653 |
| 2008/0260757 A1 | | 10/2008 | Holt et al. | |
| 2017/0095570 A1 | | 4/2017 | Dragovich et al. | |
| 2018/0339058 A1 | | 11/2018 | Kunz et al. | |

FOREIGN PATENT DOCUMENTS

| | | | | |
|---|---|---|---|---|
| CN | 103421112 A | * | 12/2013 | |
| WO | WO-2012067670 A1 | * | 5/2012 | A61K 31/437 |
| WO | 2019041024 A1 | | 3/2019 | |

OTHER PUBLICATIONS

Paul, Fundamental Immunology, 3rd Edition, 1993, pp. 292-295 (Year: 1993).*
Almagro & Fransson, Frontiers in Bioscience 2008; 13:1619-33 (Year: 2008).*
Rudikoff et al(Proc. Natl. Acad. Sci. USA 1982 vol. 79: p. 1979) (Year: 982).*
Pascalis et al(The Journal of Immunology (2002) 169, 3076-3084) (Year: 2002).*
Casset et al. (2003) BBRC 307, 198-205, (Year: 2003).*
D'Angelo et al, Frontiers in Immunology vol. 9 p. 1 (2018) (Year: 2018).*
Brown et al (J. Immunol. May 1996; 156(9):3285-3291 (Year: 1996).*
Vajdos et al (J. Mol. Biol. Jul. 5, 2002;320(2); 415-428) (Year: 2002).*
CN 103421112 Translation, 15 pages. (Year: 2013).*
Balthasar et al J. Pharmaceutical Sciences vol. 85 p. 1035 (1996) (Year: 1996).*
Kim et al Mol. Cells vol. 20 p. 17 (2005) (Year: 2005).*
Lobo et al., "Application of Anti-Methotrexate Fab Fragments for the Optimization of Intraperitoneal Methotrexate Therapy in Murine Model of Peritoneal Cancer," Journal of Pharmacological Sciences, Sep. 2005, pp. 1957-1964, vol. 94, No. 9.
Chen et al., "Development and Characterization of High-Affinity Anti-Topotecan IgG and Fab Fragments," Pharmaceutical Sciences Encyclopedia: Drug Discovery, Development, and Manufacturing, Mar. 15, 2010, pp. 1-16.
Wolska-Washer et al., "Safety and Tolerability of Antibody-Drug Conjugates in Cancer," Drug Safety, Jan. 16, 2019, pp. 295-314, vol. 42, No. 2.

* cited by examiner

*Primary Examiner* — Julie Wu
(74) *Attorney, Agent, or Firm* — Hodgson Russ LLP

(57) ABSTRACT

Provided are compositions and methods for reducing off-target toxicity of antibody-drug conjugates (ADCs). The compositions comprise an ADC, and an agent targeted to the drug (payload) that is delivered by or derived from the ADC. The ADC and the agent targeted to the payload may be delivered together or separately in the treatment of various conditions (such as tumors) by ADCs. Examples of agents targeted to payload include antibodies, fragments, or modifications thereof.

11 Claims, 60 Drawing Sheets
Specification includes a Sequence Listing.

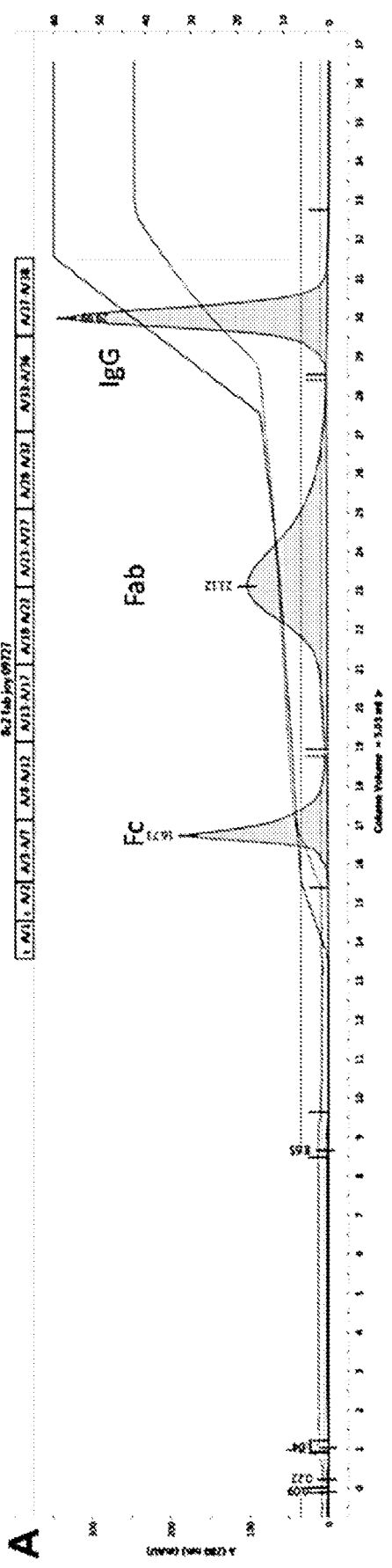
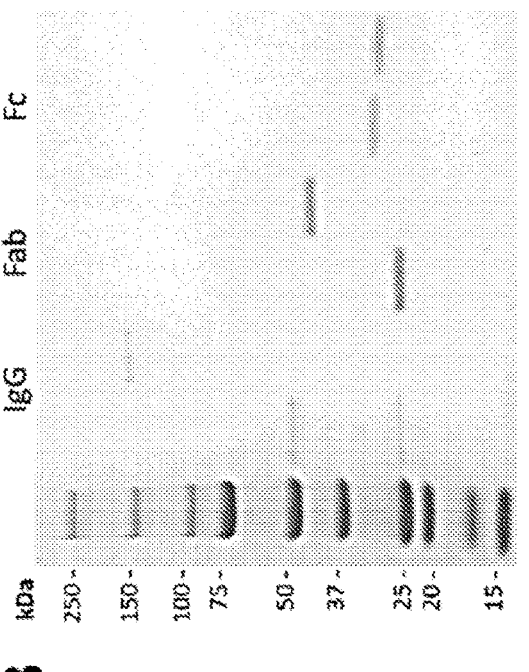
Fig. 2

Competitive ELISA with 8C2 mAb and SN38/TPT

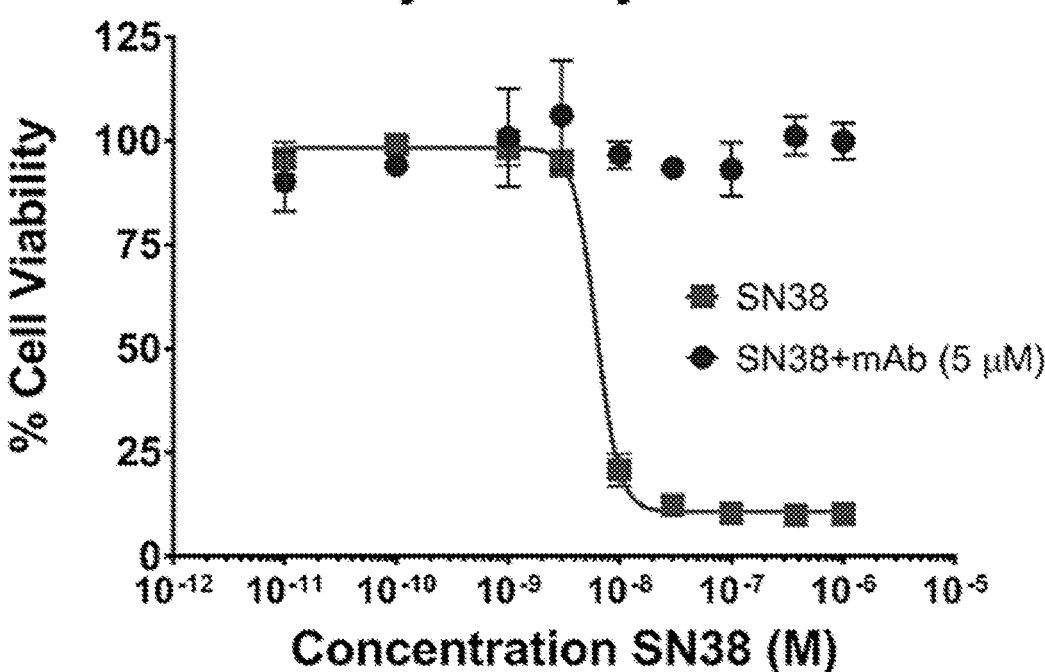
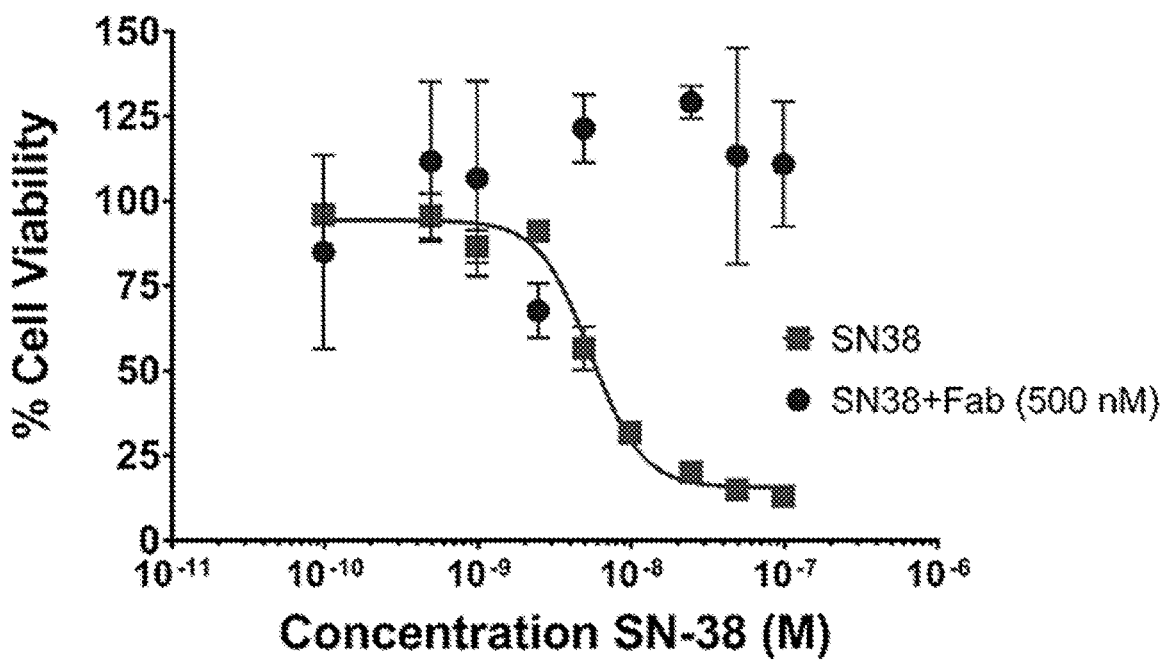
Fig. 6

Treatment for 24h and let grow for 4 days

Treatment for 48h
Let cells grow for 48 h

Treatment for 24h and let grow for 4 days

Phage library by free drug elution
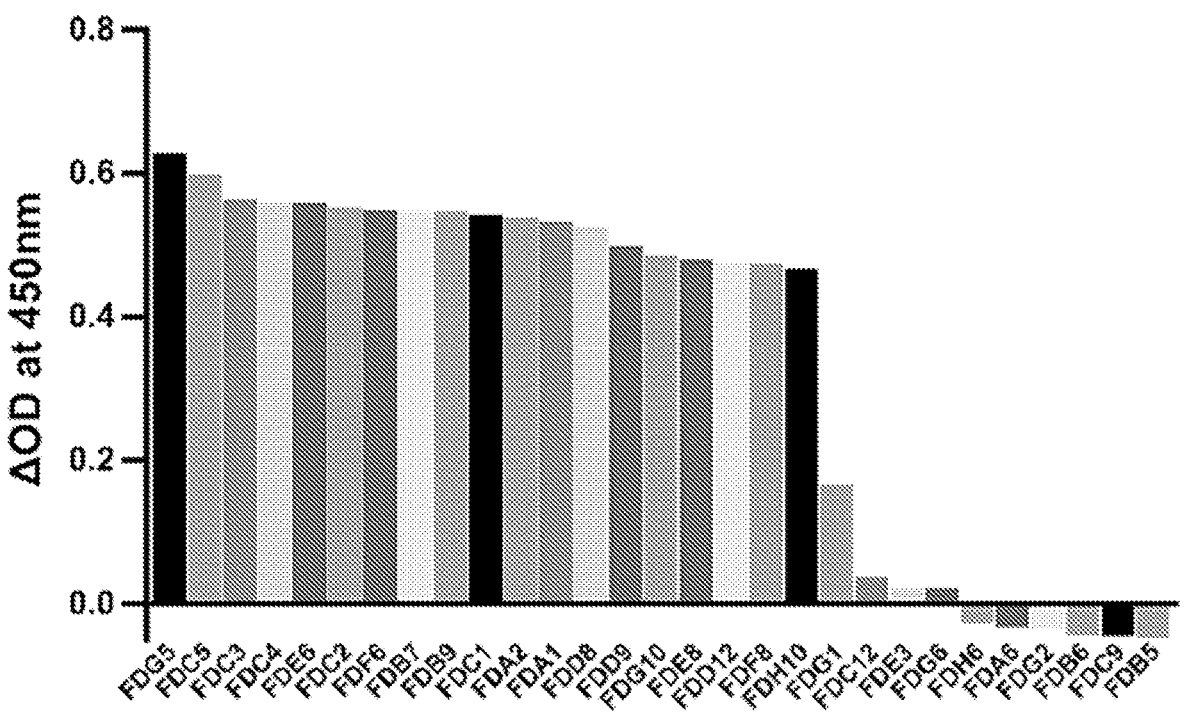
Phage library by trypsin elution
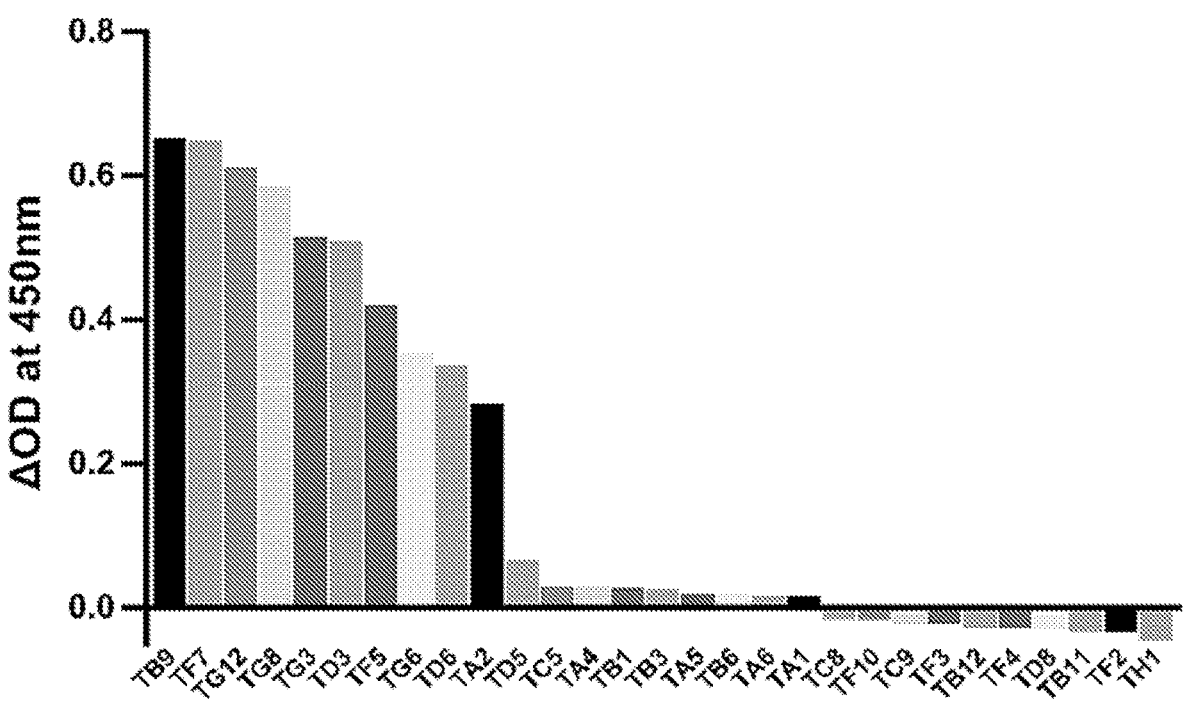
Fig. 13

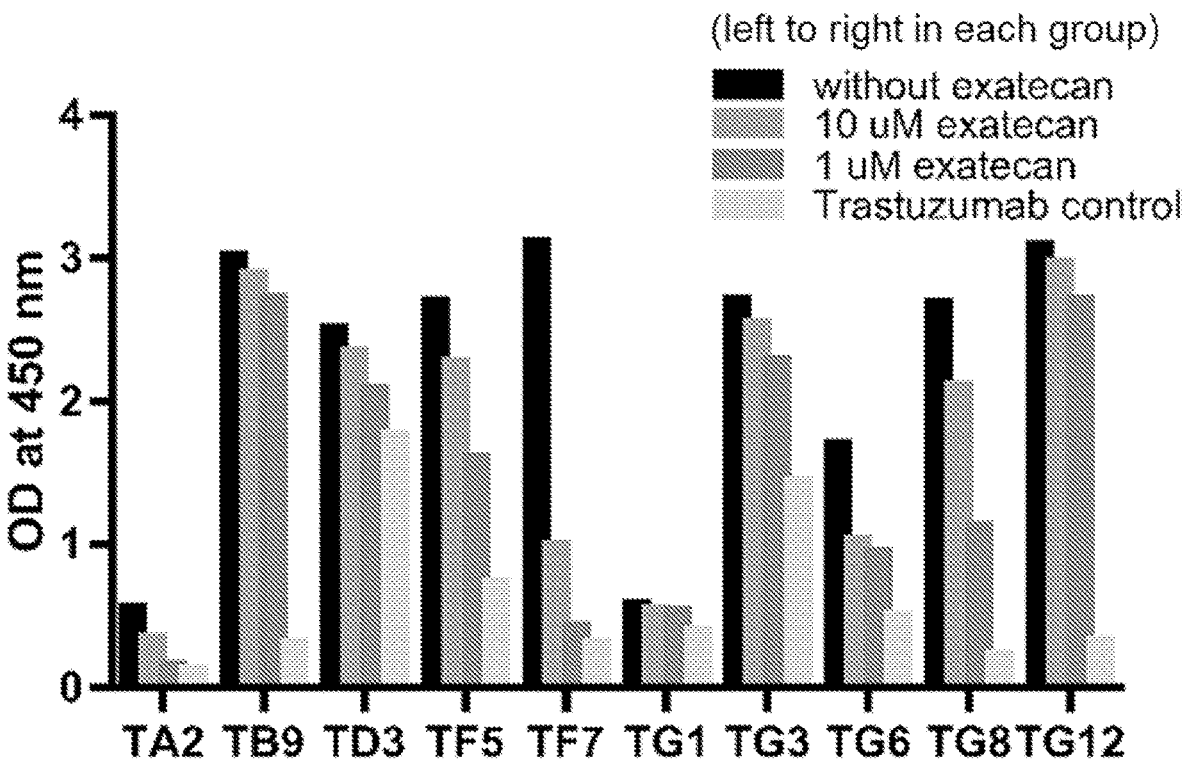
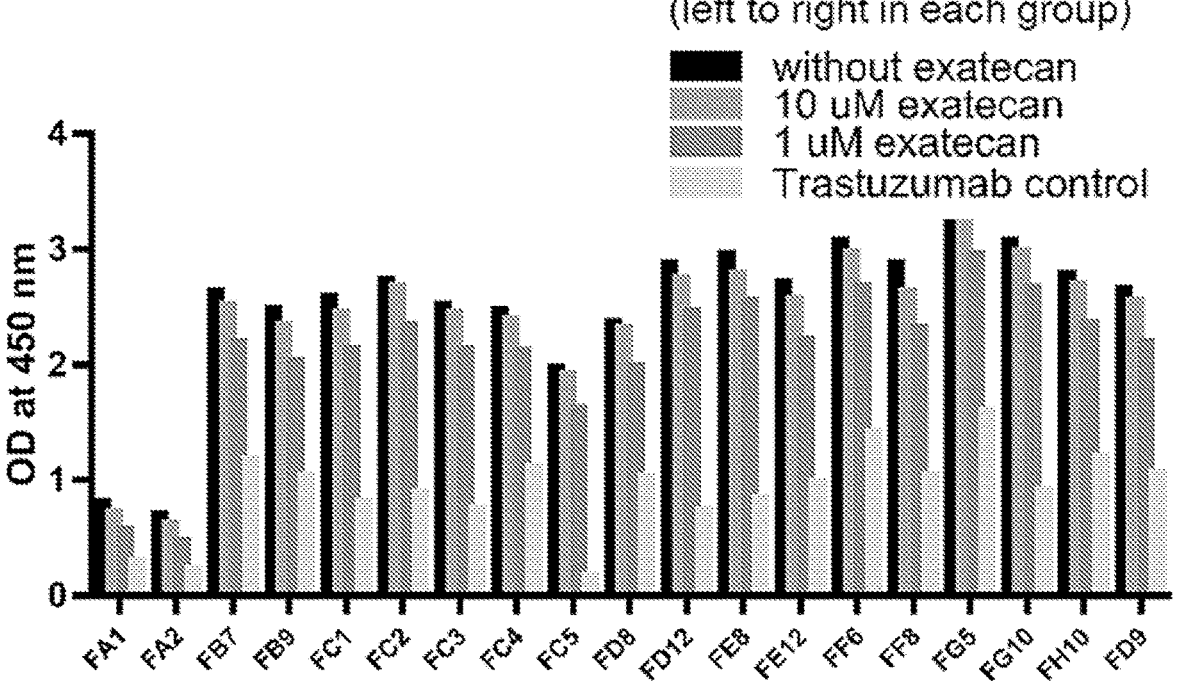
Fig. 14

| Positive Exatecan Binding sdAb Sequences | |
| --- | --- |
| Name (First Letter: T = Trypsin eluted library, F = exatecan eluted library, Second Letter: + # = Colony Identification) | |
| TA2 | QVQLQESGGGLVQPGGSLRVSCAASGFTFSSYYMSWVRQAPGKGLEWVSAINT GTGSTYYADSVKGRFTISSDNAKNTVYLQMSSLKPEDTALYYCARSSLEGRVEKPY DYWGQGTQVTVSS |
| TB9 | QVQLQESGGGLVQPGGSLRLSCAASGFTFGSNYYISWVRQAPGKGLEWVSAINT GGGSTYYADSVKGRFTISRDNAKNTLYLQMNSLKPEDTALYYCARSSLEGRVEKPY DYWGQGTQVTVSS |
| TF5 | QVQLQESGGGLVQPGGSLRLSCAASGFTFGSYYMSWVRQAPGKGLEWVSAINT GDGNTYYPDSVKGRFTISRDNAKNTLYLQMNSLKPEDTALYYCARSSYEGRVEKPY DYWGQGTQVTVSS |
| TF7 | QVQLQESGGGLAQPGGSLRVSCATSGFTFSSNYYISWVRQAPGRGLEWVSAINT GDGSTYYAHSVKGRFTISRDNAKNTLYLQMNSLKPEDTALYYCARSSLEGRIEKPYD YWGQGTQVTVSS |
| FA1 | QVQLQESGPGLVKPSQTLSLICTVSGGSITTNYYYWSWIRQAPGKGLEWMGGIN YWGSTYYSPSLKSRTSIFRDTSKNQFTLQLSSVTPEDTAIYYCARGFAAYGSSWYGY DYWGQGTQVTVSS |
| FA2 | EVQLVESGPGLVKPSQTLSLTCTVSGGSITTNYYYWSWIRQAPGKGLEWMGGIN YWGSTYYSPSLKSRTSIFRDTSKNQFTLQLSSVTPEDTAIYYCARGFAAYGSSWYGY DYWGQGTQVTVSS |

Fig. 15

Total    1ˢᵗ    2ⁿᵈ    1ˢᵗ    2ⁿᵈ    3ʳᵈ
Protein Wash Wash Elution Elution Elution
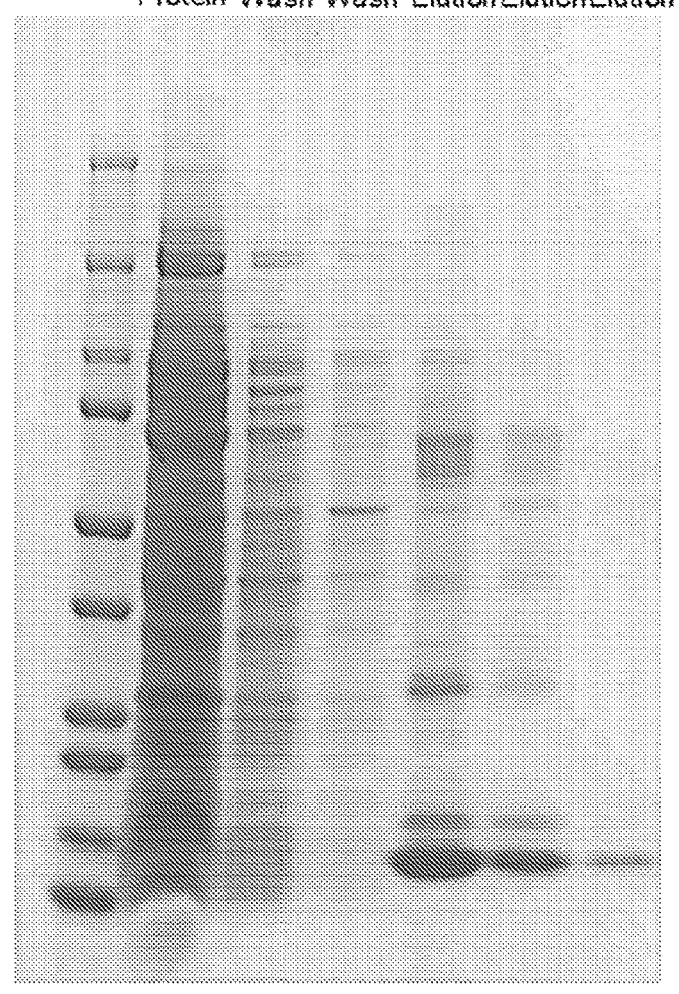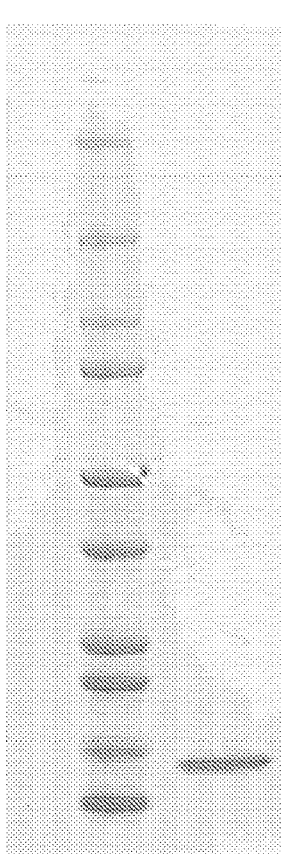
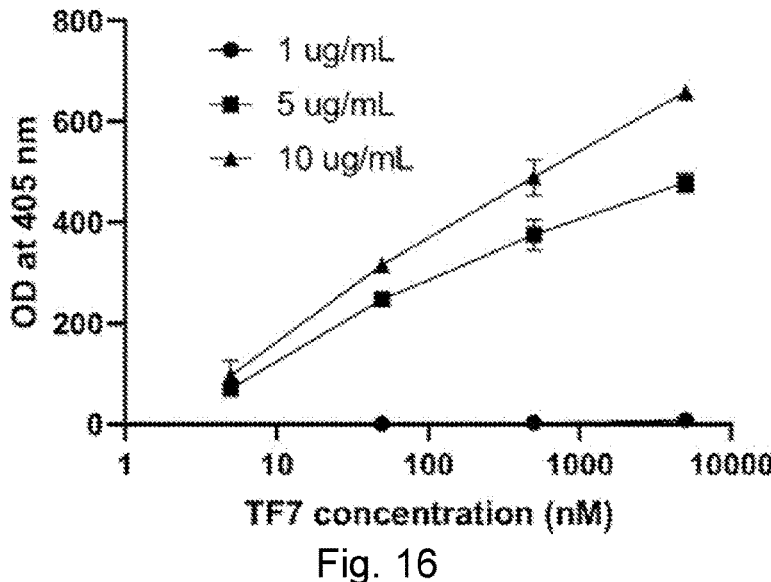
Fig. 16

A Biotin-Calich Llama plasma
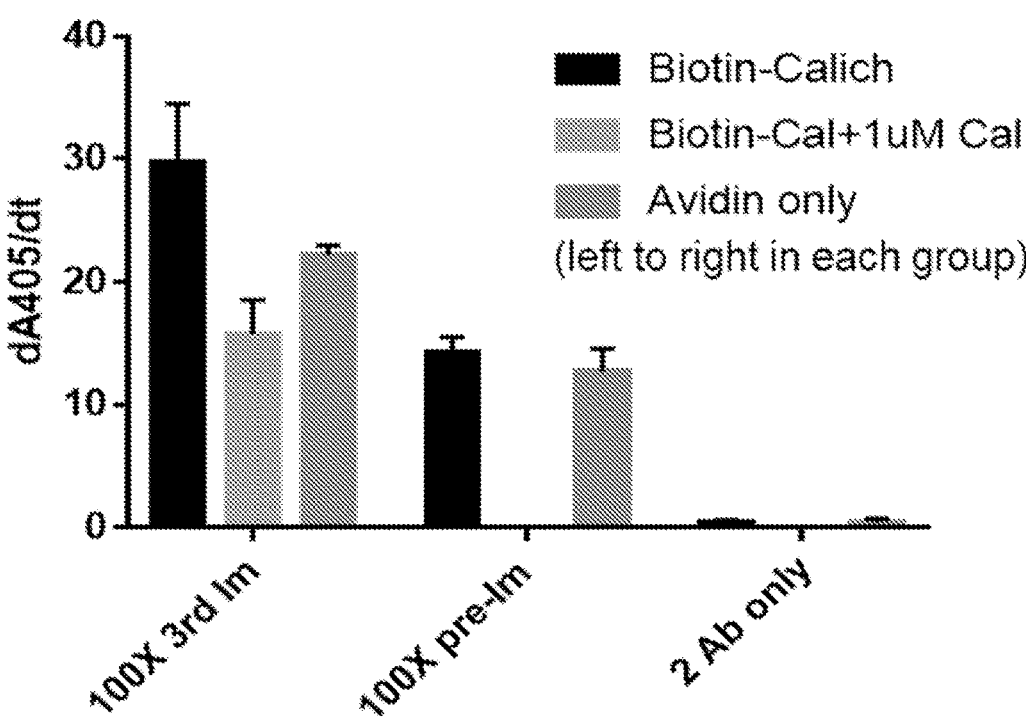
B beads-calich conjugation test
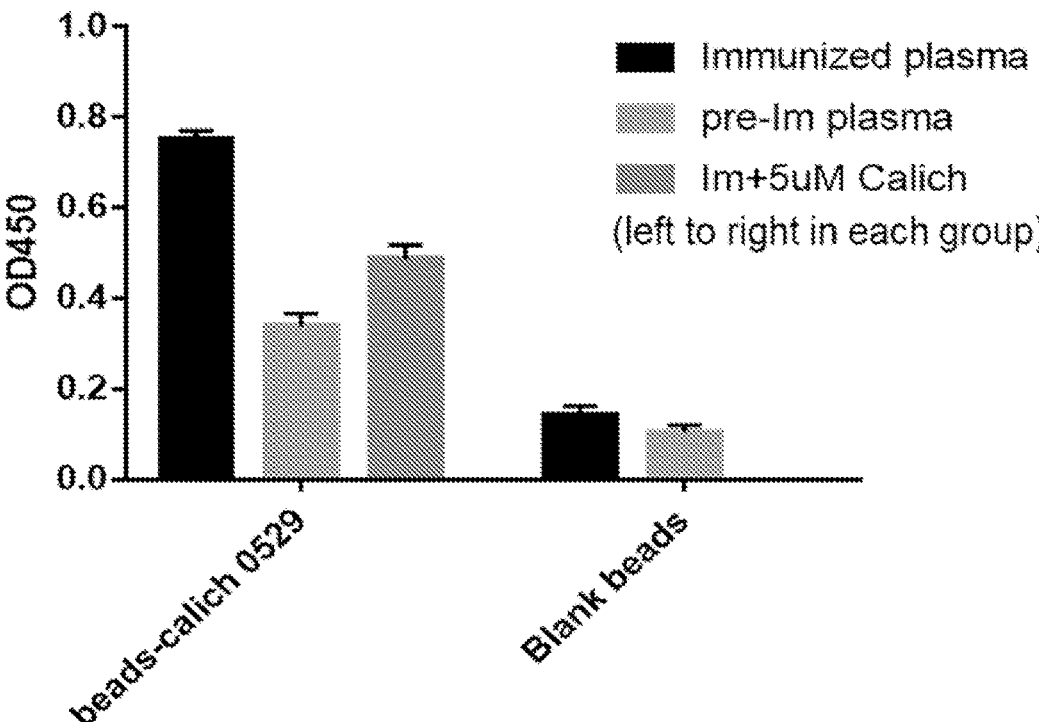
Fig. 21

A          Phage ELISA (06012018)

phage (1:100 dilution)

B  calicheamicin on molm14 cells with peptide C2 (100uM)
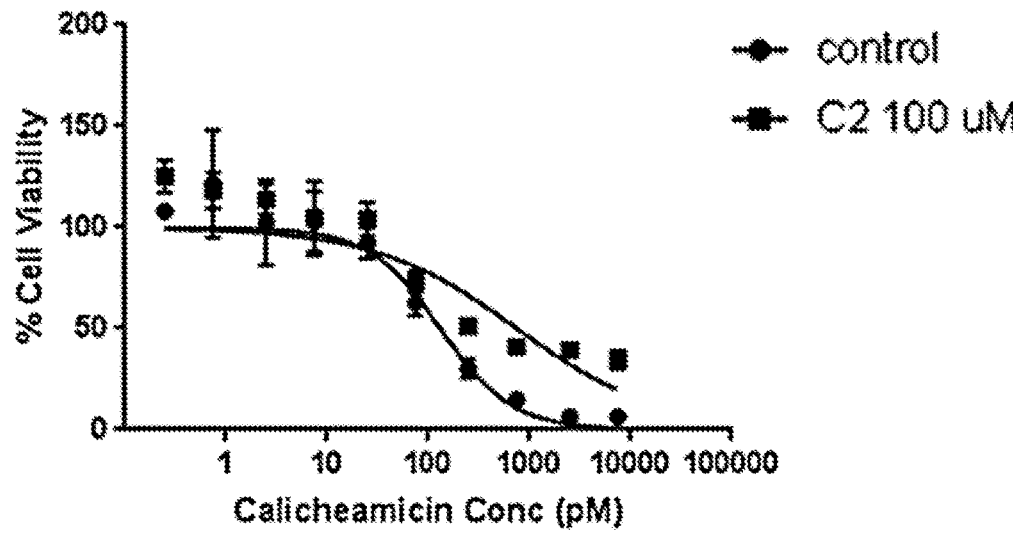
C  calicheamicin on molm14 cells with peptide C9 (100uM)
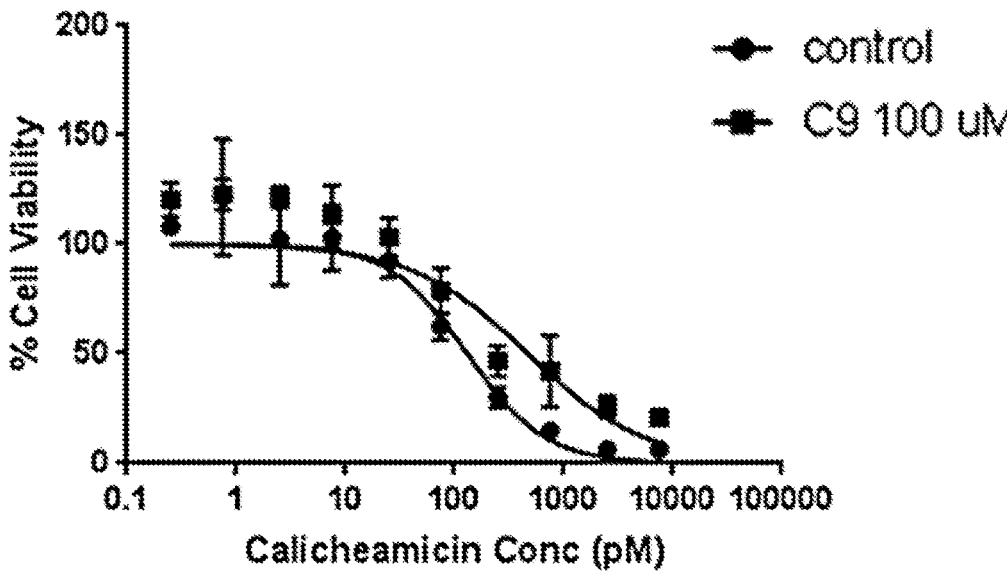
Fig. 23 (continued)

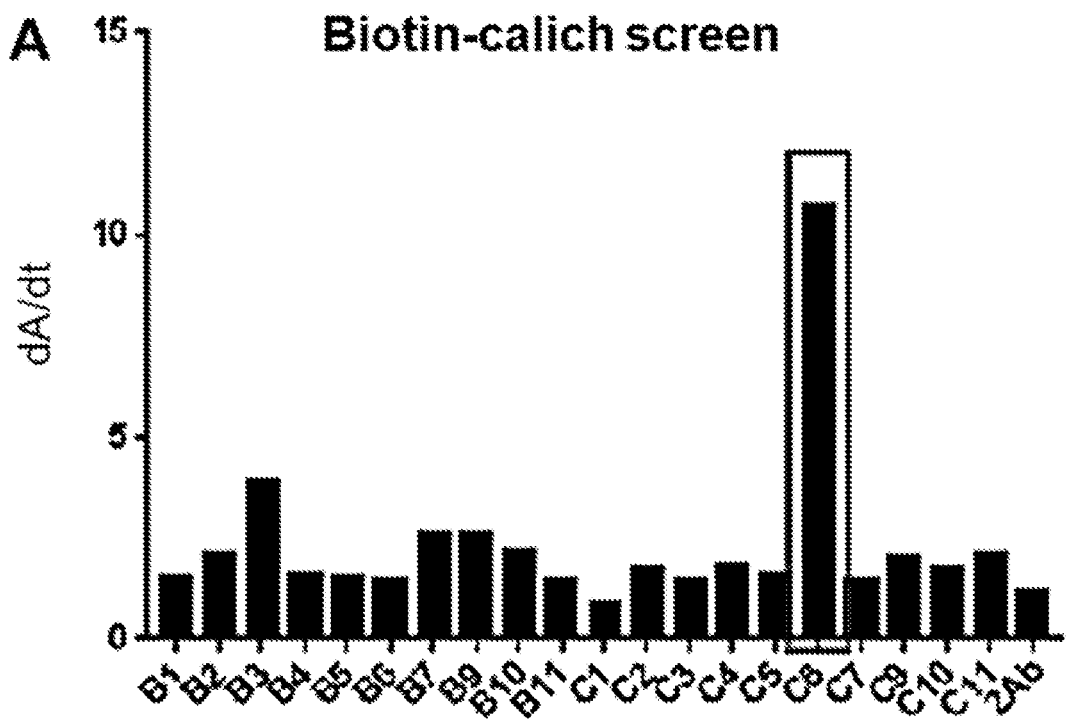
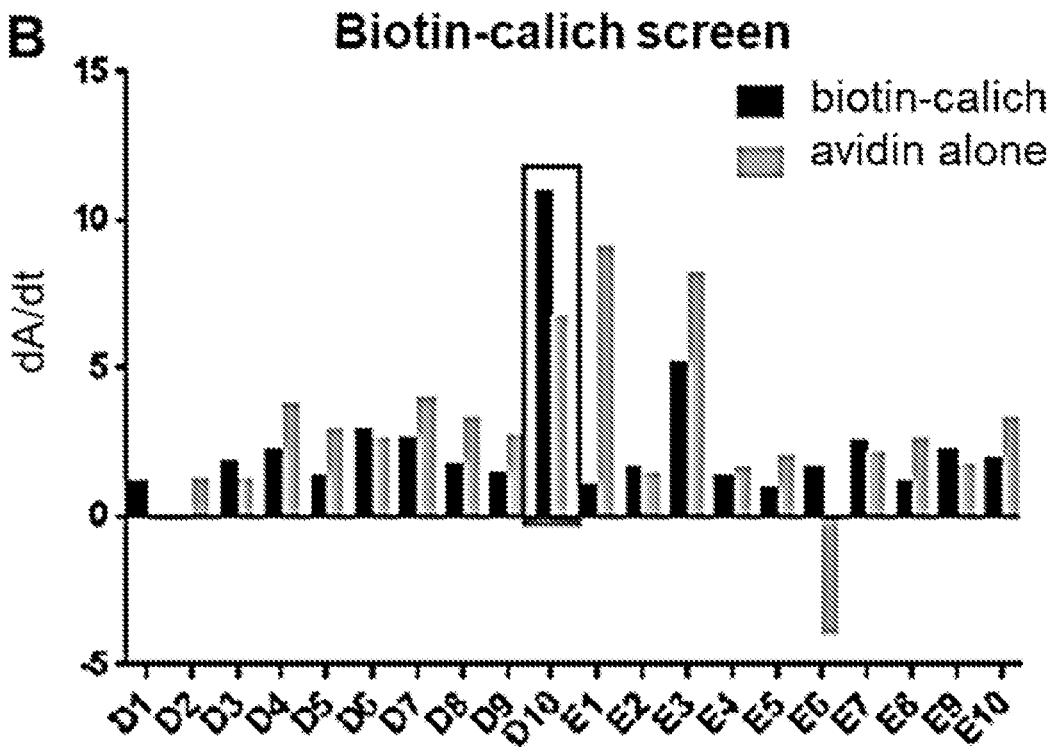
Fig. 25

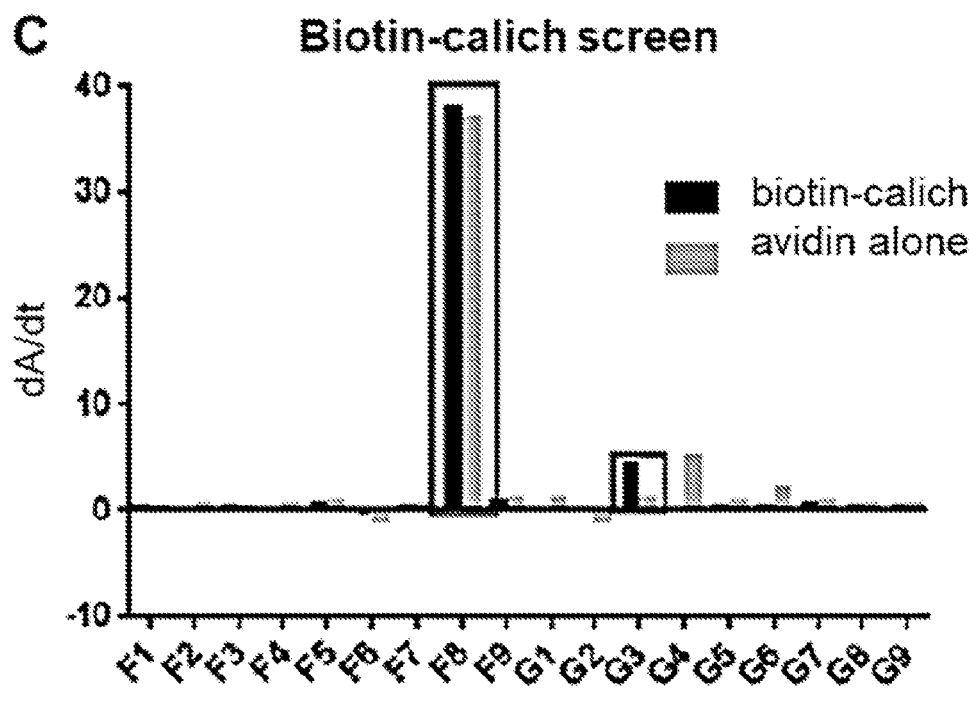
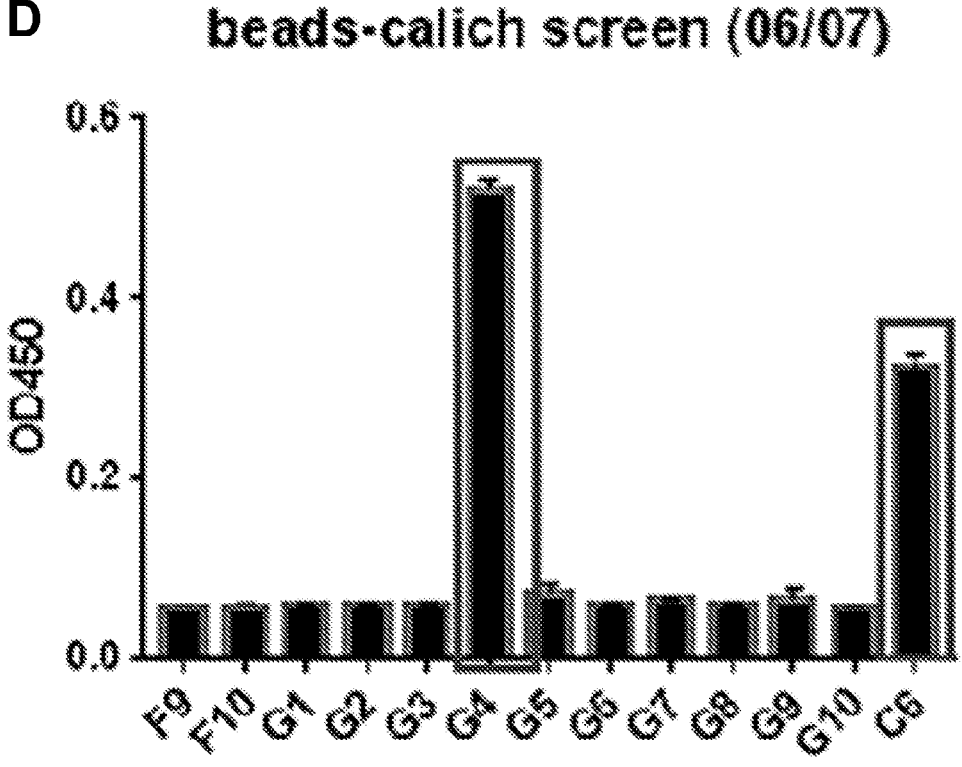
Fig. 25 (continued)

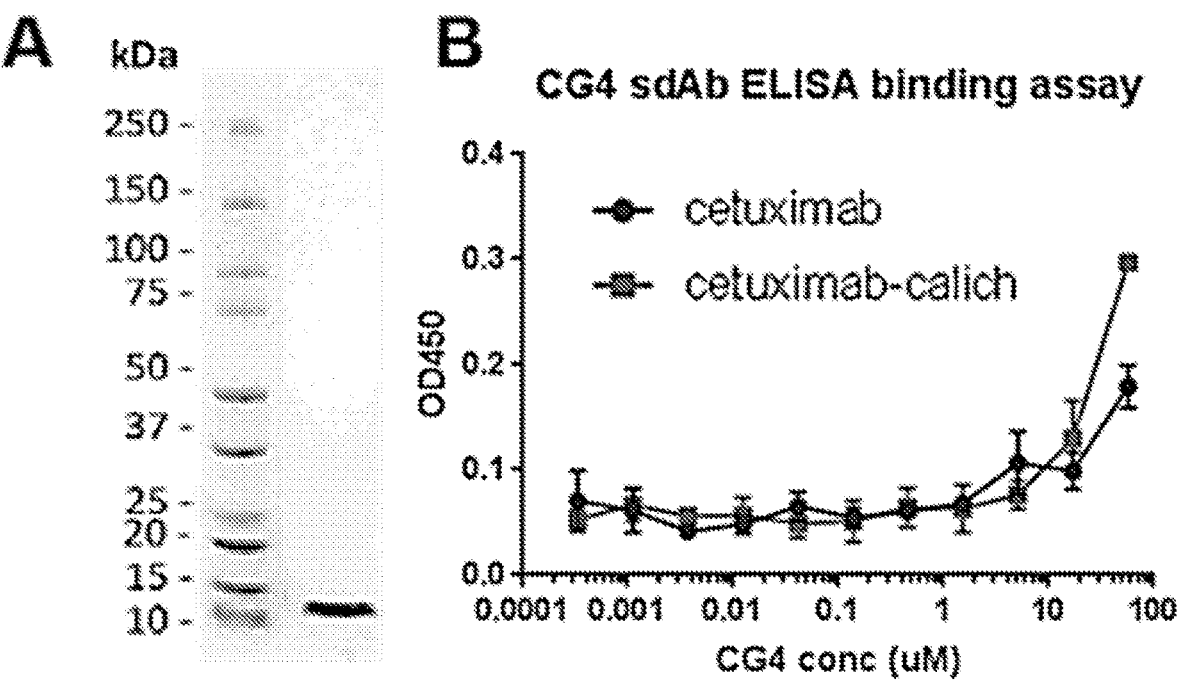
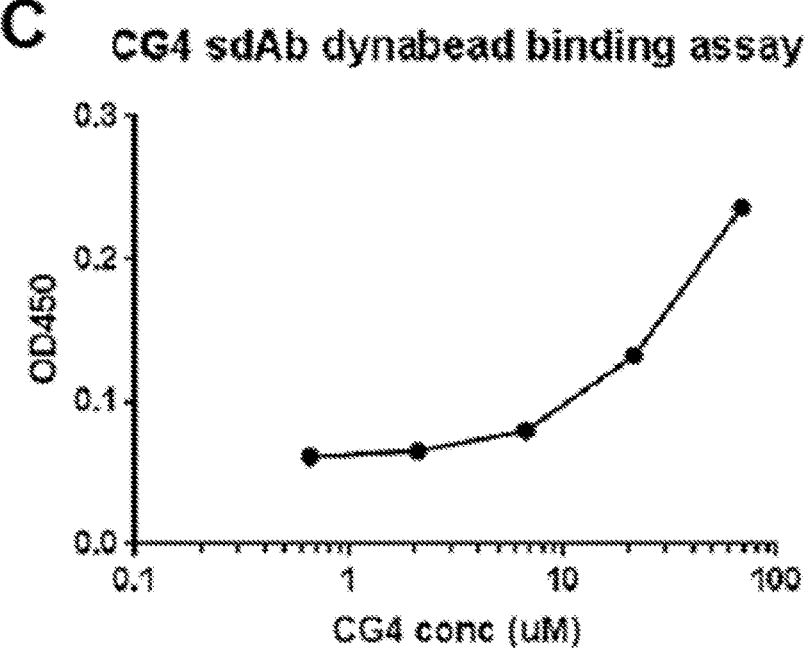
Fig. 26

D
Competitive ELISA coated with cetuximab-calicheamicin
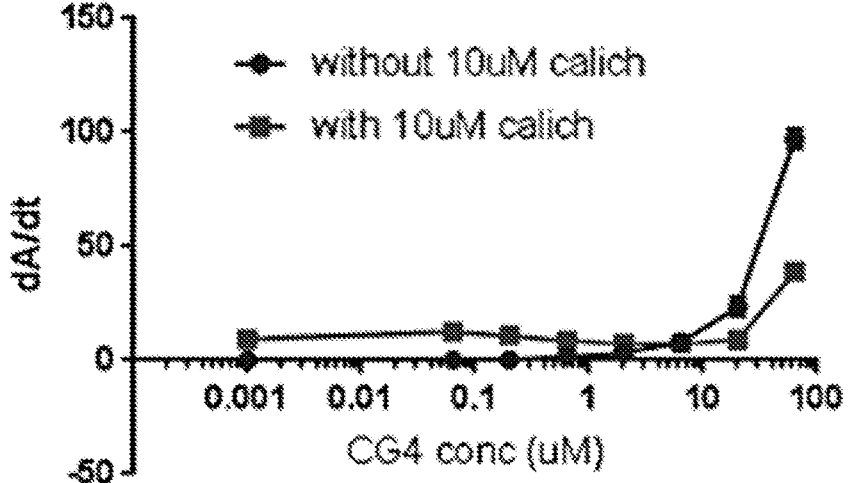
E
Competitive ELISA with Avidin-biotin-calicheamicn
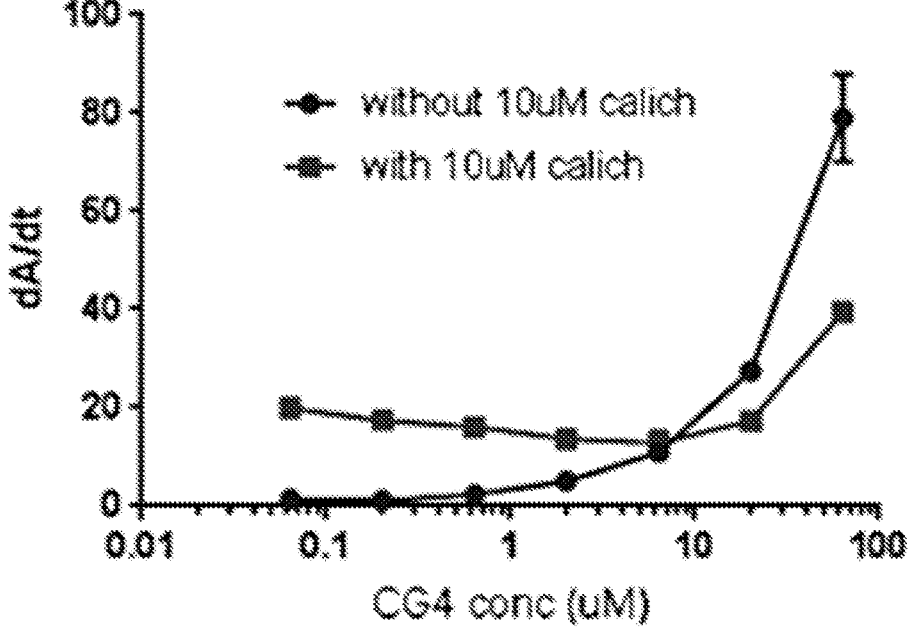
Fig. 26 (continued)

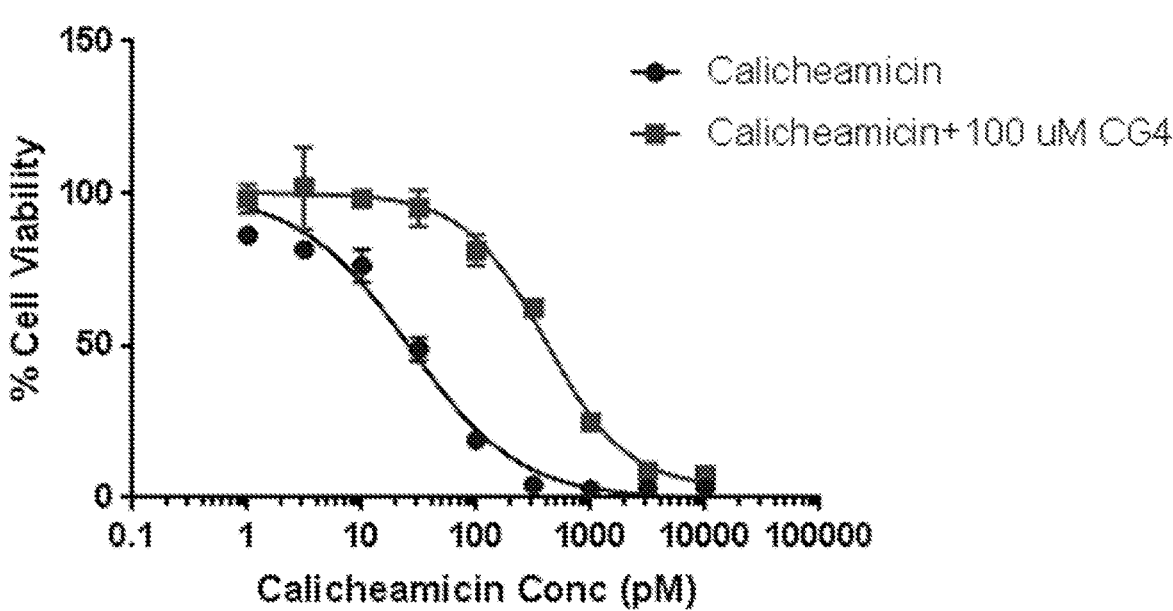
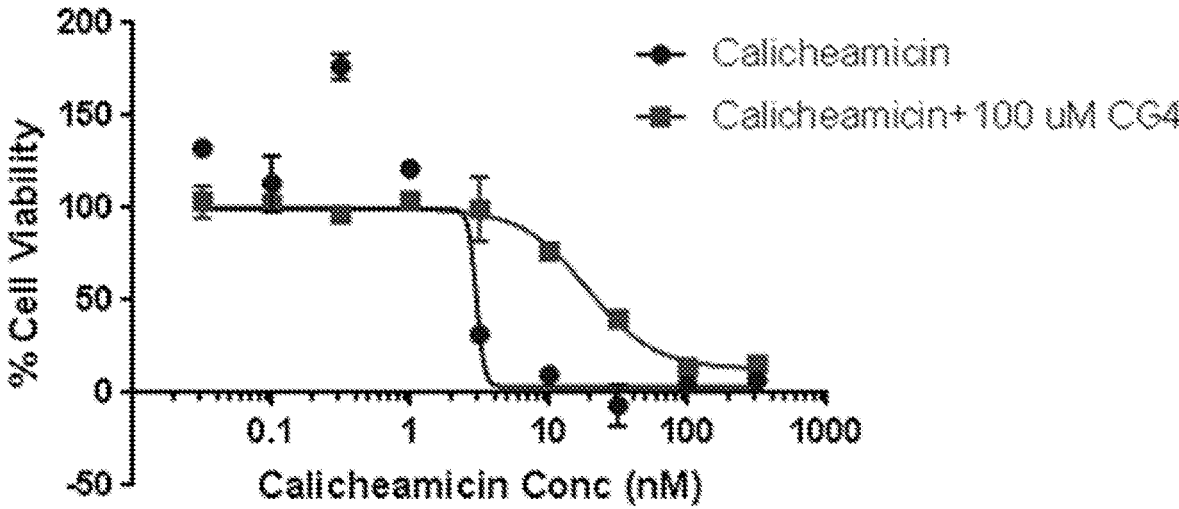
Fig. 27

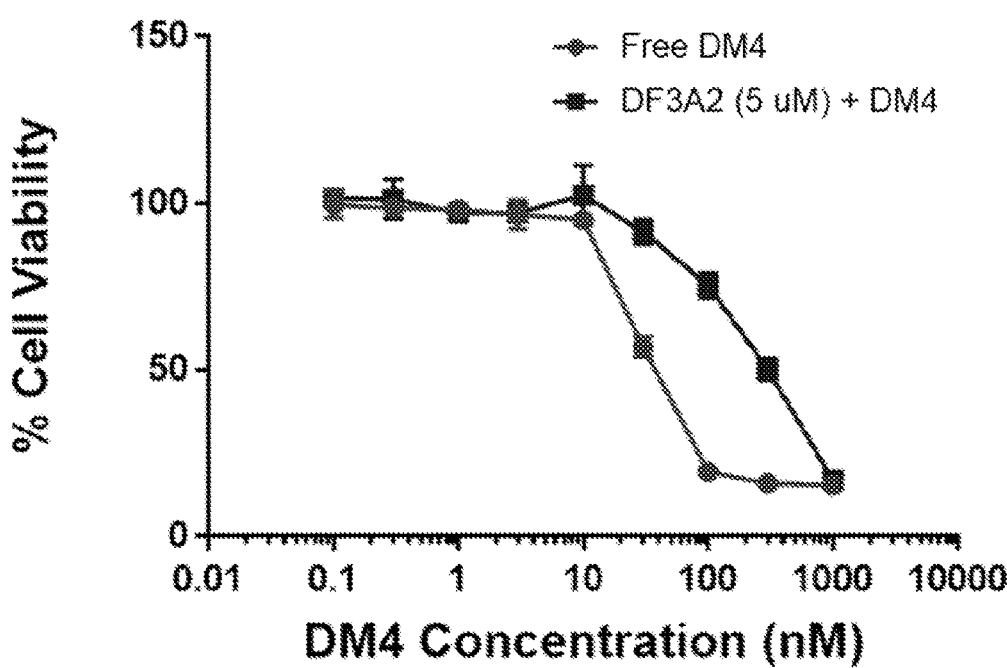
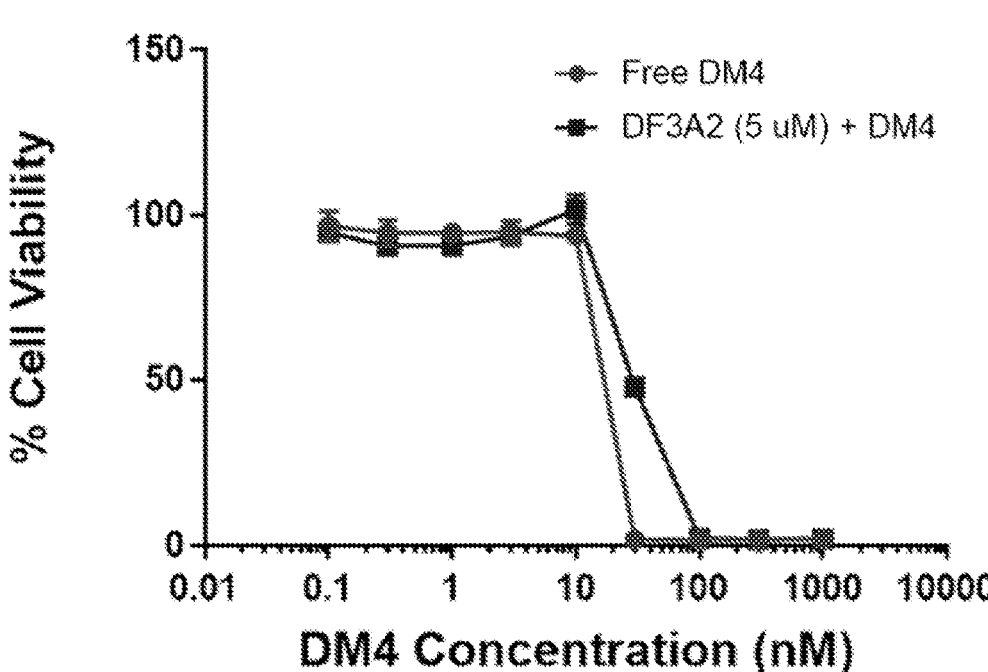
Fig. 33

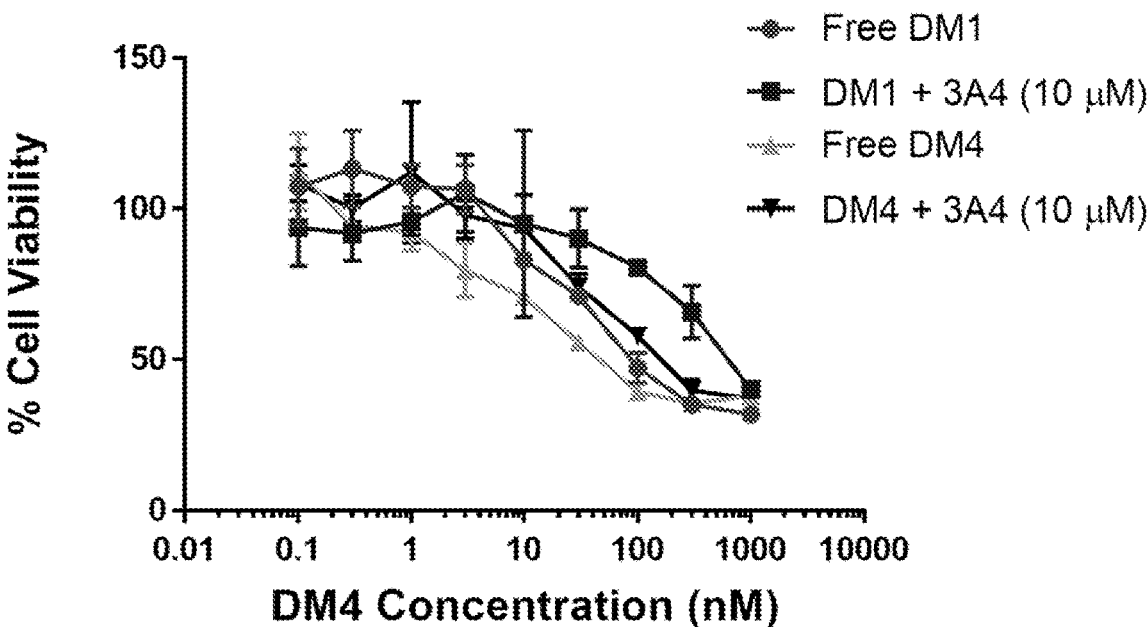
Lovo 6h Exposure
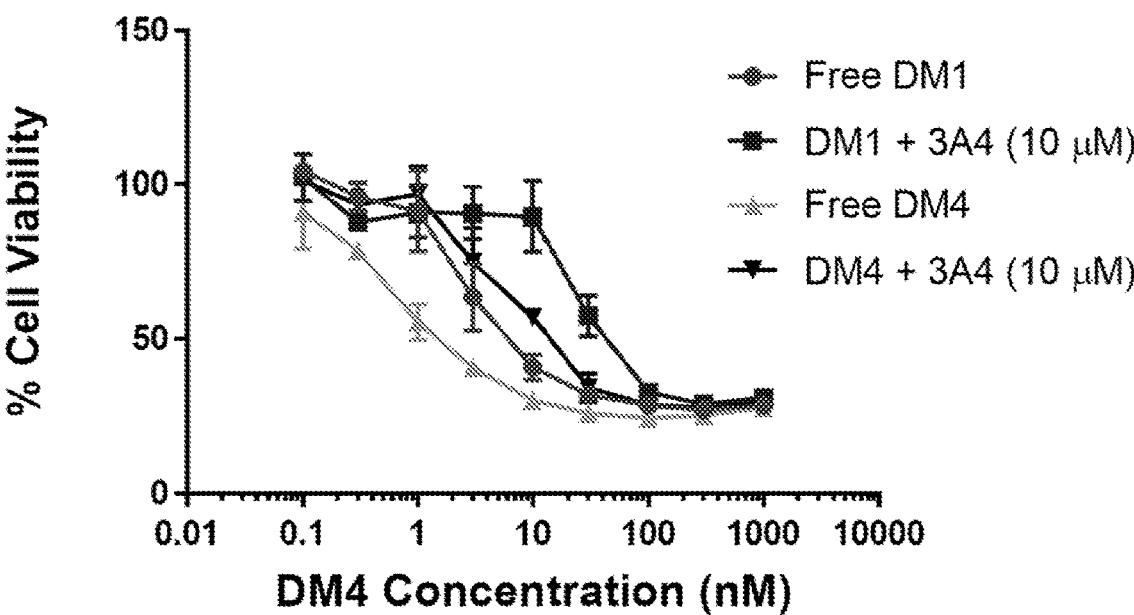
Lovo 24h Exposure
Fig. 35

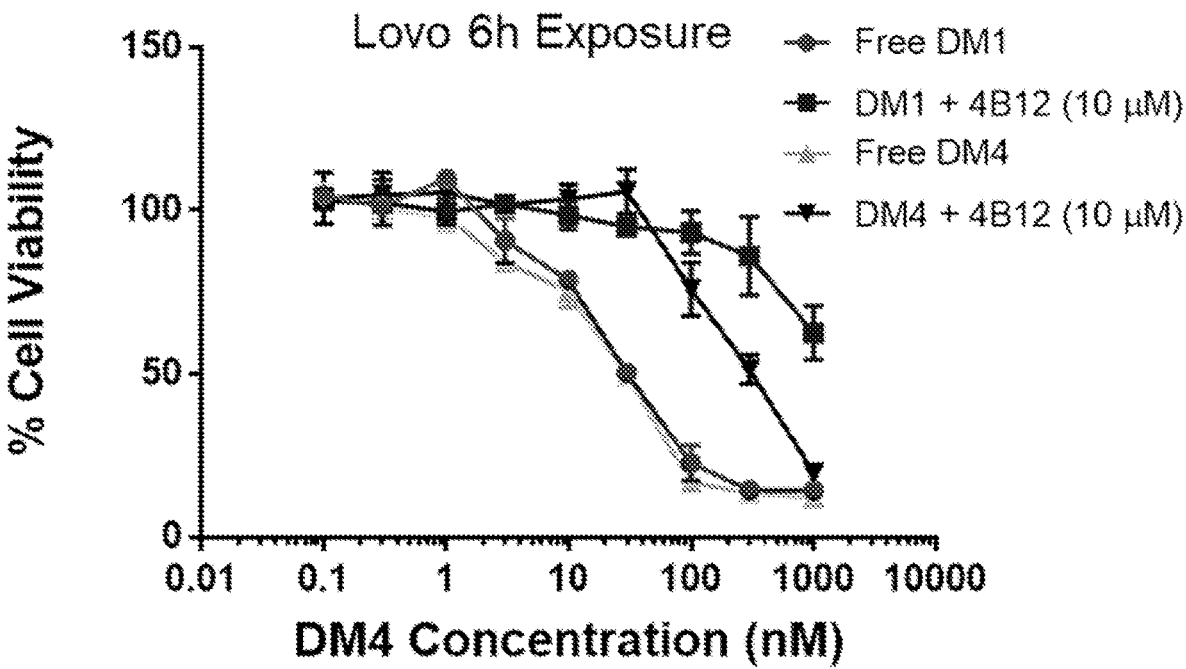
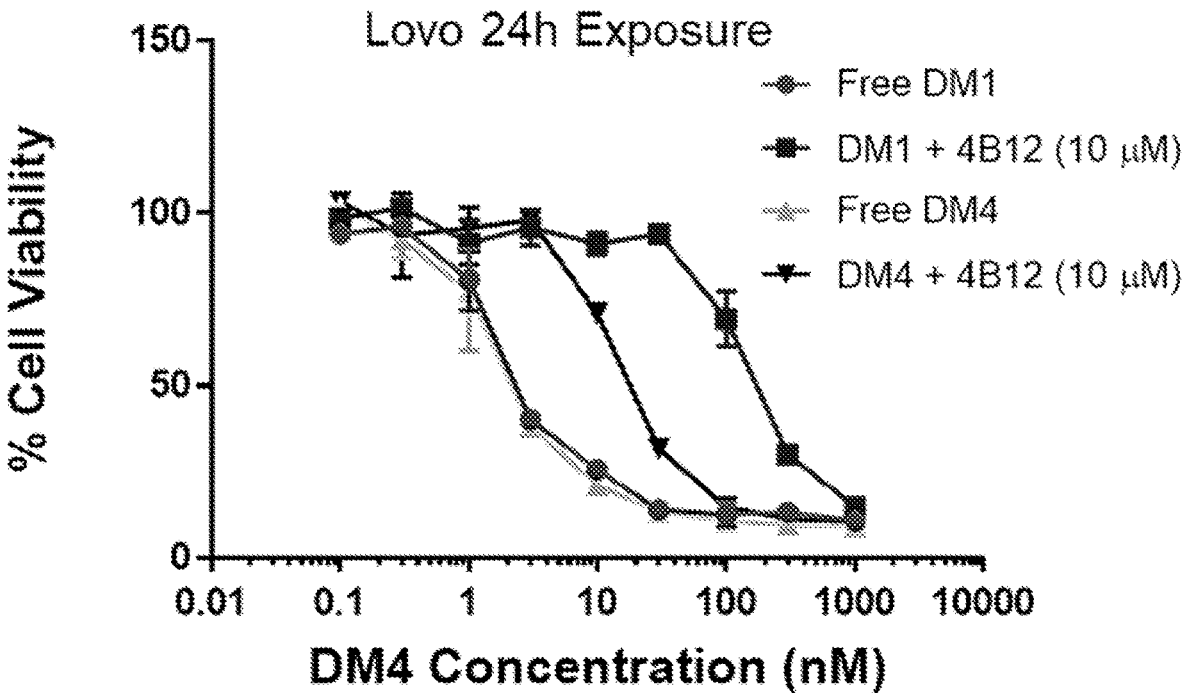
Fig. 37

D9 Media Dilution

[MMAE] (nM)

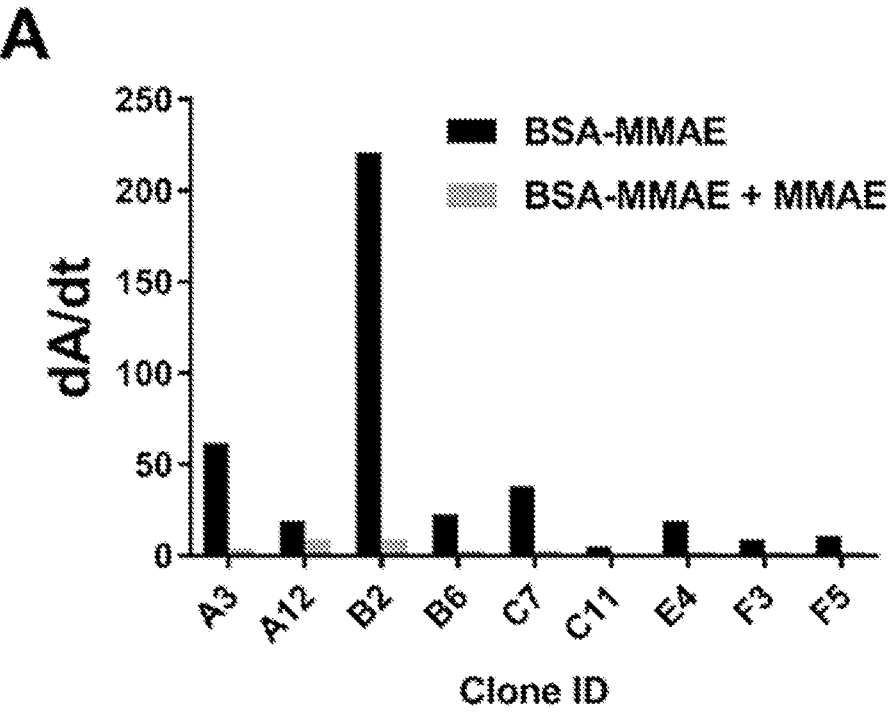
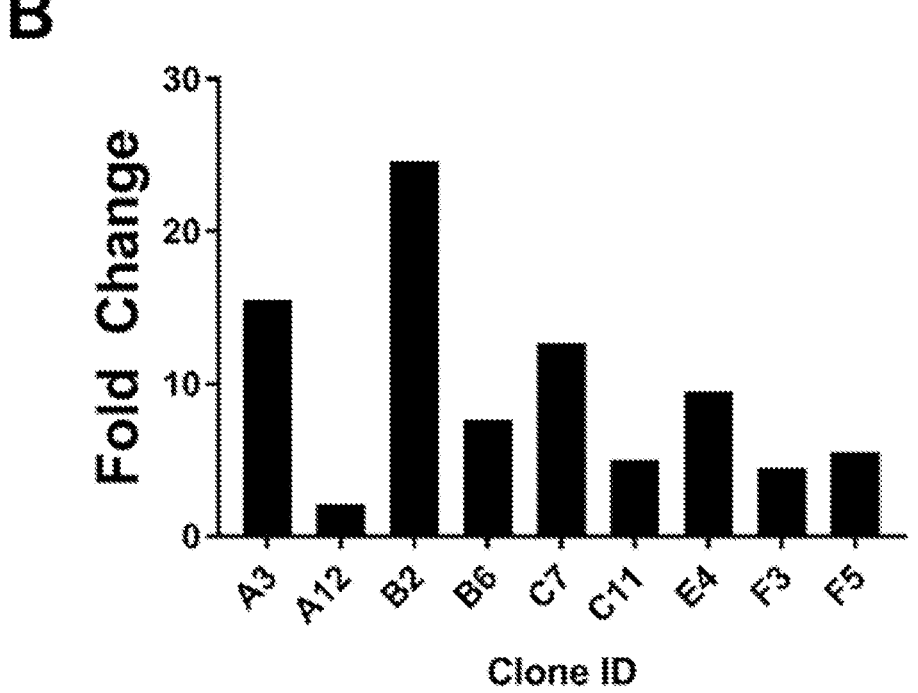
Fig. 42

A
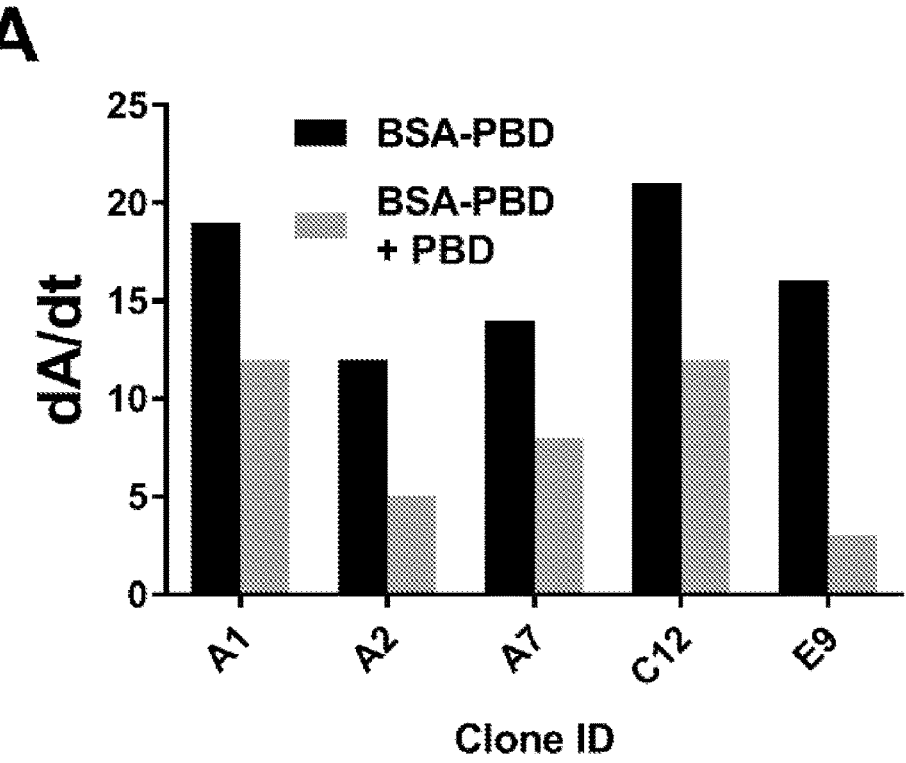
B
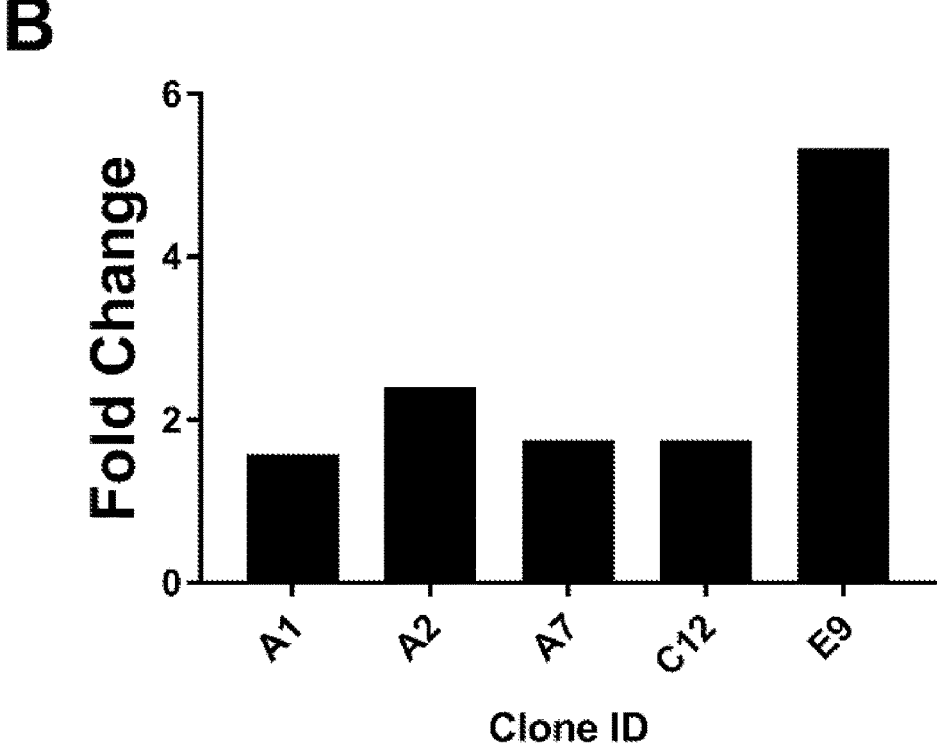
Fig. 44

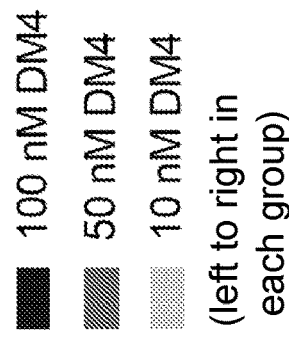
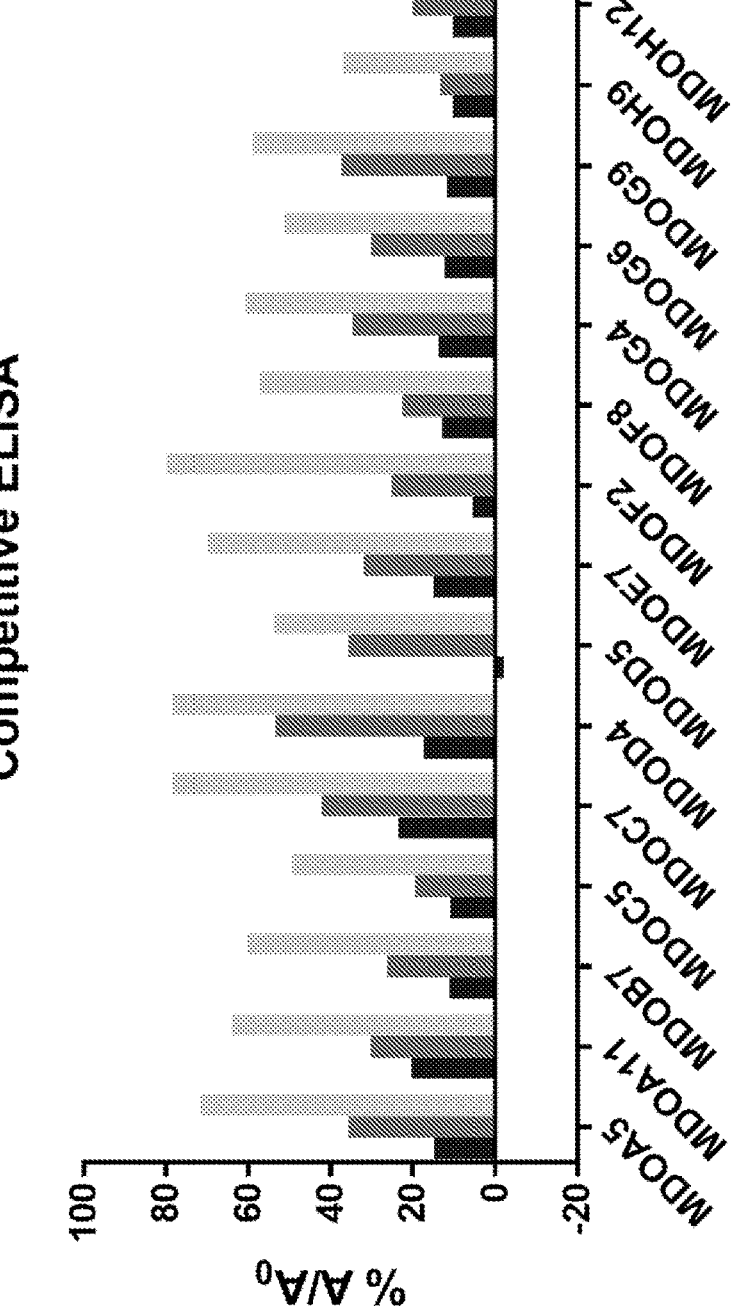
Fig. 45 (continued)

KG-1
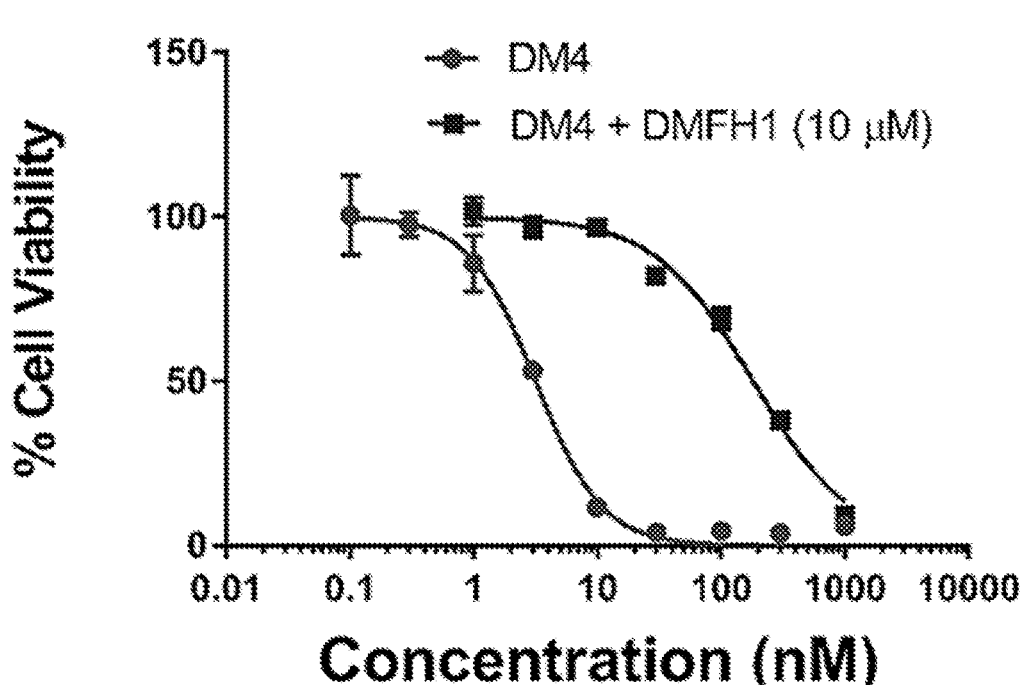
MV-4-11
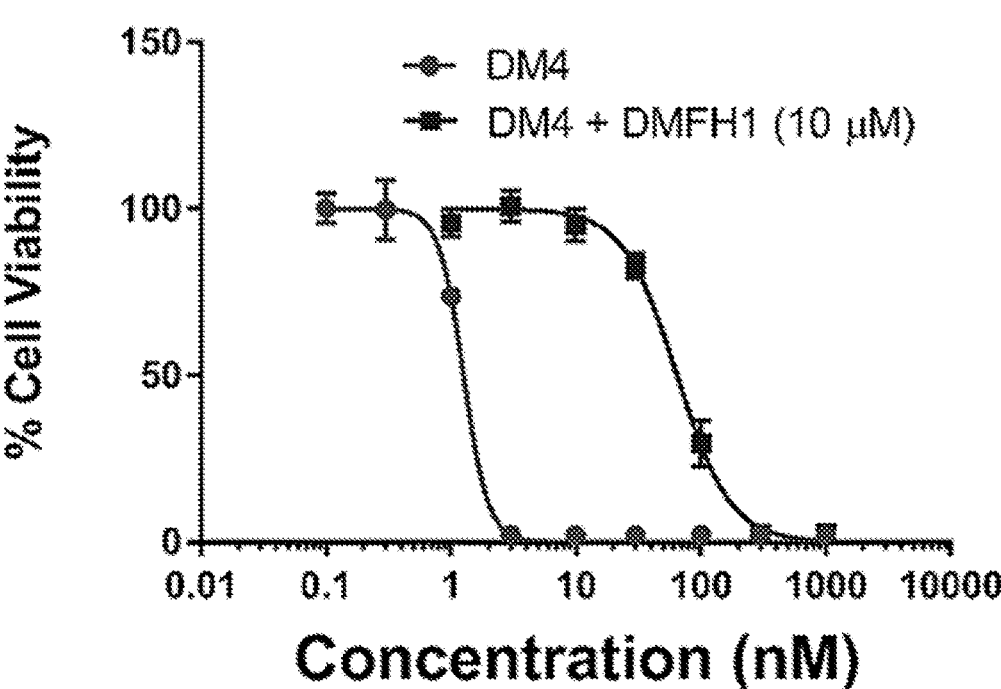
Fig. 48 (continued)

```
Murine    1 D I QMTQSPASL SASVGETVT I TCRASGN I HNSLAWYQQ I KGRSPQLLVYNAKTL  54
Chimeric  1 . . . . . . . . . . . . . . . . . . . . . . . . . . . . . . . . . . . . . . . . . . . . . . . . . . . .  54
Human     1 . . VL . . . . S . . . . . . . . . . . . . . . . . . . . . . . . . . . . . . . . . KA . K . . I . . . . . .  54

Murine    55 ADGVPSRFSGSGSGTQYSLK I NSLHPEDFGSYYCQHFWSTPFTFGSGTKLE I KR 108
Chimeric  55 . . . . . . . . . . . . . . . . . . . . . . . . . . . . . . . . . . . . . . . . . . . . . . V . . . . 108
Human     55 . . . . . . . . . . . . . . DF . . T . S . . E . . . . AT . . . . . . . . . . . . . . . Q . . . V . . . . 108

Murine    109 ADAAPTVS I FPPSSEQLTSGGASVVCFLNNFYPKD I NVKWK I DGSERQNGVLNS 162
Chimeric  109 TV . . . S . F . . . . . D . . . K . . T . . . . . L . . . . . . REAK . Q . . V . NALQSGNSQE . 162
Human     109 TV . . . S . F . . . . . D . . . K . . T . . . . L . . . . . . REAK . Q . . V . NALQSGNSQE . 162

Murine    163 WTDQDSKDSTYSMSSTLTLTKDEYERHNSYTCEATHKTSTSP I VKSFNRNEC  214
Chimeric  163 V . E . . . . . . . . . . L . . . . . . S . AD . . K . KV . A . . V . . QGLS . . VT . . . . . G . . 214
Human     163 V . E . . . . . . . . . . L . . . . . . S . AD . . K . KV . A . . V . . QGLS . . VT . . . . . G . . 214

Murine    1 EVQLQQSGAELVKPGASVKLSCTASGFN I KDTY I HW - - - VKQRPEQGLEW I GM I DLAND  56
Chimeric  1 . . . . . . . . . . . . . . . . . . . . . . . . . . . . . . ^ - - . . . . . . . . . . . . . . . . . . .  56
Human     1 . . . . . E . . . . . . . . . . . . . . . . . A . . . . . . . . . - - - . R . . . G . . . . . . . . . . . .  56
VHH       1 Q . . . V . . . GG . . Q . . G . LR . . . A . . . . . . . . . . . . . MSW . R . A . GK . . . . VS - P . . . . .  58

Murine    57 NTKYDPKFQ - - - - - GKAT I I TDTSSNKAYLQVSSLTSEDTAVYYCATWGA I I TLGGWGQ 110
Chimeric  57 . . . . . . . . . . - - - - - . . . . . . . . . . . . . . . . . . . . . . . . . . . . . . . . . . . . . . . . 110
Human     57 . . . . . . . . . . - - - - - RV . . TV . . . T . . . . . . L . . . . . . . . . . . . . . . . . . . . . . . . 110
VHH       59 . . . . . . . YYADSVK . RF . . SR . N . K . TL . . . MNT . RA . . . . . . . . . . . . . . . . . . . . . . 117

Murine    111 GTLVTVSAAKTTPPSVYPLAPGSAAQTNSMVTLGCLVKGYFPEPVTVTWNSGSLSSGVH 169
Chimeric  111 . . . . . . . S . S . KG . . . F . . . . S . KSTSGGTAA . . . . . . D . . . . . . . . S . . . . A . T . . . . 169
Human     111 . . . . . . . S . S . KG . . . F . . . . S . KSTSGGTAA . . . . . . D . . . . . . . . S . . . . A . T . . . . 169
VHH       118 TMVTVS . - - - - - - - - - - - - - - - - - - - - - - - - - - - - - - - - - - - - - - - - - - - - - - - - - - 124

Murine    170 TFPAVLQS - DLYTLSSSVTVPSSTWPSETVTCNVANPASSTKVDKK I VPRDC - - - - -   220
Chimeric  170 . . . . . . . . SG . . S . . . V . . . . . . SLGTQ . Y I . . . NHKP . N . . . . . . VE . KS . DKTHL 226
Human     170 . . . . . . . . SG . . S . . . V . . . . . . SLGTQ . Y I . . . NHKP . N . . . . . . VE . KS . DKTHL 226
VHH          - - - - - - - - - - - - - - - - - - - - - - - - - - - - - - - - - - - - - - - - - - - - - - - - - - - - - -
```

Fig. 58

|  | Mouse | Human | Chimeric |
|---|---|---|---|
| IC50 Dxd | 2.9E-09 | 6.0E-09 | 3.1E-09 |
| 95% CI | 1.807e-009 to 4.633e-009 | 4.946e-009 to 7.304e-009 | 2.613e-009 to 3.636e-009 |
| IC50 T-Dxd | 3.5E-06 | 2.6E-06 | 8.9E-07 |
| 95% CI | 2.317e-006 to 5.413e-006 | 1.772e-006 to 3.802e-006 | 6.662e-007 to 1.200e-006 |
| IC50 SN38 | 1.6E-09 | 1.4E-09 | 1.1E-09 |
| 95% CI | 1.4e-09 to 1.8e-09 | 1.1e-09 to 1.7e-09 | 7.9e-10 to 1.6e-09 |

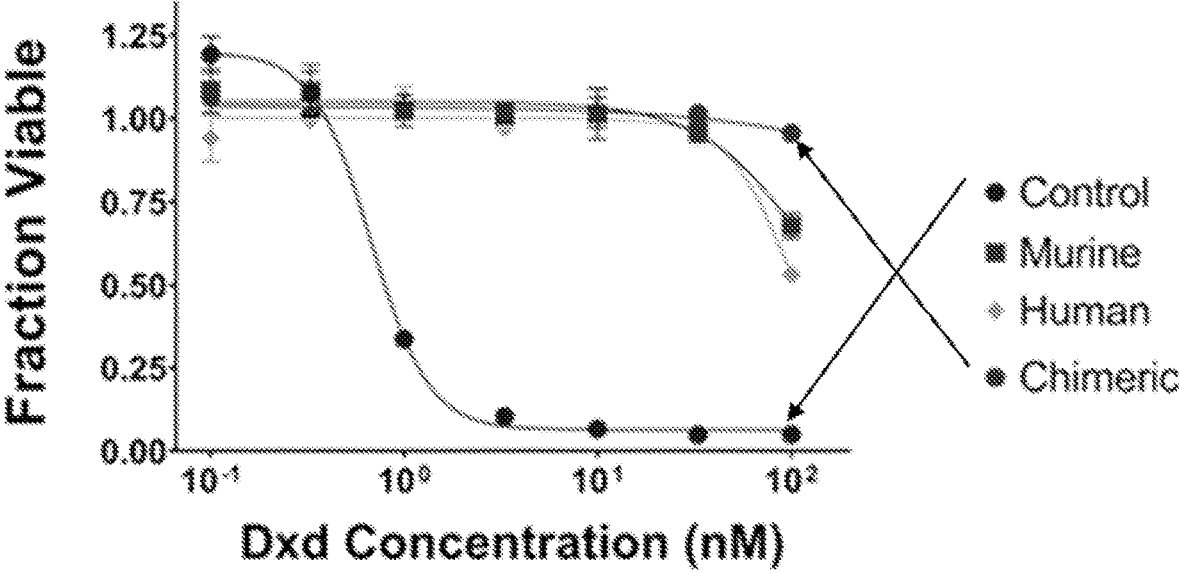
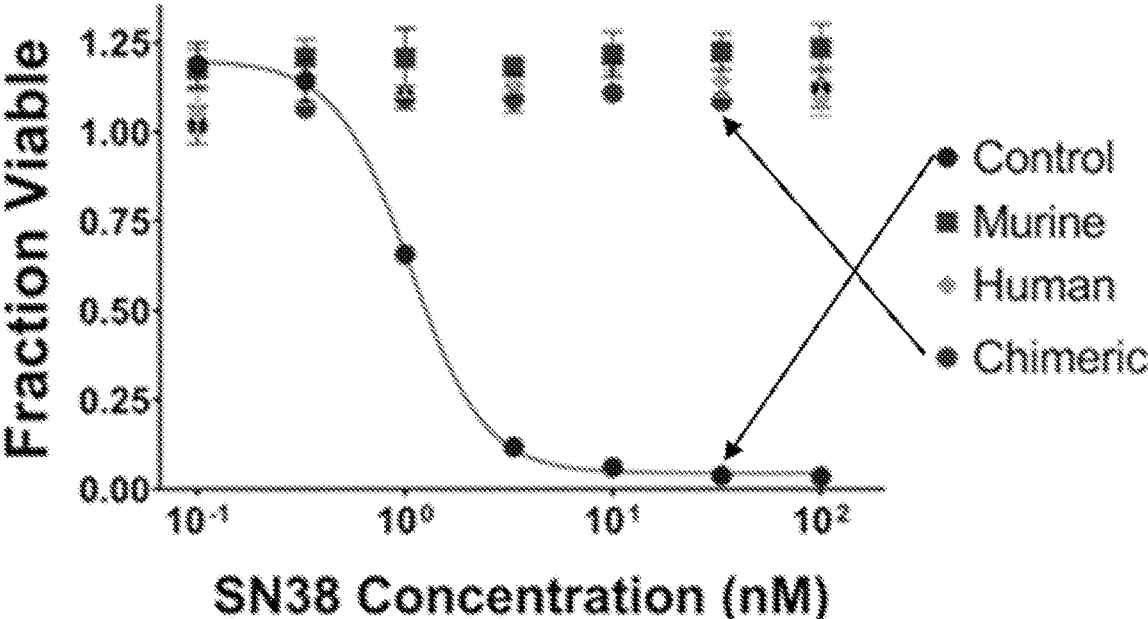
Fig. 60

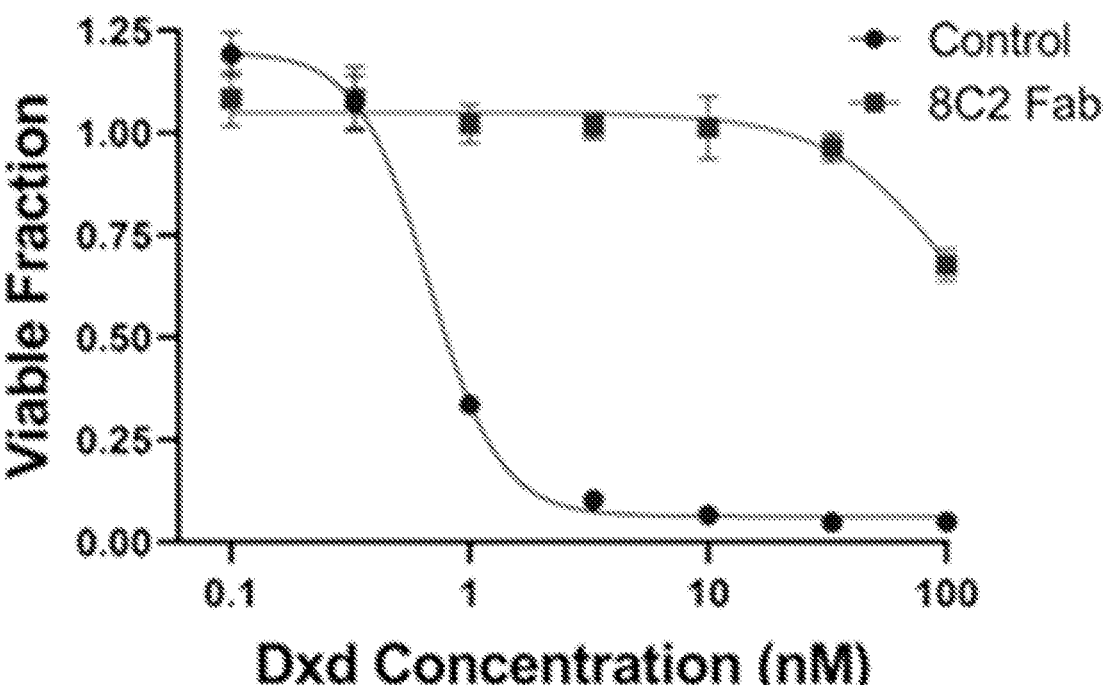
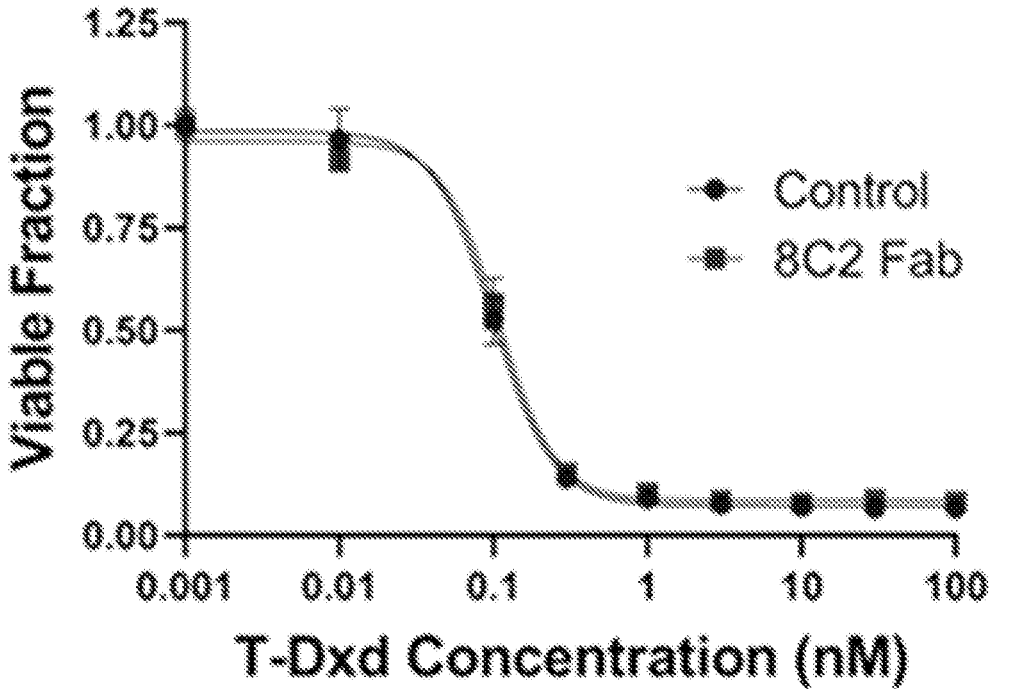
Fig. 61

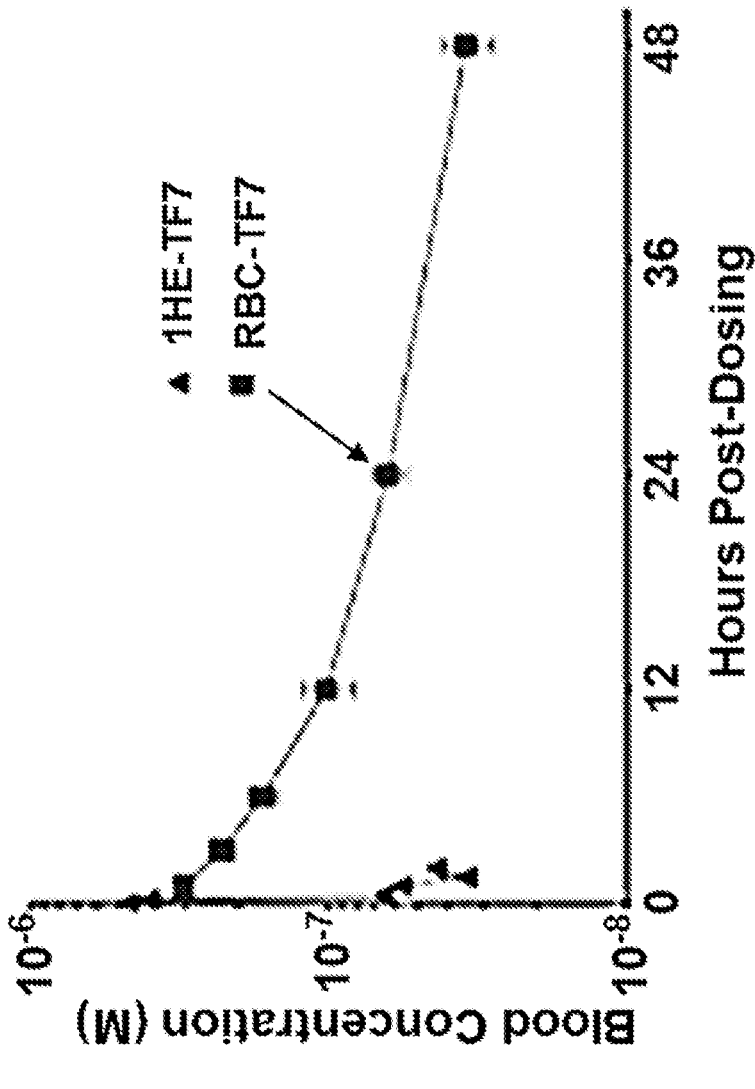
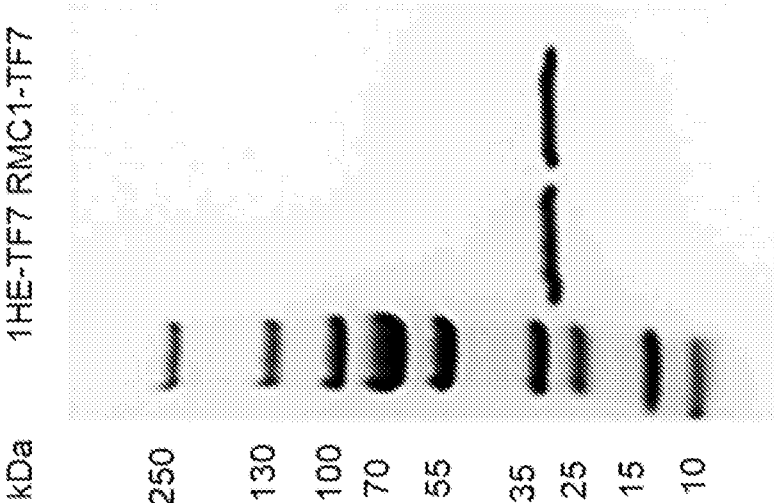
Fig. 63

SEQUENCE LISTING

```
<160> NUMBER OF SEQ ID NOS: 69

<210> SEQ ID NO 1
<211> LENGTH: 16
<212> TYPE: PRT
<213> ORGANISM: Artificial Sequence
<220> FEATURE:
<223> OTHER INFORMATION: C2 peptide

<400> SEQUENCE: 1

His Ser Trp His Trp Pro Ser Trp Trp Ala Gly Gly Gly Gly Gly Ser
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: C9 peptide

<400> SEQUENCE: 2

Ser Trp Trp Phe Pro Gln Trp Met Ala Gln Tyr Pro Gly Gly Gly Ser
1               5                   10                  15

<210> SEQ ID NO 3
<211> LENGTH: 255
<212> TYPE: PRT
<213> ORGANISM: Artificial Sequence
<220> FEATURE:
<223> OTHER INFORMATION: 8C2 scFv

<400> SEQUENCE: 3

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
```

-continued

```
               20              25              30

Tyr Ile His Trp Val Lys Gln Arg Pro Glu Gln Gly Leu Glu Trp Ile
        35              40              45

Gly Met Ile Asp Leu Ala Asn Asp Asn Thr Lys Tyr Asp Pro Lys Phe
    50              55              60

Gln Gly Lys Ala Thr Ile Ile Thr Asp Thr Ser Ser Asn Lys Ala Tyr
65              70              75              80

Leu Gln Val Ser Ser Leu Thr Ser Glu Asp Thr Ala Val Tyr Tyr Cys
            85              90              95

Ala Thr Trp Gly Ala Ile Ile Thr Leu Gly Gly Trp Gly Gln Gly Thr
            100             105             110

Leu Val Thr Val Ser Ala Ala Lys Gly Gly Gly Gly Ser Gly Gly Gly
        115             120             125

Gly Ser Gly Gly Gly Gly Ser Gly Gly Gly Gly Ser Asp Ile Gln Met
    130             135             140

Thr Gln Ser Pro Ala Ser Leu Ser Ala Ser Val Gly Glu Thr Val Thr
145             150             155             160

Ile Thr Cys Arg Ala Ser Gly Asn Ile His Asn Ser Leu Ala Trp Tyr
            165             170             175

Gln Gln Ile Lys Gly Arg Ser Pro Gln Leu Leu Val Tyr Asn Ala Lys
            180             185             190

Thr Leu Ala Asp Gly Val Pro Ser Arg Phe Ser Gly Ser Gly Ser Gly
            195             200             205

Thr Gln Tyr Ser Leu Lys Ile Asn Ser Leu His Pro Glu Asp Phe Gly
        210             215             220

Ser Tyr Tyr Cys Gln His Phe Trp Ser Thr Pro Phe Thr Phe Gly Ser
225             230             235             240

Gly Thr Lys Leu Glu Ile Lys Arg Glu Asn Leu Tyr Phe Gln Gly
            245             250             255
```

```
<210> SEQ ID NO 4
<211> LENGTH: 224
<212> TYPE: PRT
<213> ORGANISM: Artificial Sequence
<220> FEATURE:
<223> OTHER INFORMATION: 8C2 Fab heavy chain

<400> SEQUENCE: 4

Met Lys Cys Ser Trp Val Ile Phe Phe Leu Met Ala Val Val Thr Gly
1               5               10              15

Val Asn Ser Glu Glu Val Gln Leu Gln Gln Ser Gly Ala Glu Leu Val
            20              25              30

Lys Pro Gly Ala Ser Val Lys Leu Ser Cys Thr Ala Ser Gly Phe Asn
        35              40              45

Ile Lys Asp Thr Tyr Ile His Trp Val Lys Gln Arg Pro Glu Gln Gly
    50              55              60

Leu Glu Trp Ile Gly Met Ile Asp Leu Ala Asn Asp Asn Thr Lys Tyr
65              70              75              80

Asp Pro Lys Phe Gln Gly Lys Ala Thr Ile Ile Thr Asp Thr Ser Ser
            85              90              95

Asn Lys Ala Tyr Leu Gln Val Ser Ser Leu Thr Ser Glu Asp Thr Ala
            100             105             110

Val Tyr Tyr Cys Ala Thr Trp Gly Ala Ile Ile Thr Leu Gly Gly Trp
        115             120             125

Gly Gln Gly Thr Leu Val Thr Val Ser Ala Ala Lys Thr Thr Pro Pro
```

-continued

```
        130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
                180                 185                 190

Ala Val Leu Gln Ser Asp Leu Tyr Thr Leu Ser Ser Ser Val Thr Val
                195                 200                 205

Pro Ser Ser Thr Trp Pro Ser Glu Thr Val Thr Cys Asn Val Ala Asn
        210                 215                 220

<210> SEQ ID NO 5
<211> LENGTH: 205
<212> TYPE: PRT
<213> ORGANISM: Artificial Sequence
<220> FEATURE:
<223> OTHER INFORMATION: 8C2 Fab light chain

<400> SEQUENCE: 5

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
                35                  40                  45

Ile His Asn Ser Leu Ala Trp Tyr Gln Gln Ile Lys Gly Arg Ser Pro
        50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu His Pro Glu Asp Phe Gly Ser Tyr Tyr Cys Gln His Phe Trp
                100                 105                 110

Ser Thr Pro Phe Thr Phe Gly Ser Gly Thr Lys Leu Glu Ile Lys Arg
        115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Glu Arg
                165                 170                 175

Gln Asn Gly Val Leu Asn Ser Trp Thr Asp Gln Asp Ser Lys Asp Ser
                180                 185                 190

Thr Tyr Ser Met Ser Ser Thr Leu Thr Leu Thr Lys Asp
        195                 200                 205

<210> SEQ ID NO 6
<211> LENGTH: 123
<212> TYPE: PRT
<213> ORGANISM: Artificial Sequence
<220> FEATURE:
<223> OTHER INFORMATION: TF7 clone

<400> SEQUENCE: 6

Gln Val Gln Leu Gln Glu Ser Gly Gly Gly Leu Ala Gln Pro Gly Gly
1               5                   10                  15
```

-continued

```
Ser Leu Arg Val Ser Cys Ala Thr Ser Gly Phe Thr Phe Ser Ser Asn
        20                  25                  30

Tyr Tyr Ile Ser Trp Val Arg Gln Ala Pro Gly Arg Gly Leu Glu Trp
        35                  40                  45

Val Ser Ala Ile Asn Thr Gly Asp Gly Ser Thr Tyr Tyr Ala His Ser
        50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Arg Ser Ser Leu Glu Gly Arg Ile Glu Lys Pro Tyr Asp Tyr
            100                 105                 110

Trp Gly Gln Gly Thr Gln Val Thr Val Ser Ser
        115                 120
```

```
<210> SEQ ID NO 7
<211> LENGTH: 122
<212> TYPE: PRT
<213> ORGANISM: Artificial Sequence
<220> FEATURE:
<223> OTHER INFORMATION: TA2 clone

<400> SEQUENCE: 7

Gln Val Gln Leu Gln Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
        20                  25                  30

Tyr Met Ser Trp Val Arg Gln Ala Pro Gly Lys Gly Leu Glu Trp Val
        35                  40                  45

Ser Ala Ile Asn Thr Gly Thr Gly Ser Thr Tyr Tyr Ala Asp Ser Val
        50                  55                  60

Lys Gly Arg Phe Thr Ile Ser Ser Asp Asn Ala Lys Asn Thr Val Tyr
65                  70                  75                  80

Leu Gln Met Ser Ser Leu Lys Pro Glu Asp Thr Ala Leu Tyr Tyr Cys
                85                  90                  95

Ala Arg Ser Ser Leu Glu Gly Arg Val Glu Lys Pro Tyr Asp Tyr Trp
            100                 105                 110

Gly Gln Gly Thr Gln Val Thr Val Ser Ser
        115                 120
```

```
<210> SEQ ID NO 8
<211> LENGTH: 124
<212> TYPE: PRT
<213> ORGANISM: Artificial Sequence
<220> FEATURE:
<223> OTHER INFORMATION: FA1 clone

<400> SEQUENCE: 8

Gln Val Gln Leu Gln Glu Ser Gly Pro Gly Leu Val Lys Pro Ser Gln
1               5                   10                  15

Thr Leu Ser Leu Ile Cys Thr Val Ser Gly Gly Ser Ile Thr Thr Asn
        20                  25                  30

Tyr Tyr Tyr Trp Ser Trp Ile Arg Gln Ala Pro Gly Lys Gly Leu Glu
        35                  40                  45

Trp Met Gly Gly Ile Asn Tyr Trp Gly Ser Thr Tyr Tyr Ser Pro Ser
        50                  55                  60

Leu Lys Ser Arg Thr Ser Ile Phe Arg Asp Thr Ser Lys Asn Gln Phe
65                  70                  75                  80
```

-continued

```
Thr Leu Gln Leu Ser Ser Val Thr Pro Glu Asp Thr Ala Ile Tyr Tyr
                85                  90                  95

Cys Ala Arg Gly Phe Ala Ala Tyr Gly Ser Ser Trp Tyr Gly Tyr Asp
            100                 105                 110

Tyr Trp Gly Gln Gly Thr Gln Val Thr Val Ser Ser
        115                 120
```

<210> SEQ ID NO 9
<211> LENGTH: 124
<212> TYPE: PRT
<213> ORGANISM: Artificial Sequence
<220> FEATURE:
<223> OTHER INFORMATION: FA2 clone

<400> SEQUENCE: 9

```
Glu Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
            20                  25                  30

Tyr Tyr Tyr Trp Ser Trp Ile Arg Gln Ala Pro Gly Lys Gly Leu Glu
        35                  40                  45

Trp Met Gly Gly Ile Asn Tyr Trp Gly Ser Thr Tyr Tyr Ser Pro Ser
    50                  55                  60

Leu Lys Ser Arg Thr Ser Ile Phe Arg Asp Thr Ser Lys Asn Gln Phe
65                  70                  75                  80

Thr Leu Gln Leu Ser Ser Val Thr Pro Glu Asp Thr Ala Ile Tyr Tyr
                85                  90                  95

Cys Ala Arg Gly Phe Ala Ala Tyr Gly Ser Ser Trp Tyr Gly Tyr Asp
            100                 105                 110

Tyr Trp Gly Gln Gly Thr Gln Val Thr Val Ser Ser
        115                 120
```

<210> SEQ ID NO 10
<211> LENGTH: 123
<212> TYPE: PRT
<213> ORGANISM: Artificial Sequence
<220> FEATURE:
<223> OTHER INFORMATION: TB9 clone

<400> SEQUENCE: 10

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Gly Ser Asn
            20                  25                  30

Tyr Tyr Ile Ser Trp Val Arg Gln Ala Pro Gly Lys Gly Leu Glu Trp
        35                  40                  45

Val Ser Ala Ile Asn Thr Gly Gly Gly Ser Thr Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Arg Ser Ser Leu Glu Gly Arg Val Glu Lys Pro Tyr Asp Tyr
            100                 105                 110

Trp Gly Gln Gly Thr Gln Val Thr Val Ser Ser
        115                 120
```

```
<210> SEQ ID NO 11
<211> LENGTH: 122
<212> TYPE: PRT
<213> ORGANISM: Artificial Sequence
<220> FEATURE:
<223> OTHER INFORMATION: TF5 clone

<400> SEQUENCE: 11

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Tyr Met Ser Trp Val Arg Gln Ala Pro Gly Lys Gly Leu Glu Trp Val
        35                  40                  45

Ser Ala Ile Asn Thr Gly Asp Gly Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Ser Ser Tyr Glu Gly Arg Val Glu Lys Pro Tyr Asp Tyr Trp
            100                 105                 110

Gly Gln Gly Thr Gln Val Thr Val Ser Ser
        115                 120

<210> SEQ ID NO 12
<211> LENGTH: 113
<212> TYPE: PRT
<213> ORGANISM: Artificial Sequence
<220> FEATURE:
<223> OTHER INFORMATION: CG4

<400> SEQUENCE: 12

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Ile Ser Gly Tyr
            20                  25                  30

Ala Met Gly Trp Phe Arg Gln Ala Pro Gly Lys Glu Arg Asp Leu Val
        35                  40                  45

Ala Ala Ile Ser Arg Ser Gly Thr Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Pro Gly Gly Ile Trp Gly Gln Gly Thr Gln Val Thr Val Ser
            100                 105                 110

Ser

<210> SEQ ID NO 13
<211> LENGTH: 121
<212> TYPE: PRT
<213> ORGANISM: Artificial Sequence
<220> FEATURE:
<223> OTHER INFORMATION: DF3A2

<400> SEQUENCE: 13

Gln Val Gln Leu Gln Glu Ser Gly Gly Gly Leu Val Gln Pro Gly Gly
1               5                   10                  15
```

```
Ser Leu Arg Leu Ser Cys Ala Ala Ser Gly Gly Ile Phe Gly Ile Ser
            20                  25                  30

Tyr Met Gly Trp Tyr Arg Gln Ala Pro Gly Lys Gln Arg Glu Pro Val
        35                  40                  45

Ala Leu Ile Thr Ser Gly Gly Asp Thr Ala Tyr Gly Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Asp Asp Thr Ser Ala Tyr Tyr Cys Ala
                85                  90                  95

Ala Gly Phe Tyr Arg Ser Asp Ser Pro Asn Arg Tyr Asp Tyr Trp Gly
            100                 105                 110

Gln Gly Thr Gln Val Thr Val Ser Ser
        115                 120
```

<210> SEQ ID NO 14
<211> LENGTH: 121
<212> TYPE: PRT
<213> ORGANISM: Artificial Sequence
<220> FEATURE:
<223> OTHER INFORMATION: DF3A4

<400> SEQUENCE: 14

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
        35                  40                  45

Ala Leu Ile Thr Ser Gly Gly Ser Thr Tyr Tyr Ala Asp Ser Val Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Phe Tyr Arg Ser Asp Ser Pro Asn Arg Tyr Asp Tyr Trp Gly
            100                 105                 110

Gln Gly Thr Gln Val Thr Val Ser Ser
        115                 120
```

<210> SEQ ID NO 15
<211> LENGTH: 121
<212> TYPE: PRT
<213> ORGANISM: Artificial Sequence
<220> FEATURE:
<223> OTHER INFORMATION: DF4B12

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
        35                  40                  45

Ala Leu Ile Thr Ser Gly Gly Asp Thr Ala Tyr Gly Asp Ser Val Lys
    50                  55                  60

Gly Arg Phe Thr Ile Ser Arg Asp Asn Ala Lys Asn Thr Val Tyr Leu
65                  70                  75                  80
```

```
Gln Met Asn Ser Leu Thr Pro Glu Asp Thr Ser Thr Phe Tyr Cys Ala
            85                  90                  95

Ala Gly Phe Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: DT3B3

<400> SEQUENCE: 16

Glu Val Gln Leu Val Glu Ser Gly Gly Gly Leu Val Gln Ala Gly Gly
1               5                   10                  15

Ser Leu Arg Leu Ser Cys Ala Leu Ser Gly Gly Thr Leu Arg Ser Tyr
            20                  25                  30

Thr Met Gly Trp Ile Arg Gln Ala Pro Gly Lys Glu Arg Glu Phe Val
            35                  40                  45

Ala Gly Asn Arg Trp Ser Gly Gly Arg Thr Tyr Tyr Ala Asp Ser Val
            50                  55                  60

Lys Gly Arg Phe Thr Ile Ser Gly Asp Asn Ala Glu Asn Thr Val Tyr
65                  70                  75                  80

Leu Gln Met Asn Ser Leu Lys Pro Glu Asp Thr Ala Val Tyr Tyr Cys
                    85                  90                  95

Thr Ala Asp Val Thr Glu Tyr Gly Glu Asp Ser Ser Ala Tyr Trp Gly
            100                 105                 110

Arg Gly Thr Gln Val Thr Val Ser Ser
        115                 120

<210> SEQ ID NO 17
<211> LENGTH: 112
<212> TYPE: PRT
<213> ORGANISM: Artificial Sequence
<220> FEATURE:
<223> OTHER INFORMATION: DT3H3

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser His Asp
            20                  25                  30

His Met Gly Trp Phe Arg Gln Ala Pro Gly Lys Glu Arg Glu Phe Val
            35                  40                  45

Ala Ala Ile Ser Trp Thr Ser Ser Thr Tyr Tyr Gly Asp Ser Val Lys
        50                  55                  60

Gly Arg Phe Thr Ile Ser Arg Ser Asn Ala Lys Asn Thr Val Tyr Leu
65                  70                  75                  80

Gln Met Asn Ser Leu Lys Pro Glu Asp Thr Ala Ile Tyr Tyr Cys Ser
                    85                  90                  95

Trp Gly Val Gly Tyr Trp Gly Gln Gly Thr Gln Val Thr Val Ser Ser
            100                 105                 110

<210> SEQ ID NO 18
<211> LENGTH: 116
<212> TYPE: PRT
```

```
<213> ORGANISM: Artificial Sequence
<220> FEATURE:
<223> OTHER INFORMATION: DT3B5

<400> SEQUENCE: 18

Gln Val Gln Leu Val Gln Ser Gly Gly Gly Leu Val Gln Pro Gly Gly
1               5                   10                  15

Ser Leu Arg Leu Ser Cys Thr Ala Ser Gly Arg Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Ser Thr Gly Gly Leu Arg Gln Tyr Phe Gly Asp Ser Val
    50                  55                  60

Arg Gly Arg Cys Thr Ile Ser Arg Asp Asn Ala Lys Ser Thr Val Tyr
65                  70                  75                  80

Leu Gln Met Asp Ser Leu Lys Pro Glu Asp Thr Ala Val Tyr Tyr Cys
                85                  90                  95

Ala Ala Asn Trp Gly Thr Ser Tyr Tyr Trp Gly Gln Gly Thr Gln Val
            100                 105                 110

Thr Val Ser Ser
        115

<210> SEQ ID NO 19
<211> LENGTH: 115
<212> TYPE: PRT
<213> ORGANISM: Artificial Sequence
<220> FEATURE:
<223> OTHER INFORMATION: DT3B4

<400> SEQUENCE: 19

Gln Val Gln Leu Gln Glu Ser Gly Gly Gly Leu Val Gln Ala Gly Asp
1               5                   10                  15

Ser Leu Arg Leu Ser Cys Thr Ala Ser Gly Arg Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Ser Thr Gly Gly Leu Arg Gln Tyr Phe Gly Asp Ser Val
    50                  55                  60

Arg Gly Arg Cys Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Thr Gly Asn Glu Tyr His Trp Gly Arg Gly Thr Gln Val Thr
            100                 105                 110

Val Ser Ser
        115

<210> SEQ ID NO 20
<211> LENGTH: 126
<212> TYPE: PRT
<213> ORGANISM: Artificial Sequence
<220> FEATURE:
<223> OTHER INFORMATION: DF4C7

<400> SEQUENCE: 20

Glu Val Gln Leu Val Glu Ser Gly Gly Gly Leu Val Gln Pro Gly Gly
1               5                   10                  15

Ser Leu Ser Leu Ser Cys Ala Ala Ala Gly Arg Ile Ala Thr Ile Asn
            20                  25                  30
```

-continued

```
Ala Met Gly Trp Ile Arg Gln Ala Pro Gly Lys Glu Arg Glu Phe Val
        35                  40                  45

Ala Ala Val Ser Trp Ser Gly Gly Ser Thr Tyr Tyr Ser Glu Ser Val
    50                  55                  60

Lys Gly Arg Phe Thr Val Ser Arg Asp Asn Gly Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Ala Gly Thr Phe Tyr Leu Asp Asp Pro Ser Tyr His Arg Ser
                100                 105                 110

Phe Thr Ser Trp Gly Gln Gly Thr Gln Val Thr Val Ser Ser
                115                 120                 125

<210> SEQ ID NO 21
<211> LENGTH: 126
<212> TYPE: PRT
<213> ORGANISM: Artificial Sequence
<220> FEATURE:
<223> OTHER INFORMATION: DF4B7

<400> SEQUENCE: 21

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Val Tyr
                20                  25                  30

Thr Met Gly Trp Phe Arg Gln Ala Pro Gly Lys Glu Arg Glu Phe Val
        35                  40                  45

Ala Ala Ile Thr Arg Asn Gly Gly Asn Thr Tyr Tyr Gly Asp Ser Val
    50                  55                  60

Lys Gly Arg Phe Thr Ile Ser Arg Ala Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Ala Gly Thr Phe Tyr Leu Asp Asp Pro Ser Tyr His Arg Ser
                100                 105                 110

Phe Thr Ser Trp Gly Gln Gly Thr Gln Val Thr Val Ser Ser
                115                 120                 125

<210> SEQ ID NO 22
<211> LENGTH: 126
<212> TYPE: PRT
<213> ORGANISM: Artificial Sequence
<220> FEATURE:
<223> OTHER INFORMATION: DF4D12

<400> SEQUENCE: 22

Glu Val Gln Leu Val Glu Ser Gly Gly Gly Leu Val Gln Ala Gly Gly
1               5                   10                  15

Ser Leu Arg Leu Ser Cys Val Val Ser Gly Arg Thr Phe Ser Thr Tyr
                20                  25                  30

Thr Met Gly Trp Ile Arg Gln Ala Pro Gly Lys Glu Arg Glu Phe Val
        35                  40                  45

Ala Gly Ile Arg Trp Ser Gly Gly Arg Thr Tyr Tyr Ala Asp Ser Val
    50                  55                  60

Lys Gly Arg Phe Thr Ile Ser Gly Asp Asn Ala Glu Asn Thr Val Tyr
65                  70                  75                  80

Leu Gln Met Asn Ser Leu Lys Pro Glu Asp Thr Ala Val Tyr Tyr Cys
```

```
                      85                  90                  95

Asn Ala Ala Gly Thr Phe Tyr Leu Asp Asp Pro Ser Tyr His Arg Ser
                100                 105                 110

Phe Thr Ser Trp Gly Gln Gly Thr Gln Val Thr Val Ser Ser
                115                 120                 125

<210> SEQ ID NO 23
<211> LENGTH: 123
<212> TYPE: PRT
<213> ORGANISM: Artificial Sequence
<220> FEATURE:
<223> OTHER INFORMATION: DF4D11

<400> SEQUENCE: 23

Gln Val Gln Leu Gln Glu Ser Gly Gly Gly Leu Val Gln Val Gly Gly
1               5                   10                  15

Ser Leu Arg Leu Ser Cys Ala Ala Ser Gly Arg Thr Phe Ser Ile Asn
                20                  25                  30

Thr Met Gly Trp Phe Arg Gln Ala Pro Gly Lys Glu Arg Glu Phe Val
                35                  40                  45

Ala Ala Ile Ser Trp Arg Gly Glu Thr Ile Tyr Tyr Ala Asp Ser Val
            50                  55                  60

Arg Gly Arg Phe Thr Phe Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Val Arg Thr Val Val Gly Thr Asp Tyr Gly Met His Tyr
                100                 105                 110

Trp Gly Lys Gly Thr Gln Val Thr Val Ser Ser
            115                 120

<210> SEQ ID NO 24
<211> LENGTH: 122
<212> TYPE: PRT
<213> ORGANISM: Artificial Sequence
<220> FEATURE:
<223> OTHER INFORMATION: DF4B10

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
                20                  25                  30

Trp Met Tyr Trp Val Arg Gln Ala Pro Gly Lys Gly Leu Glu Trp Val
                35                  40                  45

Ser Gly Ile Asp Asn Gly Gly Gly Ser Thr Tyr Tyr Ala Asp Ser Val
            50                  55                  60

Lys Gly Arg Phe Thr Ile Ser Arg Asp Asn Ala Glu Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Lys His Tyr Tyr Ser Asp Leu Glu Arg Arg Tyr Asp Tyr Trp
                100                 105                 110

Gly Gln Gly Thr Gln Val Thr Val Ser Ser
            115                 120

<210> SEQ ID NO 25
<211> LENGTH: 123
```

-continued

```
<212> TYPE: PRT
<213> ORGANISM: Artificial Sequence
<220> FEATURE:
<223> OTHER INFORMATION: DF4A11

<400> SEQUENCE: 25

Gln Val Gln Leu Gln Glu Ser Gly Gly Gly Leu Val Gln Ala Gly Gly
1               5                   10                  15

Ser Leu Arg Leu Ala Cys Ala Ala Ser Gly Gly His Ser Gly Leu Thr
            20                  25                  30

Phe Ser Arg Tyr Ala Met Gly Trp Phe Arg Gln Ala Pro Gly Lys Glu
        35                  40                  45

Arg Glu Phe Val Ala Ala Ile Ser Gln Gly Gly Gly Ser Thr Tyr Tyr
    50                  55                  60

Ser Asp Pro Val Lys Gly Arg Phe Thr Ile Ser Arg Asp His Ala Lys
65                  70                  75                  80

Lys Gln Val Tyr Leu Gln Met Asp Ser Leu Lys Pro Glu Asp Thr Ala
                85                  90                  95

Val Tyr Tyr Cys Asn Trp His Ser Asp Tyr Pro Arg Asn Gln Leu Tyr
            100                 105                 110

Trp Gly Gln Gly Thr Gln Val Thr Val Ser Ser
        115                 120

<210> SEQ ID NO 26
<211> LENGTH: 123
<212> TYPE: PRT
<213> ORGANISM: Artificial Sequence
<220> FEATURE:
<223> OTHER INFORMATION: DF3A1

<400> SEQUENCE: 26

Gln Val Gln Leu Gln Glu Ser Gly Gly Gly Leu Val Gln Ala Gly Gly
1               5                   10                  15

Ser Leu Arg Leu Ala Cys Ala Ala Ser Gly Gly His Ser Gly Leu Thr
            20                  25                  30

Phe Ser Arg Tyr Ala Met Gly Trp Phe Arg Gln Ala Pro Gly Lys Glu
        35                  40                  45

Arg Glu Phe Val Ala Ala Ile Ser Gln Gly Gly Gly Ser Thr Tyr Tyr
    50                  55                  60

Ser Asp Pro Val Lys Gly Arg Phe Thr Ile Ser Arg Asp His Ala Lys
65                  70                  75                  80

Lys Gln Val Tyr Leu Gln Met Asp Ser Leu Lys Pro Glu Asp Thr Ala
                85                  90                  95

Val Tyr Tyr Cys Asn Trp His Ser Asp Tyr Pro Arg Asn Gln Leu Tyr
            100                 105                 110

Trp Gly Gln Gly Thr Gln Val Thr Val Ser Ser
        115                 120

<210> SEQ ID NO 27
<211> LENGTH: 115
<212> TYPE: PRT
<213> ORGANISM: Artificial Sequence
<220> FEATURE:
<223> OTHER INFORMATION: DF4C12

<400> SEQUENCE: 27

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
```

-continued

```
                    20                  25                  30

Asp Met Gly Trp Leu Arg Gln Ala Pro Gly Lys Gly Arg Glu Phe Val
            35                  40                  45

Ala Ser Ile Asn Trp Ser Gly Thr Thr Lys Tyr Tyr Ala Asp Ser Ala
    50                  55                  60

Lys Gly Arg Phe Thr Ile Asp Arg Asp Asp Ala Lys Ser Met Ala Tyr
65                  70                  75                  80

Leu Gln Met Asn Ser Leu Lys Pro Glu Asp Thr Ala Val Tyr Tyr Cys
                    85                  90                  95

Ala Ala Ile Gly Asn Glu Tyr Tyr Trp Gly Gln Gly Thr Gln Val Thr
            100                 105                 110

Val Ser Ser
            115
```

<210> SEQ ID NO 28
<211> LENGTH: 122
<212> TYPE: PRT
<213> ORGANISM: Artificial Sequence
<220> FEATURE:
<223> OTHER INFORMATION: MA3

<400> SEQUENCE: 28

```
Gln Val Gln Leu Val Gln Ser Gly Gly Gly Leu Val Gln Ala Gly Asp
1               5                   10                  15

Ser Leu Thr Leu Ser Cys Val Ala Ser Gly Arg Pro Phe Arg Arg Tyr
                    20                  25                  30

Ser Ile Gly Trp Phe Arg Gln Ala Pro Gly Lys Glu Arg Glu Phe Val
            35                  40                  45

Ala Ala Ile Ser Trp Ser Gly Ser Ser Thr Ser Tyr Leu Asp Ser Leu
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                    85                  90                  95

Asn Val Arg Ala Arg Ala Thr Met Phe Arg Ser Pro Ser Asp Tyr Trp
            100                 105                 110

Gly Gln Gly Thr Gln Val Thr Val Ser Ser
        115                 120
```

<210> SEQ ID NO 29
<211> LENGTH: 116
<212> TYPE: PRT
<213> ORGANISM: Artificial Sequence
<220> FEATURE:
<223> OTHER INFORMATION: MB2

<400> SEQUENCE: 29

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Arg Thr Leu Arg Ser Tyr
                    20                  25                  30

Ala Met Gly Trp Phe Arg Gln Ala Pro Gly Lys Glu Arg Glu Phe Val
            35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Gly Val Lys Asn Thr Val Tyr
65                  70                  75                  80
```

-continued

```
Leu Gln Met Asn Ser Leu Lys Pro Glu Asp Thr Ala Val Tyr Tyr Cys
                85                  90                  95

Ser Ala Arg Val Leu Phe Arg Thr Ser Trp Gly Gln Gly Thr Gln Val
               100                 105                 110

Thr Val Ser Ser
        115

<210> SEQ ID NO 30
<211> LENGTH: 125
<212> TYPE: PRT
<213> ORGANISM: Artificial Sequence
<220> FEATURE:
<223> OTHER INFORMATION: MC7

<400> SEQUENCE: 30

Gln Val Gln Leu Val Gln Ser Gly Gly Gly Leu Val Gln Ala Gly Gly
1               5                   10                  15

Ser Leu Arg Leu Ser Cys Val Ala Ser Gly Arg Thr Phe Ser Met Tyr
               20                  25                  30

Arg Met Gly Trp Phe Arg Gln Ala Pro Gly Lys Glu Arg Glu Phe Val
            35                  40                  45

Ala Ser Ile Arg Trp Ser Gly Gly Ser Thr Tyr Tyr Thr Asp Ser Val
         50                  55                  60

Lys Asp Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Val Trp Arg Leu Asn Ser Trp Tyr Arg Gly Ala Val
               100                 105                 110

Gly Tyr Trp Gly Gln Gly Thr Gln Val Thr Val Ser Ser
        115                 120                 125

<210> SEQ ID NO 31
<211> LENGTH: 121
<212> TYPE: PRT
<213> ORGANISM: Artificial Sequence
<220> FEATURE:
<223> OTHER INFORMATION: DMFH1

<400> SEQUENCE: 31

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
               20                  25                  30

Tyr Met Gly Trp Tyr Arg Gln Ala Pro Gly Lys Gln Arg Glu Pro Val
            35                  40                  45

Ala Met Ile Thr Ser Gly Gly Ser Thr Tyr Tyr Ala Asp Ser Val Lys
         50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Ala Ser Thr Tyr Tyr Cys Ala
                85                  90                  95

Ala Gly Cys Tyr Arg Ser Asp Ser Pro Asn Arg Tyr Asp Tyr Trp Gly
               100                 105                 110

Gln Gly Thr Gln Val Thr Val Ser Ser
        115                 120

<210> SEQ ID NO 32
```

```
<211> LENGTH: 121
<212> TYPE: PRT
<213> ORGANISM: Artificial Sequence
<220> FEATURE:
<223> OTHER INFORMATION: DMOH9

<400> SEQUENCE: 32

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Thr
            20                  25                  30

Tyr Met Gly Trp Tyr Arg Gln Ala Pro Gly Lys Gln Arg Glu Pro Val
        35                  40                  45

Ala Met Ile Thr Ser Gly Gly Ser Thr Tyr Tyr Ala Asp Ser Val Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 33
<211> LENGTH: 121
<212> TYPE: PRT
<213> ORGANISM: Artificial Sequence
<220> FEATURE:
<223> OTHER INFORMATION: DMOF8

<400> SEQUENCE: 33

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
        35                  40                  45

Ala Met Ile Thr Ser Ser Gly Ser Thr Tyr Tyr Ala Asp Ser Val Arg
    50                  55                  60

Gly Arg Val Thr Ile Ser Arg Ala Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 34
<211> LENGTH: 121
<212> TYPE: PRT
<213> ORGANISM: Artificial Sequence
<220> FEATURE:
<223> OTHER INFORMATION: DMFH2

<400> SEQUENCE: 34

Gln Val Gln Leu Gln Glu Ser Gly Gly Gly Leu Val Gln Pro Gly Gly
1               5                   10                  15
```

-continued

Ser Leu Arg Leu Ser Cys Ala Ala Ser Gly Ser Thr Phe Gly Ile Ser
        20                    25                    30

Tyr Met Gly Trp Tyr Arg Gln Ala Pro Gly Lys Gln Arg Glu Pro Val
        35                    40                    45

Ala Met Ile Thr Ser Gly Gly Ser Thr Tyr Tyr Val Asp Ser Val Lys
    50                    55                    60

Gly Arg Val Thr Ile Ser Arg Asp Asn Ala Lys Lys Thr Val Tyr Leu
65                    70                    75                    80

Gln Met Asn Ser Leu Arg Pro Glu Asp Thr Ser Thr Tyr Tyr Cys Ala
                85                    90                    95

Ala Gly Phe Tyr Arg Ser Asp Ser Pro Asn Arg Tyr Asp Tyr Trp Gly
            100                   105                   110

Gln Gly Thr Gln Val Thr Val Ser Ser
        115                   120

<210> SEQ ID NO 35
<211> LENGTH: 121
<212> TYPE: PRT
<213> ORGANISM: Artificial Sequence
<220> FEATURE:
<223> OTHER INFORMATION: DMFF2

<400> SEQUENCE: 35

Gln Val Gln Leu Gln Glu Ser Gly Gly Gly Leu Val Gln Pro Gly Gly
1                   5                    10                    15

Ser Leu Arg Leu Ser Cys Ala Ala Ser Gly Ser Ile Phe Gly Ile Ser
        20                    25                    30

Tyr Met Gly Trp Tyr Arg Gln Ala Pro Gly Lys Gln Arg Glu Pro Val
        35                    40                    45

Ala Leu Ile Thr Ser Gly Gly Ser Thr Tyr Tyr Val Asp Ser Val Lys
    50                    55                    60

Gly Arg Val Thr Ile Ser Arg Asp Asn Ala Lys Lys Thr Val Tyr Leu
65                    70                    75                    80

Gln Met Asn Ser Leu Arg Pro Glu Asp Thr Ser Thr Tyr Tyr Cys Ala
                85                    90                    95

Ala Gly Tyr Tyr Arg Ser Asp Ser Pro Asn Arg Tyr Asp Tyr Trp Gly
            100                   105                   110

Gln Gly Thr Gln Val Thr Val Ser Ser
        115                   120

<210> SEQ ID NO 36
<211> LENGTH: 121
<212> TYPE: PRT
<213> ORGANISM: Artificial Sequence
<220> FEATURE:
<223> OTHER INFORMATION: DMFB8

<400> SEQUENCE: 36

Gln Val Gln Leu Gln Glu Ser Gly Gly Gly Leu Val Gln Pro Gly Gly
1                   5                    10                    15

Ser Leu Arg Leu Ser Cys Ala Ala Ser Gly Ser Ile Phe Gly Ile Ser
        20                    25                    30

Tyr Met Gly Trp Tyr Arg Gln Ala Pro Gly Lys Gln Arg Glu Pro Val
        35                    40                    45

Ala Met Ile Thr Ser Gly Gly Ser Thr Tyr Tyr Ala Asp Ser Val Lys
    50                    55                    60

Gly Arg Val Thr Ile Ser Arg Asp Asn Ala Lys Lys Thr Val Tyr Leu
65                    70                    75                    80

```
Gln Met Tyr Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 37
<211> LENGTH: 121
<212> TYPE: PRT
<213> ORGANISM: Artificial Sequence
<220> FEATURE:
<223> OTHER INFORMATION: DMFA2

<400> SEQUENCE: 37

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
        35                  40                  45

Ala Leu Ile Thr Ser Gly Gly Ser Thr His Tyr Val Asp Ser Val Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Ser Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 38
<211> LENGTH: 121
<212> TYPE: PRT
<213> ORGANISM: Artificial Sequence
<220> FEATURE:
<223> OTHER INFORMATION: DMFA4

<400> SEQUENCE: 38

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Met Phe Gly Ile Ser
            20                  25                  30

Tyr Met Gly Trp Tyr Arg Gln Ala Pro Gly Lys Gln Arg Glu Pro Val
        35                  40                  45

Ala Leu Ile Thr Ser Gly Gly Ser Thr Tyr Tyr Ala Asp Ser Ala Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120
```

<210> SEQ ID NO 39
<211> LENGTH: 121
<212> TYPE: PRT
<213> ORGANISM: Artificial Sequence
<220> FEATURE:
<223> OTHER INFORMATION: DMFA9

<400> SEQUENCE: 39

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Asn Gln Arg Glu Pro Val
        35                  40                  45

Ala Met Ile Thr Ser Gly Gly Ser Thr Tyr Tyr Ala Asp Ser Val Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 40
<211> LENGTH: 121
<212> TYPE: PRT
<213> ORGANISM: Artificial Sequence
<220> FEATURE:
<223> OTHER INFORMATION: DMFC5

<400> SEQUENCE: 40

Gln Val Gln Leu Gln Glu Ser Gly Gly Gly Gln Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
        35                  40                  45

Ala Leu Ile Thr Ser Gly Gly Ser Thr Tyr Tyr Val Asp Ser Val Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 41
<211> LENGTH: 121
<212> TYPE: PRT
<213> ORGANISM: Artificial Sequence
<220> FEATURE:
<223> OTHER INFORMATION: DMFD3

<400> SEQUENCE: 41

Gln Val Gln Leu Gln Glu Ser Gly Gly Gly Leu Val Gln Pro Gly Gly
1               5                   10                  15

-continued

```
Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
            35                  40                  45

Ala Met Ile Thr Ser Gly Gly Ser Thr Tyr Tyr Ala Asp Ser Val Lys
        50                  55                  60

Gly Arg Val Thr Ile Ser Arg Asp Asn Ala Glu Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Cys Tyr Arg Ser Asp Ser Pro Asn Arg Tyr Asp Tyr Trp Gly
            100                 105                 110

Gln Gly Thr Gln Val Thr Val Ser Ser
        115                 120
```

<210> SEQ ID NO 42
<211> LENGTH: 121
<212> TYPE: PRT
<213> ORGANISM: Artificial Sequence
<220> FEATURE:
<223> OTHER INFORMATION: DMFD7

<400> SEQUENCE: 42

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
            35                  40                  45

Ala Met Ile Thr Ser Gly Gly Ser Thr Tyr Tyr Ala Asp Ser Val Lys
        50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120
```

<210> SEQ ID NO 43
<211> LENGTH: 121
<212> TYPE: PRT
<213> ORGANISM: Artificial Sequence
<220> FEATURE:
<223> OTHER INFORMATION: DMFE1

<400> SEQUENCE: 43

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Asn Gln Arg Glu Pro Val
            35                  40                  45

Ala Met Ile Thr Ser Gly Gly Ser Thr Tyr Tyr Ala Asp Ser Val Lys
        50                  55                  60

Gly Arg Val Thr Ile Ser Arg Asp Asn Ala Lys Lys Thr Val Tyr Leu
```

```
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
               100                 105                 110

Gln Gly Thr Gln Val Thr Val Ser Ser
        115                 120
```

<210> SEQ ID NO 44
<211> LENGTH: 121
<212> TYPE: PRT
<213> ORGANISM: Artificial Sequence
<220> FEATURE:
<223> OTHER INFORMATION: DMFE5

<400> SEQUENCE: 44

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
                20                  25                  30

Tyr Met Gly Trp Tyr Arg Gln Ala Pro Gly Lys Gln Arg Glu Pro Val
            35                  40                  45

Ala Met Ile Thr Ser Gly Gly Ser Thr Tyr Tyr Ala Asp Ser Val Lys
        50                  55                  60

Gly Arg Val Thr Val Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
               100                 105                 110

Gln Gly Thr Gln Val Thr Val Ser Ser
        115                 120
```

<210> SEQ ID NO 45
<211> LENGTH: 121
<212> TYPE: PRT
<213> ORGANISM: Artificial Sequence
<220> FEATURE:
<223> OTHER INFORMATION: DMFE8

<400> SEQUENCE: 45

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
                20                  25                  30

Tyr Met Gly Trp Tyr Arg Gln Ala Pro Gly Lys Gln Arg Glu Pro Val
            35                  40                  45

Ala Met Ile Thr Ser Gly Gly Ser Thr Tyr Tyr Ala Asp Ser Val Lys
        50                  55                  60

Gly Arg Val Thr Ile Ser Arg Asp Asn Ala Lys Lys Thr Ile Tyr Leu
65                  70                  75                  80

Gln Met Asn Ser Leu Arg Pro Glu Asp Thr Ser Thr Tyr Tyr Cys Ala
                85                  90                  95

Ala Gly Phe Tyr Arg Ser Asp Ser Pro Asn Arg Tyr Asp Tyr Trp Gly
               100                 105                 110

Arg Gly Thr Gln Val Thr Val Ser Ser
        115                 120
```

<210> SEQ ID NO 46
<211> LENGTH: 121
<212> TYPE: PRT
<213> ORGANISM: Artificial Sequence
<220> FEATURE:
<223> OTHER INFORMATION: DMFF1

<400> SEQUENCE: 46

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
        35                  40                  45

Ala Met Ile Thr Ser Gly Gly Ser Thr Tyr Tyr Ala Asp Ser Val Lys
    50                  55                  60

Gly Arg Val Thr Ile Ser Arg Asp Asn Ala Lys Lys Thr Ile Tyr Leu
65                  70                  75                  80

Gln Met Asn Ser Leu Arg Pro Glu Asp Thr Ser Thr Tyr Tyr Cys Ala
            85                  90                  95

Ala Gly Phe Tyr Arg Ser Asp Ser Pro Asn Arg Tyr Asp Tyr Trp Gly
            100                 105                 110

Arg Gly Thr Gln Val Thr Val Ser Ser
        115                 120

<210> SEQ ID NO 47
<211> LENGTH: 121
<212> TYPE: PRT
<213> ORGANISM: Artificial Sequence
<220> FEATURE:
<223> OTHER INFORMATION: DMFF6

<400> SEQUENCE: 47

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
        35                  40                  45

Ala Leu Ile Thr Ser Gly Gly Ser Thr Tyr Tyr Val Asp Ser Val Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Gly Asp Thr Ser Thr Tyr Tyr Cys Ala
            85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 48
<211> LENGTH: 121
<212> TYPE: PRT
<213> ORGANISM: Artificial Sequence
<220> FEATURE:
<223> OTHER INFORMATION: DMFG2

<400> SEQUENCE: 48

Gln Val Gln Leu Gln Glu Ser Gly Gly Gly Leu Val Gln Pro Gly Gly

-continued

```
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
            35                  40                  45

Ala Met Ile Thr Ser Gly Gly Ser Thr Tyr Tyr Ala Asp Ser Val Lys
    50                  55                  60

Gly Arg Val Thr Ile Ser Arg Asp Asn Ala Lys Lys Thr Ile Tyr Leu
65                  70                  75                  80

Gln Leu Ile Ser Leu Arg Pro Glu Asp Thr Ser Thr Tyr Tyr Cys Ala
            85                  90                  95

Ala Gly Phe Tyr Arg Ser Asp Ser Pro Asn Arg Tyr Asp Tyr Trp Gly
            100                 105                 110

Gln Gly Thr Gln Val Thr Val Ser Ser
        115                 120
```

<210> SEQ ID NO 49
<211> LENGTH: 121
<212> TYPE: PRT
<213> ORGANISM: Artificial Sequence
<220> FEATURE:
<223> OTHER INFORMATION: DMFG3

<400> SEQUENCE: 49

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Leu Ala Pro Gly Asn Gln Arg Glu Pro Val
            35                  40                  45

Ala Met Ile Thr Ser Gly Gly Ser Thr Tyr Tyr Ala Asp Ser Val Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
            85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120
```

<210> SEQ ID NO 50
<211> LENGTH: 63
<212> TYPE: PRT
<213> ORGANISM: Artificial Sequence
<220> FEATURE:
<223> OTHER INFORMATION: DMFG5

<400> SEQUENCE: 50

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
            35                  40                  45

Ala Met Ile Thr Ser Gly Gly Ser Thr Tyr Tyr Ala Asp Ser Val
    50                  55                  60
```

-continued

<210> SEQ ID NO 51
<211> LENGTH: 113
<212> TYPE: PRT
<213> ORGANISM: Artificial Sequence
<220> FEATURE:
<223> OTHER INFORMATION: DMOA3

<400> SEQUENCE: 51

```
Gln Val Gln Leu Gln Glu Arg Gly Gly Gly Leu Val Gln Ala Gly Gly
1               5                   10                  15

Ser Leu Arg Leu Ser Cys Ala Ala Ser Gly Arg Thr Ile Ser Gly Tyr
            20                  25                  30

Ala Met Gly Trp Phe Arg Gln Ala Pro Gly Lys Glu Arg Asp Leu Val
            35                  40                  45

Ala Ala Ile Ser Arg Ser Gly Thr Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Pro Gly Gly Ile Trp Gly Gln Gly Thr Gln Val Thr Val Ser
            100                 105                 110

Ser
```

<210> SEQ ID NO 52
<211> LENGTH: 121
<212> TYPE: PRT
<213> ORGANISM: Artificial Sequence
<220> FEATURE:
<223> OTHER INFORMATION: DMOA5

<400> SEQUENCE: 52

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Ile Gly Trp Tyr Arg Gln Ala Pro Gly Lys Gln Arg Glu Pro Val
            35                  40                  45

Ala Leu Ile Thr Ser Gly Gly Ser Thr Tyr Tyr Val Asp Ser Val Lys
        50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120
```

<210> SEQ ID NO 53
<211> LENGTH: 121
<212> TYPE: PRT
<213> ORGANISM: Artificial Sequence
<220> FEATURE:
<223> OTHER INFORMATION: DMOA11

<400> SEQUENCE: 53

```
Gln Val Gln Leu Gln Glu Ser Gly Gly Gly Leu Val Gln Pro Gly Gly
1               5                   10                  15
```

```
Ser Leu Arg Leu Ser Cys Ala Ala Ser Gly Ser Ile Phe Gly Ile Ser
        20                  25                  30

Tyr Met Gly Trp Tyr Arg Gln Ala Pro Gly Arg Gln Arg Glu Pro Val
        35                  40                  45

Ala Leu Ile Thr Ser Gly Gly Ser Thr Tyr Tyr Thr Asp Ser Val Lys
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 54
<211> LENGTH: 121
<212> TYPE: PRT
<213> ORGANISM: Artificial Sequence
<220> FEATURE:
<223> OTHER INFORMATION: DMOB5

<400> SEQUENCE: 54

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
        20                  25                  30

Tyr Met Gly Trp Tyr Arg Gln Ala Pro Gly Lys Gln Arg Glu Pro Val
        35                  40                  45

Ala Leu Ile Thr Ser Gly Gly Ser Thr Tyr Tyr Val Asp Ser Val Asn
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Phe Tyr Arg Ser Asp Ser Pro Asn Arg Tyr Asp Tyr Trp Gly
            100                 105                 110

Gln Gly Thr Gln Val Thr Val Ser Ser
        115                 120

<210> SEQ ID NO 55
<211> LENGTH: 121
<212> TYPE: PRT
<213> ORGANISM: Artificial Sequence
<220> FEATURE:
<223> OTHER INFORMATION: DMOB7

<400> SEQUENCE: 55

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
        20                  25                  30

Tyr Met Gly Trp Tyr Arg Gln Ala Pro Gly Lys Gln Arg Glu Pro Val
        35                  40                  45

Ala Met Ile Thr Ser Gly Gly Ser Thr Tyr Tyr Ala Asp Ser Val Lys
    50                  55                  60

Gly Arg Val Thr Ile Ser Arg Asp Asn Ala Lys Lys Thr Val Tyr Leu
```

-continued

```
65              70              75              80

Gln Met Asn Ser Leu Arg Pro Glu Asp Thr Ser Thr Tyr Tyr Cys Ala
                85              90              95

Ala Gly Phe Tyr Arg Ser Asp Ser Pro Asn Arg Tyr Asp Tyr Trp Gly
            100             105             110

Gln Gly Thr Gln Val Thr Val Ser Ser
        115             120

<210> SEQ ID NO 56
<211> LENGTH: 121
<212> TYPE: PRT
<213> ORGANISM: Artificial Sequence
<220> FEATURE:
<223> OTHER INFORMATION: DMOC10

<400> SEQUENCE: 56

Gln Val Gln Leu Gln Glu Ser Gly Gly Gly Leu Val Gln Pro Gly Gly
1               5               10              15

Ser Leu Arg Leu Ser Cys Ala Ala Ser Gly Ser Ile Phe Gly Ile Ser
            20              25              30

Tyr Met Gly Trp Tyr Arg Gln Ala Pro Gly Lys Gln Arg Glu Pro Val
        35              40              45

Ala Leu Ile Thr Ser Gly Gly Ser Thr Tyr Tyr Val Asp Ser Val Asn
    50              55              60

Gly Arg Val Thr Ile Ser Arg Asp Asn Ala Lys Lys Thr Val Tyr Leu
65              70              75              80

Gln Met Asn Ser Leu Arg Pro Glu Asp Thr Ser Thr Tyr Tyr Cys Ala
                85              90              95

Ala Gly Phe Tyr Arg Ser Asp Ser Pro Asn Arg Tyr Asp Tyr Trp Gly
            100             105             110

Gln Gly Thr Gln Val Thr Val Ser Ser
        115             120

<210> SEQ ID NO 57
<211> LENGTH: 121
<212> TYPE: PRT
<213> ORGANISM: Artificial Sequence
<220> FEATURE:
<223> OTHER INFORMATION: DMOD4

<400> SEQUENCE: 57

Gln Val Gln Leu Gln Glu Ser Gly Gly Gly Leu Val Gln Pro Gly Gly
1               5               10              15

Ser Leu Arg Leu Ser Cys Ala Ala Ser Gly Ser Ile Phe Gly Ile Ser
            20              25              30

Tyr Met Gly Trp Tyr Arg Gln Ala Pro Gly Lys Gln Arg Glu Pro Val
        35              40              45

Ala Leu Ile Thr Ser Gly Gly Ser Ala Tyr Tyr Val Asp Ser Val Lys
    50              55              60

Gly Arg Val Thr Ile Ser Arg Asp Asn Ala Lys Lys Thr Val Tyr Leu
65              70              75              80

Gln Met Asn Ser Leu Arg Pro Glu Asp Thr Ser Thr Tyr Tyr Cys Ala
                85              90              95

Ala Gly Phe Tyr Arg Ser Asp Ser Pro Asn Arg Tyr Asp Tyr Trp Gly
            100             105             110

Gln Gly Thr Gln Val Thr Val Ser Ser
        115             120
```

<210> SEQ ID NO 58
<211> LENGTH: 121
<212> TYPE: PRT
<213> ORGANISM: Artificial Sequence
<220> FEATURE:
<223> OTHER INFORMATION: DMOE7

<400> SEQUENCE: 58

Gln Val Gln Leu Gln Glu Ser Gly Gly Gly Arg Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
        35                  40                  45

Ala Leu Ile Thr Ser Gly Gly Ser Thr Tyr Tyr Val Asp Ser Val Glu
    50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
            85                  90                  95

Ala Gly Tyr Tyr Arg Ser Asp Ser Pro Asn Arg Tyr Asp Tyr Trp Gly
        100                 105                 110

Gln Gly Thr Gln Val Thr Val Ser Ser
        115                 120

<210> SEQ ID NO 59
<211> LENGTH: 113
<212> TYPE: PRT
<213> ORGANISM: Artificial Sequence
<220> FEATURE:
<223> OTHER INFORMATION: DMOF6

<400> SEQUENCE: 59

Gln Val Gln Leu Gln Glu Ser Gly Gly Gly Leu Val Gln Val Gly Gly
1               5                   10                  15

Ser Leu Arg Leu Ser Cys Ala Ala Ser Gly Arg Thr Ile Ser Gly Tyr
            20                  25                  30

Ala Met Gly Trp Phe Arg Gln Ala Pro Gly Lys Glu Arg Asp Leu Val
        35                  40                  45

Ala Ala Ile Ser Arg Ser Gly Thr Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
            85                  90                  95

Asn Ala Pro Gly Gly Ile Trp Gly Gln Gly Thr Gln Ala Thr Val Ser
        100                 105                 110

Ser

<210> SEQ ID NO 60
<211> LENGTH: 121
<212> TYPE: PRT
<213> ORGANISM: Artificial Sequence
<220> FEATURE:
<223> OTHER INFORMATION: DMOG1

<400> SEQUENCE: 60

Gln Val Gln Leu Gln Glu Ser Gly Gly Gly Leu Val Gln Pro Gly Gly
1               5                   10                  15

-continued

```
Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
            35                  40                  45

Ala Leu Ile Thr Ser Gly Gly Ser Thr Tyr Tyr Ala Asp Ser Val Asn
        50                  55                  60

Gly Arg Val Thr Ile Ser Arg Asp Asn Ala Lys Lys Thr Val Tyr Leu
65                  70                  75                  80

Gln Met Asn Ser Leu Arg Pro Glu Asp Thr Ser Thr Tyr Tyr Cys Ala
                85                  90                  95

Ala Gly Tyr Tyr Arg Ser Asp Ser Pro Asn Arg Tyr Asp Tyr Trp Gly
                100                 105                 110

Gln Gly Thr Gln Val Thr Val Ser Ser
            115                 120
```

<210> SEQ ID NO 61
<211> LENGTH: 121
<212> TYPE: PRT
<213> ORGANISM: Artificial Sequence
<220> FEATURE:
<223> OTHER INFORMATION: DMOG4

<400> SEQUENCE: 61

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Lys Gln Arg Glu Pro Val
            35                  40                  45

Ala Met Ile Thr Ser Gly Gly Ser Thr Tyr Tyr Ala Asp Ser Val Lys
        50                  55                  60

Gly Arg Val Thr Ile Ser Arg Asp Asn Ala Lys Lys Thr Val His Leu
65                  70                  75                  80

Gln Met Asn Ser Leu Arg Pro Glu Asp Thr Ser Thr Tyr Tyr Cys Ala
                85                  90                  95

Ala Gly Phe Tyr Arg Ser Asp Ser Pro Asn Arg Tyr Asp Tyr Trp Gly
                100                 105                 110

Gln Gly Thr Gln Val Thr Val Ser Ser
            115                 120
```

<210> SEQ ID NO 62
<211> LENGTH: 121
<212> TYPE: PRT
<213> ORGANISM: Artificial Sequence
<220> FEATURE:
<223> OTHER INFORMATION: DMOH12

<400> SEQUENCE: 62

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Gly Ile Ser
            20                  25                  30

Tyr Met Gly Trp Tyr Arg Gln Ala Pro Gly Arg Gln Arg Glu Pro Val
            35                  40                  45

Ala Met Ile Thr Ser Gly Gly Ser Thr Tyr Tyr Val Asp Gly Val Lys
        50                  55                  60

Gly Arg Val Thr Ile Ser Arg Asp Asn Ala Lys Lys Thr Val Tyr Leu
```

-continued

```
65              70              75              80

Gln Met Lys Ser Leu Arg Pro Glu Asp Thr Ser Thr Tyr Tyr Cys Ala
            85              90              95

Ala Gly Phe Tyr Arg Ser Asp Ser Pro Asn Arg Tyr Asp Tyr Trp Gly
            100             105             110

Gln Gly Thr Gln Val Thr Val Ser Ser
        115             120
```

```
<210> SEQ ID NO 63
<211> LENGTH: 214
<212> TYPE: PRT
<213> ORGANISM: Artificial Sequence
<220> FEATURE:
<223> OTHER INFORMATION: 8C2 murine light chain

<400> SEQUENCE: 63

Asp Ile Gln Met Thr Gln Ser Pro Ala Ser Leu Ser Ala Ser Val Gly
1               5               10              15

Glu Thr Val Thr Ile Thr Cys Arg Ala Ser Gly Asn Ile His Asn Ser
            20              25              30

Leu Ala Trp Tyr Gln Gln Ile Lys Gly Arg Ser Pro Gln Leu Leu Val
        35              40              45

Tyr Asn Ala Lys Thr Leu Ala Asp Gly Val Pro Ser Arg Phe Ser Gly
    50              55              60

Ser Gly Ser Gly Thr Gln Tyr Ser Leu Lys Ile Asn Ser Leu His Pro
65              70              75              80

Glu Asp Phe Gly Ser Tyr Tyr Cys Gln His Phe Trp Ser Thr Pro Phe
            85              90              95

Thr Phe Gly Ser Gly Thr Lys Leu Glu Ile Lys Arg Ala Asp Ala Ala
            100             105             110

Pro Thr Val Ser Ile Phe Pro Pro Ser Ser Glu Gln Leu Thr Ser Gly
        115             120             125

Gly Ala Ser Val Val Cys Phe Leu Asn Asn Phe Tyr Pro Lys Asp Ile
    130             135             140

Asn Val Lys Trp Lys Ile Asp Gly Ser Glu Arg Gln Asn Gly Val Leu
145             150             155             160

Asn Ser Trp Thr Asp Gln Asp Ser Lys Asp Ser Thr Tyr Ser Met Ser
            165             170             175

Ser Thr Leu Thr Leu Thr Lys Asp Glu Tyr Glu Arg His Asn Ser Tyr
            180             185             190

Thr Cys Glu Ala Thr His Lys Thr Ser Thr Ser Pro Ile Val Lys Ser
        195             200             205

Phe Asn Arg Asn Glu Cys
    210
```

```
<210> SEQ ID NO 64
<211> LENGTH: 214
<212> TYPE: PRT
<213> ORGANISM: Artificial Sequence
<220> FEATURE:
<223> OTHER INFORMATION: 8C2 chimeric light chain

<400> SEQUENCE: 64

Asp Ile Gln Met Thr Gln Ser Pro Ala Ser Leu Ser Ala Ser Val Gly
1               5               10              15

Glu Thr Val Thr Ile Thr Cys Arg Ala Ser Gly Asn Ile His Asn Ser
            20              25              30
```

```
Leu Ala Trp Tyr Gln Gln Ile Lys Gly Arg Ser Pro Gln Leu Leu Val
        35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu His Pro
65                  70                  75                  80

Glu Asp Phe Gly Ser Tyr Tyr Cys Gln His Phe Trp Ser Thr Pro Phe
                85                  90                  95

Thr Phe Gly Ser Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 65
<211> LENGTH: 214
<212> TYPE: PRT
<213> ORGANISM: Artificial Sequence
<220> FEATURE:
<223> OTHER INFORMATION: 8C2 human light chain

<400> SEQUENCE: 65

Asp Ile Val Leu Thr Gln Ser Pro Ser Ser Leu Ser Ala Ser Val Gly
1               5                   10                  15

Glu Thr Val Thr Ile Thr Cys Arg Ala Ser Gly Asn Ile His Asn Ser
                20                  25                  30

Leu Ala Trp Tyr Gln Gln Ile Lys Gly Lys Ala Pro Lys Leu Leu Ile
        35                  40                  45

Tyr Asn Ala Lys Thr Leu Ala Asp Gly Val Pro Ser Arg Phe Ser Gly
        50                  55                  60

Ser Gly Ser Gly Thr Asp Phe Ser Leu Thr Ile Ser Ser Leu Glu Pro
65                  70                  75                  80

Glu Asp Phe Ala Thr Tyr Tyr Cys Gln His Phe Trp Ser Thr Pro Phe
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

-continued

```
Ser Thr Leu Thr Leu Ser Lys Ala Asp Tyr Glu Lys His Lys Val Tyr
        180             185             190

Ala Cys Glu Val Thr His Gln Gly Leu Ser Ser Pro Val Thr Lys Ser
    195             200             205

Phe Asn Arg Gly Glu Cys
    210

<210> SEQ ID NO 66
<211> LENGTH: 220
<212> TYPE: PRT
<213> ORGANISM: Artificial Sequence
<220> FEATURE:
<223> OTHER INFORMATION: 8C2 murine heavy chain

<400> SEQUENCE: 66

Glu Val Gln Leu Gln Gln Ser Gly Ala Glu Leu Val Lys Pro Gly Ala
1               5               10              15

Ser Val Lys Leu Ser Cys Thr Ala Ser Gly Phe Asn Ile Lys Asp Thr
        20              25              30

Tyr Ile His Trp Val Lys Gln Arg Pro Glu Gln Gly Leu Glu Trp Ile
        35              40              45

Gly Met Ile Asp Leu Ala Asn Asp Asn Thr Lys Tyr Asp Pro Lys Phe
    50              55              60

Gln Gly Lys Ala Thr Ile Ile Thr Asp Thr Ser Ser Asn Lys Ala Tyr
65              70              75              80

Leu Gln Val Ser Ser Leu Thr Ser Glu Asp Thr Ala Val Tyr Tyr Cys
            85              90              95

Ala Thr Trp Gly Ala Ile Ile Thr Leu Gly Gly Trp Gly Gln Gly Thr
        100             105             110

Leu Val Thr Val Ser Ala Ala Lys Thr Thr Pro Pro Ser Val Tyr Pro
        115             120             125

Leu Ala Pro Gly Ser Ala Ala Gln Thr Asn Ser Met Val Thr Leu Gly
    130             135             140

Cys Leu Val Lys Gly Tyr Phe Pro Glu Pro Val Thr Val Thr Trp Asn
145             150             155             160

Ser Gly Ser Leu Ser Ser Gly Val His Thr Phe Pro Ala Val Leu Gln
            165             170             175

Ser Asp Leu Tyr Thr Leu Ser Ser Ser Val Thr Val Pro Ser Ser Thr
            180             185             190

Trp Pro Ser Glu Thr Val Thr Cys Asn Val Ala Asn Pro Ala Ser Ser
        195             200             205

Thr Lys Val Asp Lys Lys Ile Val Pro Arg Asp Cys
    210             215             220

<210> SEQ ID NO 67
<211> LENGTH: 226
<212> TYPE: PRT
<213> ORGANISM: Artificial Sequence
<220> FEATURE:
<223> OTHER INFORMATION: 8C2 chimeric heavy chain

<400> SEQUENCE: 67

Glu Val Gln Leu Gln Gln Ser Gly Ala Glu Leu Val Lys Pro Gly Ala
1               5               10              15

Ser Val Lys Leu Ser Cys Thr Ala Ser Gly Phe Asn Ile Lys Asp Thr
        20              25              30

Tyr Ile His Trp Val Lys Gln Arg Pro Glu Gln Gly Leu Glu Trp Ile
        35              40              45
```

```
Gly Met Ile Asp Leu Ala Asn Asp Asn Thr Lys Tyr Asp Pro Lys Phe
    50              55              60

Gln Gly Lys Ala Thr Ile Ile Thr Asp Thr Ser Ser Asn Lys Ala Tyr
65              70              75              80

Leu Gln Val Ser Ser Leu Thr Ser Glu Asp Thr Ala Val Tyr Tyr Cys
                85              90              95

Ala Thr Trp Gly Ala Ile Ile Thr Leu Gly Gly Trp Gly Gln Gly Thr
            100             105             110

Leu Val Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
    130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
            195             200             205

Asn Thr Lys Val Asp Lys Lys Val Glu Pro Lys Ser Cys Asp Lys Thr
    210             215             220

His Leu
225

<210> SEQ ID NO 68
<211> LENGTH: 226
<212> TYPE: PRT
<213> ORGANISM: Artificial Sequence
<220> FEATURE:
<223> OTHER INFORMATION: 8C2 human heavy chain

<400> SEQUENCE: 68

Glu Val Gln Leu Gln Glu Ser Gly Ala Glu Leu Val Lys Pro Gly Ala
1               5               10              15

Ser Val Lys Leu Ser Cys Ala Ala Ser Gly Phe Asn Ile Lys Asp Thr
            20              25              30

Tyr Ile His Trp Val Arg Gln Arg Pro Gly Gln Gly Leu Glu Trp Ile
        35              40              45

Gly Met Ile Asp Leu Ala Asn Asp Asn Thr Lys Tyr Asp Pro Lys Phe
    50              55              60

Gln Gly Arg Val Thr Ile Thr Val Asp Thr Ser Thr Asn Lys Ala Tyr
65              70              75              80

Leu Gln Leu Ser Ser Leu Thr Ser Glu Asp Thr Ala Val Tyr Tyr Cys
                85              90              95

Ala Thr Trp Gly Ala Ile Ile Thr Leu Gly Gly Trp Gly Gln Gly Thr
            100             105             110

Leu Val Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
    130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175
```

-continued

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Leu
225

<210> SEQ ID NO 69
<211> LENGTH: 124
<212> TYPE: PRT
<213> ORGANISM: Artificial Sequence
<220> FEATURE:
<223> OTHER INFORMATION: 8C2 VHH

<400> SEQUENCE: 69

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Met Ser Trp Val Arg Gln Ala Pro Gly Lys Gly Leu
            35                  40                  45

Glu Trp Val Ser Pro Asp Leu Ala Asn Asp Asn Thr Lys Tyr Asp Pro
    50                  55                  60

Lys Tyr Tyr Ala Asp Ser Val Lys Gly Arg Phe Thr Ile Ser Arg Asp
65                  70                  75                  80

Asn Ser Lys Asn Thr Leu Tyr Leu Gln Met Asn Thr Leu Arg Ala Glu
            85                  90                  95

Asp Thr Ala Val Tyr Tyr Cys Ala Thr Trp Gly Ala Ile Ile Thr Leu
            100                 105                 110

Gly Gly Trp Gly Gln Thr Met Val Thr Val Ser Ser
            115                 120
```

COMPOSITIONS AND METHODS FOR REDUCING OFF-TARGET TOXICITY OF ANTIBODY DRUG CONJUGATES

CROSS-REFERENCE TO RELATED APPLICATIONS

This application claims priority to U.S. Provisional patent application No. 62/943,358, filed on Dec. 4, 2019, the disclosure of which is incorporated herein by reference.

SEQUENCE LISTING

The instant application contains a Sequence Listing which has been submitted electronically in txt format and is hereby incorporated by reference in its entirety. Said txt copy was created on Dec. 4, 2020, is named "011520_01569_ST25.txt" and is 82,000 bytes in size.

BACKGROUND OF THE DISCLOSURE

Anti-cancer antibody-drug conjugates (ADCs) are being employed for targeted delivery of drugs, which may be toxins or other cell growth inhibitors (termed here as drug or payload molecules) to cancer cells. Nine ADCs are currently marketed in the US, and approximately 100 ADCs are in development (Chau et al., Lancet. 2019; 394(10200):793-804; Coats et al., Clin Cancer Res. 2019. Epub Apr. 14, 2019. doi: 10.1158/1078-0432.CCR-19-0272; Wolska-Washer et al., Drug Saf. 2019; 42(2):295-314; Beck et al., Nat Rev Drug Discov. 2017; 16(5):315-37). However, clinical application of ADCs has been somewhat disappointing; many ADCs have failed in clinical trials as a result of substantial off-target toxicity, which has limited tolerable doses below levels needed for tumor eradication (Coats et al., Clin Cancer Res. 2019. Epub Apr. 14, 2019. doi: 10.1158/1078-0432.CCR-19-0272; Kim et al., Biomol Ther (Seoul). 2015; 23(6):493-509; de Goeij et al., Curr Opin Immunol. 2016; 40:14-23; Khera et al., BioDrugs. 2018; 32(5):465-80). As a result of associated toxicity to non-target sites, the early promise of ADCs is not fully realized and therefore, there is an ongoing need in the area of cancer therapy to develop new approaches to minimize non-target toxicity of therapeutic payload drug molecules without compromising their anti-tumor efficacy.

SUMMARY OF THE DISCLOSURE

This disclosure provides compositions and methods for reducing off-target toxicity of ADCs. For example, the present compositions and methods can be used for treatment of tumors with ADCs, while reducing off-target toxicity of the ADCs. The drug in the ADC may be referred to herein as "payload". The compositions comprise an ADC and an agent targeted to the payload that is delivered by or derived from the ADC. The agent targeted to the payload is termed herein as "payload-binding agent" or PBA. The ADC and the payload-binding agent may be provided in the same composition or in different compositions. The payload binding agent may be a peptide or an antibody or a fragment or an antibody mimetic or a modification thereof directed to the ADC payload, and which binds to the payload. If the payload binding agent is an antibody or a fragment or modification thereof, it may be referred to as "anti-payload antibody".

In an aspect, this disclosure provides a method for inhibiting or preventing the growth of one or more tumors comprising administering to an individual in need of treatment, an ADC and a payload binding agent, wherein the payload binding agent has specific affinity for the ADC payload. The ADC and the payload binding agent may be administered in the same composition or different compositions, via the same routes or via different routes, or using the same regimen or different regimen.

In an aspect, this disclosure provides peptides or antibodies or antibody fragments or modifications, which are specific for an ADC payload molecule. The anti-payload antibody may be whole immunoglobulin molecules such as polyclonal or monoclonal antibodies or chimeric antibodies including humanized antibodies. The antibody fragments or modification can be antigen-binding fragments thereof, including, but not limited to, Fab, F(ab'), F(ab')2, Fv, dAb, Fd, CDR fragments, single-chain antibodies (scFv), bivalent single-chain antibodies, single-chain phage antibodies, diabodies, or single domain antibodies (nanobodies) and the like. Antibody mimetics may include affibodies, nanofitins, or the like. The fragments of the antibodies may be produced synthetically or by enzymatic or chemical cleavage of intact immunoglobulins or may be genetically engineered by recombinant DNA techniques. These techniques are well known in the art. The antibody or fragments or modifications thereof may be modified so as to impart longer half-life, stability and the like. In an embodiment, the disclosure provides antibodies or fragments or derivatives thereof directed to several ADC payload, including full length antibodies, scFv, Fab and other fragments directed specifically to maytansinoids, auristatins, camptothecins, pyrrolobenzdiazepines, and calicheamicin.

BRIEF DESCRIPTION OF THE FIGURES

FIG. 2. 8C2 Fab production. A) Purification of 8C2 Fab using a hydroxyapatite chromatography. B) Purity analysis of fractions collected during purification. Samples were loaded under reducing and non-reducing conditions. 8C2 Fab purity and integrity was assessed by examining a single band at 25 kDa under reducing conditions and a primary band at 50 kDa under non-reducing conditions.

FIG. 6. Inhibition of SN38 cytotoxicity by intact 8C2 mAb and 8C2 Fab fragment in HT-29 colorectal cancer cells. Intact 8C2 antagonizes SN38 cytotoxicity up to 1 μM, >300-fold increase, while 8C2 Fab prevents cytotoxicity of SN38 up to 100 nM.

FIG. 13. Positive clones from ELISA screening with phage media. Phage media was diluted 5-fold with PBST before adding to ELISA wells coated with either Trastuzumab-deruxtecan or Trastuzumab. The positive ΔOD at 450 nm indicates phage binding to Trastuzumab-deruxtecan more than Trastuzumab.

FIG. 14. Competitive ELISA. Phage media from identified positive clones was tested for binding against Trastuzumab deruxtecan with or without pre-incubation of exatecan.

FIG. 15. Unique sdAb sequences obtained from phages with positive exatecan binding (from FIGS. 13,14). The sequence for TA2 is SEQ ID NO:7, TB9 is SEQ ID NO:10, TF5 is SEQ ID NO:11, TF7 is SEQ ID NO:6, FA1 is SEQ ID NO:8, and FA2 is SEQ ID NO:9.

FIG. 16. SDS-PAGE and Indirect ELISA. TF7 is ~80% pure after Ni-NTA column and ~95% pure after CHT column, and shows concentration-dependent binding to Trastuzumab deruxtecan.

FIG. 21. Evaluation of polyclonal antibody response to calicheamicin from llama plasma. Llama was immunized with KLH-calicheamicin. Llama plasma before the immunization and after the immunization were collected and tested for response against calicheamicin. Plasma was pre-incubated with free drug to compete for binding to biotin-calicheamicin (A) or bead-bound calicheamicin (B). The third immunization demonstrated antibodies present within llama plasma that bind to free calicheamicin.

FIG. 26. sdAb CG4 ELISA binding assay. A) Anti-calicheamicin sdAb CG4 was expressed and purified by $Ni^{2+}$-NTA resin. SDS-PAGE showed good purity with a single band around 12 kDa. B) Binding to Cetuximab-calicheamcin conjugate increased with increasing concentration of CG4 (CG4 is the same as G4 from FIG. 25). C) Binding to Dynabeads-calicheamicin increased with increasing concentration of CG4. D) 10 µM calicheamicin lowered the binding of 64 µM CG4 by 2.5-fold based on the ADC coated ELISA. E) 10 µM calicheamicin lowered the binding of 64 µM CG4 by 2-fold based on the ADC coated ELISA. And considering the higher background of calicheamicin group, the actual fold reduction could be around 3.3-fold and 4.3.

FIG. 27. MTT Cell based assay with CG4 (CG4 is the same as G4 from FIG. 25). Fresh media containing a range of calicheamicin were pre-incubated with or without 100 µM purified sdAb CG4 at room temperature for 30 minutes. Log-phase MOLM-14 cells or ramos cells were seeded at 96-well microtiter plates at a density of 20,000 cells/well, and received treatment for 24 h. CG4 increased the calicheamicin $IC_{50}$ by 15.4-fold from 26.03 pM to 400.2 pM on MOLM-14 cells, and increased the IC50 by 6.34-fold from 2.979 nM to 18.88 nM on ramos cells, respectively.

FIG. 33. MTT Cell based assay. Cell cytotoxicity of DM4 on Lovo and MOLM-14 cells with and without 5 µM of DF3A2 sdAb. DM4 exhibited an $IC_{50}$ of 35.81 nM and 18.36 nM in Lovo and MOLM-14 cells, respectively. DM4 cytotoxicity was inhibited by DF3A2 to 376.2 nM and 39.17 nM in Lovo and MOLM-14, respectively.

FIG. 35. MTT Cell based assay with DF3A4. Cell cytotoxicity of DM1 and DM4 on Lovo cells with and without 10 µM of DF3A4 sdAb for 6 and 24 h exposure periods. In the 6 h exposure duration, DM1 and DM4 exhibited $IC_{50}$ of 30.48 nM and 7.699 nM on Lovo cells. DM1 and DM4 cytotoxicity was inhibited by DF3A4 to 450.5 nM and 45.32 nM, respectively. In the 24 h exposure duration, DM1 and DM4 exhibited $IC_{50}$ of 3.067 nM and 0.7131 nM on Lovo cells. DM1 and DM4 cytotoxicity was inhibited by DF3A4 (referred to as 3A4 in the figure) to 29.38 nM and 6.175 nM, respectively.

FIG. 37. MTT Cell based assay with DF4B12. Cell cytotoxicity of DM1 and DM4 on Lovo cells with and without 10 µM of DF4B12 sdAb for 6 and 24 h exposure periods. In the 6 h exposure duration, DM1 and DM4 exhibited $IC_{50}$ of 22.15 nM and 21.53 nM on Lovo cells. DM1 and DM4 cytotoxicity was inhibited by DF4B12 to 1174 nM and 334.4 nM, respectively. In the 24 h exposure duration, DM1 and DM4 exhibited $IC_{50}$ of 2.124 nM and 1.837 nM on Lovo cells. DM1 and DM4 cytotoxicity was inhibited by DF4B12 to 224.1 nM and 17.22 nM, respectively.

FIG. 42. Positive clones identified from screening of the llama single domain antibody phage library against MMAE. A) Single colonies obtained following three panning steps were expanded and culture media was tested for binding against BSA-MMAE with or without pre-incubation of MMAE. B) Fold change between responses of sdAbs when pre-incubated with MMAE. B2, A3, and C7 demonstrated the highest fold change, >10-fold.

FIG. 44. Positive clones identified from screening of the llama single domain antibody phage library against PBD. A) Single colonies obtained following three panning steps were expanded and culture media was tested for binding against BSA-PBD with or without pre-incubation of PBD. B) Fold change between responses of sdAbs when pre-incubated with PBD. E9 demonstrated the highest fold change, about 5.

FIG. 58. 8C2 Fab sequences. Sequences of light and heavy chains of murine, chimeric and human antibodies and VHH are provided. The top panel shows the sequence of the light chain and the bottom panel shows the sequences of the heavy chain. Also provided is the sequence for a 8C2 VHH with the CDRs of 8C2 placed into a stable human framework. Dots represent positions of identify with the parent murine sequence and dashed represent regions without a matching amino acid site. The sequence of murine light chain is represented by SEQ ID NO:59, the sequence of chimeric light chain is represented by SEQ ID NO:60, the sequence of human light chain is represented by SEQ ID NO:61, the sequence of murine heavy chain is represented by SEQ ID NO:62, the sequence of chimeric heavy chain is represented by SEQ ID NO:63, the sequence of human heavy chain is represented by SEQ ID NO:64, and the sequence of VHH Is represented by SEQ ID NO:65.

FIG. 60. Effects of 8C2 Fab Constructs on Dxd and SN38 Cytotoxicity: Free payload (SN38 left plot, Dxd right plot) was incubated with SKBR3 cells with or without coincubation with the 8C2 Fab constructs. Cell viability evaluated on day 7.

FIG. 61. Effects of Murine Recombinant 8C2 Fab on Dxd and T-Dxd Cytotoxicity: Demonstration of the selectivity of 8C2 Fab in inhibiting the cytotoxicity of free payload in comparison to intact antibody drug conjugate. Free payload Dxd (Left) cytotoxicity is inhibited by >100-fold without impacting the cytotoxicity of the intact ADC trastuzumab deruxtecan (T-Dxd, right).

FIG. 63. Engineered constructs with improved pharmacokinetics. (Left): SDS-PAGE gels showing purified sdAb-sdAb bispecific fusion proteins, combining the anti-camptothecin sdAb (TF7) with an anti-RBC sdAb (RMC1) or with a non-binding control sdAb (1HE). Each construct has a MW of ~27 kDa. Fusion of TF7 with RMC1 led to a substantial reduction in clearance, increasing plasma half-life to 27.6 h (relative to 3.5 h for the fusion of TF7 and the non-binding sdAb). Use of anti-RBC domains allows dramatic alterations in sdAb pharmacokinetics, enabling greater convenience of dosing while also increasing the blood:

Figure 1:
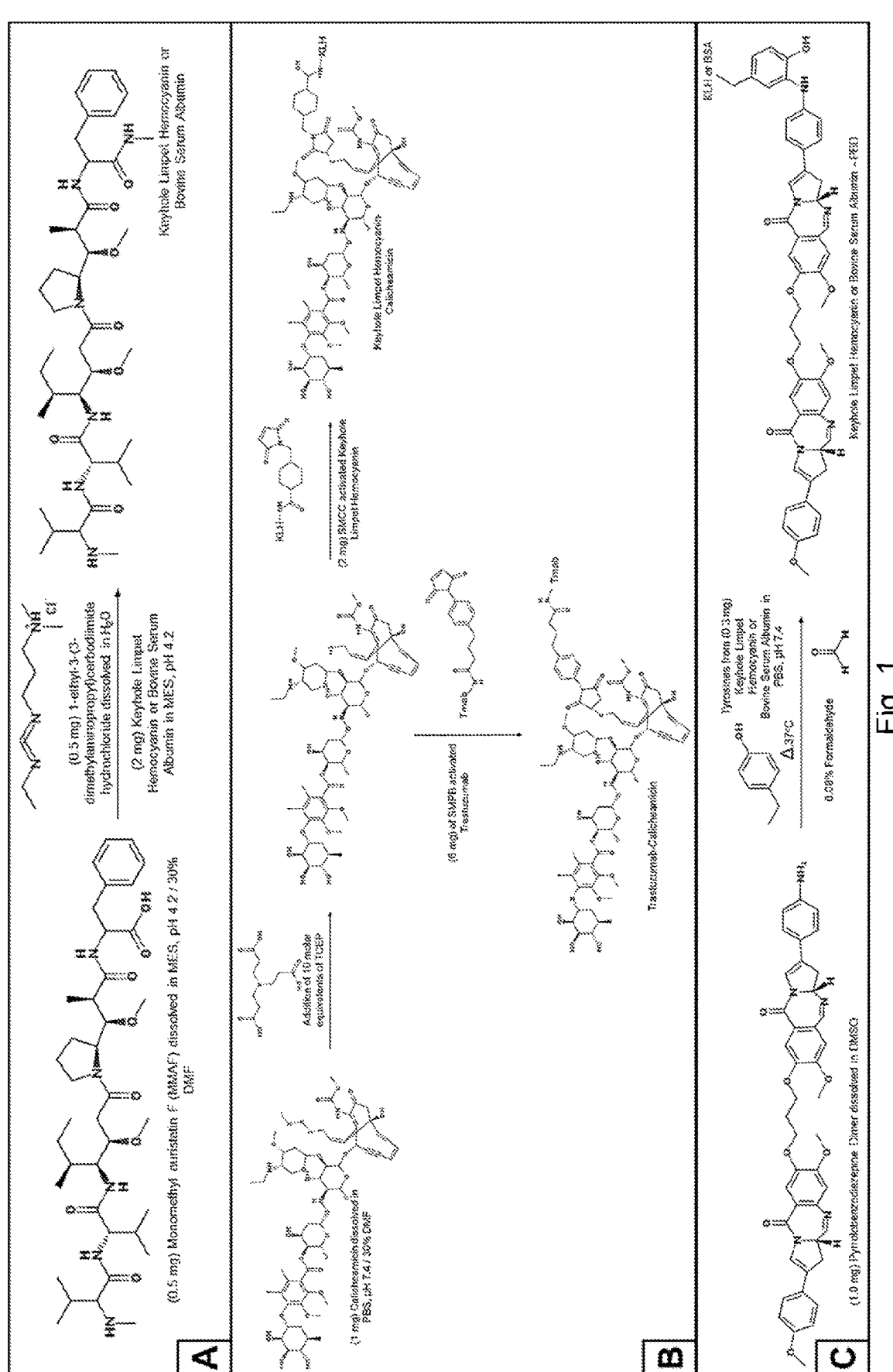
FIG. 1. Chemical reaction schematics for developing immunogen conjugates. A) MMAF was reacted with 1-ethyl-3-(3-dimethylaminopropyl)carbodiimide hydrochloride in MES buffer, pH 4.2 with carrier proteins keyhole limpet hemocyanin (KLH) or bovine serum albumin (BSA). The reaction favors the carboxylic acid group resulting in an amide bond between MMAF and the carrier protein. B) Calicheamicin was reacted with 10 molar equivalents of TCEP for 2 h at 37° C. in order to reduce the tri-sulfide bond. Following reduction, the r-Calicheamicin was reacted with either SMCC modified KLH or SMPB modified trastuzumab. C) Mannich condensation chemistry was employed to conjugate pyrrolobenzodiazepine (PBD) to carrier proteins. PBD was reacted with either KLH or BSA in presence of 0.08% formaldehyde under constant heating at 37° C. for 17 h. KLH immunogens were used for animal immunizations while BSA and trastuzumab conjugates were utilized for ELISA.

tumor exposure ratio, which is expected to promote inhibition of the systemic toxicity of released payload without altering beneficial within-tumor bystander effects.

DETAILED DESCRIPTION OF THE DISCLOSURE

The present disclosure provides compositions and methods for treatment of diseases (e.g., cancer) using ADC, while reducing off-target toxicity associated with the ADC. The method comprises administering to an individual in need of treatment an ADC and one or more payload binding agents directed to the drug portion of the ADC. The payload binding agent is effective in reducing the non-target toxicity of the ADC or the non-target toxicity derived from the free drug dissociated therefrom. The compositions comprise antibodies (including fragments or modifications thereof), which are directed to the drug of the ADC. Compositions are also provided that comprise the ADC and an agent (such as an antibody) which is directed to the drug that makes up the ADC. The agents bind to free drug and may or may not bind to the drug when it is part of the ADC.

An ADC comprises an antibody group, a linking group, and a drug group. The antibody group targets an antigen, such as a tumor cell antigen, the linking group is used to attached the drug group to the antibody group, and the drug group is an agent that is cytotoxic to the targeted cell. The antibody group may be referred to as an antibody or by the name of the antibody. Similarly, the drug group may be referred to as a drug or by the name of the drug.

The term "treatment" as used herein refers to reduction or delay in one or more symptoms or features associated with the presence of the particular condition being treated Treatment does not necessarily mean complete cure and does not preclude relapse, but may be used in connection with any such relapse.

The term "therapeutically effective amount" as used herein is the amount sufficient to achieve, in a single or multiple doses, the intended purpose of treatment. The exact amount desired or required will vary depending on the mode of administration, patient specifics and the like. Appropriate effective amounts can be determined by one of ordinary skill in the art (such as a clinician) with the benefit of the present disclosure.

Where a range of values is provided in this disclosure, it should be understood that each intervening value, to the tenth of the value of the lower limit of that range, and any other intervening value and ranges in that stated range are encompassed within the disclosure, unless clearly indicated otherwise. The upper and lower limits of these smaller ranges may independently be included in the smaller ranges encompassed within the disclosure.

As used in this disclosure, the singular forms include the plural forms and vice versa unless the context clearly indicates otherwise. The indefinite articles "a" and "an" as used in the specification and claims should be understood to mean "at least one" unless clearly indicated otherwise.

A general reference to an antibody in this disclosure is also intended to include all full-length antibodies, antibody fragments containing antigen binding domains, as well as modified antibodies or fragments containing substitutions or modifications of the amino acid residues, and including where antibody fragments, modified or not, may be linked together via covalent linkages with or without linkers.

The terms "off-target" and "non-target" in reference to toxicity refer to toxicity that accompanies the administration of many chemotherapeutic agents. While the intended purpose of administration of a chemotherapeutic agent is to reduce or inhibit the growth of tumors or any accompanying metastases, the growth, function, and/or physiology of normal cells are often adversely affected in the course of treatment of cancer. A reduction of off-target or non-target toxicity is intended to reduce any adverse effects on the non-tumor or non-metastatic cells.

The term "payload binding agent" (PBA) as used in this disclosure refers to an agent that specifically binds to a payload (drug) portion of an ADC. The PBA may be an antibody, a fragment or modification thereof, a peptide, an aptamer, a Spiegelmer, a fibronectin, a DARPin, a cyclo-dextrin, or an affitin. When the PBA is an antibody, the PBA may be referred to herein as an anti-drug antibody or anti-payload antibody. The anti-payload antibody may be whole immunoglobulin molecules such as polyclonal or monoclonal antibodies or chimeric antibodies including humanized antibodies or may be antigen-binding fragments thereof, including, but not limited to, Fab, F(ab'), F(ab')2, Fv, dAb, Fd, CDR fragments, single-chain antibodies (scFv), bivalent single-chain antibodies, single-chain phage antibodies, diabodies, single domain antibodies (nanobodies) and the like. The fragments of the antibodies may be produced synthetically or by enzymatic or chemical cleavage of intact immunoglobulins or may be genetically engineered by recombinant DNA techniques. These techniques are well known in the art.

The term "chimeric antibody" refers to an antibody that has framework residues from one species, such as human, and CDRs (which generally confer antigen binding) from another species, such as a murine antibody that specifically binds a payload. In a chimeric antibody, some portions of the heavy and/or light chains may be identical or homologous to sequences from a particular species while other portions may be identical or homologous to sequences from a different species. Chimeric antibodies generally exhibit decreased immunogenicity and increased stability. Techniques for cloning murine immunoglobulin variable domains known in the art—such as, for example, see Orlandi et al., Proc. Natl Acad. Sci. USA 86: 3833 (1989), and Leung et al., Hybridoma 13:469 (1994). As an example of a chimeric antibody, polynucleotides encoding the variable domains of the light chain or the heavy chain of an antibody derived from an animal (e.g., mouse, rat, or chicken) other than human can be linked to polynucleotides encoding the constant domains of the light chain or the heavy chain derived from a human antibody to produce a polynucleotide (such as DNA) encoding a chimeric antibody.

A "human" antibody (also called a "fully human" antibody) is an antibody that includes human framework regions and all of the CDRs from a single or different human immunoglobulins. Thus, frameworks from one human antibody can be engineered to include CDRs from a different human antibody. Methods for producing human antibodies are known in the art—such as, for example, see Mancini et al., 2004, New Microbiol. 27:315-28; Conrad and Scheller, 2005, Comb. Chem. High Throughput Screen. 8:117-26.

A "humanized antibody" is typically a human antibody that has one or more amino acid residues imported into it (i.e., introduced into it) from a source that is non-human. For example, a humanized antibody is a recombinant protein in which the CDRs of an antibody from a species such as rodent, rabbit, dog, goat, or horse are imported into human heavy and light variable domains. The constant domains (also referred to as framework regions) of the antibody molecule are generally the same as those of a human antibody. The non-human immunoglobulin providing the CDRs can be termed as "donor" and the human immuno-globulin providing the framework can be termed as "acceptor". For example, all the CDRs can be from the donor immunoglobulin in a humanized immunoglobulin. Constant regions need not be always present, but if they are, they can be substantially identical to human immunoglobulin constant regions, i.e., at least about 85-90%, such as about 95% or more identical. A humanized antibody binds to the same payload as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions that have substantially no effect on antigen binding or other immunoglobulin functions. Humanized immunoglobulins can be constructed by means of genetic engineering (see for example, U.S. Pat. No. 5,585,089, and U.S. Publication No. 2010/0196266). For example, murine monoclonal antibodies may be isolated or generated and then humanized.

Antibody fragments can be produced by enzymatic digestion. For example, papain digestion of antibodies produces two identical antigen-binding fragments, called "Fab" fragments, and a "Fc" fragment. The Fab fragment contains an entire L chain and the variable region domain of the H chain (VH), and the first constant domain of one heavy chain. Each Fab fragment is monovalent with respect to antigen binding, i.e., it has a single antigen-binding site. Pepsin treatment of an antibody yields a single large $F(ab')_2$ fragment that roughly corresponds to two disulfide linked Fab fragments having divalent antigen-binding activity and is capable of cross-linking antigen. "Fv" is the minimum antibody fragment that contains a complete antigen-recognition and -binding site and single-chain Fv also abbreviated as "sFv" or "scFv" are antibody fragments that comprise the VH and VL antibody domains connected into a single polypeptide chain. The term "diabodies" refers to small antibody fragments prepared by constructing sFv fragments with short linkers between the VH and VL domains such that inter-chain but not intra-chain pairing of the V domains is achieved, resulting in a bivalent fragment, i.e., fragment having two antigen-binding sites. A single domain antibody (sdAb) is an antibody fragment which has a single mono-meric variable antibody domain. ScAbs can be made from heavy-chain antibodies found in camelids. An antibody fragment can be a single variable region or a peptide consisting of or comprising a single CDR. A single-chain antibody has a heavy chain variable domain and a light chain variable domain linearly linked to each other via a linker. A polynucleotide (such as DNA) encoding the single-chain antibody can be produced by binding a polynucleotide encoding the heavy chain variable domain, a polynucleotide encoding the linker (typically 10-20 nucleotides), and a polynucleotide encoding the light chain variable domain, with the heavy chain variable domain and the light chain variable domain being both derived from a human antibody.

The antibodies useful for the present method may be obtained from a human or a non-human animal. The antibody may be of any class (for example, IgG, IgE, IgM, IgD, IgA and IgY), or any subclass (e.g., IgG1, IgG2, IgG3, IgG4, IgA1 and IgA2). In an embodiment, single domain antibodies or nanobodies produced by camelids in response to introducing APP cleavage products (or peptide fragments thereof) into the camelids can be used. The nanobodies are typically heavy chain antibodies and thus contain heavy chain homodimers and do not contain antibody light chains.

These antibodies typically comprise a single variable domain and two constant domains (CH2 and CH3).

The present disclosure also provides sequences that have homology with the protein or peptides sequences (including antibody sequences) described herein. In various examples, the homologous sequences have at least 85%, 86%, 87%, 88%, 89%, 90%, 91%, 92%, 93%, 94%, 95%, 96%, 97%, 98%, or 99% identity with a protein or peptide sequence of the present disclosure.

Payload molecule is typically a drug molecule that causes cell toxicity. For example, any molecule that is used for treatment of cancer may be used. Examples include compounds, DNA, RNA, peptides and the like. In an embodiment, the drug molecule may be covalently bound to an N-terminal amino acid of the antibody via a reactive group or via a linker. Examples of reactive groups that cross link with the N-terminal alpha amine group of the antibody (such as light or heavy chain) include isothiocyanate, isocyate, acyl azide, NHS ester, sulfonyl ester, aldehyde, glyoxal, epoxide, carbonate, aryl halide, imidoester, carbodiimide, anhydride, fluorophenyl ester and the like. The reactive groups aldehyde or NHS ester are commonly used. Reduced cysteines (free sulfhydryls) may also be used. Conjugation methods of payload molecules to antibody are known. For example, conjugation of payload molecules to antibody is described in U.S. Pat. No. 10,071,170, the description of which is incorporated herein by reference.

Examples of payload molecules include microtubule formation inhibitors, meiosis inhibitors, topoisomerase inhibitors, RNA polymerase inhibitors, DNA intercalators or alkylators, ribosome inhibitors, siRNA, enzymes (carboxypeptidase, alkaline phosphatase, cytosine deaminase), immunocytokines (e.g. Interleukin-2) and the like. Examples of cytotoxic drugs include, but are not limited to, maytansinoid, auristatin, dolastatin, tubulysin, camptothecin, pyrrolobenzodiazepines, calicheamicin, gelonin, doxorubicin, duocamysin, carboplatin, cisplatin, cyclophosphamide, ifosfamide, nidran, bleomycin, mitomycin C, cytarabin, fluorouracil, methotrexate, trimetrexate, vinblastine, alimta, altretamine, procarbazine, taxol, taxotere, diphtheria toxin, *Pseudomonas* exotoxin and derivatives (e.g. PE38, PE40), alpha-emitters (Ac-225, At-211, Th-227, Ra-223, Pb-212, Bi-212, Ra-224). Compounds include their stereoisomers and derivatives. Auristatin may be monomethyl auristatin E (MMAE) or monomethyl auristatin F (MMAF).

In various embodiments, the ADC, which includes conjugates of antibodies with cytotoxic agents, may comprise any antibody or a fragment or modification thereof that is useful against a tumor antigen or that is useful for delivering the cytotoxic drug to the tumor cells. For example, there are several monoclonal antibodies that have been demonstrated as successful therapeutic agents for the treatment of human cancers. These include rituximab, trastuzumab, cetuximab, panitumumab, bevacizumab and many others.

Examples of monoclonal antibodies indicated against solid tumors include pertuzumab, ramucirumab, nivolumab, pembrolizumab, necitumumab, dinutuximab, olaratumab, atezolizumab, avelumab, cemiplimab, carotuximab, margetuximab, bemarituzumab, naxitamab, relatlimab, brentuximab, lorvotuzumab, glembatumumab, BCD-100, spartalizumab, IBI308, CS1001, tremelimumab, TSR-042). Any of these antibodies may be used to make an antibody drug conjugate.

Examples of ADCs include, but are not limited to, gemtuzumab ozogamicin, brentuximab vedotin, trastuzumab emtansine (TDM1), inotuzumab ozogamicin, polatuzumab vedotin, trastuzumab deruxtecan, trastuzumab duocarmazine, sacituzumab govitecan, loncastuximab tesirine, oportuzumab monatox, zolbetuximab claudiximab, depatuxizumab mafodotin, mirvetuximab sorvatansine, rovalpituzumab tesirine, enfortumab vedotin, BAT8001, L19IL2, and L19TNF.

When the PBA is an antibody, the anti-drug antibody can be directed to the toxin (also referred to herein as the drug or payload) part of the ADC. In embodiments, the anti-drug antibody can be a fragment of the whole antibody. The fragment of the anti-drug antibody may be Fab, a Fab', a F(ab')2, a Fv, a scFv, a single domain antibody, or a diabody, or any other epitope binding fragment. The fragment of the antibody can be in the range of 0.5 kDa-110 kDa (Note: F(ab')2 is ~100 kDa), including all Da values and ranges therebetween. In an embodiment, the antibody fragment is about 15 kDa. In an embodiment, the antibody is a single domain antibody (nanobody) containing only $V_HH$ (generally, 13 kDa to 15 kDa). The anti-drug antibody has a binding affinity for the drug that may be expressed in terms of dissociation constant ($K_D$). In an embodiment, the $K_D$ of the anti-drug antibody is from 10 pM to 50 nM, including all 0.1 pM values and ranges therebetween. In an embodiment, the $K_D$ is less than 1 nM. In an embodiment, the $K_D$ is from 10 pM to 100 pM. In an embodiment, the $K_D$ can be from 5-100 pM. In an embodiment, the anti-drug antibody is a Camelid, chimeric, or humanized single domain antibody—also termed as a nanobody. These antibodies possess many characteristics that are ideal for the present competitive inhibition approach. Single domain antibodies are a small antibody format (~15 kDa), are highly stable, can be expressed in *E. coli* and can be humanized to limit immunogenicity. Additionally, camelid immunization and phage display technologies allow rapid and inexpensive development of novel inhibitors.

The antibody (including fragments or modifications) may bind to the free payload or payload cleaved from the ADC. When the payload is cleaved from the ADC, such as via enzymatic action, hydrolysis, oxidation, or some other mechanism, the cleaved payload may comprise a portion of the linking group, all of the linking group, or none of the linking group. The cleaved payload may further comprise substituents that may be added during or after cleavage, or functional groups formed as a result of the cleavage process. Examples of substituents and/or functional groups formed from the cleavage process include, but are not limited to, alkyl groups (e.g., methyl, ethyl, propyl, isopropyl, and the like), alcohol groups, amines, thiols, sulfonic acids, sulfoxides, sulfides, sulfones, carboxylic acids, esters, amides, and the like, and combinations thereof.

Several antibodies (including fragments or modifications) are described in the examples herein, and sequences are disclosed. For example, full-length antibodies, scFv, Fab and others, directed specifically to maytansinoids, auristatins, camptothecins, pyrrolobenzdiazepines, calicheamicin, including derivatives of the foregoing. Generation of the antibodies, screening of the antibodies to identify the candidates with the desired binding specificity and affinity, and their binding and inhibitory characteristics are described.

The sequences of any of the antibodies or fragments described herein may include a polyhistidine tag, or the sequences may be used without the polyhistidine tag (e.g., to reduce immunogenicity). Any specific sequences disclosed here with polyhistidine tags also include the corresponding sequences without the polyhistidine tags, and any sequences disclosed herein without the polyhistidine tags also include sequences with the polyhistidine tags. Variants of the sequences of antibodies or fragments disclosed herein include sequences which have at least 85% identity with the disclosed sequences providing the binding affinity is not adversely affected. For example, the binding affinity of variants may be 10% less, the same, or better than the disclosed sequences. In embodiments, the variants may have at least 90%, at least 95%, at least 98%, at least 99% homology (identity) with the disclosed sequences without adversely affecting the binding affinity. The disclosure also includes nucleotide sequences that encode for the amino acid sequences or their variants as described herein.

The PBA may be a peptide comprised of ten or more amino acids, and with an equilibrium dissociation constant ($K_D$) for binding to the payload that is 50.0 nM or lower.

It was surprising that a binding agent, such as an antibody, directed to the payload (drug) portion of the ADC does not adversely affect its efficacy with respect to cytotoxicity for cancer cells, at least to any significant extent, but is able to reduce toxicity associated with the unconjugated payload. While not intending to be bound by any particular theory, it is possible the entry and intra-cellular processing of an ADC may be affected by binding to payload binding agents, and that the cellular entry of unconjugated payload is affected (reduced) by binding to a payload binding agent. However, the ability of payload binding agents to reduce toxicity of unconjugated payload relative to the anti-cancer cytotoxicity of ADCs, thereby enabling enhanced anti-cancer selectivity, is unexpected. In an embodiment, the potency of ADC may increase when used in conjunction with a PBA (such as an antibody). In such a case, not only does the non-target toxicity reduce, but the ADC efficacy is unexpectedly enhanced. In some embodiments, the PBA may not bind to the drug when it is a part of the ADC. Rather, it may bind to only free drug. In this case, there would be little or no impact on ADC efficacy, but a significant reduction in non-target toxicity.

The present disclosure provides a composition for reducing off-target toxicity comprising means for reducing toxicity of an unconjugated or cleaved payload (e.g., drug) from an ADC while not adversely affecting the efficacy of the ADC in the intended treatment (such as treatment for cancer cells). The means for reducing off-target toxicity includes anti-drug antibodies and fragments and modifications thereof, a peptide, an aptamer, a Spiegelmer, a fibronectin, a DARPin, a cyclodextrin, and/or an affitin.

When a reference is made to an antibody being "targeted to payload" or "directed to payload" or similar phrases, it means the antibody has specific affinity for the payload, when the payload is in the form of free payload, including when it is cleaved from the ADC. The anti-payload antibody may or may not bind to the payload when the payload is conjugated to the antibody part of the ADC.

In embodiments, the PBA may be engineered for binding to formed elements within blood (e.g., albumin, red blood cell membrane proteins, etc.). PBA that have been engineered for binding to formed elements in blood may be expected to demonstrate reduced clearance (i.e., enabling greater convenience in dosing) and increased blood:tumor exposure, enabling greater pharmacokinetic selectivity (i.e., enabling greater inhibition of released payload molecules in blood relative to inhibition of released payload molecules within tumors).

In an aspect, the disclosure provides pharmaceutical compositions comprising or consisting essentially of the ADCs and the anti-payload agents as described herein. The formulations typically contain physiologically acceptable carriers, excipients, or stabilizers and may be in the form of aqueous solutions, lyophilized or other dried or solid formulations. Examples of suitable pharmaceutical preparation components can be found in Remington: The Science and Practice of Pharmacy 22th edition (2012). Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, polyethylene glycol (PEG) and the like. In an embodiment, the pharmaceutical composition may comprise buffer components and stabilizers, including, but not limited to, sucrose, polysorbate 20, NaCl, KCl, sodium acetate, sodium phosphate, arginine, lysine, trehalose, glycerol, and maltose. In embodiments, the ADCs and the anti-payload antibodies or fragments or modifications thereof are the only protein molecules present in the compositions. In embodiments, the ADCs and the anti-payload antibodies or fragments or modifications thereof, are the only antibodies present in the composition.

Compositions comprising the ADC and the payload binding agent may be administered together, or separately and independently using any suitable route including parenteral, subcutaneous, intraperitoneal, intrapulmonary, and intranasal. Parenteral infusions include intramuscular, intravenous, intraarterial, intraperitoneal, or subcutaneous administration. The administration(s) may be carried out in a continuous manner or may be intermittent. Appropriate dosage will depend upon the particular tumor being treated, the specifics and condition of the individual patient, the mode of administration etc. Determination of appropriate dosage is within the purview of one skilled in the art, such as a treating physician. In an embodiment, the ADC may be delivered locally, while the PBA is delivered so as to be available systemically. For example, and ADC may be delivered at or near the site of a tumor or intraperitoneally, while the PBA may be delivered i.v. In an embodiment, the ADC may be delivered locally, while the anti-payload antibody is delivered so as to be available systemically. For example, and ADC may be delivered at or near the site of a tumor or intraperitoneally, while the anti-payload antibody may be delivered i.v.

The ADC and the PBA may be administered as a single composition or may be administered as separate compositions. When administered as separate compositions, they may be administered sequentially or concurrently. The two compositions may be administered at the same or different times, by the same or different routes, for same or different lengths of time, on the same or different regimens.

In an embodiment, the amount of the ADC and the PBA separately or together are in amounts sufficient enough to reduce the non-target toxicity of the ADC by at least 5% relative to that expected with the ADC alone at the same concentration as used in the combination. In embodiments, the reduction in toxicity may be 10%, 20%, 30%, 40%, 50% or more. Reduction in non-target toxicity can be evaluated by methods known in the art. For example, reduction could be classified as a reduction in the percent of patients at a specific dose that experience a grade 3 or higher adverse reaction with and without the PBA (Clin. Invest. (2013) 3(12), 1157-1165). Additionally, within an individual patient, reduction in non-target toxicity could be classified as a reduction in the severity of an adverse reaction (e.g., neutropenia) with, versus without the PBA.

The ADC and the PBA can be administered to an individual in need of treatment at dose(es) that is/are effective to treat a solid tumor. In general, suitable dosages of the PBA and the ADC can range from about 0.1 mg/kg to 100 mg/kg, including all 0.1 mg/kg values and ranges therebetween. Examples of dosages include 0.1, 0.5, 1, 5, 10, 15, 20, 25, 30, 35, 40, 45, 50, 55, 60, 65, 70, 75, 80, 85, 90, 95 and 100 mg/kg. A variety of dosage regimens are contemplated including dosage regimens in which the ADC and the PBA may be administered repeatedly, e.g., on a daily, weekly or monthly schedule, over a short period or an extended period of time, e.g., months to years (e.g., maintenance therapy). The range for administration of the PBA may be from 0.01-100 mg/kg, including all 0.01 mg/kg values and ranges therebetween. A suitable ratio of the ADC to the PBA may be determined by one skilled in the art. For example, a molar ratio can be from 1:1 to 1:100 ADC:PBA.

The amount of ADC and the anti-payload antibody can be administered to an individual in need of treatment at a dose that is effective to treat a solid tumor. In general, suitable dosages of the antibodies or fragments thereof—for both the ADC and the anti-payload antibody—can range from about 0.1 mg/kg to 100 mg/kg, including all 0.1 mg/kg values and ranges therebetween. Examples of dosages include 0.1, 0.5, 1, 5, 10, 15, 20, 25, 30, 35, 40, 45, 50, 55, 60, 65, 70, 75, 80, 85, 90, 95 and 100 mg/kg. A variety of dosage regimens are contemplated including dosage regimens in which the ADC and the anti-payload antibody may be administered repeatedly, e.g., on a daily, weekly or monthly schedule, over a short period or an extended period of time, e.g., months to years (e.g., maintenance therapy). The range for administration of the anti-payload antibody may be from 0.01-100 mg/kg, including all 0.01 mg/kg values and ranges therebetween. A suitable ratio of the ADC to the anti-drug antibody may be determined by one skilled in the art. In an embodiment, the molar ratio can be from 1:1 to 1:100 ADC:anti-Drug antibody.

In an embodiment, half-life extension strategies can be used to increase plasma half-life of the anti-payload antibodies including fusion of moieties to the sdAb that bind blood components such as albumin, red blood cells (e.g., Band 3 of RBCs) or endogenous IgG as well as PASylation and PEGylation. Thus, in embodiments, the anti-payload antibody may be fused to moieties that bind to albumin, red blood cells or endogenous IgG, or fragments thereof, or may be PASylated and/or PEGylated. As an example, a bispecific antibody may have an arm that binds to the payload and another arm that binds to albumin or red blood cells (e.g., Band 3 of RBCs). In an embodiment, the antibodies or fragments do not contain a polyhistidine tag. Data presented in FIG. 63 show fusion proteins of a candidate anti-camptothecin sdAb (TF7) and either RMC1, a sdAb that we have developed to bind to a red blood cell antigen (Band 3), or 1HE, a control sdAb that does not bind to mouse proteins. The TF7-RMC1 fusion protein exhibits a ~9-fold increase in half-life compared to TF7 fused to the non-binding control sdAb (TF7-1HE). It is therefore considered that sdAb-sdAb fusion proteins that combine anti-payload binding activity with desirable pharmacokinetic attributes (restricted distribution to blood, elimination via renal filtration due to low molecular weight, long half-life) can provide optimal enhancement of ADC therapeutic selectivity (increasing the ratio of efficacy to off-site toxicity).

The present composition/compositions may be administered alone or in combination with other types of treatments (e.g., surgical resection, radiation therapy, chemotherapy, hormonal therapy, immunotherapy, or other anti-tumor agents).

The present compositions may be used for any type of cancer, including carcinoma, lymphoma, sarcoma, melanoma, and leukemia. Non-limiting examples include squamous cell cancer, small-cell lung cancer, non-small cell lung cancer, adenocarcinoma of the lung, squamous carcinoma of the lung, cancer of the peritoneum, myeloma (including multiple myeloma), hepatocellular cancer, gastrointestinal cancer, pancreatic cancer, glioblastoma/glioma (e.g., anaplastic astrocytoma, glioblastoma multiforme, anaplastic oligodendroglioma, anaplastic oligodendroastrocytoma), cervical cancer, ovarian cancer, liver cancer, bladder cancer, hepatoma, breast cancer, brain cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

In an aspect, this disclosure provides a method for generating and identifying anti-payload antibodies that are suitable to be used in combination with an ADC therapy to reduce non-target cytotoxicity. The method comprises generating or obtaining a library of antibodies, identifying specific antibodies based upon positive binding to the payload molecule by ELISA and/or by surface plasmon resonance techniques, identifying antibodies that have the desired affinity (such as $K_D$ equal to or less than 50 nM), identifying cytotoxicity potential of the antibodies, determining binding kinetic parameters, and determining in vivo efficacy.

In an embodiment, the present disclosure provides compositions and methods for treatment of cancer using ADC, where the drug portion of the ADC is camptothecin or a camptothecin derivative, analog, or metabolite. The camptothecin derivative, analog, or metabolite thereof may be topotecan, irinotecan, exatecan, or SN38. The method comprises administering to an individual in need of treatment an ADC, where the drug portion is a camptothecin group and a payload binding agent directed to the camptothecin portion of the ADC. The ADC and the PBA may be administered in the same composition or in separate compositions as described elsewhere in this disclosure. The camptothecin derivative, analog, or metabolite thereof can be topotecan. The camptothecin derivative, analog, or metabolite thereof can be irinotecan. The camptothecin derivative, analog, or metabolite thereof can be exatecan. The camptothecin derivative, analog, or metabolite thereof can be SN38. An example of an ADC where the camptothecin derivative, analog, or metabolite thereof is exatecan is trastuzumab deruxtecan. An example of an ADC where the camptothecin derivative, analog, or metabolite thereof is SN38 is sacituzumab govitecan. Another example of an ADC where the camptothecin derivative, analog, or metabolite thereof is SN38 is labetuzumab govitecan. When the drug portion of an ADC is a camptothecin group, an example of an antibody that can be used as a payload binding agent is 8C2, or a fragment or modification thereof. A fragment or a modification may be Fab, scFv, sdAb and the like. The PBA may be an antibody fragment such as sdAbs TF7, TA2, FA1/FA2, TB2, and TFS. The fragment may be Fab sequence of 8C2, such as a murine, human or a chimeric Fab sequence, or a VHH. A method is also provided for the treatment of cancer (such as a solid tumor) comprising administering to an individual in need of treatment an ADC and a PBA, wherein the drug is a camptothecin group or derivative, analog, or metabolite thereof (e.g., topotecan, irinotecan, exatecan, SN38, etc.) and the PBA is an anti-camptothecin antibody (e.g., 8C2) or a fragment or modification thereof.

In an embodiment, the present disclosure provides compositions and methods for treatment of cancer using an ADC, where the drug portion of the ADC is calicheamicin or a calicheamicin derivative, analog, or metabolite. The method comprises administering to an individual in need of treatment an ADC, where the drug portion is a calicheamicin group, and a payload binding agent directed to the calicheamicin portion of the ADC. The ADC and the PBA may be administered in the same composition or in separate compositions as described elsewhere in this disclosure. An example of an ADC where the drug is calicheamicin is gemtuzumab ozogamicin. Another example of an ADC where the drug is calicheamicin is inotuzumab ozogamicin. When the drug portion of an ADC is calicheamicin, examples of a payload binding agent are peptides C2 and C9 as described in the Examples herein, or sdAb CG4. A method is also provided for the treatment of cancer (such as a solid tumor) comprising administering to an individual in need of treatment an ADC, wherein the drug in the ADC is calicheamicin, and a peptide C2 or C9, or sdAb CG4.

In an embodiment, the present disclosure provides compositions and methods for treatment of cancer using ADC, where the drug portion of the ADC is a maytansinoid or a maytansinoid derivative, analog or metabolite. The maytansinoid or derivative, analog, or metabolite thereof may be DM1, DM2, DM3, DM4, DM5, DM6, or DM7. The method comprises administering to an individual in need of treatment an ADC, where the drug portion is a maytansinoid (such as DM1 or DM4), and a PBA directed to the maytansinoid portion of the ADC. The ADC and the PBA may be administered in the same composition or in separate compositions as described elsewhere in this disclosure. An example of an ADC where the drug is maytansinoid is ado-trastuzumab emtansine (TDM1). When the drug portion of an ADC is a maytansinoid, an example of a PBA that can be used is sdAbs DF3A2, DT3B3, DT3H3, DF3A4, DF4B12, DT3B5, DT3B4, DF4C7, DF4B7, DF4D12, DF4D11, DF4B10, DF4A11, DF3A1, DF4C12, DMFH1, DMOH9, DMOF8, DMFH2, DMFF2, DMFB8, DMFA2, DMFA4, DMFA9, DMFC5, DMFD3, DMFD7, DMFE1, DMFE5, DMFE8, DMFF1, DMFF6, DMFG2, DMFG3, DMFG5, DMOA3, DMOA5, DMOA11, DMOB5, DMOB7, DMOC10, DMOD4, DMOE7, DMOF6, DMOG1, DMOG4, DMOH12, or combinations thereof. A method is also provided for the treatment of cancer (such as a solid tumor) comprising administering to an individual in need of treatment an ADC, wherein the drug is a maytansinoid (e.g., DM1, DM4) and an antibody which may be a sdAbs DF3A2, DT3B3, DT3H3, DF3A4, DF4B12, DT3B5, DT3B4, DF4C7, DF4B7, DF4D12, DF4D11, DF4B10, DF4A11, DF3A1, DF4C12, DMFH1, DMOH9, DMOF8, DMFH2, DMFF2, DMFB8, DMFA2, DMFA4, DMFA9, DMFC5, DMFD3, DMFD7, DMFE1, DMFE5, DMFE8, DMFF1, DMFF6, DMFG2, DMFG3, DMFG5, DMOA3, DMOA5, DMOA11, DMOB5, DMOB7, DMOC10, DMOD4, DMOE7, DMOF6, DMOG1, DMOG4, DMOH12, or combinations thereof.

In an embodiment, the present disclosure provides compositions and methods for treatment of cancer using ADC, where the drug portion of the ADC is an auristatin E (MMAE) or auristatin E derivative, analog, or metabolite. The method comprises administering to an individual in need of treatment an ADC, where the drug portion is auristatin E, and a PBA directed to auristatin E portion of the ADC. The ADC and the PBA may be administered in the same composition or in separate compositions as described elsewhere in this disclosure. An example of an ADC where the drug portion is auristatin E is brentuximab vedotin. Another example of an ADC where the drug portion is auristatin E is polatuzumab vedotin. When the drug portion of an ADC is auristatin E, an example of a PBA that can be used is IgM D9, sdAb MA3, MB2, and MC7. A method is also provided for the treatment of cancer (such as a solid tumor) comprising administering to an individual in need of treatment an ADC, wherein the drug is auristatin E and an antibody which may be a IgM D9, sdAb MA3, MB2, and MC7.

In an embodiment, the present disclosure provides compositions and methods for treatment of cancer using ADC, where the drug portion of the ADC is a pyrrolobenzodiazepine (PBD) or PBD derivative, analog or metabolite. The method comprises administering to an individual in need of treatment an ADC, where the drug portion is a PBD, and a PBA directed to PBD portion of the ADC. The ADC and the PBA may be administered in the same composition or in separate compositions as described elsewhere in this disclosure. An example of an ADC where the drug portion is PBD is camidanlumab tesirine. When the drug portion of an ADC is PBD, a suitable PBA can be identified by screening of single domain libraries, and specific clones can be isolated, sequenced, and tested for specificity.

In an aspect, this disclosure provides kits comprising an ADC and components for reducing non-target toxicity of the ADC. The kits may comprise in the same or different composition, i) ADC, and ii) an anti-payload antibody, wherein the anti-payload antibody is specific for the drug portion of the ADC. The ADC and the anti-payload antibody may be provided in a powdered, lyophilized form, along with reconstitution media, where the antibody and the ADC can be reconstituted prior to use. The kit may also optionally comprise instructions for administration of the compositions comprising the ADC, and the composition comprising the anti-payload antibody, which may be administered via different routes.

Some non-limiting examples are provided in the following paragraphs.

Example 1. A method for reducing non-target toxicity of an antibody-drug conjugate (ADC) comprising administering to an individual in need of treatment the ADC and a payload binding agent (PBA) which is directed to the drug portion of the ADC. In various examples, the drug portion is a cleaved payload from an ADC.

Example 1a. The method of Example 1, wherein the PBA is an antibody of a fragment or modification thereof, which is directed to the drug portion of the ADC (anti-drug antibody).

Example 1b. The method of Example 1, wherein PBA is a peptide.

Example 2. The method of Example 1, wherein the ADC and the PBA are administered in the same composition.

Example 3. The method of Example 1, wherein the ADC and the PBA are administered in different compositions.

Example 4. The method of Example 3, wherein the ADC and the PBA are administered via different routes.

Example 4a. The method of Example 4, wherein the ADC is administered by intraperitoneal route and the PBA is administered intravenous route.

Example 5. The method of Example 1, wherein the drug is camptothecin, calicheamicin, auristatin E, PBD or maytansinoid.

Example 6. The method of Example 1, wherein the $K_D$ of the PBA is less than or equal to 50 nM.

Example 6a. The method of Example 1, wherein the $K_D$ of the anti-drug antibody is less than or equal to 50 nM.

Example 7. The method of Example 6 or 6a, wherein the $K_D$ of the PBA (Example 6) or the anti-drug antibody (Example 6a) is less than 1 nM.

Example 8. The method of Example 7, wherein the $K_D$ of the PBA or the anti-drug antibody is from 10 pM to 100 pM.

Example 9. A composition comprising an ADC and a PBA, which is directed to the drug portion of the ADC.

Example 9a. The composition of Example 9, wherein the PBA is an antibody of a fragment or modification thereof, which is directed to the drug portion of the ADC (anti-drug antibody).

Example 10. A kit comprising: i) a composition comprising an ADC; ii) a composition comprising an anti-drug antibody which is specific for the drug in the ADC; iii) optionally, instructions for use including instructions for administration of i) and ii).

The invention is further demonstrated by way of the figures and data presented herein, whether provided in the detailed description or the figures.

EXAMPLE 1

This example describes the general methods used in this disclosure.

Single Domain Antibody Phage Display Library

Immunization and RNA Isolation

To establish a single domain antibody (sdAb) phage display library a llama provided by Capralogics (Hardwick, MA) was subcutaneously immunized with 300 μg of KLH-MMAF in incomplete Freund's adjuvant every three weeks for a total of four immunizations. Ten days after the fourth immunization, 600 mL of freshly harvested blood was used to isolate PBMCs. Circulating PBMCs were isolated from whole blood using Sepmate-50 conical tubes containing 15 mL of Lymphoprep density gradient medium. The cassette was filled with 20 mL of 1:1 diluted llama blood in 1× PBS/2% FBS and centrifuged 1200×g for 20 min at room temperature. After centrifugation, the thin white film above the red blood cells were carefully pipetted out using 3 mL sterile pipettes. The volume was brought up to 10 mL with 1× PBS/3% FBS. All fractions from each round of PBMC isolation were combined and centrifuged at 300×g for 8 minutes at room temperature to pellet the PBMCs. Pelleted cells were resuspended with TRIzol Reagent and pipetted several times to help lyse the cells and fragment DNA. The cell suspension was incubated on ice for 5 minutes to permit complete dissociation of nucleoprotein complexes. Separation of RNA from TRIzol suspension was completed by addition of chloroform. The chloroform-TRIzol solution was then vortexed for 30 s and incubated for 2-3 minutes. The solution was then centrifuged for 15 minutes at 12,000×g at 4° C. After centrifugation, the aqueous supernatant was transferred to a new tube for RNA precipitation by 0.5 mL of isopropanol. The solution was incubated for 10 minutes and centrifuged at 12,000×g for 10 min at 4° C. Supernatant was aspirated off and the RNA pellet was resuspended with 75% ethanol and centrifuged at 10,000×g for 5 minutes. The supernatant was discarded and the RNA pellet was washed once more with 75% ethanol. After centrifugation, the pellet was dried using nitrogen blanket. RNA pellet was resuspended in 50 μL of RNase-free water by pipetting up and down. The water was incubated on a heat block set at 60° C. for 10-15 minutes to ensure complete solubilization.

Reverse Transcription PCR and Amplification

RT-PCR was conducted using 2.5 μg of total RNA with the following volumes of reagents: (1 μL) 50 μM Oligo d(T)20 primer, (1 μL) 10 mM dNTP mix, diH$_2$O to 13 μL. The primer mixture was incubated at 65° C. for 5 min followed by incubation on ice for 1 min. The annealed RNA was then added to GoScript Reverse Transcriptase mixture (4 μL GoScript 5× Reaction Buffer, 1 μL GoScript Reverse Transcriptase, 1 μL 100 mM DTT) and incubated at 50-55° C. for 10 min followed by an inactivation period at 80° C. for 10 min. Llama heavy chains were amplified by PCR. PCR reaction solutions contained the following reagents and volumes: (25 μL) OneTaq 2× Master Mix, (1 μL) cDNA, (1 μL) 10 μM 5'-VH1/VH3/VH4 primers, (1 μL) 10 μM 3'-CH2 primer, (1 μL) DMSO, (21 μL) DNase/RNase free H$_2$O. PCR reactions were performed with a BioRad C1000 Touch Thermocycler using the following temperature program: initial phase of 94° C. for 2 min followed by 37 cycles of 94° C. for 30 s, 55° C. for 1 min, 68° C. for 1 min, followed by a final extension at 68° C. for 5 min. PCR products were then purified by DNA gel electrophoresis using a 1.2% agarose gel and E.Z.N.A gel extraction kit (Omega Bio-tek, Norcross, GA). Amplification of llama VHH DNA was conducted in triplicate with the following reaction set-up: (25 μL) OneTaq 2× Master Mix, (20 ng) VHH DNA, (1 μL) 10 μM 5'-VHH primers, (1 μL) 10 μM 3'-JH primer, (1 μL) DMSO, and DNase/RNase free H$_2$O up to 50 μL. Amplification was conducted using the temperature gradient: initial phase of 94° C. for 3 min, followed by 30 cycles of 94° C. for 30 s, 61° C. for 1 min, 68° C. for 1 min, and a final extension at 68° C. for 5 min. PCR products were then purified by DNA gel electrophoresis using a 1.2% agarose gel and E.Z.N.A gel extraction kit (Omega Bio-tek, Norcross, GA).

Phagemid Production and Transformation

Amplified PCR product (1 μg/replicate) and pComb3XSS phagemid vector (2 μg/replicate) were digested in triplicate with SfiI restriction enzyme according to the manufacturer's recommendation. Reactions were incubated at 50° C. for 16 h. Cut products were recovered through DNA gel electrophoresis using a 1% agarose gel. A test library was first developed by ligating digested DNA into the phagemid vector. Ligated vector was purified with an E.Z.N.A cycle pure kit. Electrocompetent cells were transformed by electroporation with 5 μL of DNA according to the following conditions: 1.0 mm cuvette, 10 μF, 600 Ohms, 1800 Volts, time constants 3.5 to 4.5 msec. Immediately after pulsating cells, 975 μL of Recovery Medium to was added to cells. Cell suspension was then transferred into a 3 mL tube and incubated at 250 rpm for 1 h at 37° C. Cell suspension was then serially diluted to 1:1000 on LB agar plates containing 100 μg/ml ampicillin and 2% (wt/v) glucose and grown overnight at 37° C. Electroporation efficiency was determined by counting the colonies and multiplying by the corresponding dilution factor.

sdAb Library Construction

For test library construction, approximately 10-20 clones were isolated, re-suspended in water, and incubated at 95° C. for 5 min, followed by centrifugation at 4° C. for 5 min. DNA within the supernatant was amplified as described previously using 5' and 3' sequencing primers. PCR products were purified, digested using 2.5 U of BstNI for 1 h at 60° C. DNA was loaded onto a 2.5% agarose gel for confirmation. Digested products were purified and sequenced.

For full library construction, sufficient amount of VHH DNA was ligated into pCom3XSS to yield a library of at least 10$^7$ individual transformants (i.e. 6-8 ligations, with each ligation containing 150 ng of digested VHH and 350 ng of digested phagemid). Several separate electroporations were carried out using 3 μL as described previously and 25 μL of TG1 cells. All electroporations were combined into a 50 mL conical tube. Transformed bacteria were serially diluted to 1:10000 on LB agar plates containing 100 μg/ml ampicillin and 2% (wt/v) glucose and grown overnight at 37° C. Library size was evaluated by colony counting. Fragmentation PCR and sequencing were conducted as described above. Remaining bacteria suspension was plated onto four 245 mm square LB agar dishes containing 100 μg/ml ampicillin and 2% (wt/v) glucose and grown overnight at 37° C. This process was repeated until the library size was ≥10$^7$, upon which the library was recovered by first scraping bacteria from the 245 mm dishes in 8 mL of LB medium and combined into a 50 mL conical. Collected cell suspension was mixed with sterile glycerol (20%, v/v). Cell library aliquots were stored in −80° C.

sdAb Phage Isolation

A thawed library aliquot was used to inoculate 60 mL of 2×YT medium supplemented with 100 μg/ml ampicillin and 2% (wt/v) glucose in a baffled 250 mL Erlenmeyer. Inoculated medium was grown at 37° C. until OD$_{600}$≈0.5. To rescue phage, 10 mL of broth was transferred to a 50 mL conical where 1 μL of CM13 helper phage was added and incubated for 1 h at 37° C. at 250 rpm. Infected cells were then isolated by centrifugation at 2,800×g for 10 min at RT. Cells were re-suspend in 50 ml of 2×YT supplemented with 100 μg/mL ampicillin and 50 μg/mL kanamycin into a baffled 250-ml Erlenmeyer flask and incubated overnight at 30° C. and 200 rpm. Bacterial culture was transferred to two 50-ml conical tubes and centrifuged for 15 min at 3,200×g and 4° C. to pellet cells. Supernatants were isolated into new 50 mL conicals, where 6 mL of 20% (wt/v) PEG6000/2.5 M NaCl solution was added, mixed by inversion, and chilled on ice for 30 min. Phage particles were pelleted by centrifugation for 10 min at 3,200×g and 4° C. Precipitated phage particles were re-suspended in 1 mL of ice-cold PBS, and transferred microcentrifuge tubes. Phage particle suspension was centrifuged for 90 s at 16,000×g and 4° C. in a microcentrifuge to pellet any residual bacteria. Phage particles from the supernatant were re-precipitated by adding 250 μl of ice-cold 20% (wt/v) PEG6000/2.5 M NaCl solution, mixed by inversion, and incubated on ice for 10 min. Phage particles were pelleted by centrifugation at 16,000 g and 4° C. for 20 min and re-suspended in 0.5 mL of ice-cold PBS. Remaining bacterial debris was removed by centrifugation for 90 s at 16,000 g and 4° C. The phage was then used to pan against ADC payload conjugates by ELISA.

Phage concentration was determined prior to panning via a titration method. Briefly, phage was serially diluted by factors of 10 in PBS. To a single well on a low-binding 96-well round-bottom culture plate, 10 μL of each dilution to a well with 90 μL of TG1 cells (pre-grown suspension). Plates were incubated for 15 min at 37° C. to infect TG1 cells. Approximately 5 μL of the infected TG1 cells from each dilution was transferred to solid selective medium (LB+100 μg/mL ampicillin+2% glucose) and grown overnight at 37° C. Phage concentration is determined by counting colonies on the highest diluted plate that showed growth.

sdAb Affinity Matured ELISA

Nunc Maxisorp 96-well plates were coated with 100 μL of 1 μg/mL antigen (i.e. BSA-MMAF, BSA-PBD, Tmab-Calicheamicin) solution in $Na_2HPO_4$, pH unadjusted, and incubated overnight at 4° C. Plates were washed three times with PBST (PBS+0.05% Tween 20) and blocked with MPBS (PBS+5% non-fat dry milk) at RT for 2 h. Following five washes with PBST, phage solutions of $10^{11}/100$ μL in MPBS were incubated for at RT for 2 h with agitation. Wells were then washed 10-times with PBST, incubated with PBST for 30 min at 4° C., and washed another 10-times with PBST. Bound phages were eluted with 100 μL of 100 mM glycine/HCl, pH 2.8 at RT for 10 min. Solutions were then neutralized with 10 μL of 1 M Tris-HCl, pH 9.8. Free payload at 1 ng/mL concentration was then incubated with eluate for 30 min at RT. After incubation, 50 μL of phage solution was incubated with a second antigen coated plate (i.e. Tmab-vc-MMAE, BSA-PBD, Tmab-Caliceamicin) and incubated at RT for 1 h. Supernatant was collected and used to infect 10 mL of TG1 cells in a 50 mL conical tube for 30 min at 37° C. Phage suspension was then serially diluted onto LB agar plates (100 μg/mL ampicillin and 2% (wt/vol) glucose). Remaining phage was cultured overnight at 37° C. in 25 mL of LB supplemented with 100 μg/mL ampicillin and 2% (wt/vol) glucose. Phage was rescued as described previously and used for two further pans. For the second and third pans, eluted phage was incubated with 0.1 and 0.01 ng/mL of free drug, respectively.

Screening of sdAb Binders

Phage infected TG1 cells were grown overnight, serially diluted in LB, spread over individual culture plates containing selective medium (LB agar+100 μg/mL ampicillin+2% (wt/v) glucose), and incubated overnight at 37° C. A master plate was generated by inoculating a single colony into wells of a 96-well round-bottom culture plate filled with 100 of 2×TY supplemented with 100 μg/mL ampicillin, 2% (wt/vol) glucose and 10% (vol/vol) glycerol, and grown overnight at 37° C. These wells were then used to inoculate wells of 96-deepwell plates containing 1 mL of 2×TY medium (100 μg/mL ampicillin+0.1% (wt/v) glucose per well). Plates were incubated them for 3 h at 37° C. and 250 rpm until $OD_{600}≈0.5$. Nanobody expression was induced with 4 μL of 0.5 M IPTG per well (final concentration of 2 mM) and incubated for an additional 15-24 h at 37° C. and 250 rpm. Nunc Maxisorp 96-well plates were coated as described previously. Plates were washed three times with PBST and blocked with MPBS for 2 h at RT. Plates were then washed three times with PBST and incubated with 1:1 diluted supernatant from induced bacteria at RT for 2 h, with or without pre-incubation with free drug at 1 μg/mL. Plates were then washed three times with PBST, where bound phage was detected using an anti-HA tag HRP-conjugated Ab diluted 1:1000 in PBST. Following incubated and five washed with PBST, 100 μL of 1-Step Turbo TMB-ELISA solution was added to each well and incubated for 30 minutes. The reaction was quenched by adding 100 μL of Stop solution to each well and absorbance was measured at 450 nm.

Sanger Sequencing was carried out by the DNA Sequencing Laboratory at Roswell Park Comprehensive Cancer Center to obtain DNA sequences of positive binding sdAbs. Amino sequences translated using IgBlast database are provided in Table I. Aligned sequences have also been provided as compared to MC7. Highlighting in black represents 100% sequence homology across all queries, grey represents sequences that are different, but contain similar characteristics/properties as those in the same position, and white highlight means divergence of the sequence.

Development of Mouse Hybridomas Secreting Anti-Drug Antibodies

Immunogens were synthesized using the linker chemistry described in FIG. 1. Briefly, keyhole limpet hemocyanin, bovine serum albumin, or trastuzumab were used to generate hapten conjugates. Monomethyl auristatin F (MMAF) was linked via an EDC linker and calicheamicin was linked via either SMCC or SMPB following protein reduction by TCEP. Approximately 50 μg of immunogen emulsified in Freund's incomplete adjuvant was used for a single animal immunization. Five female Balb/c mice were injected with 200 μL of emulsion subcutaneously and given a booster every 3 weeks. The mouse with the highest level of anti-drug antibody in plasma was selected for hybridoma development. Briefly, $5×10^6$ SP 2/0-Ag 14 myeloma cells were transferred to RPMI1640, containing 20% fetal bovine serum (FBS), and 1× oxaloacetate pyruvate insulin media supplement (OPI). Harvested spleen tissue was teased apart with an 18-gauge needle, where disrupted tissue was then mixed with 10 mL of warmed RPMI1640 media. After centrifuging the spleen cell suspension and the myeloma cell suspension at 500×g for 5 minutes, both pellets were resuspended in warmed RPMI1640 media. The resuspended cells were then combined and centrifuged at 800×g for 5 minutes. Exactly 1 mL of 50% polyethylene glycol was added dropwise to the pellet and then gently mixed, before the addition of 10 mL of pre-warmed RPMI1640, which was slowly added and gently mixed over the course of 3 minutes. The mixture was then centrifuged and the pellet was resuspended with 200 mL RPMI1640 media containing 20% FBS, 1× OPI, HAT (hypoxanthine, aminopterin, and thymidine), and 5 mg/L gentamicin. The media was then dispensed (175 μL/well) into 96-well plates. 8C2 was previously established (REFs).

Hybridoma Screening and Subcloning

ELISA plates were coated with 250 μL of 4 μg/mL of BSA-MMAF or trastuzmab-calicheamicin conjugate at 4° C. overnight. The plates were washed three times with 0.05% Tween in 20 mM $Na_2HPO_4$, and then three times with diH2O. Samples (100 μL of either plasma diluted 100-fold in pH 7.4 1× PBS, or 100 μL of cell culture media) were incubated for 2 hours at room temperature. Plates were washed as described previously and then incubated for 1 hour with PB-Tween (20 mM $Na_2HPO_4$, 0.05% Tween) containing 0.2% v/v alkaline phosphatase (AP) conjugated to murine specific goat secondary IgG, and 3% v/v bovine serum albumin (BSA). After the final plate wash, 200 μL of freshly prepared 4 mg/mL p-nitro phenyl phosphate (PNPP) in pH 9.8 diethanolamine buffer was added to each well. The change in absorbance with time (dA/dt) at 405 nm was assessed using a Spectra Max 340 plate reader.

Individual hybridoma colonies identified by ELISA as positive for anti-drug antibodies were then cloned by the method of single cell picking. Briefly, a small portion of cells from each well containing uncloned anti-drug antibodies, positive hybridoma cells were diluted and transferred to a sterile 96-well plate lid. Single cells were identified under 40× magnification and transferred to individual wells of a 96-well plate (containing 175 μL of fresh RPMI1640 cell culture media, with 20% FBS, 1×HT, and 1× OPI). Individual cells were allowed to divide until colonies became visible (10-14 days), before testing cell culture supernatant for anti-drug antibody activity. This cloning process was then repeated to ensure monoclonality. Antibody isotyping was determined using Pierce Rapid Antibody Isotyping Kits—Mouse.

Cell Cytotoxicity

Log-phase MOLM-14, Ramos (RA 1), HT-29, LS174T, or NCI-N87 cells were seeded in 96-well microtiter plates at a density of 20,000 cells/well, 20,000 cells/well, 5,000 cells/well, 5,000 cells/well, and 10,000 cells/well, respectively, in 100 µL of culture medium. HT-29, LS174T, and NCI-N87 cells were allowed to adhere for 24 h before cell culture media was aspirated and replaced with 100 µL of fresh media containing a range of treatment for, 48 (LS174T), 96 (NCI-N87), or 120 (HT-29) h. MOLM-14 and Ramos cells were re-suspended with treatment solutions, where 100 µL of cell-treatment suspension was aliquoted into wells of a 96-well plate for 24 h. Treatment solutions consisted of calicheamicin, MMAE, topotecan, or SN38 with or without immunized animal plasma, purified anti-drug antibody, or antibody-drug conjugate (ADC) with or without plasma or anti-drug antibody. For MOLM-14 and Ramos cells, 25 µL of MTT solution (5 mg/mL in pH 7.4 1× PBS) was added directly to wells following treatment incubation. For adherent cells, treatment media was aspirated from wells and cells were washed three times with 100 µL of fresh media. Following the final wash, 100 µL of complete media and 25 µL of MTT solution were added to each well. Cells were incubated for 4 h in order to allow cells to reduce MTT to formazan dye. Once MTT was reduced, 100 µL of 10% SDS prepared in 0.01 M HCl was added to each well and incubated overnight to solubilize the formazan crystals. Formazan dye was measured at 570 nm and normalized by cell debris at 690 nm.

EXAMPLE 2

This example describes antibodies or fragments against camptothecin derivatives.

8C2 Fab and scFv Expression and Purification

8C2 is an antibody directed against topotecan, a camptothecin. IgG was produced in 1 L spinner flasks containing serum free media. One week after inoculation with 8C2 hybridoma cells, 750 mL of media was collected and replaced with 750 mL of fresh media. The collected media was centrifuged at 10,000×g for 10 min at 4° C. and then filtered using a 0.22 µm bottle-top filter. This process was repeated every three days until 2 L of media was harvested. Centrifuged and filtered media was then applied to a protein G column using a BioRad NGC Liquid Chromatography System. Protein G bound 8C2 was eluted using 100 mM glycine, pH 2.8. Collected fractions were immediately neutralized with 1 M Tris-HCl, pH 9.0 and then dialyzed into 20 mM $Na_2HPO_4$, 10 mM EDTA, pH 7.0. Immobilized papain resin was equilibrated in 20 mM $Na_2HPO_4$, 20 mM cysteine-HCl, pH 7.0 prior to mAb digestion. Approximately 10 mg of 8C2 was prepared in 20 mM $Na_2HPO_4$, 20 mM cysteine-HCl, pH 7.0. Immobilized papain slurry was mixed with 8C2 IgG and incubated at 37° C. overnight with constant mixing. The digestion solution was centrifuged at 1000×g for 5 min to pellet the immobilized papain resin. Supernatant was collected and diluted 20× in loading buffer (10 mM $Na_2HPO_4$, 5 mg/L $CaCl_2$, pH 6.5). 8C2 Fab was then purified using a Bio-Scale Mini CHT Ceramic Hydroxyapatite Multimodal Chromatography Type I Cartridge, 40 µm. Briefly, the CHT resin was pre-equilibrated with 3 column volumes (CV) of elution buffer (500 mM $Na_2HPO_4$, 5 mg/L $CaCl_2$, pH 6.5) and then equilibrated with 10 CV of loading buffer at a rate of 2.0 mL/min. Sample was then loaded onto the column at a rate of 2.0 mL/min followed by 5 CV of loading buffer. The elution process consisted of four gradients at a rate of 2.0 mL/min: 1) 2 CV of 0-10% elution buffer, 2) 8 CV of 10-18% elution buffer, 3) 4 CV of 18-25% elution buffer, and 4) 4 CV of 25-100% elution buffer. Fractions were collected during the elution process based on an $A_{280} \geq 0.05$ (FIG. 2). Purity was assessed by SDS-PAGE analysis.

8C2 amino acid sequence was converted to DNA and codon optimized for *E. coli* expression. DNA was synthesized by GeneArt in the VH-VL orientation with a $(G_4S)_4$ linker. The 8C2 construct was ligated into the pET22b(+) expression vector, using NdeI and XhoI restriction sites, which contains a gene for ampicillin resistance, Lac operon for IPTG induction, and contains a C-terminal hexahistidine tag for IMAC purification. The pET22b plasmid containing 8C2 scFv was transfected into *E. coli* BL21(DE3). To express the construct a glycerol stock containing transfected cells was struck onto a LB agar plate containing 100 µg/mL of ampicillin and incubated at 37° C. for 18 h. Using a sterile pipet tip, a single colony was used to inoculate a 10 mL starter culture of LB media, which was grown overnight at 37° C. The starter culture was then used to inoculate a 2 L culture of LB and grown to an optical density of 0.6-0.8. Once the proper OD was reached, the culture was induced with 1 mM IPTG and incubated for 20 h at 20° C. After expression, cells were centrifuged at 15,000×g for 10 minutes, excess media was decanted and the pelleted cells were placed at −80° C. for a minimum of 1 h. For purification, cells were lysed using a triton X-100 based buffer containing lysozyme and DNase. Cell lysate suspension was then centrifuged at 15,000×g for 20 minutes. The cell pellet, containing 8C2 scFv inclusion bodies, was denatured in an 8 M urea buffer, pH 10. Inclusion bodies were applied to a HisPur™ Ni-NTA Spin Column, where refolding was achieved on-column using a urea gradient. 8C2 scFv was eluted using a 0.5 M imidazole buffer. Eluted scFv was dialyzed twice against 2 L of PBS at 4° C. for a minimum of 12 hours to remove excess imidazole.

```
8C2 scFv amino acid sequence:
                                        (SEQ ID NO: 3)
EVQLQQSGAELVKPGASVKLSCTASGFNIKDTYIHWVKQRPEQGLEWIG

MIDLANDNTKYDPKFQGKATIITDTSSNKAYLQVSSLTSEDTAVYYCAT

WGAIITLGGWGQGTLVTVSAAKGGGGSGGGGSGGGGSGGGGSDIQMTQS

PASLSASVGETVTITCRASGNIHNSLAWYQQIKGRSPQLLVYNAKTLAD

GVPSRFSGSGSGTQYSLKINSLHPEDFGSYYCQHFWSTPFTFGSGTKLE

IKRENLYFQG
```

8C2 Fab amino acid sequence: Signal peptide sequence is italicized, complementarity determining region is bolded, variable region is underlined and the remaining denotes constant region.

```
Heavy Chain:
                                        (SEQ ID NO: 4)
MKCSWVIFFLMAVVTGVNSEEVQLQQSGAELVKPGASVKLSCTASGFNI

KDTYIHWVKQRPEQGLEWIGMIDLANDNTKYDPKFQGKATIITDTSSNK

AYLQVSSLTSEDTAVYYCATWGAIITLGGWGQGTLVTVSAAKTTPPSVY
```

-continued

```
PLAPGSAAQTNSMVTLGCLVKGYFPEPVTVTWNSGSLSSGVHTFPAVLQ

SDLYTLSSSVTVPSSTWPSETVTCNVAN

Light Chain
                                          (SEQ ID NO: 5)
MSVLTQVLALLLLWLTGARCDIQMTQSPASLSASVGETVTITCRASGNI

HNSLAWYQQIKGRSPQLLVYNAKTLADGVPSRFSGSGSGTQYSLKINSL

HPEDFGSYYCQHFWSTPFTFGSGTKLEIKRADAAPTVSIFPPSSEQLTS

GGASVVCFLNNFYPKDINVKWKIDGSEERQNGVLNSWTDQDSKDSTYSM

SSTLTLTKD
```

In embodiments, the disclosure provides a heavy chain sequence which comprises the CDRs shown for SEQ ID NO:4, and a light chain sequence which comprises the CDRs shown for SEQ ID NO:5.

Competitive ELISA

A competitive ELISA was employed to determine the affinity of intact 8C2 mAb for SN38 and topotecan. A BSA-topotecan conjugate was synthesized and immobilized as previously described (Shah et al., Int J Pharm. 2014; 465(1-2):228-238. doi:10.1016/j.ijpharm.2014.01.038) 8C2 concentration was held constant at 10 nM with increasing concentrations of topotecan or SN38. 8C2 drug samples were incubated for 2 hours at room temperature with agitation. Following incubation, wells were washed three times with 250 µL of PBS-T and three times with dH2O. Wells were then incubated with a 1:500 dilution anti-mouse AP conjugate secondary in PBS-T with 3% BSA for 1 h. After washing, 250 µL of 4 mg/ml PNPP in diethanolamine buffer pH 9.8 with absorbance being read at 405 nm. The change in absorbance over time data was fit to a four-parameter function in GraphPad Prism 7. The results indicate that 8C2 has a similar affinity for SN38 as its native antigen topotecan, which was previously characterized to have a 0.95 nM affinity using surface plasmon resonance.

Trastuzumab Deruxtecan Development

Trastuzumab at a concentration of 5 mg/ml was reduced with an 8× molar excess of TCEP for 2 hours at 37° C. Following reduction, deruxtecan dissolved in DMSO was added at 16× molar excess for 2 hours at room temperature. Trastuzumab deruxetecan was passed over a PD-10 column to remove free deruxtecan and unreacted TCEP. The drug antibody ratio was assessed through absorbance readings at 280 and 370 nm.

Cell Cytotoxicity with Exatecan and Trastuzumab Deruxtecan

100 µL cell culture media containing 5000 cells of the gastric adenocarcinoma cell line NCI-N87(ATCC® CRL-5822™) was allowed to adhere to a 96 well plate for 24 hours. Exatecan mesylate (DX8951f) or Trastuzumab deruxtecan (DS-8201a) dilutions with and without 8C2 mAb/Fab in 100 µL of RPMI was added to each well in replicates of 3. Cells were incubated with the drug mixture for 24 hours at 37° C., 5% CO2. After incubation drug containing cell culture media was aspirated and 250 µL of fresh RPMI was added, allowing cells to grow for another 4 days. Then cell culture media was aspirated and 125 µL of RPMI with a final concentration of 1 mg/ml MTT was added followed by a four-hour incubation. MTT crystals were dissolved in 0.01 M HCL/10% SDS overnight at 37° C. followed by absorbance reading at 570 nm (corrected to 640 nm).

sdAb Affinity Matured ELISA

Nunc Maxisorp 96-well plates were coated with either 100 µL of 1 µg/mL Trastuzumab deruxtecan or Trastuzumab solution in PBS pH 7.4 and incubated overnight at 4° C. Plates were washed three times with PBST (PBS+0.05% Tween 20) and blocked with MPBS (PBS+2% non-fat dry milk) at RT for 2 h. Following five washes with PBST, phage solutions of $10^{11}/100$ µL in MPBS were incubated with Trastuzumab coated wells at RT for 1 h with agitation. Phage solutions were then aspirated out and added into Trastuzumab deruxtecan coated wells, incubated at RT for 2 h with agitation. Wells were washed and tapped dry on clean paper towels 5, 10, 15 and times with PBST for the $1^{st}$, $2^{nd}$, $3^{rd}$ and $4^{th}$ panning. Bound phages were eluted with either 100 µL of freshly prepared 1 mg/mL Trypsin at RT for 30 min for all four panning processes, or with decreasing concentration (1000, 100, 10 and 1 nM) of exatecan solution in PBST. Phage eluted with Trypsin were then neutralized with 5 µL of 4 mg/mL ABESF per 100 µL of Trypsin. 10 µL solutions from two eluted phage libraries were saved for output titration. Remaining phages eluted with different solutions were collected and used to infect 3 mL of TG1 cells per 300 µL of eluted solutions for 30 min at 37° C. without shaking. 5 mL of pre-warmed 2×YT media containing 200 µg Ampicillin was added to the tube containing the infected cells and incubated for 1 h at 37° C. 250 rpm. Another 500 µg of Ampicillin was then added and incubated for another 1 h at 37° C. 250 rpm. After that 20 µL of CM13 helper phage was added and incubated for 1 h. Last, 8 mL TG1 cells were transferred into a 250 mL flask and supplied with 42 mL of 2×YT media containing 4.3 mg Ampicillin and 250 uL of stock Kanamycin. The infected TG1 cells were allowed to grow overnight at 30° C. 200 rpm.

Screening of sdAb Binders

Phage infected TG1 cells were grown overnight, serially diluted in 2×YT media, spread over individual culture plates containing selective medium (LB agar+100 µg/mL ampicillin+2% (wt/v) glucose), and incubated overnight at 37° C. A master plate was generated by inoculating a single colony into wells of a 96-well round-bottom culture plate filled with 125 µL of 2×TY supplemented with 100 µg/mL ampicillin, 2% (wt/vol) glucose and 10% (vol/vol) glycerol, and grown overnight at 37° C. These wells were then used to inoculate wells of 96-deep well plates containing 1 mL of 2×TY medium (100 µg/mL ampicillin+0.1% (wt/v) glucose per well). Plates were incubated for 3 h at 37° C. and 250 rpm until OD$_{600}$ reached 0.5. 1 uL of CM13 helper phages were added into each well and incubated at for 1 h at 37° C. 1 uL of stock Kanamycin were then added into each well and incubated overnight at 30° C. 200 rpm.

Nunc Maxisorp 96-well plates were coated as described previously. Plates were washed three times with PBST and blocked with MPBS for 2 h at RT. Plates were then washed three times with PBST and incubated with 1:4 diluted phage media from deep well with or without pre-incubation with exatecan (1 and 10 µM for 30 min) at RT for 2 h. Plates were then washed three times with PBST, where bound phage was detected using an anti-HA tag HRP-conjugated Ab diluted 1:1000 in PBST. Following incubated and five washed with PBST, 100 µL of 1-Step Turbo TMB-ELISA solution was added to each well and incubated for 30 minutes. The reaction was quenched by adding 100 µL of Stop solution to each well and absorbance was measured at 450 nm. Sanger Sequencing was carried out by the DNA Sequencing Laboratory at Roswell Park Comprehensive Cancer Center to obtain DNA sequences of positive binding sdAbs.

Results

Evaluation of SN38 Antagonists

Figure 3:
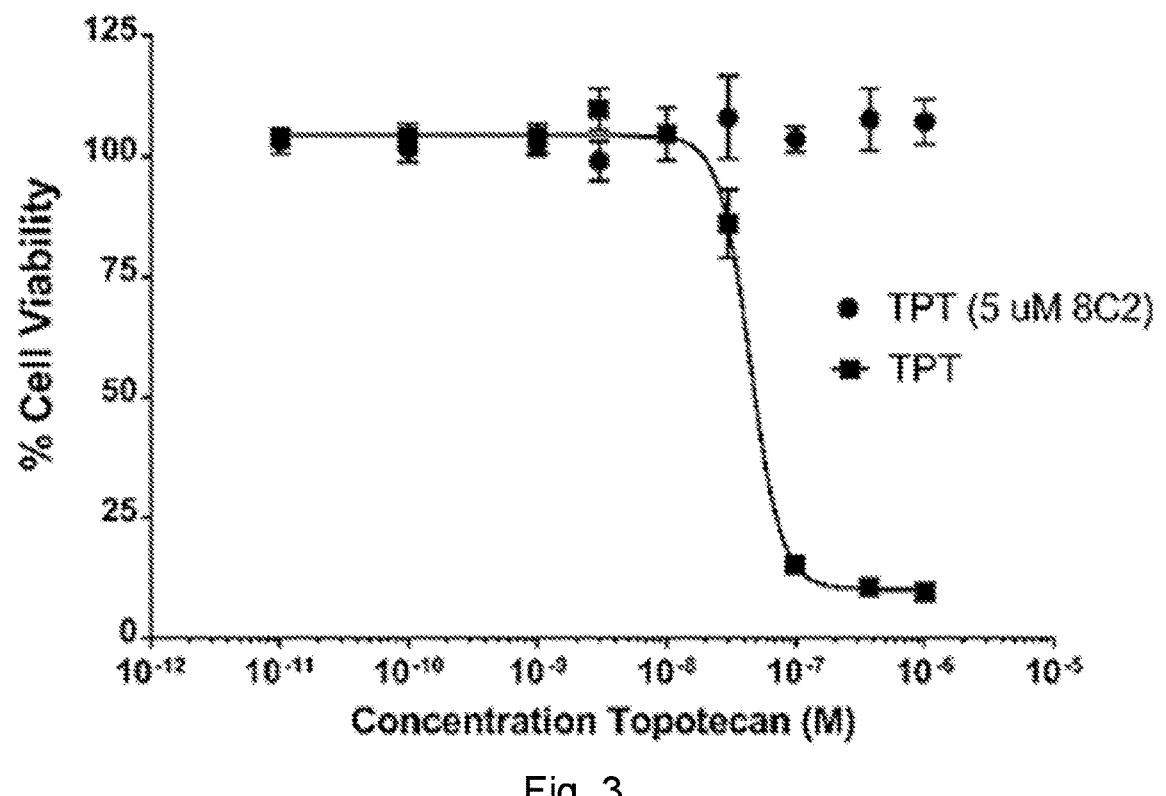
FIG. 3. Competitive Cell Cytotoxicity assay with HT-29 cells. 8C2 mAb prevents topotecan cytotoxicity of HT-29 cells up to 1.0 µM of topotecan.
Figure 4:
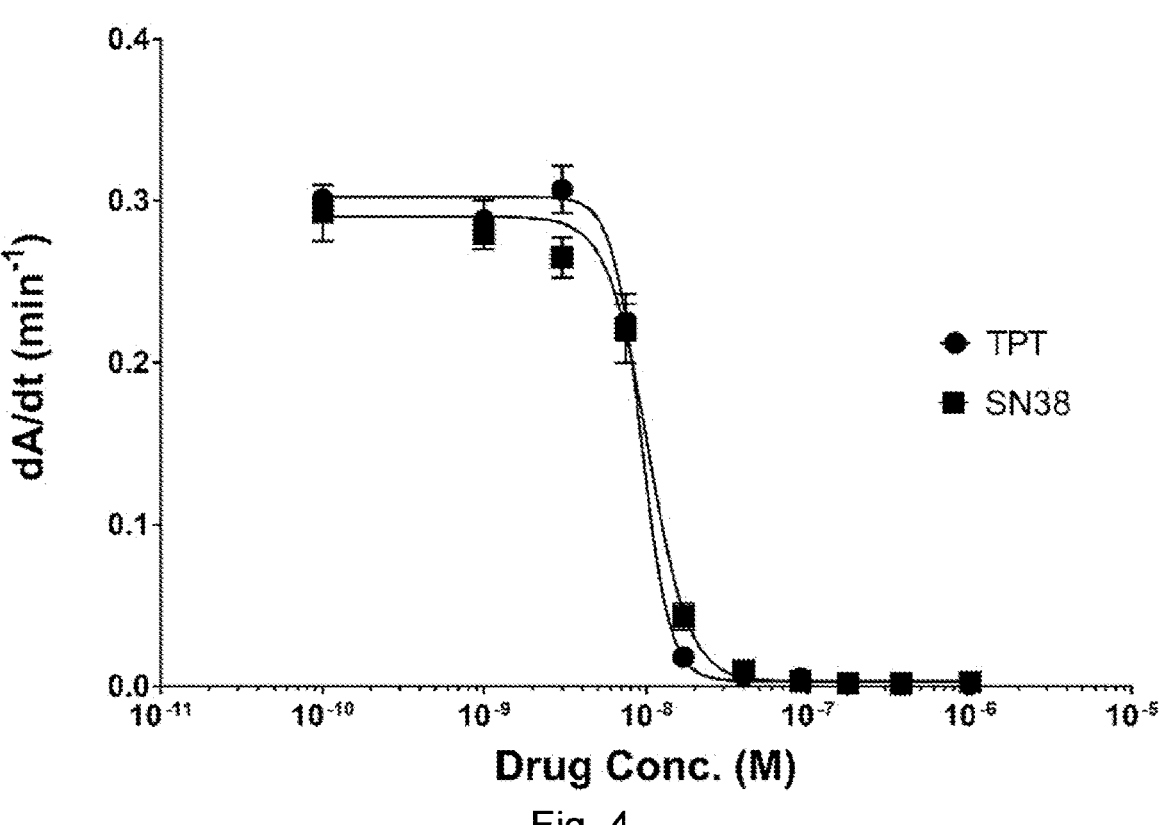
FIG. 4. Competitive ELISA 8C2 with TPT and SN38. The results of the competitive ELISA of SN38 and topotecan vs. intact 8C2 indicates a similar affinity of 8C2 towards both camptothecin derivatives. The IC50 was 9.3 nM for topotecan and 10.29 nM for SN38.

Previously, we have established an anti-drug antibody against topotecan, named 8C2 [PMID 24508555 or 24368689]. This antibody has demonstrated high affinity for topotecan with inhibition of topotecan cytotoxicity on HT-29 cells up to 1.0 µM (FIG. 3). Although 8C2 was developed to antagonize topotecan, we determined if it also binds to another camptothecin currently being employed as an antibody-drug conjugate payload, SN38. 8C2 IgG binding to SN38 was evaluated using a competitive ELISA and compared to topotecan. 8C2 demonstrated a similar affinity for topotecan and SN38, with $IC_{50}$ values of 9.3 nM for topotecan and 10.29 nM for SN38 (FIG. 4). Antagonism of SN38 by 8C2 mAb in vitro was evaluated using HT-29 cells and an MTT cell viability assay. The $IC_{50}$ of SN38 on HT-29 cells was 8 nM in absence of 8C2; however, in presence of 8C2, SN38 toxicity was abolished up to 1.0 µM (FIG. 6 top). Although intact 8C2 abolished SN38 cytotoxicity, intact IgG is not an optimal construct for enhancing ADC selectivity as intact IgG may result in pharmacokinetic limitations when bound to SN38 antibody-drug conjugates. Considering this, two 8C2 fragments were produced: 1) Fab & 2) scFv. 8C2 Fab was generated via papain digestion as described in methods above. Hydroxyapatite chromatography was employed to separate Fab from Fc fragments and intact IgG (FIG. 2A). 8C2 Fab purity and integrity was assessed by examining a single band at 25 kDa under reducing conditions and a primary band at 50 kDa under non-reducing conditions (FIG. 2B). The ability of Fab fragment to prevent cytotoxicity of SN38 in vitro was assessed using HT-29 cells. Consistent with mAb, 500 nM of Fab fragment prevented the cytotoxicity of SN38 on HT-29 cells, shifting the $IC_{50}$ by >30-fold (FIG. 6 bottom).

Figure 5:
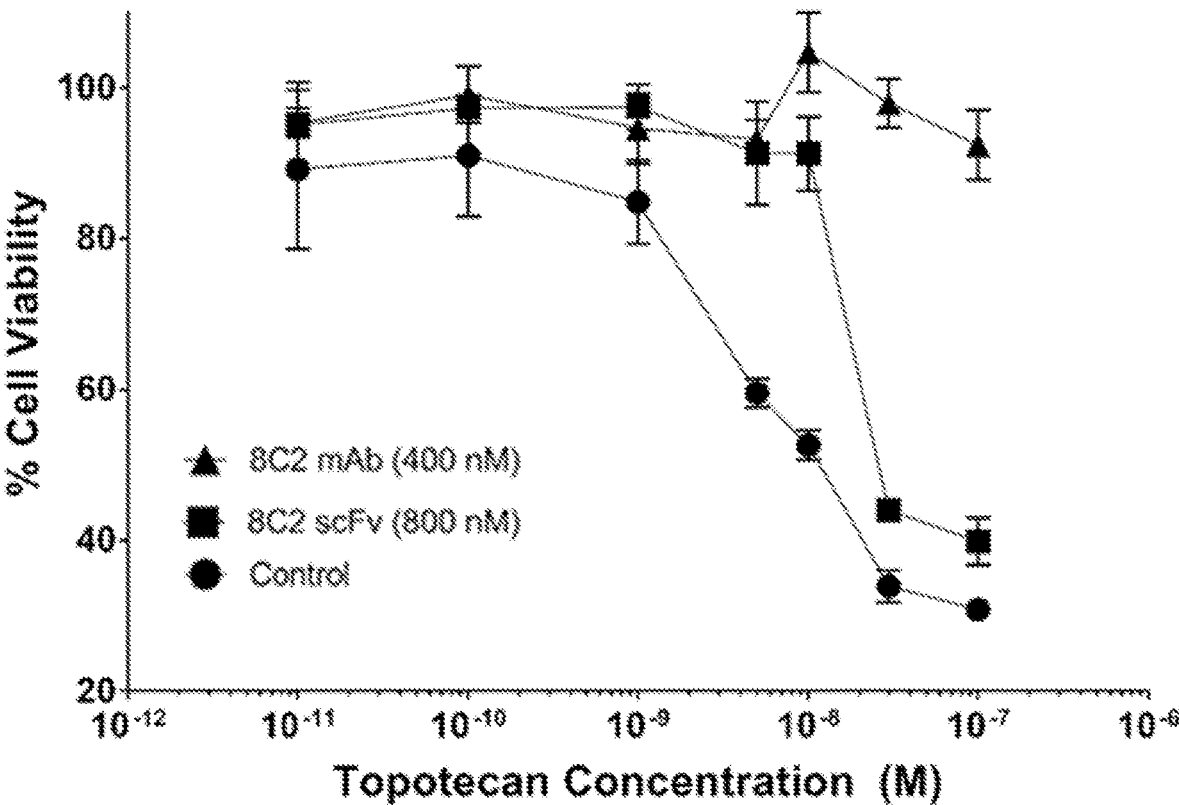
FIG. 5. Competitive Cell Cytotoxicity Assay with Topotecan and 8C2 mAb/scFv. LS174T cells were used for preliminary investigation of the effect of 8C2 mAb and scFv on topotecan cytotoxicity. Significant cell death was observed at 2.5 nM topotecan in the absence of 8C2 or 8C2 scFv. In the presence of the anti-camptothecin mAb and scFv, the concentration v. cytotoxicity relationship for topotecan was right-shifted, indicating inhibition of topotecan-induced cytotoxicity.
Figure 7:
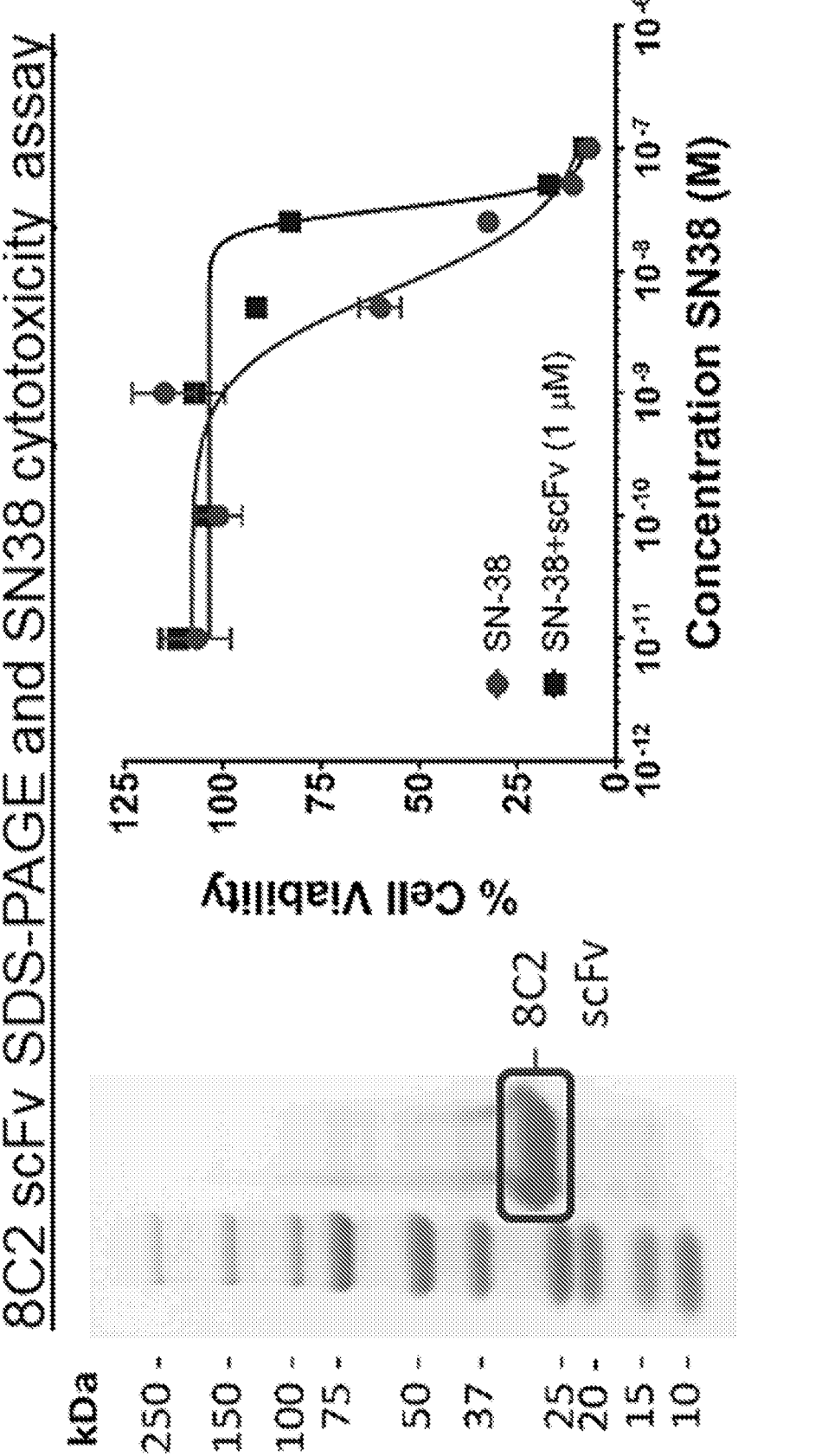
FIG. 7. Purification and cytotoxicity competition of 8C2 scFv. 8C2 scFv was expressed in *E. coli* BL21(DE3), purified through inclusion bodies, and refolded. HT-29 cells were seeded in a 96 well microtiter plate and treated with a 100 μL of SN38 solutions with or without 8C2 scFv. Cell cytotoxicity of SN38 decreased with incubation of 8C2 scFv by 4.6-fold.
Figure 8:
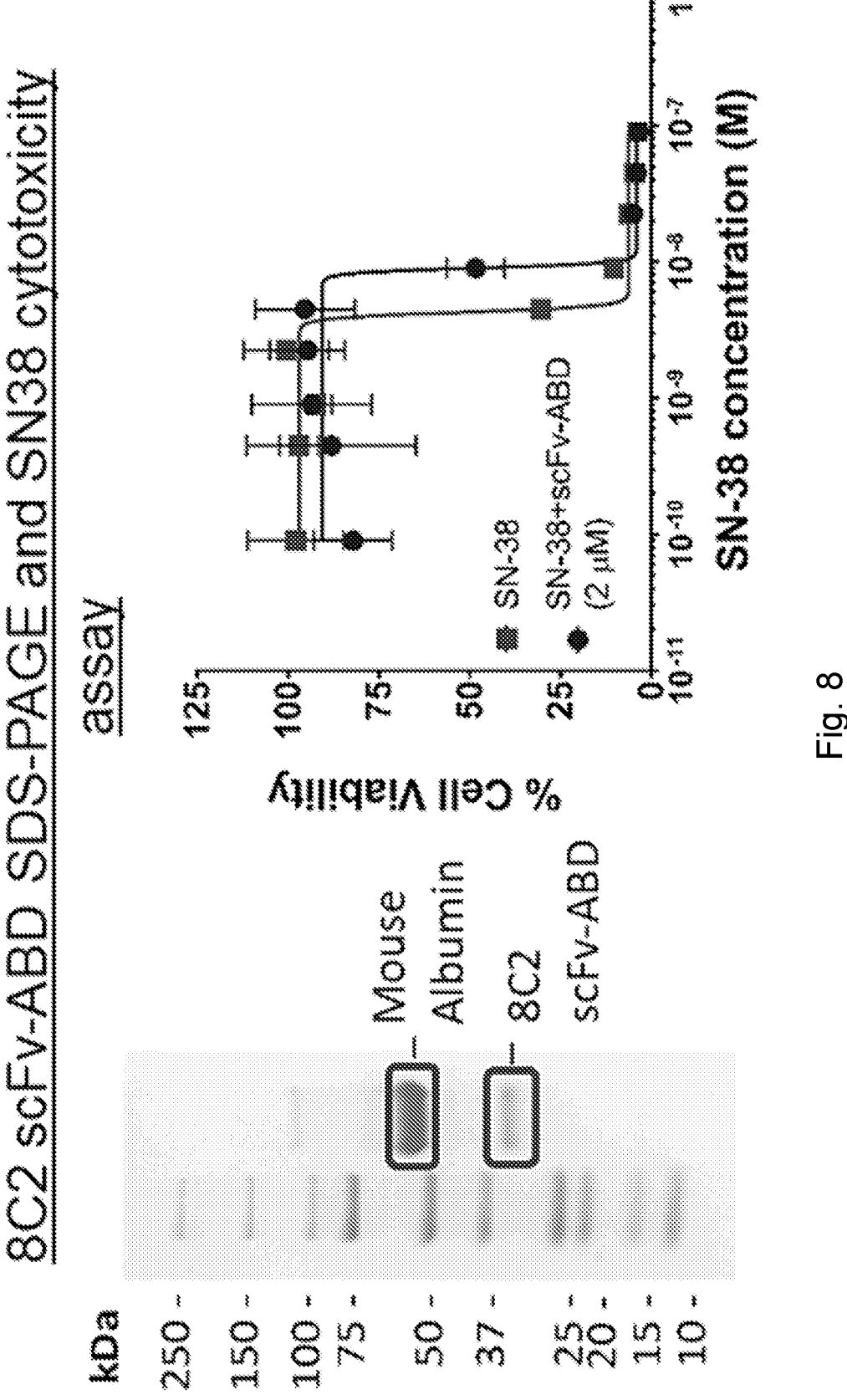
FIG. 8. Purification and cytotoxicity competition of 8C2 scFv containing an albumin binding domain (ABD). 8C2 scFv-ABD was expressed in *E. coli* BL21(DE3), purified through inclusion bodies, and refolded. HT-29 cells were seeded in a 96 well microtiter plate and treated with a 100 μL of SN38 solutions with or without 8C2 scFv-ABD. Cell cytotoxicity of SN38 decreased with incubation of 8C2 scFv by 2.1-fold.
Figure 9:
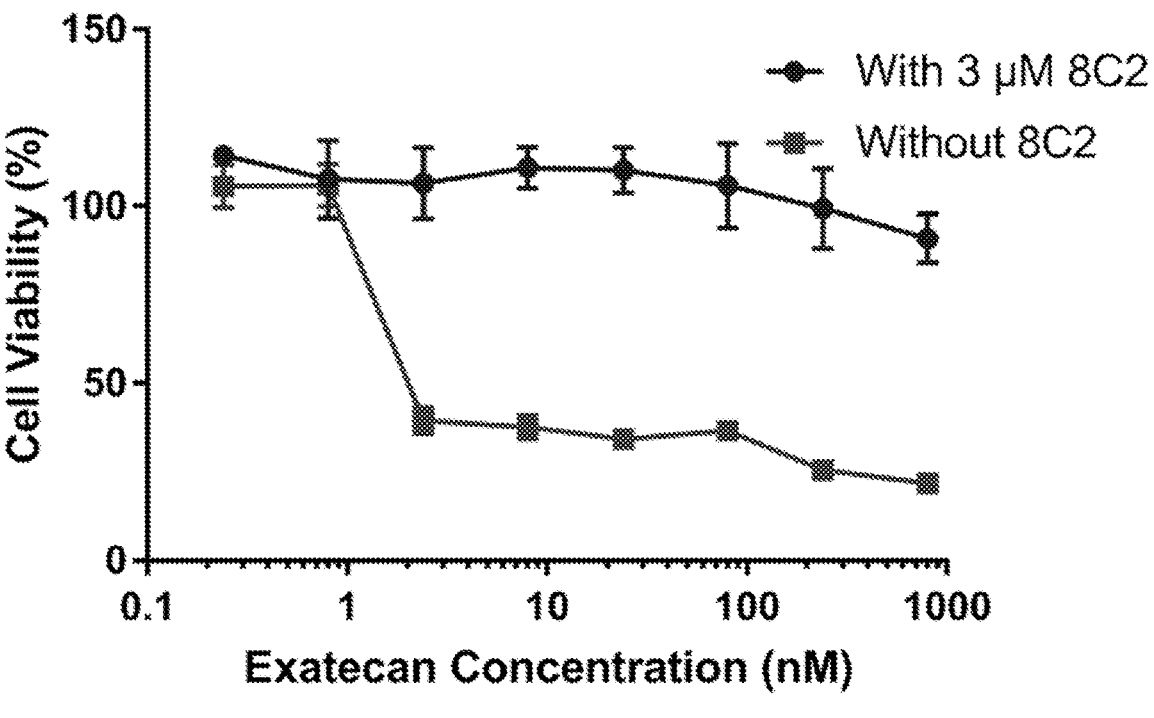
FIG. 9. Exatecan Competitive Cell Cytotoxicity assay with NCI-N87 cells. 8C2 mAb prevents exatecan cytotoxicity up to 1.0 μM.
Figure 10:
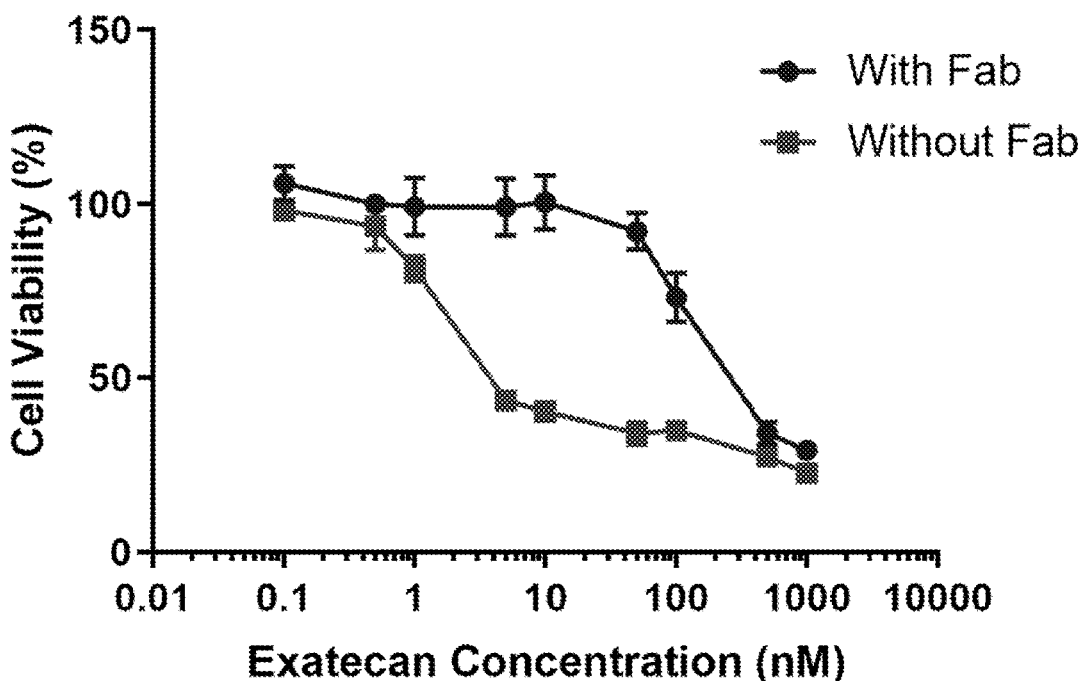
FIG. 10. Exatecan Competitive Cell Cytotoxicity assay with NCI-N87 cells. 8C2 Fab increased the IC50 for exatecan from 2.1 nM to 128.2 nM.

An anti-topotecan/SN38 single-chain Fv was generated using E. coli BL21(DE3) cells and purified from inclusion bodies (FIG. 7). Based on SDS-PAGE analysis, 8C2 scFv was produced with good purity. Initially, the ability of 8C2 scFv to antagonize topotecan (the molecule used to generate 8C2 mAb) was evaluated using a cell viability assay. Based on this work, scFv increased the viability of LS174T cells in response to topotecan treatment (FIG. 5). Next, viability of HT-29 cells was assessed in response to SN38 with and without 8C2 scFv. The cytotoxicity of SN38 was inhibited by 4.6-fold by 8C2 scFv, as described in FIG. 7. Although there was a shift in cytotoxicity, 8C2 scFv experienced significant instability in storage buffer and precipitated at 4° C. and −80° C. It is well established scFvs exhibit a short half-life in vivo, thus, a second scFv was produced with an albumin binding domain tethered to the C-terminus in order to enhance the systemic half-life of the construct (FIG. 8). 8C2 scFv-ABD was expressed in E. coli BL21(DE3) and purified from inclusion bodies in a similar manner to 8C2 scFv. In an attempt to increase stability, mouse serum albumin (MSA) was spiked into the refolded product. MSA-scFv product was then incubated with HT-29 cells exposed to SN38. Based on MTT analysis, the 8C2-ABD construct reduced cytotoxicity of SN38 by 2.1-fold. Based on the presented results, 8C2 Fab fragments are a suitable candidate for enhancing SN38 ADCs selectivity considering Fab stability, yield, and shift in free SN38 toxicity.

Figure 11:
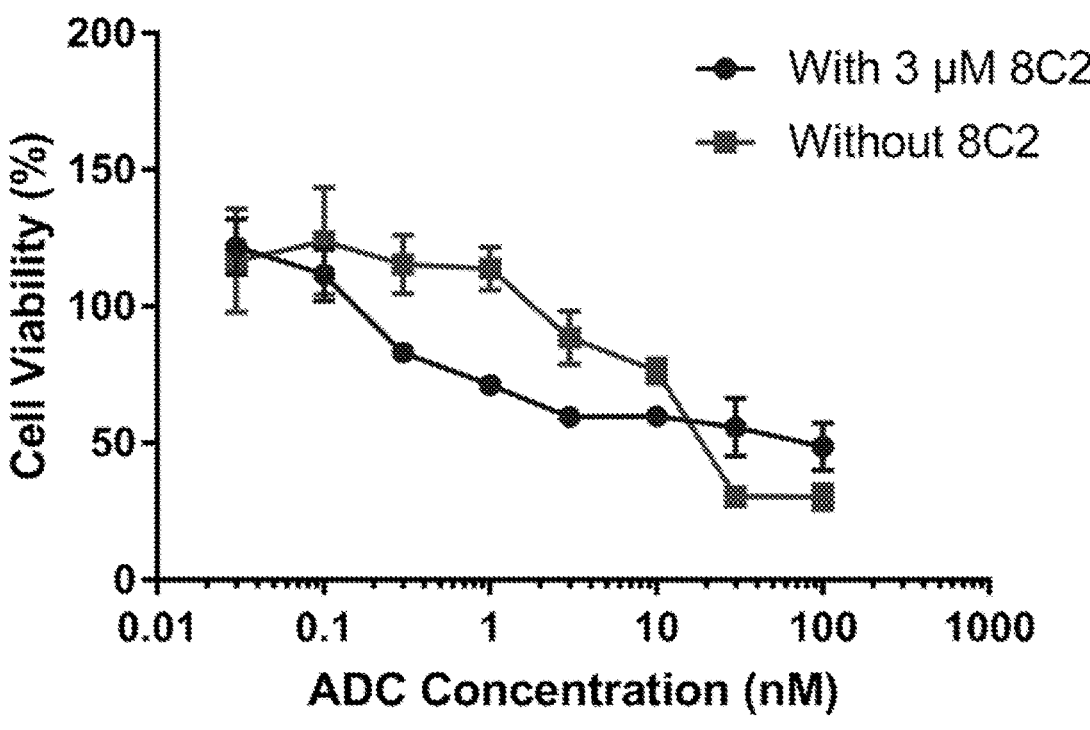
FIG. 11. Competitive Cell Cytotoxicity assay with NCI-N87 cells. 8C2 mAb does not prevent trastuzumab deruxectan cytotoxicity, in-fact higher cytotoxicity of ADC with 8C2 was observed for a majority of the ADC concentrations.
Figure 12:
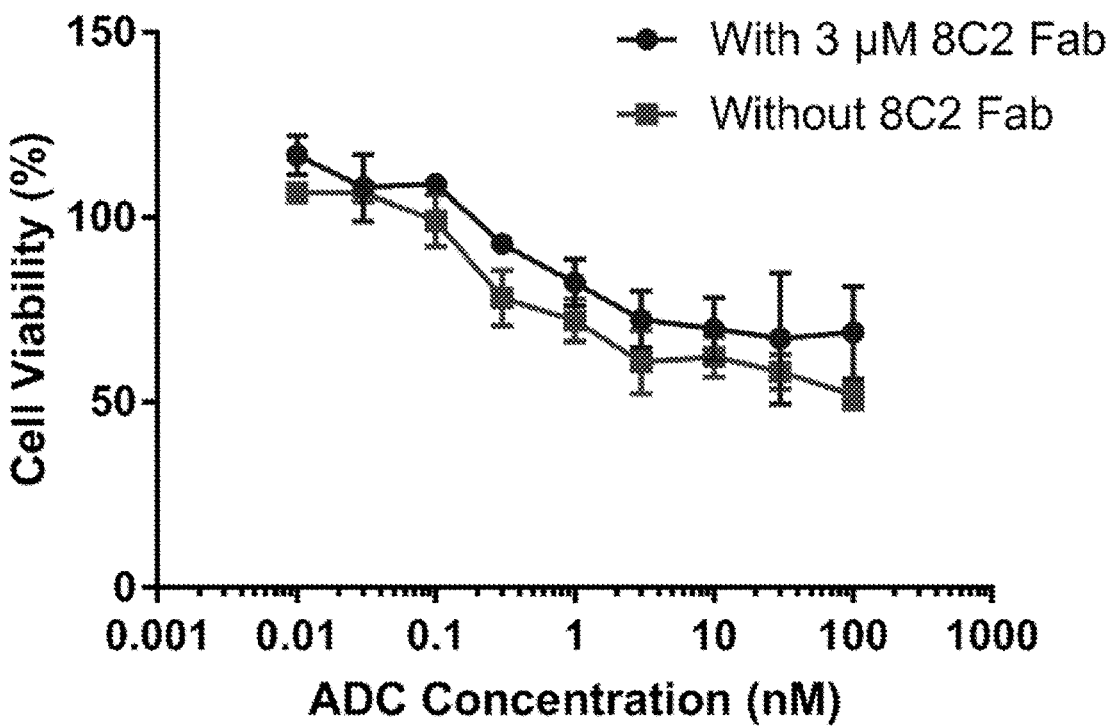
FIG. 12. Competitive Cell Cytotoxicity assay with NCI-N87 cells. 8C2 Fab does not significantly alter trastuzumab deruxectan cytotoxicity.

Currently, the antibody drug conjugate trastuzumab deruxtecan is in phase III clinical trials for several indications. Trastuzumab deruxtecan consists of the monoclonal antibody trastuzumab conjugated to the camptothecin derivative exatecan. We determined if 8C2 could inhibit cellular cytotoxicity of exatecan. No cytotoxicity of exatecan up to 1 µM was observed with 8C2, whereas significant cell death was observed with free exatecan with an IC50 of 1.5 nM (Figures). Addition of 8C2 Fab also decreased exatecan cytotoxicity with addition of 3 uM 8C2 Fab increasing the exatecan IC50 from 2.1 to 128.2 nM. In contrast to free exatecan, addition of intact 8C2 or 8C2 Fab with the ADC trastuzumab deruxtecan did not prevent cell death (FIGS. 11 and 12). Interestingly, addition of intact 8C2 to trastuzumab deruxtecan increased the observed cellular cytotoxicity in comparison to ADC alone across most concentrations. This observation of a decrease in free payload toxicity with 8C2 and an increase in toxicity of ADC with 8C2 is unexpected. It may be attributable to several mechanisms including enhanced internalization of ADC-bound antibody, however this has not been elucidated.

In parallel with work being done with 8C2, the llama single domain phage library has been panned against the ADC trastuzumab deruxtecan. Following panning, many potential exatecan binders were identified (FIGS. 13 and 14). 20 clones from free drug eluted phage library and 10 clones from trypsin eluted phage library show positive binding to Trastuzumab-deruxtecan and negligible binding to Trastuzumab (FIG. 13). Phage media from all 30 clones were re-screened by competitive ELISA with the presence of free exatecan at 10 µM and 1 µM (FIG. 14), which indicate the binding activity of phages to Trastuzumab-deruxtecan can be reduced by exatecan. DNA sequencing results of all 30 clones show that there are 6 unique clones.

Positive phage clones were sequenced leading to identification of 6 unique single domain antibody sequences (FIG. 15). DNA encoding for the listed sequences can be synthesized for recombinant expression. Expressed single domains can be evaluated for SN38/exatecan binding and cell cytotoxicity inhibition.

Figure 17:
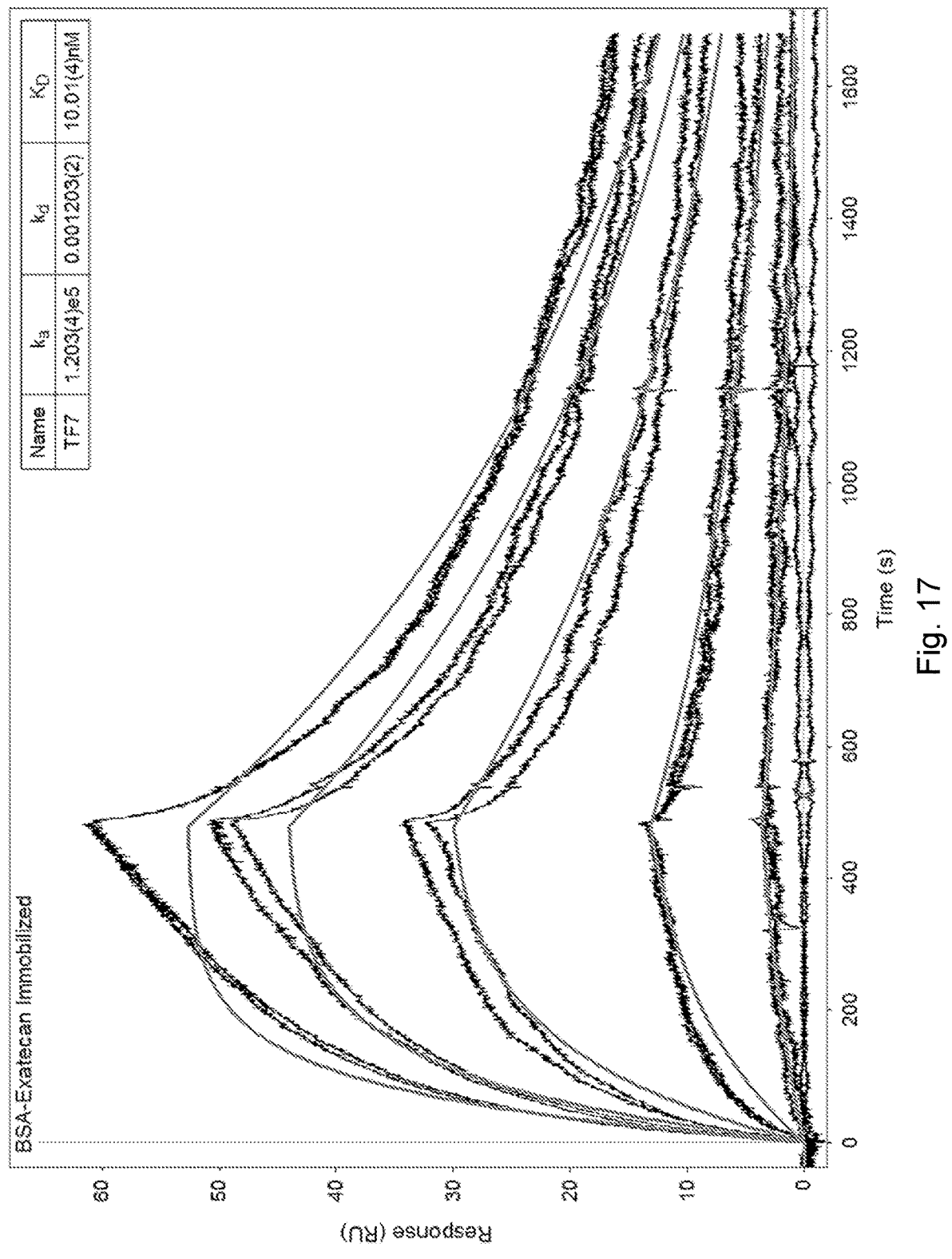
FIG. 17. SPR binding assessment of TF7: Binding analysis for sdAb TF7 against BSA conjugated Exatecan. Kinetic assessment with a predicted equilibrium binding assessment of 10.01 nM.

Anti-Exatecan sdAb TF7 clone. TF7 expressed in SHuffle is purified by Ni-NTA column and CHT chromatography with yield of 12 mg/L and purity over 95%. TF7 shows concentration-dependent binding to ELISA coated Trastuzumab-deruxtecan and SPR chip immobilized exatecan conjugated BSA. (FIGS. 16 and 17).

TF7 Amino acid sequence (SEQ ID NO: 6)

QVQLQESGGGLAQPGGSLRVSCATSGFTFSSNYYISWVRQAPGRGLEWV
SAINTGDGSTYYAHSVKGRFTISRDNAKNTLYLQMNSLKPEDTALYYCA
RSSLEGRIEKPYDYWGQGTQVTVSS

Figure 18:
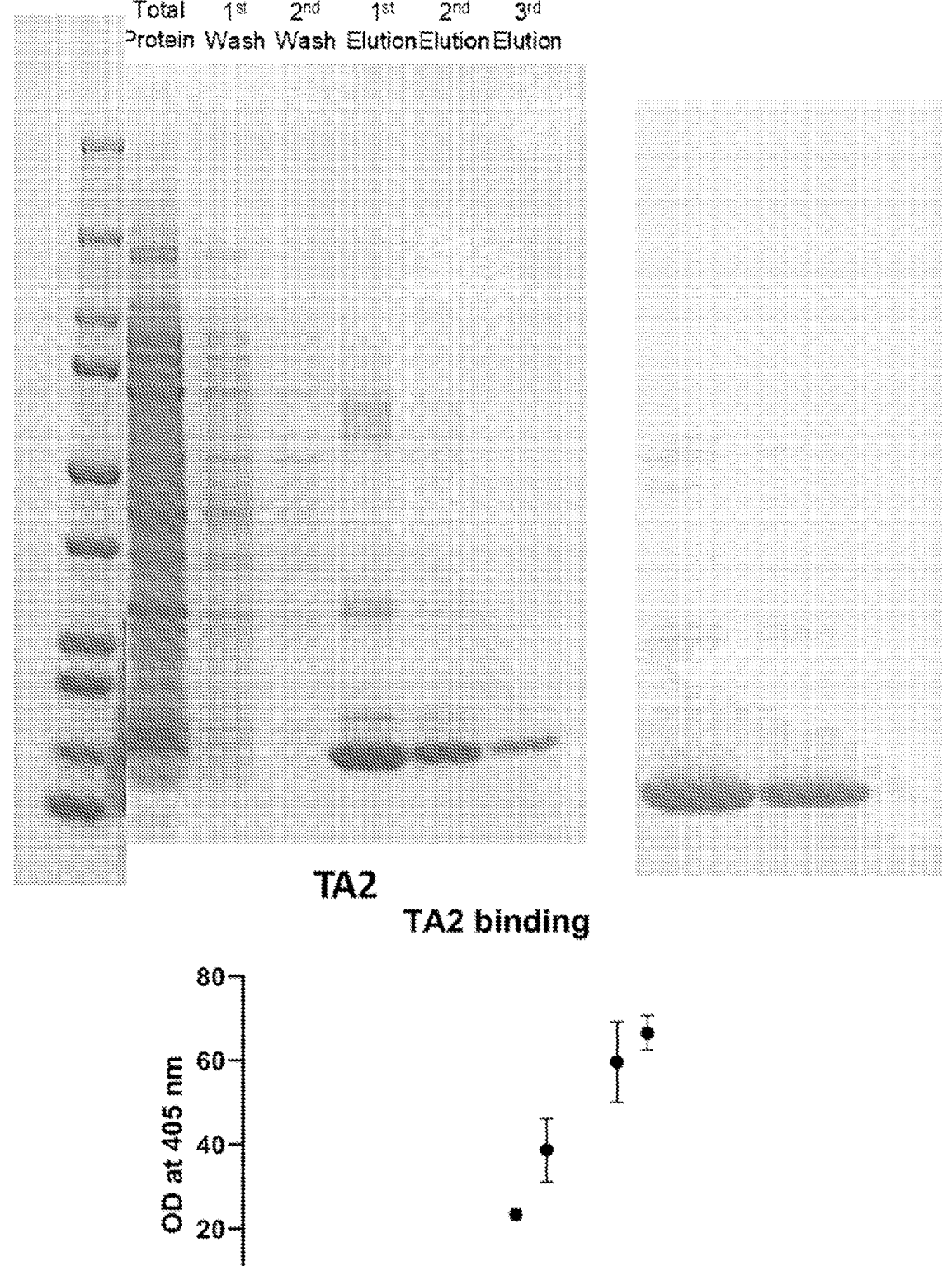
FIG. 18. SDS-PAGE and Indirect ELISA. TA2 is ~80% pure after Ni-NTA column and ~95% pure after CHT column, and shows concentration-dependent binding to Trastuzumab deruxtecan.

Anti-Exatecan sdAb TA2 clone. TA2 expressed in SHuffle is purified by Ni-NTA column and CHT chromatograph with yield of 10 mg/L and purity over 95%. TA2 shows concentration-dependent binding to Trastuzumab-deruxtecan. (FIG. 18).

TA2 Amino acid sequence (SEQ ID NO: 7)

QVQLQESGGGLVQPGGSLRVSCAASGFTFSSYYMSWVRQAPGKGLEWVS
AINTGTGSTYYADSVKGRFTISSDNAKNTVYLQMSSLKPEDTALYYCAR
SSLEGRVEKPYDYWGQGTQVTVSS

Figure 19:
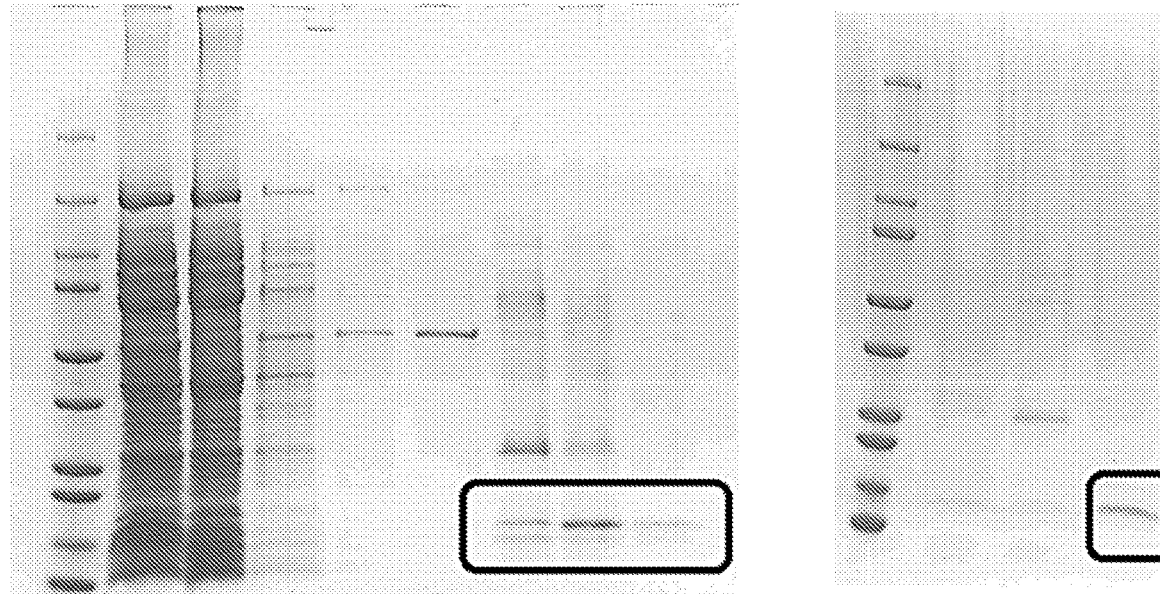
FIG. 19. SDS-PAGE. The last three columns of left gel image are FA2 after Ni-NTA column purification and the last column of right gel image is FA2 after CHT column purification, indicating FA2 is not expressed well. (FA1 is the same case).

Anti-Exatecan sdAb FA1/FA2 clone. FA1 and FA2 expressed in SHuffle are purified by Ni-NTA column and CHT chromatograph. However, both constructs are poorly expressed based on SDS-PAGE results. (FIG. 19).

```
Amino acid sequences
FA1
                                   (SEQ ID NO: 8)
QVQLQESGPGLVKPSQTLSLICTVSGGSITTNYYYWSWIRQAPGKGLEW
MGGINYWGSTYYSPSLKSRTSIFRDTSKNQFTLQLSSVTPEDTAIYYCA
RGFAAYGSSWYGYDYWGQGTQVTVSS FA2
                                   (SEQ ID NO: 9)
EVQLVESGPGLVKPSQTLSLTCTVSGGSITTNYYYWSWIRQAPGKGLEW
MGGINYWGSTYYSPSLKSRTSIFRDTSKNQFTLQLSSVTPEDTAIYYCA
RGFAAYGSSWYGYDYWGQGTQVTVSS Additional sdAb clones
TB9
                                   (SEQ ID NO: 10)
QVQLQESGGGLVQPGGSLRLSCAASGFTFGSNYYISWVRQAPGKGLEWV
SAINTGGGSTYYADSVKGRFTISRDNAKNTLYLQMNSLKPEDTALYYCA
RSSLEGRVEKPYDYWGQGTQVTVSS TF5
                                   (SEQ ID NO: 11)
QVQLQESGGGLVQPGGSLRLSCAASGFTFGSYYMSWVRQAPGKGLEWVS
AINTGDGNTYYPDSVKGRFTISRDNAKNTLYLQMNSLKPEDTALYYCAR
SSYEGRVEKPYDYWGQGTQVTVSS
```

In summary, we have established an anti-drug antibody, named 8C2, against the synthetic camptothecin derivative topotecan. 8C2 has demonstrated high affinity binding against topotecan leading to a reduction in topotecan cytotoxicity>1 μM in HT-29 cells and >10 μM in LS174T cells. Although 8C2 was developed to antagonize topotecan, 8C2 also shows positive binding against the camptothecin derivatives SN38 and exatecan. 8C2 IgG binding to SN38 was evaluated using a competitive ELISA and compared to topotecan. 8C2 demonstrated a similar affinity for topotecan and SN38, with $IC_{50}$ values of 9.3 nM for topotecan and 10.29 nM for SN38. Considering high affinity for SN38, antagonism of SN38 by 8C2 mAb in vitro was evaluated using HT-29 cells and an MTT cell viability assay. The $IC_{50}$ of SN38 on HT-29 cells was 8 nM in absence of 8C2; however, in presence of 8C2, SN38 toxicity was abolished up to 1.0 μM. Although intact 8C2 abolished SN38 cytotoxicity, intact IgG is not an optimal construct for enhancing ADC selectivity as intact IgG may result in pharmacokinetic limitations when bound to SN38 antibody-drug conjugates. Considering this, two 8C2 fragments were produced: 1) Fab & 2) scFv. 8C2 Fab was generated via papain digestion as described in methods above. Hydroxyapatite chromatography was employed to separate Fab from Fc fragments and intact IgG. 8C2 Fab purity and integrity was assessed by examining a single band at 25 kDa under reducing conditions and a primary band at 50 kDa under non-reducing conditions. As previously conducted with 8C2 mAb, the ability of Fab fragment to prevent cytotoxicity of SN38 in vitro was assessed using HT-29 cells. Consistent with mAb, 500 nM of Fab fragment prevented the cytotoxicity of SN38 on HT-29 cells, shifting the $IC_{50}$ by >30-fold.

EXAMPLE 3

This example describes calicheamicin antagonists.

Materials and Methods

Anti-Drug Peptide Phage Display Library

A 10 μg/mL solution of TmAb-calicheamicin was diluted in 0.1 M tris-buffered saline (TBS), pH 8.6. Nunc MaxiSorpt 96 well plates were coated with 250 μL of antigen solution and incubated overnight at 4° C. Supernatant was discarded and plates were washed six times with TBS with 0.1%

Tween-20 (TBST). Phage library stock was diluted 100-fold with TBST and aliquoted into microtiter plate wells and incubated for 1 h. Within the phage solutions, trastuzumab was added to 25 μg/mL. After incubating for 1 h, the supernatant was discarded and plates were washed ten times with TBST. Bound phages were eluted with 0.2 M glycine-HCl, pH 2.2. Eluate was then diluted with 20 mL of culture and incubated for 4.5 h at 37° C. After incubation, the culture was centrifuged for 10 min at 12,000×g and transferred to a fresh tube where phage was precipitated with ⅙ volume of 20% PEG/2.5 M NaCl and incubated overnight at 4° C. The PEG precipitation was centrifuged at 12,000×g for 15 min at 4° C. The supernatant was discarded and the phage pellet was resuspended in 1 mL of TBS. The resuspended phage was centrifuged again at 14,000×rpm for 5 min at 4° C. to pellet residual cells. Supernatant was transferred to a new tube and reprecipitated by adding ⅙ volume of 20% PEG/2.5 M NaCl. The solution was incubated on ice for 1 h and centrifuged at 14,000×rpm for 10 min at 4° C. Supernatant was discarded. Phage pellet was resuspended in 200 μL of TBS and centrifuged to pellet any remaining debris. The supernatant was then tittered and plated on LB/IPTG/Xgal plates. Blue plaques were counted to determine diversity. Two more rounds of panning were carried out. Plaques from the third panning were harvested for sequencing.

Peptide Phage Library ELISA Binding Assay

An overnight culture of E. coli was diluted with a 1:100 ratio in 20 mL Lysogeny broth (LB) medium containing 20 μg/mL of tetracycline. An aliquot of 5 μL of each phage stock collected from phage panning (C1, C2, C3, C4, C6, C7, & C9) were added into 20 mL cultures respectively and incubated at 37° C. with shaking for 5 hours. Then each was centrifuged at 12,000×g for 10 minutes at 4° C. The supernatant was transferred to fresh tubes and centrifuged again. A volume of 16 mL of upper supernatant was transferred again and precipitated with 2.7 mL 20% PEG/2.5 M NaCL at 4° C. overnight. The PEG precipitation was spun at 12,000×g for 15 minutes at 4° C. and supernatant was removed. Then the pellet was suspended in 1 mL of TBS and spun at 14,000 rpm for 5 minutes at 4° C. to pellet residual cells. The supernatant was re-precipitated with 167 μL of 20% PEG/2.5 M NaCl and incubated on ice for 60 minutes. Then it was re-centrifuged at 14,000×rpm for 10 minutes at 4° C. and residual supernatant was removed. The pellet was suspended in 50 μl of TBS and was diluted to 1:100 for ELISA screen for binding to calicheamicin. A ELISA plate was coated with 4 μg/mL of trastuzumab-calicheamicin conjugate at 4° C. overnight. After washing with TB ST for 6 times, the plate was blocked with 3% milk and incubated with 1:100 diluted peptide phages, or negative control (PBS) or positive control (anti-calicheamicin plasma) for 2 hours at room temperature. After the plate was washed as before, 1:1000 diluted anti-M13 antibody was incubated next for 1 hour to bind to the multi-valent phages. And the goat anti-mouse IgG (Fc specific) with Alkaline Phosphatase conjugated was diluted to 1:500 in 3% milk and added to the ELISA plate for 1 hour incubation. Finally, 4 mg/ml the substrate PNPP in 1× diethanolamine buffer was added and absorbance changes of the plate was read at 405 nm.

Calicheamicin Conjugation for sdAb Library Panning

Calicheamicin was reacted with 10 molar equivalents of TCEP for 2 h at 37° C. in order to reduce the tri-sulfide bond. Following reduction, the r-Calicheamicin was reacted overnight with either maleimide modified biotin, or SMCC modified cetuximab, or tosylactivated dynabeads.

Dynabeads Phage Display

50 µl Dynabeads-calicheamicin were blocked with MPBS (PBS+2% non-fat dry milk) at RT for 30 minutes. Following pre-incubation with 1:50 preimmunized llama plasma, phage solutions were incubated with beads at RT for 30 minutes. Beads were then washed with PBST. Bound phages were eluted either with 500 µL of 1 mg/ml trypsin at RT for 30 min, or eluted with free calicheamicin. Eluted phage were used to infect TG1 cells for titration and for phage amplification and rescue for two further pans. For the second and third pans, 25 µl and 12.5 µl of beads were used for panning, respectively.

sdAb Production and Purification

The sdAb gene was ligated to a cut expression plasmid PET-22b and transformed to the *E. Coli* Shuffle T7 cells. Single colony was inoculated and overnight grown culture was diluted 1:100 to TB medium. The cells were grown at 30° C. until OD600=0.6-0.8, and 1 mM IPTG was added into the culture to induce expression. After 20 hours expression, the protein in cell pellets was extracted by Bugbuster Buffer and purified by $Ni^{2+}$-NTA resin.

ELISA Binding Assay

Figure 25:
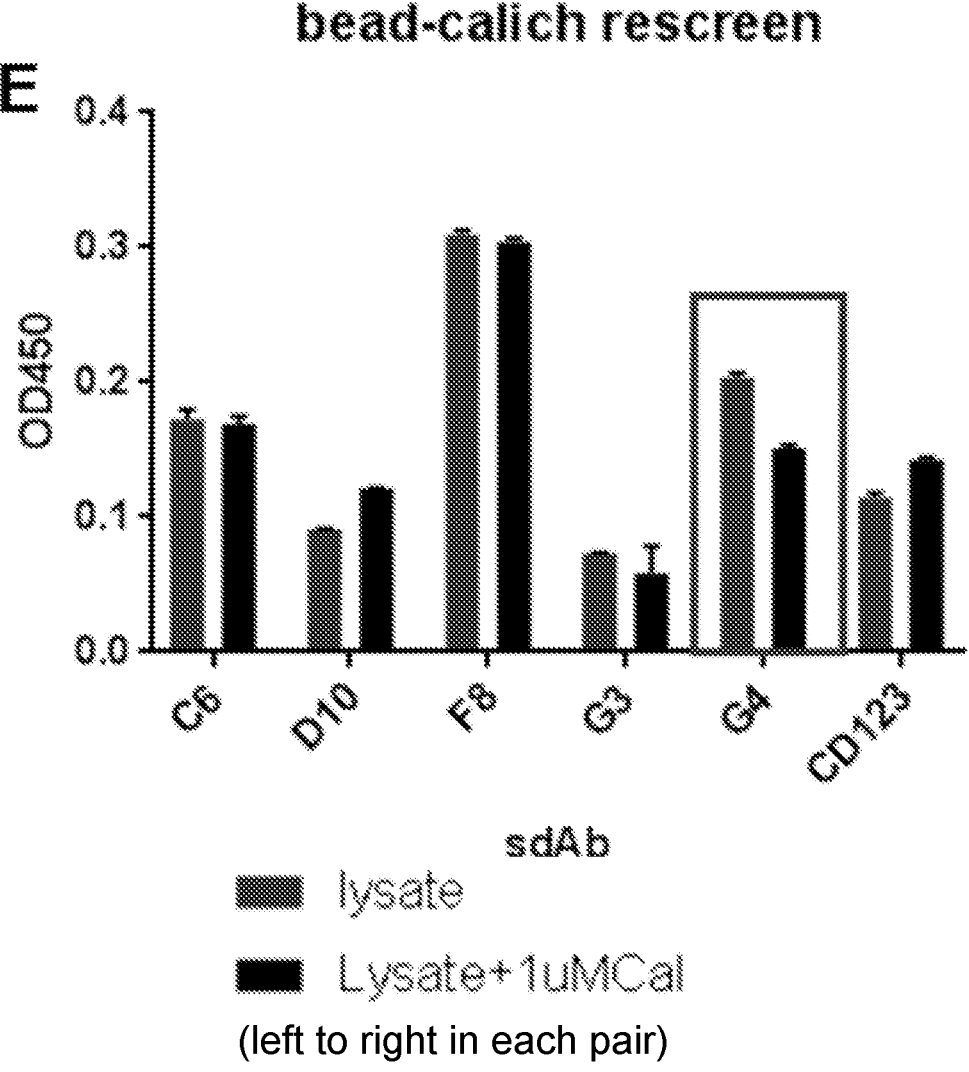
FIG. 25. Positive clones identified from screening of the llama single domain antibody phage library against calicheamicin. A-C) Single colonies were tested for binding against avidin-biotin-calicheamicin. C6, D10, F8, G3 showed binding to the calicheamicin conjugates. These colonies or clones may be referred to in this application with a preceding "C", such as CC6, CD10, CF8, CG3, CG4 etc. D) Single colonies were also screened for binding against dynabeads-calicheamicin. G4 and C6 showed high binding to the dynabeads. E) The five colonies C6, D10, F8, G3, G4 were rescreened and tested with or without pre-incubation of 1 µM free Calicheamicin. A loss of binding signal was observed for the sdAb clone CG4 with the addition of 1 µM free calicheamicin.

Nunc Maxisorp 96-well plates were coated with 4 µg/ml Cetuximab or Cetuximab-calicheamicin, or 5 µg/ml Avidin. Plates were washed three times with PBST and three times with dH2O, and blocked with MPBS for 2 h at RT. For the Avidin coated plates, plates were washed three times with PBST and incubated with 1 µM Biotin-Calicheamcin. Plates were then washed three times with PBST and incubated with increasing concentration of purified sdAb CG4 (G4 from FIG. 25) at RT for 2 h, with or without pre-incubation with free Calicheamicin at 10 µM. Plates were then washed three times with PBST, where bound sdAb was detected using an anti-His tag HRP-conjugated Ab diluted 1:1000 in MPBST. Following incubated and five washed with PBST, 100 µL of 1-Step Turbo TMB-ELISA solution was added to each well and incubated for 30 minutes. The reaction was quenched by adding 100 µL of Stop solution to each well and absorbance was measured at 450 nm. Alternatively, wells can also be incubated with 1:1000 diluted anti-His tag AP-conjugated Ab, instead of HRP conjugated Ab. After washing, 4 mg/ml PNPP in diethanolamine buffer pH 9.8 with absorbance being read at 405 nm.

Dynabeads Binding Assay

Calicheamicin conjugated dynabeads were washed with PBST and blocked with MPBS for 30 min. Beads were washed three times with PBST and incubated with sdAb for 30 minutes. Bound sdAb were detected with 1:1000 diluted anti-His tag HRP-conjugated Ab. After washed with PBST, beads were resuspended with 500 µL of 1-Step Turbo TMB-ELISA solution and incubated for 30 minutes. The reaction was quenched by adding Stop solution, and absorbance was measured at 450 nm.

Cell Cytotoxicity

Fresh media containing a range of treatment were pre-incubated with or without 100 µM purified sdAb at room temperature for 30 minutes. Log-phase MOLM-14 cells were seeded in 96-well microtiter plates at a density of 20,000 cells/well, and were re-suspended with treatment solutions, where 100 µL of cell-treatment suspension was aliquoted into wells of a 96-well plate for 24 h. 25 µL of MTT solution (5 mg/mL in pH 7.4 1× PBS) was added directly to wells following treatment incubation. Cells were incubated for 4 h in order to allow cells to reduce MTT to formazan dye. Once MTT was reduced, 100 µL of 10% SDS prepared in 0.01 M HCl was added to each well and incubated overnight to solubilize the formazan crystals. Formazan dye was measured at 570 nm and normalized by cell debris at 690 nm.

Results

Evaluation of Calicheamicin Antagonists

Figure 20:
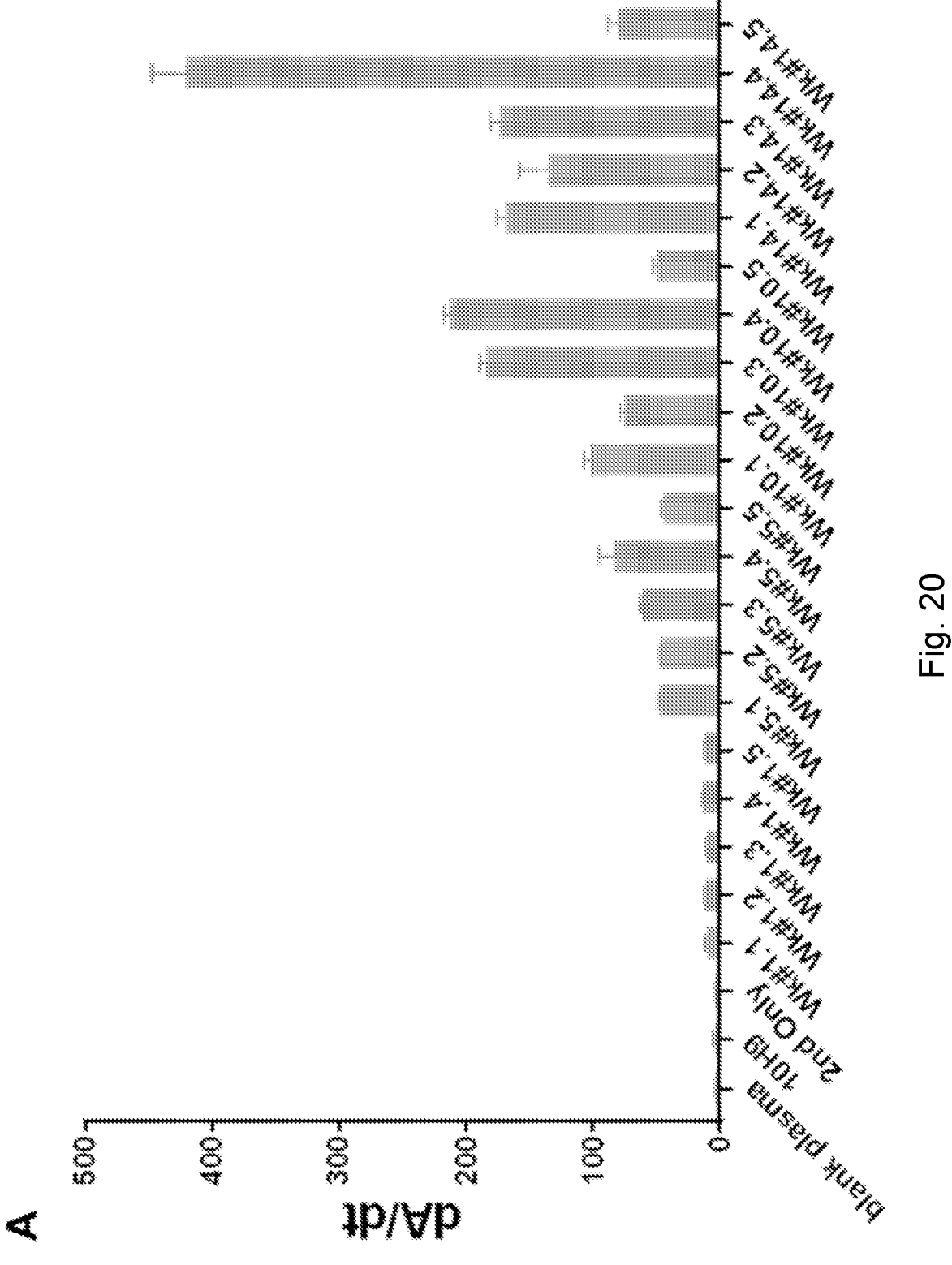
FIG. 20. Evaluation of polyclonal antibody response to Calicheamicin from mouse plasma. A) Balb/c plasma responses over the immunization course of 50 μg of KLH-calicheamicin in incomplete Freund's adjuvant. The mouse with the highest response was selected for fusion to myeloma SP2/0 cells. B) Mouse plasma was tested for cross reactivity to Tmab by ELISA. All samples were negative for binding to Tmab, but positive for Tmab-calicheamicin.
Figure 20:
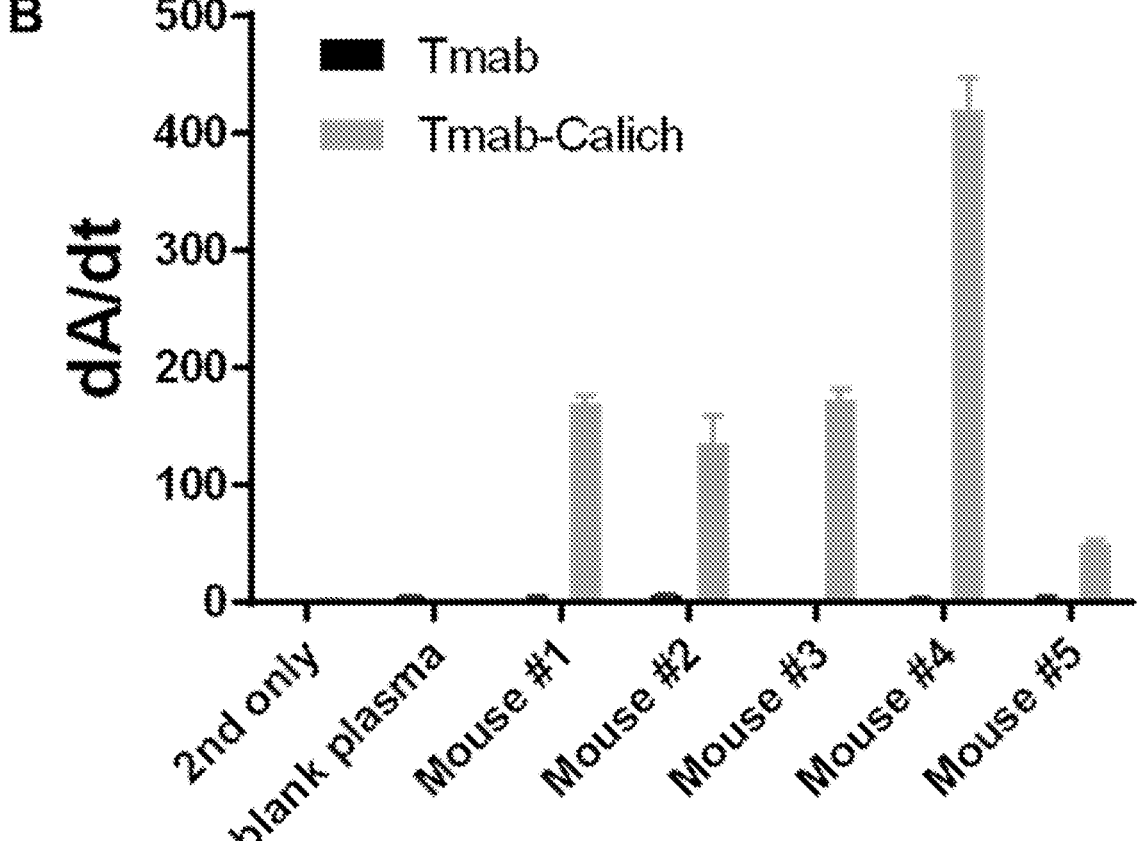

Female Balb/c mice have been immunized with KLH-calicheamicin. Plasma samples were collected from immunized mice over the course of immunization and evaluated for binding to Tmab-calicheamicin by ELISA. Over fourteen weeks, mice responded positively to KLH-calicheamicin, where the highest responding mouse was selected for fusion to mouse myeloma SP2/0 cells (FIG. 20A). Plasma was negative for cross-binding to Tmab (FIG. 20B). Mouse hybridoma were grown for two weeks after the fusion, where established cell colonies were tested for binding to Tmab-calicheamicin. Positive cells were then selected for sub-cloning by single cell picking to develop monoclonal antibodies. Colonies were grown for another two weeks and then tested for binding via ELISA. Isotyping of a single anti-calicheamicin mAb colony determined antibodies being produced were IgM.

Evaluation of plyclonal antibody response to calicheamicin from Llama plasma was also carried out (FIG. 21). A llama was immunized with KLH-Calicheamicin to produce sdAb against Calicheamicin. Llama plasma after immunization showed positive response to biotin-calich conjugate and dynabeads-calich, compared to the pre-immunized plasma. Binding was also inhibited when plasma was pre-incubated with free calicheamicin.

Figure 22:
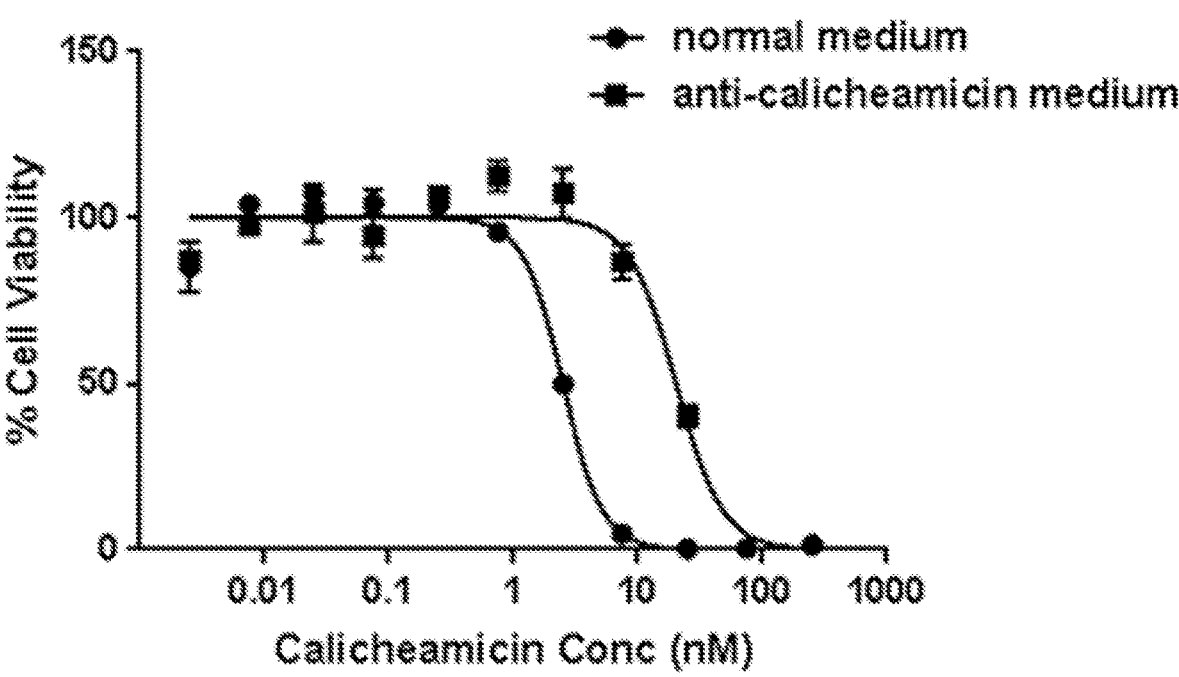
FIG. 22. MTT assay with IgM. Cell cytotoxicity of calicheamicin on Ramos cells with or without anti-calicheamicin IgM containing hybridoma media. Approximately, 20,000 cells/well were incubated with treatment solutions for 24 h and evaluated for cell viability with an MTT assay. Calicheamicin exhibited an $IC_{50}$ of $2.495 \pm 0.224$ nM, but was inhibited by anti-calicheamicin IgM to $20.300 \pm 2.941$ nM.

Anti-Calicheamicin IgM 11B9 Clone. Mouse hybridoma were grown for two weeks after the fusion, where established cell colonies were tested for binding to Tmab-calicheamicin. Positive cells were then selected for sub-cloning by single cell picking to develop monoclonal antibodies. Colonies were grown for another two weeks and then tested for binding via ELISA. Isotyping of a single anti-calicheamicin mAb colony determined antibodies being produced were IgM. Cytotoxicity assays were conducted for free calicheamicin on Ramos Burkitt Lymphoma cells in presence or absence of anti-calicheamicin medium. Caliceamicin is a highly potent DNA alkylating agent that demonstrated high cytotoxicity on Ramos cells, with an IC50 of 2.496±0.224 nM. However, in presence of anti-calicheamicin medium, cytotoxicity was inhibited by 8.13-fold, resulting in an IC50 of 20.300±2.941 nM. (FIG. 22).

Figure 23:
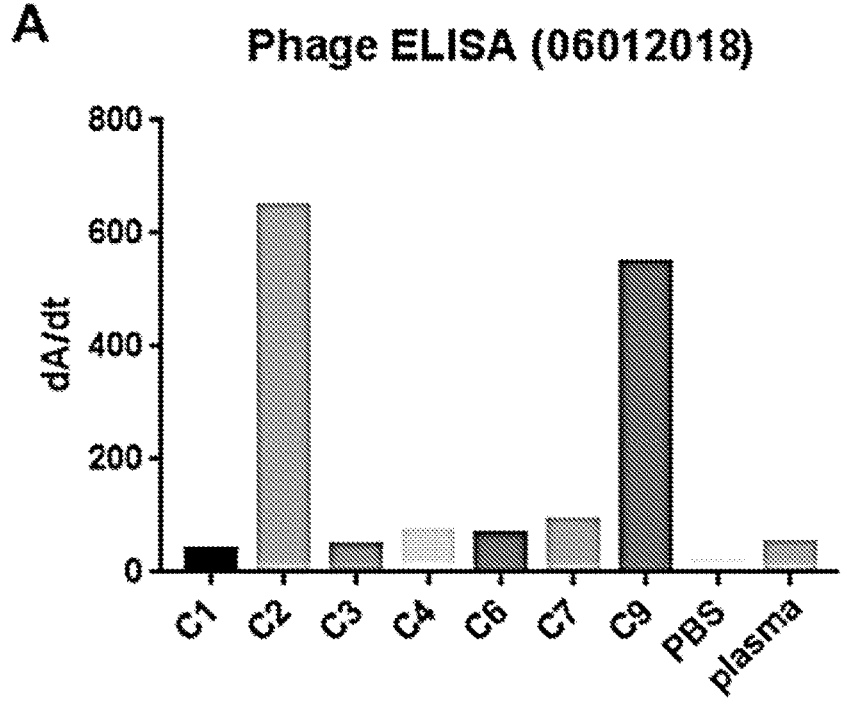
FIG. 23. ELISA screening with peptide phage. Generation of anti-calicheamicin peptides from a commercially available peptide library and the effect on cell viability. A) Clones isolated from panning and ability to bind to Tmab-calicheamicin. Two peptide candidates were identified for positive binding and synthesized for in vitro cell cytotoxicity assessment. B) MTT assay with peptide C2. Cell cytotoxicity of calicheamicin in MOLM-14 with or without C2 peptide at 100 μM. C2 reduced the $IC_{50}$ by 5.69-fold from 131.8 pM to 749.9 pM. C2 amino acid sequence is HSWHWPSWWAGGGGGS (SEQ ID NO:1). C) MTT assay with peptide C9. Cell cytotoxicity of calicheamicin in MOLM-14 with or without C9 peptide at 100 μM. C9 reduced the $IC_{50}$ by 3.56-fold from 131.8 pM to 469.7 pM. C9 amino acid sequence is SWWFPQWMAQYPGGGS (SEQ ID NO:2).
Figure 24:
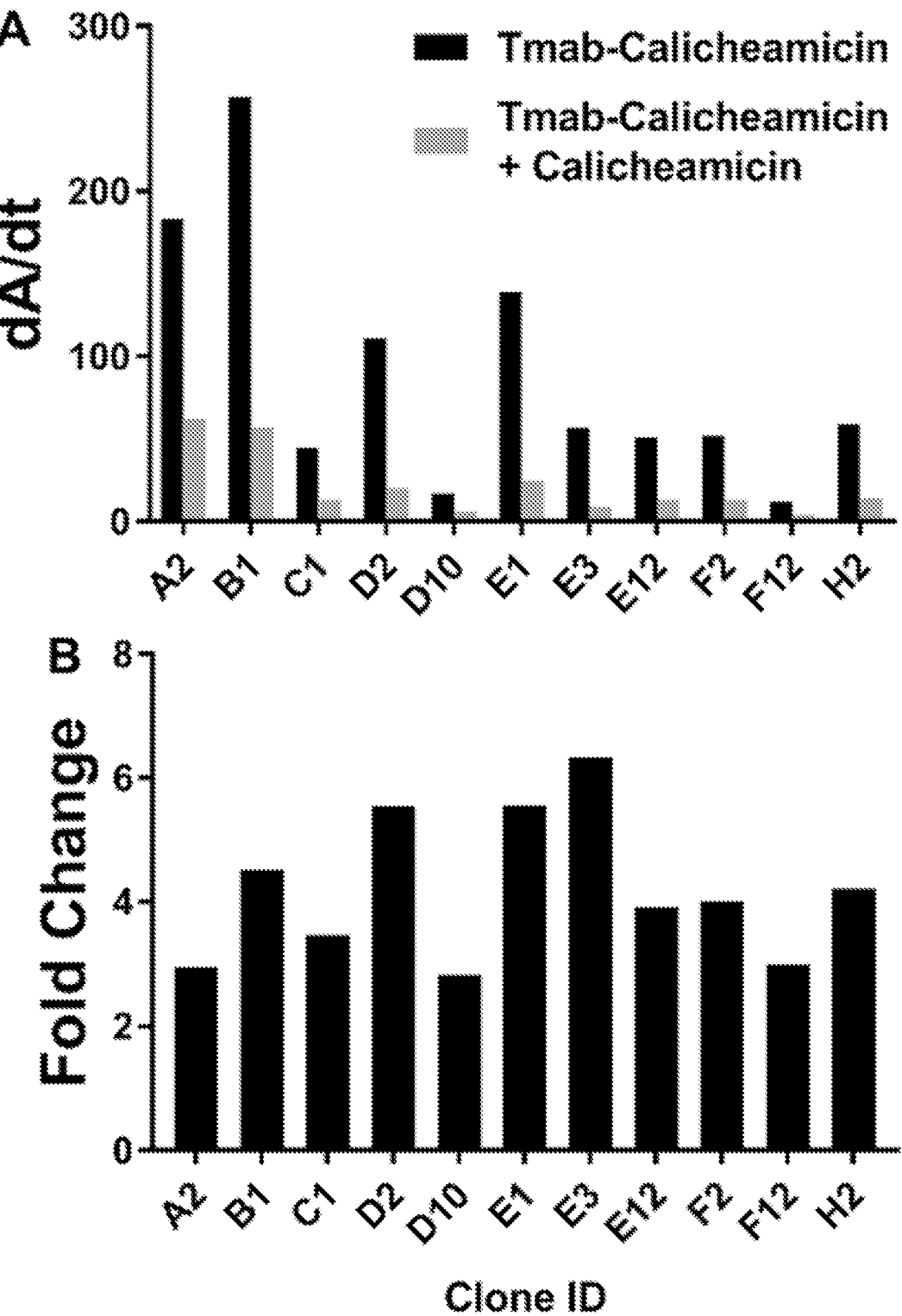
FIG. 24. Positive clones identified from screening of the llama single domain antibody phage library against calicheamicin using method: sdAb affinity matured ELISA. A) Single colonies obtained following three panning steps were expanded and culture media was tested for binding against Tmab-calicheamicin with or without pre-incubation of calicheamicin. B) Fold change between responses of sdAbs when pre-incubated with calicheamicin. B1, D2, E1, E3, and H2 demonstrated the highest fold change, >4-fold.

Anti-Calicheamicin peptide C2. A peptide phage library obtained from New England BioLabs was purchased and used to screen for anti-calicheamicin antagonists. Following the panning process, two peptides were identified by ELISA that bound to BSA-calicheamicin: C2 and C9 (FIG. 23A). These peptides were synthesized by ThermoScientific and employed in an MTT assay on MOLM-14 cells. MOLM-14 is a human cell line of acute myeloid leukemia, previously employed to evaluate calicheamicin-based antibody drug conjugates. Following a 24 h exposure period to MOLM-14 cells, calicheamicin demonstrated an IC50 of 131.8±17.33 pM. Co-incubation with 100 µM of C2 reduced calicheamicin IC50 by 5.69- and 3.56-fold to 749.9±478.7 pM (FIG. 23B).

Anti-Calicheamicin peptide C9. C9 peptides were identified by ELISA that bound to Tmab-calicheamicin. Following a 24 h exposure period to MOLM-14 cells, calicheamicin demonstrated an IC50 of 131.8±17.33 pM. Co-incubation with 100 µM of C9 peptide reduced calicheamicin IC50 3.56-fold to 469.7±238.1 pM. (FIG. 23C).

Anti-Calicheamicin sdAb CG4 clone. From the single domain library, after three rounds of panning against Dynabeads-Calicheamicin (FIGS. 25A, B, C), there were five positive hits by screening against biotin-Calicheamicin and Dynabeads-Calicheamicin (FIG. 25D). Of the 5 positive hits CG4 was the only clone inhibited by addition of 1 μM free calicheamicin (FIG. 25E). Therefore the CG4 clone was selected for further characterization and was recombinantly expressed in the *E. Coli* cell line Shuffle T7 and purified by $Ni^{2+}$-NTA resin (FIG. 26).

Both the ADC coated ELISA and the dynabeads binding assay show apparent calicheamicin binding with increasing concentration of CG4 (FIG. 26B/C). Also, different concentration of CG4 were pre-incubated with or without 10 μM calicheamicin at room temperature for 30 minutes. Addition of 10 μM Calicheamicin led to a decrease in CG4 signal by 2.5-fold and 2-fold for the cetuximab-calicheamicin coated plates (FIG. 26D) and avidin coated plates (FIG. 26E), respectively. Considering the higher background of calicheamicin group, the actual fold reduction could be around 3.3-fold (96.81/29.2619) and 4.3-fold (77.41/18.17).

Cytotoxicity assay was conducted on MOLM-14 cells using calicheamicin with or without purified CG4. 100 μM CG4 decreased the cytotoxicity of calicheamicin by 15.4 fold, from 26.03 pM to 400.2 pM. (FIG. 27).

CG4 sequence:
(SEQ ID NO: 12)
QVQLQESGGGLVQAGGSLRLSCAASGRTISGYAMGWFRQAPGKERDLVA
AISRSGTSTYYADSVKGRFTISRDNAKNTVYLQMNSLKPEDTAVYYCNA
PGGIWGQGTQVTVSS

EXAMPLE 4

This example describes maytansinoid antagonists.

Materials and Methods

Magnetic Bead Bio-Panning

Bio-panning was performed to identify high affinity binders targeting DM1 and DM4. In summary, stock StrepAvidin magnetic beads were blocked with 2% pre-immunized llama plasma for 1 hour at room temperature, then the blocked beads were either incubated with 500 μL of 1.2 μM biotin-DM1 for 30 minutes for the next binding step, or were used to pre-absorbed 300 μL of stock phage library diluted in additional 300 μL PBST for 1 hour. The pre-absorbed phages were then incubated with the Avidin-Biotin-DM1 beads for another 1 hour before elution via either competition with free DM1 or trypsin. For the first, second, third, and fourth panning, respectively, the amount of stock beads for binding was reduced from 50 μL to 20, 10 and 10 μL, and the concentration of free DM1 elution was reduced from 1 μM to 100, 10, and 1 nM.

Screening

Two hundred clones were screened with phage media, with 50 clones from the third and fourth round of each panning method. Twenty positive clones that had highest binding signal toward DM1 were sequenced and rescreened via competitive assay with free DM1 and DM4. From the sequencing results, unique anti-DM1/DM4 sdAbs were expressed in small scale with their phagemid vectors, purified, and further evaluated for the binding affinity via SPR and competitive assay.

SPR

Preliminary screening of DM1/4 binders were performed using a neutravidin SPR chip with DM1-Biotin on the left channel. Phagemid purified sdAbs were flowed over the SPR chip for 2 minutes at a flow rate of 25 ul/min. After binding, sdAb was dissociated for 20 minutes. Observed sensorgrams were fit to an individual dissociation rate constant for each construct. Equilibrium and kinetic binding of 3A2 was assessed using a CM5 SPR chip with TDM1 immobilized on the left channel. 3A2 was injected over a range of concentrations between 1.25-400 nM for 8 minutes and the Cmax at each concentration used to obtain an equilibrium binding constant $K_D$. Rate constants for 3A2-TDM1 association and dissociation were obtained through fitting of the observed sensorgrams for the 1.25, 2.5, 5, 7.5 and 10 nM injections to a 1:1 Langmuir binding model.

Cell Cytotoxicity

Log-phase Lovo or MOLM-14 cells were seeded in 96-well microtiter plates at a density of 5,000 cells/well, in 100 μL or 70 μL of culture medium, respectively. Lovo cells were allowed to adhere for 24 h before cell culture media was aspirated and replaced with 100 μL of PBS containing a range of treatment for 6h, then washed for 2 times before replacing with fresh media and incubated for additional 90 h. MOLM-14 cells were re-suspended with treatment solutions, where 100 μL of cell-treatment suspension was aliquoted into wells of a 96-well plate for 24 h. Treatment solutions consisted of DM-4 with or without purified anti-drug sdAb. For MOLM-14 cells, 10 μL of MTT solution (5 mg/mL in pH 7.4 1× PBS) was added directly to wells following treatment incubation. For adherent cells, treatment media was aspirated from wells and cells were washed three times with 100 μL of fresh media. Following the final wash, 100 μL of complete media and 25 μL of MTT solution were added to each well. Cells were incubated for 4 h in order to allow cells to reduce MTT to formazan dye. Once MTT was reduced, 100 μL of 10% SDS prepared in 0.01 M HCl was added to each well and incubated overnight to solubilize the formazan crystals. Formazan dye was measured at 570 nm and normalized by cell debris at 690 nm.

Results

Figure 29:
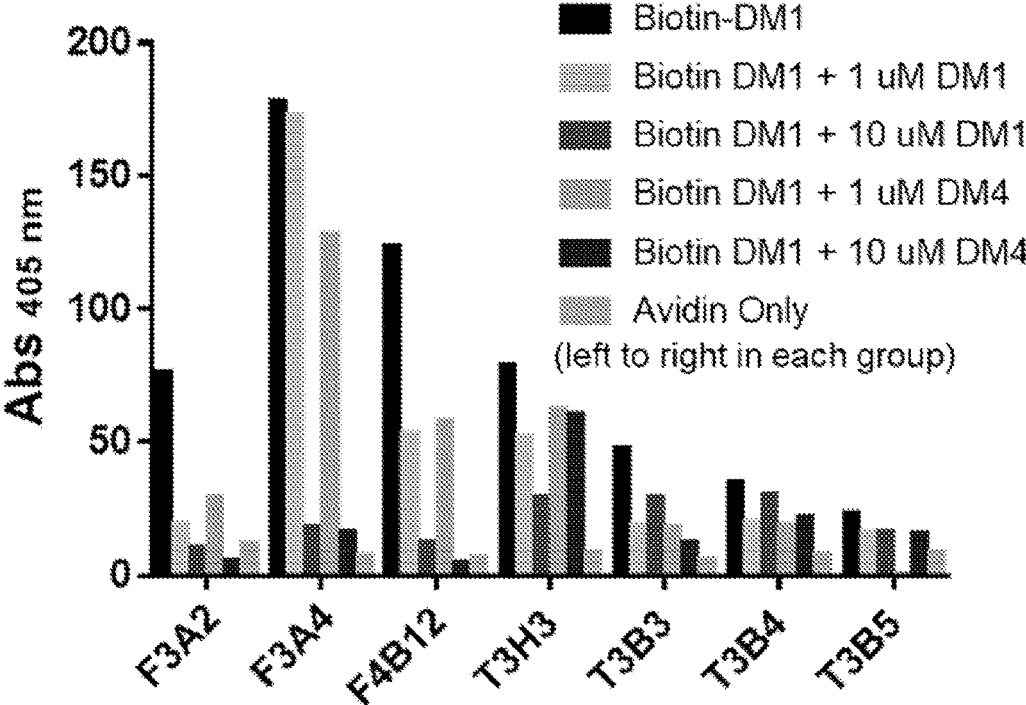
FIG. 29. Competitive binding of phage media with free DM1 or DM4. Phage media was diluted 5-fold in PBST and incubated with either 1 µM or 10 µM of DM1 for 30 minutes before adding to ELISA wells coated with avidin-biotin-DM1. Pre-incubation with DM1 inhibited binding of the sdAb in a concentration-dependent manner.

85% of the screened clones showed positive binding to avidin-biotin-DM1, with no binding observed to avidin alone. 60 clones with the highest ELISA binding signals were sequenced leading to identification of 12 unique sdAb sequences. Phage media from 7 of the unique sdAb sequences were rescreened via competitive assay with addition of either free DM1 or DM4 at concentrations of 1 or 10 μM. Addition of free DM1/4 led to a reduction in the ELISA signal in a concentration dependent manner, demonstrating specific binding activity for the sdAb clones (FIG. 29). The phage-based competitive assay is an empirical mean to assess antigen binding specificity and does not provide information on binding affinity.

Figure 30:
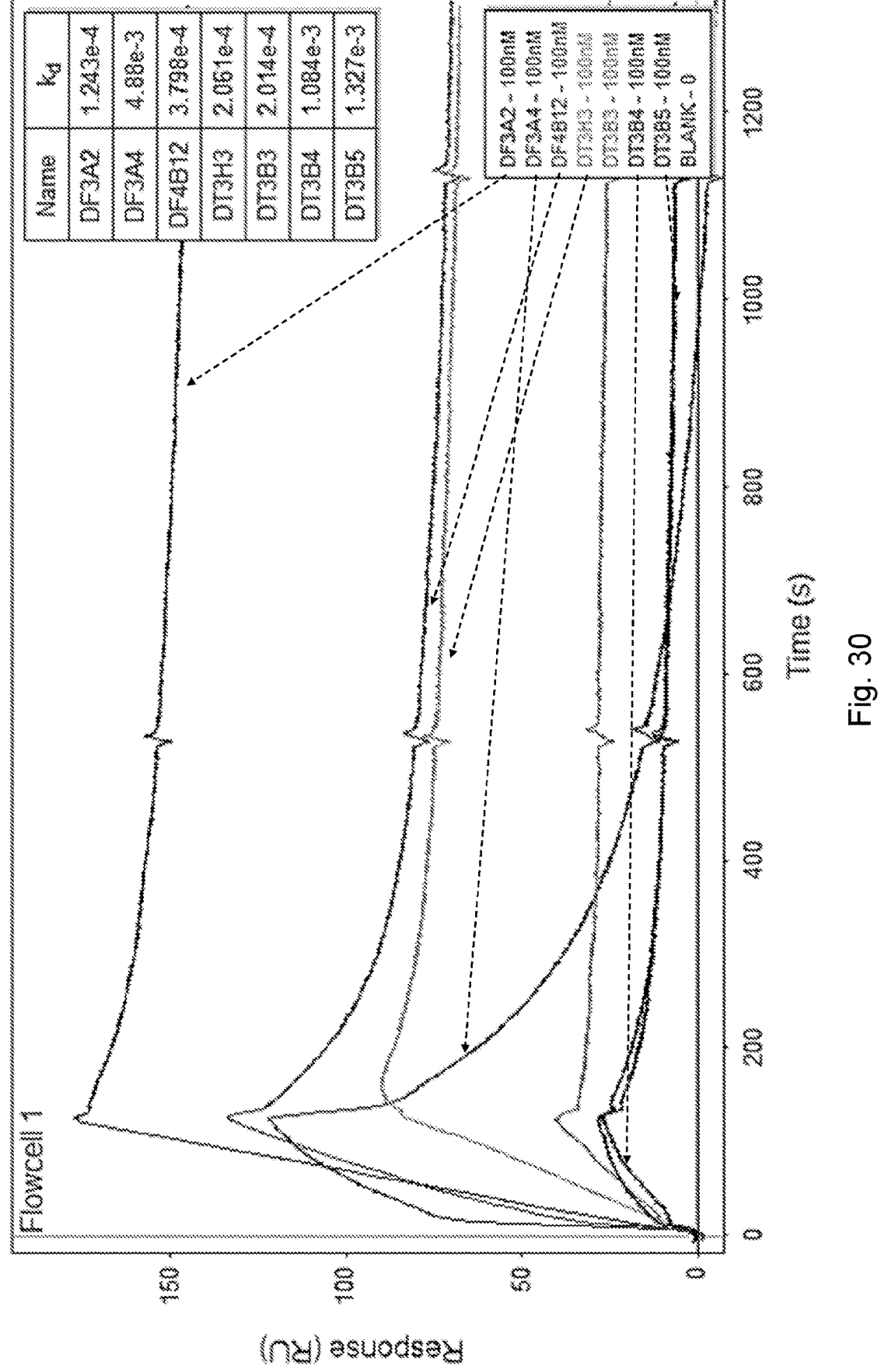
FIG. 30. Affinity assessment of the positive clones with purified sdAbs via SPR. Kinetic assessment with 20 min dissociation phase was utilized to determine dissociation rate constants (i.e., $k_{off}$) of the tested clones. DF3A2, DT3B3 and DT3H3 have longer dissociation rates, indicative of these clones showing high affinity DM1 binding.
Figures 31, 32:
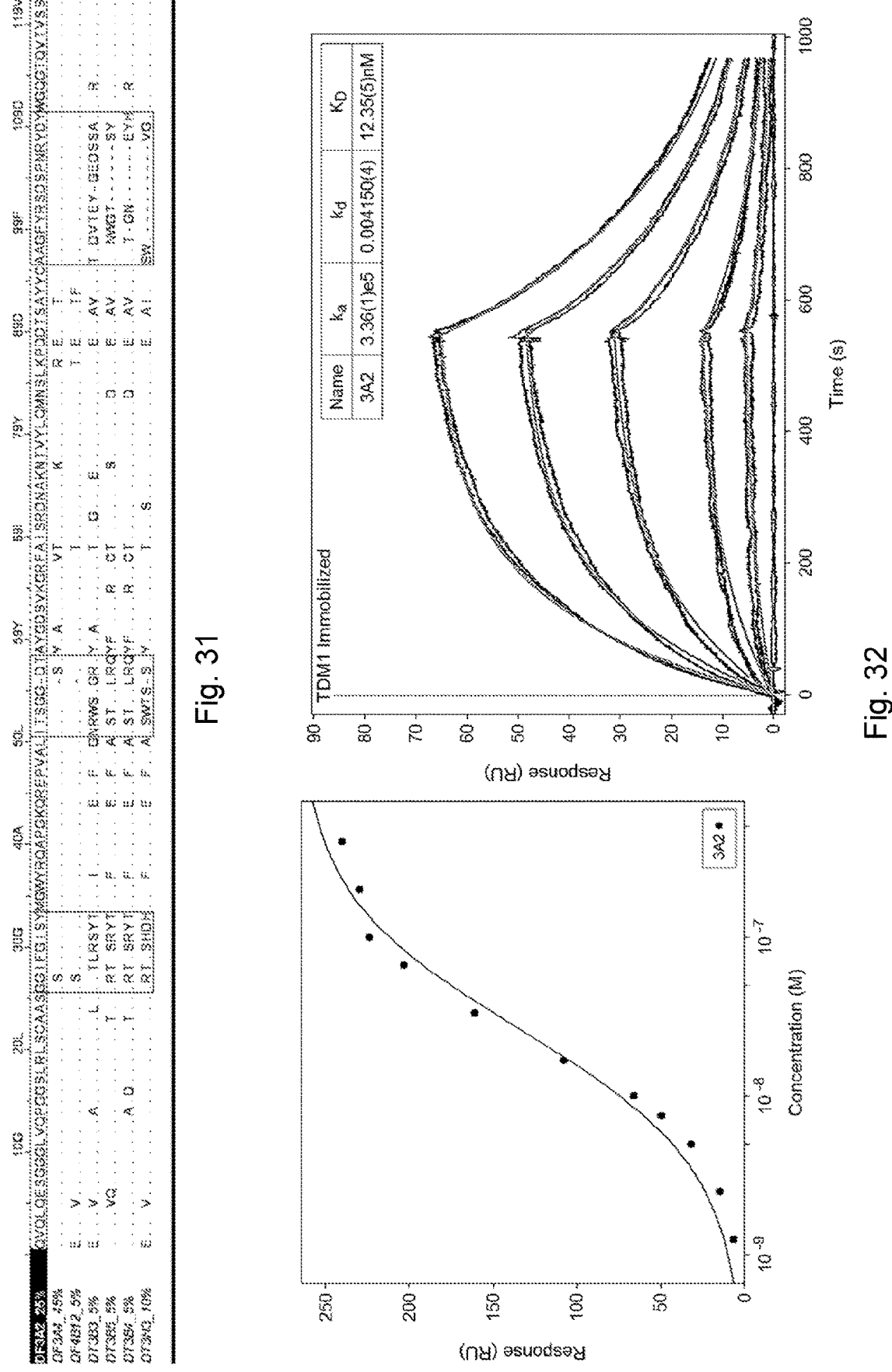
FIG. 31. Sequence alignment from positive clones with DF3A2 clone set as a reference sequence. The start of each row indicates a clone identity and proportion of that clone among 20 of the sequenced clones. Dots are used to denote residues identical to those of the reference clone. Solid-line boxes are CDR regions. Gaps were introduced to improve the alignment and are marked with dashes. The sequence for DF3A2 is SEQ ID NO:13, DF3A4 is SEQ ID NO:14, DF4B12 is SEQ ID NO:15, DT3B3 is SEQ ID NO:16, DT3B5 is SEQ ID NO:18, DT3B4 is SEQ ID NO:19 and DT3H3 is SEQ ID NO:17.
FIG. 32. SPR binding assessment of anti-DM1/4 clone: Binding analysis for sdAb 3A2 against trastuzumab conjugated DM1 (ado-trastuzumab emtansine). Left: Equilibrium binding results with a predicted $K_D$ for 3A2-TDM1 binding of 25 nM. Right: Kinetic assessment with a predicted equilibrium binding assessment of 12.35 nM. These results indicate that 3A2 binds with high affinity to DM1, however, observed multiphasic kinetics leads to a disconnect between the equilibrium and kinetic results. This indicates some trastuzumab conjugated DM1 is readily available for binding whereas other sites may be partially blocked.

The 7 positive clones were further expressed in a small scale with their phagemid vectors for affinity assessment using SPR. The SPR results illustrated the unique clones exhibited varying dissociation kinetics (FIG. 30). Among them, DF3A2, DT3B3 and DT3H3 illustrated the longest dissociation rates. Interestingly, DF3A2, DF4B12, and DF3A4 share the same CDR3 sequence (FIG. 31); however, their dissociation kinetics were remarkably different. This phenomenon indicates that the divergent residues in other CDR and FR regions might be crucially contributing to the binding activity, thus make them appealing targets for future affinity maturation via site-directed mutagenesis.

Figure 28:
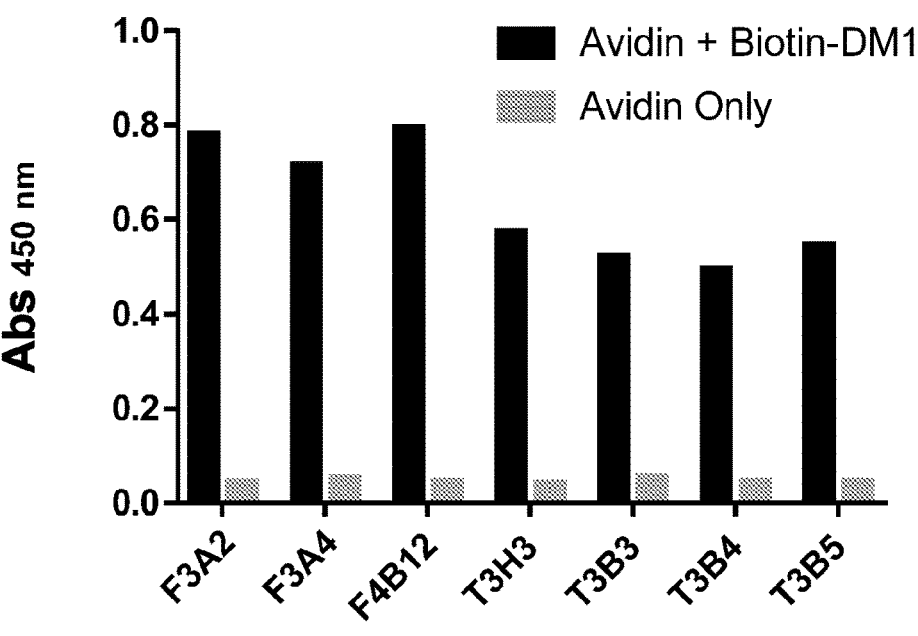
FIG. 28. Positive unique clones from ELISA screening with phage media. Phage media was diluted 5-fold with PBST before adding to ELISA wells coated with either avidin alone or avidin with biotin-DM1. All of the identified clones had significant binding activity to avidin-biotin-DM1 but not to avidin alone.

Anti-DM1/DM4 sdAb DF3A2 clone. The 3A2 clone was predicted to be the best DM1 binder based on the preliminary screening and SPR results (FIGS. 28-30). DNA encoding for 3A2 was synthesized and expressed in the *E. coli* strain SHuffle and purified using nickel chromatography.

Purified 3A2 was used to assess TDM1 binding using SPR. An equilibrium binding assessment indicated 3A2 bound TDM1 with a 25 nM $K_D$ (FIG. 32A), however, biphasic binding kinetics were observed for the equilibrium runs. The biphasic results are likely the result of the varied conjugation sites of DM1 on trastuzumab leading to sites with poor accessibility for 3A2. To obtain a secondary measure of binding kinetics sdAb injected at concentrations between 1.25-10 nM were fit to a 1:1 Langmuir binding model to obtain association and dissociation rate constants. Rate constant fits indicate 3A2 binds TDM1 with a $K_D$ of 12.35 nM (FIG. 32B). Further investigations are being pursued to determine if 3A2 binds free DM1 with equivalent affinity.

Binding affinity was estimated with a $K_D$ of 12.35 nM via SPR with immobilized T-DM1. Antagonism of DM4 by DF3A2 sdAbs in vitro was evaluated via MTT cell viability assay with Lovo and MOLM-14 cells. The $IC_{50}$ of DM4 was 35 and 18 nM in Lovo and MOLM-14 cells, respectively. DF3A2 was able to inhibit the cytotoxicity of DM4 by 11-fold in Lovo cells, and 2.1-fold in MOLM-14 cells. (FIG. 33).

DF3A2 Amino Acid Sequence (SEQ ID NO: 13)

QVQLQESGGGLVQPGGSLRLSCAASGGIFGISYMGWYRQAPGKQREPVA
LITSGGDTAYGDSVKGRFAISRDNAKNTVYLQMNSLKPDDTSAYYCAAG
FYRSDSPNRYDYWGQGTQVTVSS

Figure 34:
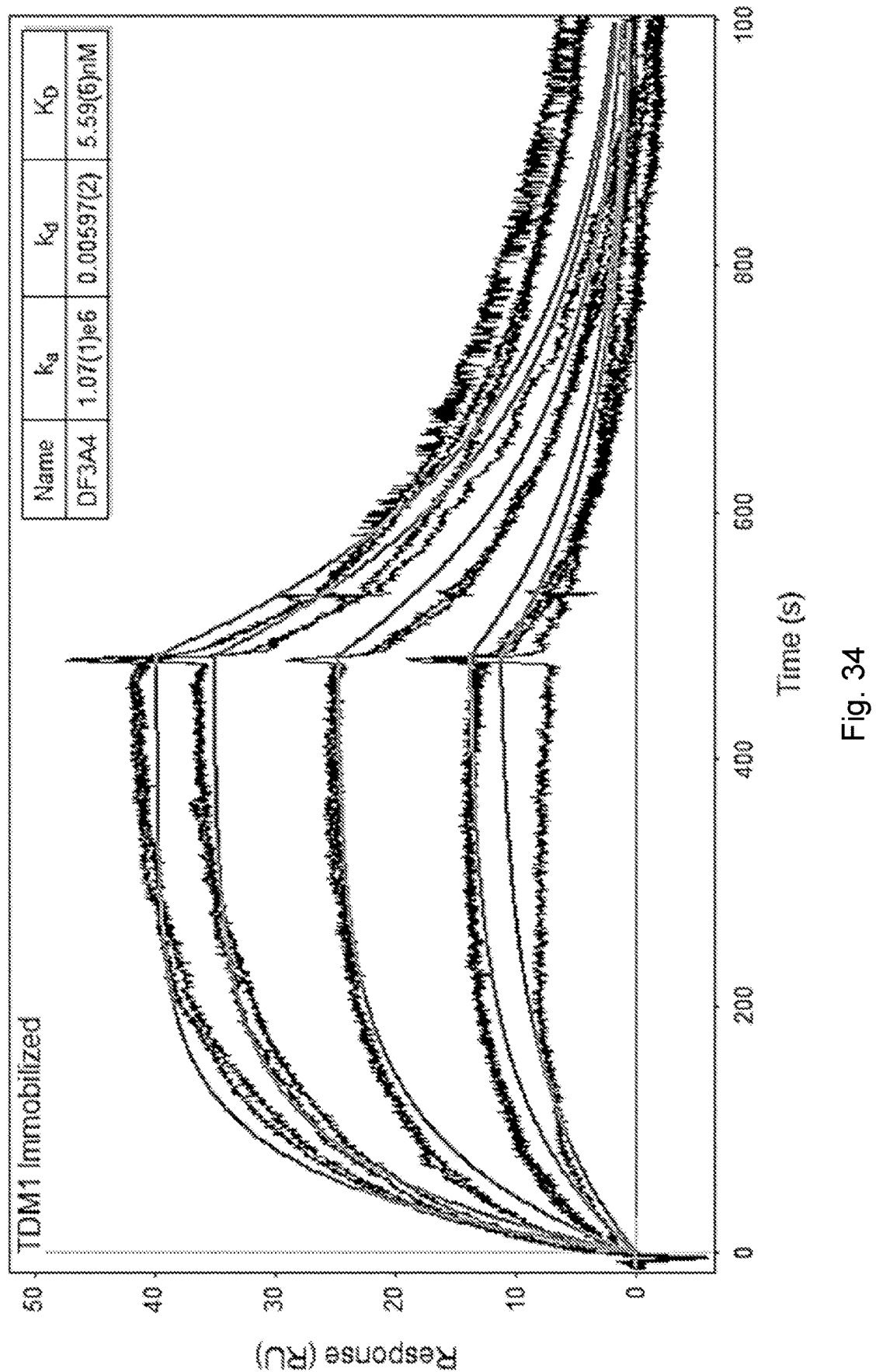
FIG. 34. SPR binding assessment of DF3A4: Binding analysis for sdAb DF3A4 against trastuzumab conjugated DM1 (ado-trastuzumab emtansine). Kinetic assessment with a predicted equilibrium binding assessment of 5.59 nM.

Anti-DM1/DM4 sdAb DF3A4 clone. Binding affinity was estimated with a $K_D$ of 5.59 nM via SPR with immobilized T-DM1 (FIG. 34). Antagonism of DM1 and DM4 by DF3A4 sdAb in vitro was evaluated at two exposure duration, 6 h and 24 h (FIG. 35). In the 6 h exposure period, with the presence of 10 µM DF3A4, the $IC_{50}$ of DM1 was shifted 14.8-fold from 30.48 nM to 450.5 nM, and the $IC_{50}$ of DM4 was shifted 5.88-fold from 7.699 nM to 45.32 nM. In the 24 h exposure period, with the presence of 10 µM DF4B12, the $IC_{50}$ of DM1 was shifted 9.58-fold from 3.067 nM to 29.38 nM, and the $IC_{50}$ of DM4 was shifted 8.66-fold from 0.7131 nM to 6.175 nM.

DF3A4 Amino acid sequence (SEQ ID NO: 14)

QVQLQESGGGLVQPGGSLRLSCAASGSIFGISYMGWYRQAPGKQREPV
ALITSGGSTYYADSVKGRVTISRDNAKKTVYLQMNSLRPEDTSTYYCA
AGFYRSDSPNRYDYWGQGTQVTVSS

Figure 36:
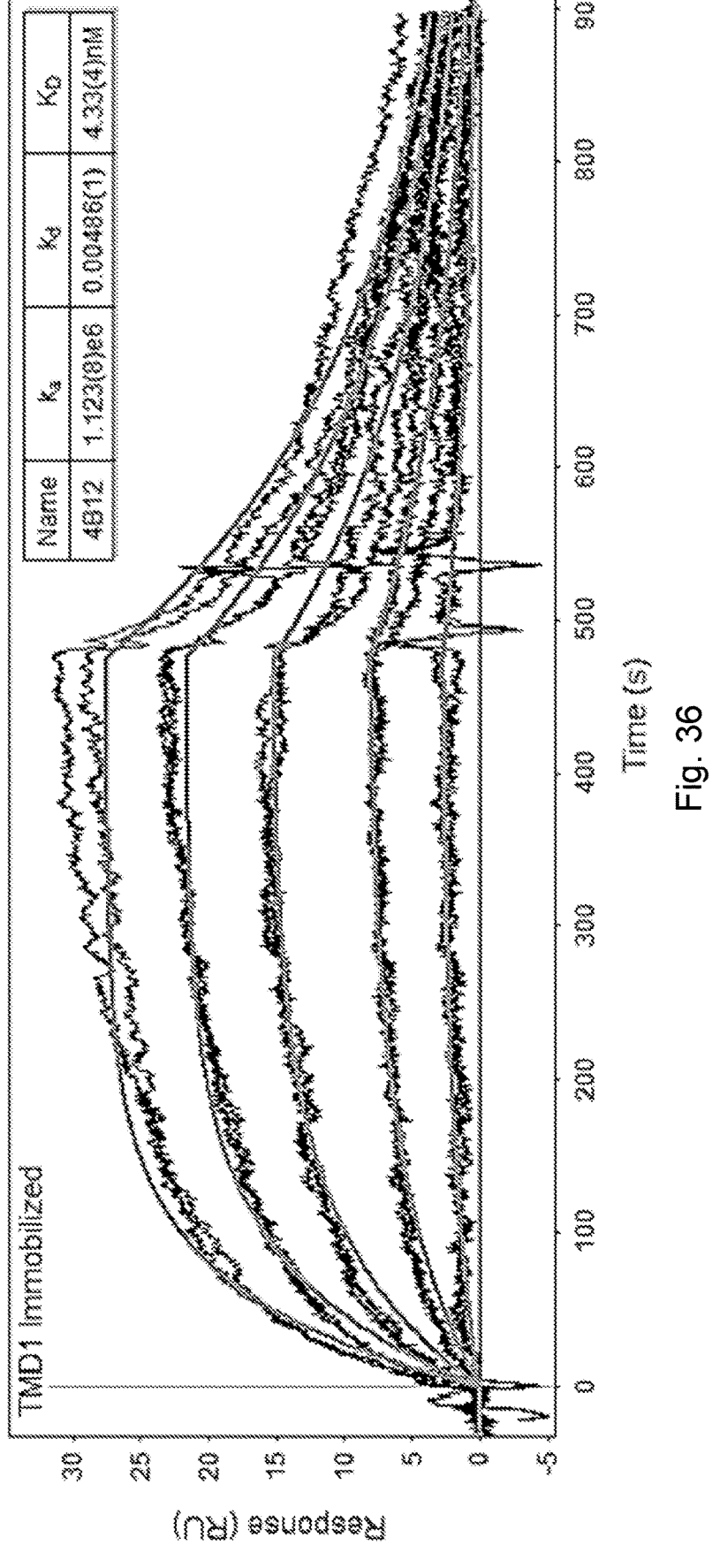
FIG. 36. SPR binding assessment of DF4B12: Binding analysis for sdAb DF4B12 against trastuzumab conjugated DM1 (ado-trastuzumab emtansine). Kinetic assessment with a predicted equilibrium binding assessment of 4.33 nM.

Anti-DM1/DM4 sdAb DF4B12 clone. Binding affinity of DF4B12 was estimated with a $K_D$ of 4.33 nM via SPR with immobilized T-DM1 (FIG. 36). Antagonism of DM1 and DM4 by DF4B12 sdAb in vitro was evaluated at two exposure duration, 6 h and 24 h (FIG. 37). In the 6 h exposure period, with the presence of 10 µM 4B12, the $IC_{50}$ of DM1 was shifted 53-fold from 22.15 nM to 1.174 and the $IC_{50}$ of DM4 was shifted 15.5-fold from 21.53 nM to 334.3 nM. In the 24 h exposure period, with the presence of 10 µM DF4B12, the $IC_{50}$ of DM1 was shifted 105.5-fold from 2.124 nM to 224.1 nM, and the $IC_{50}$ of DM4 was shifted 9.4-fold from 1.837 nM to 17.22 nM.

DF4B12 Amino acid sequence (SEQ ID NO: 15)

EVQLVESGGGLVQPGGSLRLSCAASGSIFGISYMGWYRQAPGKQREPVALI
TSGGDTAYGDSVKGRFTISRDNAKNTVYLQMNSLTPEDTSTFYCAAGFYRS
DSPNRYDYWGQGTQVTVSS

-continued

Additional Unique sdAb clones with positive ELISA
binding
DT3B3

(SEQ ID NO: 16)

EVQLVESGGGLVQAGGSLRLSCALSGGTLRSYTMGWIRQAPGKEREFVAGN
RWSGGRTYYADSVKGRFTISGDNAENTVYLQMNSLKPEDTAVYYCTADVTE
YGEDSSAYWGRGTQVTVSS

DT3H3

(SEQ ID NO: 17)

EVQLVESGGGLVQPGGSLRLSCAASGRTFSHDHMGWFRQAPGKEREFVAAI
SWTSSTYYGDSVKGRFTISRSNAKNTVYLQMNSLKPEDTAIYYCSWGVGYW
GQGTQVTVSS

DT3B5

(SEQ ID NO: 18)

QVQLVQSGGGLVQPGGSLRLSCTASGRTFSRYTMGWFRQAPGKEREFVAAI
STGGLRQYFGDSVRGRCTISRDNAKSTVYLQMDSLKPEDTAVYYCAANWGT
SYYWGQGTQVTVSS

DT3B4

(SEQ ID NO: 19)

QVQLQESGGGLVQAGDSLRLSCTASGRTFSRYTMGWFRQAPGKEREFVAAI
STGGLRQYFGDSVRGRCTISRDNAKNTVYLQMDSLKPEDTAVYYCAATGNE
YHWGRGTQVTVSS

DF4C7

(SEQ ID NO: 20)

EVQLVESGGGLVQPGGSLSLSCAAAGRIATINAMGWIRQAPGKEREFVAAV
SWSGGSTYYSESVKGRFTVSRDNGKNTVYLQMNSLKPEDTAVYYCNAAGTF
YLDDPSYHRSFTSWGQGTQVTVSS

DF4B7

(SEQ ID NO: 21)

QVQLQESGGGLVQPGGSLRLSCAASGRTFSVYTMGWFRQAPGKEREFVAAI
TRNGGNTYYGDSVKGRFTISRANAKNTVYLQMNSLKPEDTAVYYCNAAGTF
YLDDPSYHRSFTSWGQGTQVTVSS

DF4D12

(SEQ ID NO: 22)

EVQLVESGGGLVQAGGSLRLSCVVSGRTFSTYTMGWIRQAPGKEREFVAGI
RWSGGRTYYADSVKGRFTISGDNAENTVYLQMNSLKPEDTAVYYCNAAGTF
YLDDPSYHRSFTSWGQGTQVTVSS

DF4D11

(SEQ ID NO: 23)

QVQLQESGGGLVQVGGSLRLSCAASGRTFSINTMGWFRQAPGKEREFVAAI
SWRGETIYYADSVRGRFTFSRDNAKNTVYLQMNSLKPEDTAVYYCAADVRT
VVGTDYGMHYWGKGTQVTVSS

DF4B10

(SEQ ID NO: 24)

EVQLVESGGGLVQPGGSLRLSCVASGFTFSSYWMYWVRQAPGKGLEWVSGI
DNGGGSTYYADSVKGRFTISRDNAENTLYLQMNSLKPEDTAVYYCAAKHYY
SDLERRYDYWGQGTQVTVSS

DF4A11

(SEQ ID NO: 25)

QVQLQESGGGLVQAGGSLRLACAASGGHSGLTFSRYAMGWFRQAPGKEREF
VAAISQGGGSTYYSDPVKGRFTISRDHAKKQVYLQMDSLKPEDTAVYYCNW
HSDYPRNQLYWGQGTQVTVSS

DF3A1

(SEQ ID NO: 26)

EVQLVESGGGLVQPGGSLRLSCAASGSIFGISYMGWYRQAPGKQREPVALI
TSGGDTAYGDSVKGRFTISRDNAKNTVYLQMNSLKPEDTAVYYCNAQSAWR
RDDYWGQGTQVTVSS

DF4C12

(SEQ ID NO: 27)

EVQLVESGGGLVQAGGSLRLSCAASGRTFNNYDMGWLRQAPGKGREFVASI
NWSGTTKYYADSAKGRFTIDRDDAKSMAYLQMNSLKPEDTAVYYCAAIGNE
YYWGQGTQVTVSS

EXAMPLE 5

Figure 38:
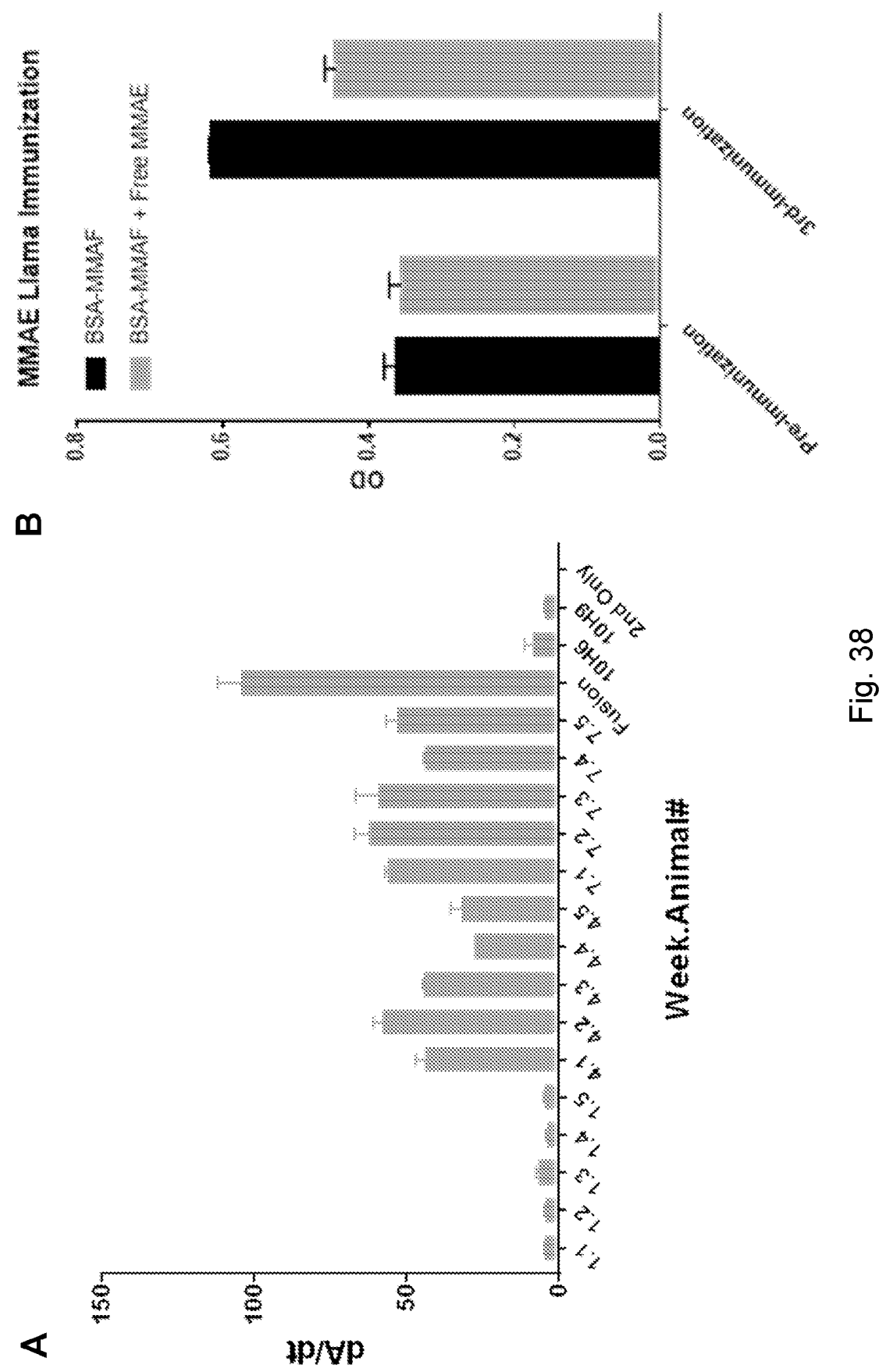
FIG. 38. Evaluation of polyclonal antibody response to MMAE/MMAF from mouse and llama plasma A) Balb/c plasma responses over the course of three immunizations of 50 µg of KLH-MMAF in incomplete Freund's adjuvant. Plasma at the time of the fusion had a high response to BSA-MMAF based on ELISA. B) Llama plasma responses over the course of 3 immunizations of approximately 150 µg of KLH-MMAF in incomplete Freund's adjuvant. Plasma was pre-incubated with free drug to compete for binding to BSA-MMAF. The third immunization demonstrated antibodies present within llama plasma that bind to free MMAE.

This example describes auristatin antagonists.
Evaluation of Monomethyl Auristatin E (MMAE) Antagonists Mice were immunized with KLH-MMAF in order to produce antibodies against MMAE. Plasma samples were collected from immunized mice over the course of immunization and evaluated for binding to BSA-MMAF by ELISA. Over seven weeks, mice responded positively to KLH-MMAF, where the highest responding mouse was selected for fusion to mouse myeloma SP2/0 cells (FIG. 38A). Mouse hybridoma were grown for two weeks after the fusion, where established cell colonies were tested for binding to BSA-MMAF. Positive cells were then selected for subcloning by single cell picking to develop monoclonal antibodies. Colonies were grown for another two weeks and then tested for binding via ELISA.

Figure 39:
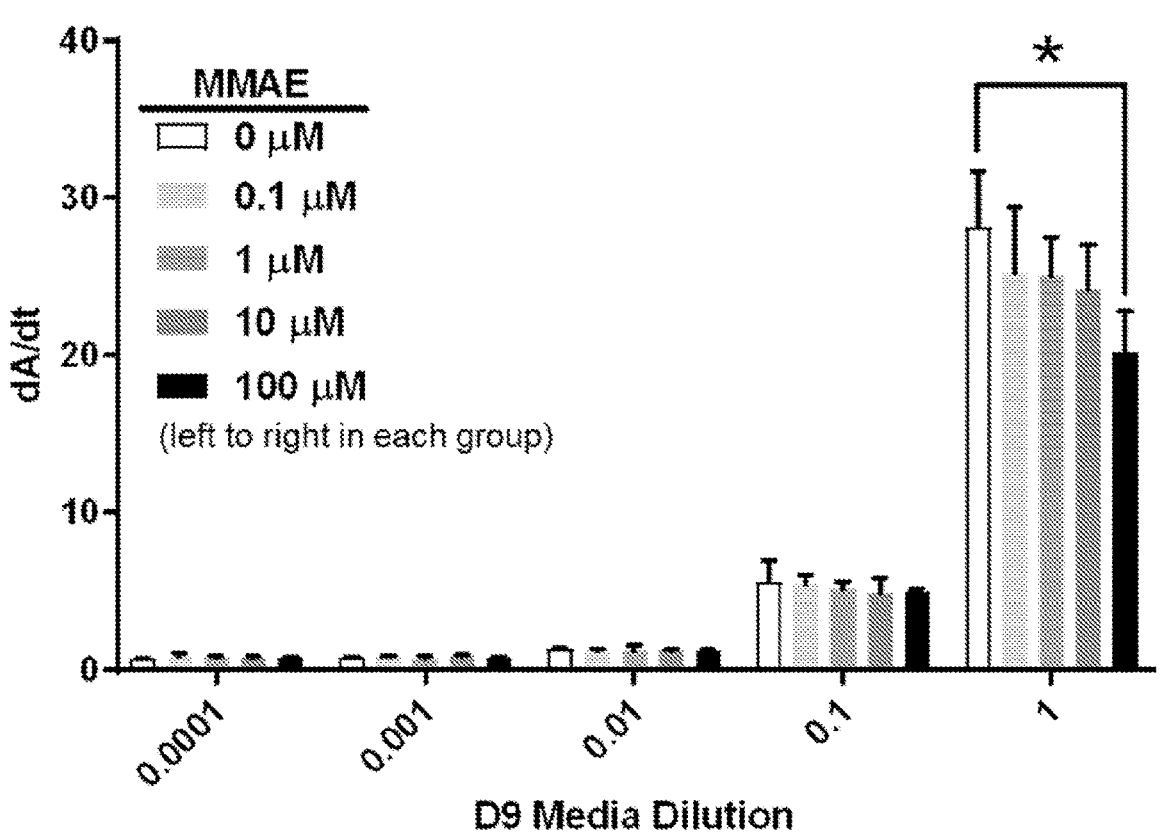
FIG. 39. Competitive ELISA with anti-auristatin IgM hybridoma (D9) media and various MMAE concentrations with BSA-MMAF coated ELISA plates. IgM within media is significantly inhibited by only 100 µM of MMAE.

Anti-MMAF/MMAE IgM D9 Clone. The highest responding colony, D9, was then confirmed for monoclonality by carrying out a second single cell picking. Although D9 was established as monoclonal, the antibodies being produced by this hybridoma were determined to be IgM. IgM is not an optimal construct, but experiments with IgMs can provide insight into mechanisms of inhibition. To determine whether the IgM is inhibited by MMAE, D9 hybridoma media was incubated with MMAE at various concentrations before incubating on an ELISA plate coated with BSA-MMAF. Based on the results, IgM was only significantly reduced by high concentrations of MMAE (FIG. 39). Due to the low inhibition of IgM by MMAE, difficulty of isolating anti-auristatin IgG, and stability issues with scFv production, a llama was immunized with KLH-MMAF to produce single domain antibodies against MMAF. Following the third immunization, plasma was evaluated for production of antibodies against BSA-MMAF. As shown in FIG. 38B, llama plasma responded positively to BSA-MMAF coated ELISA plates. Binding was also inhibited when plasma was incubated with MMAE, indicating antibodies bind to free drug.

Figure 40:
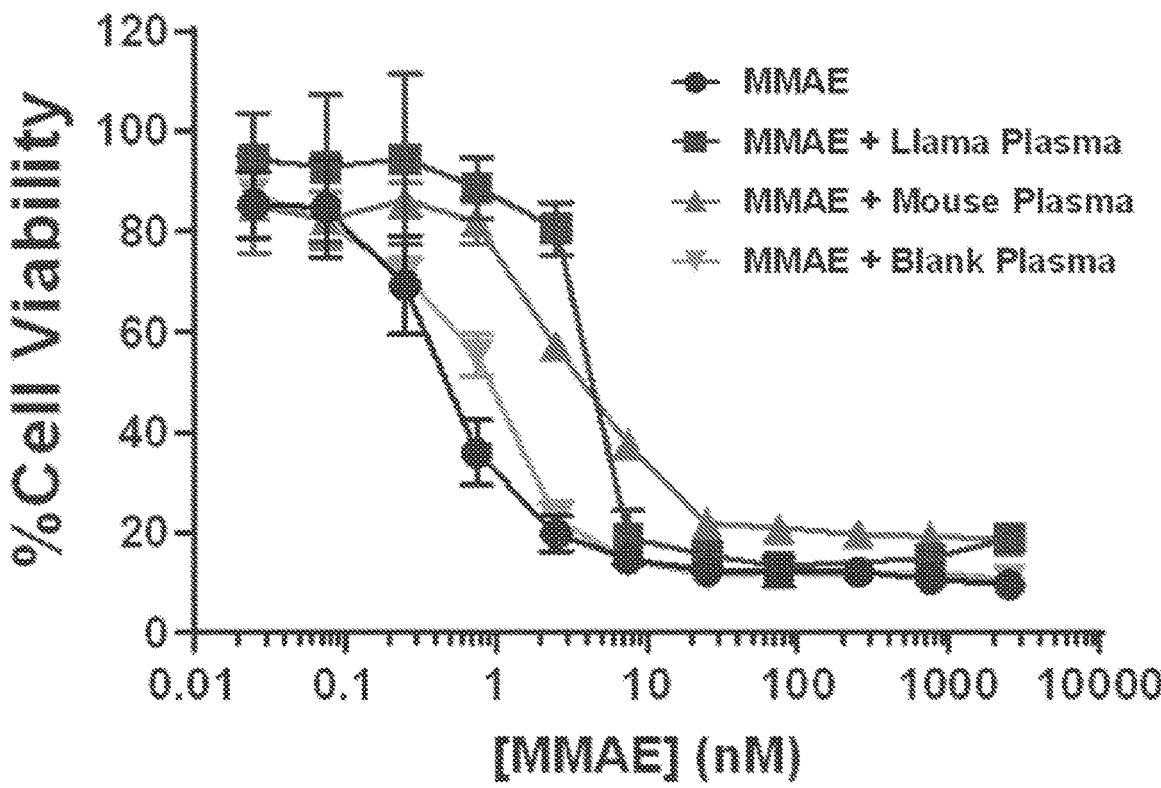
FIG. 40. Cytotoxicity of MMAE in NCI-N87 cells with or without 1:50 diluted plasma. MMAE demonstrated the highest cytotoxicity at 0.4962±0.03272 nM. When incubated with llama or mouse plasma, the cytotoxicity of MMAE was significantly reduced to 3.699±0.2973 nM and 3.393±0.3145 nM, respectively. Blank plasma did not significantly alter the cytotoxicity of MMAE.
Figure 41:
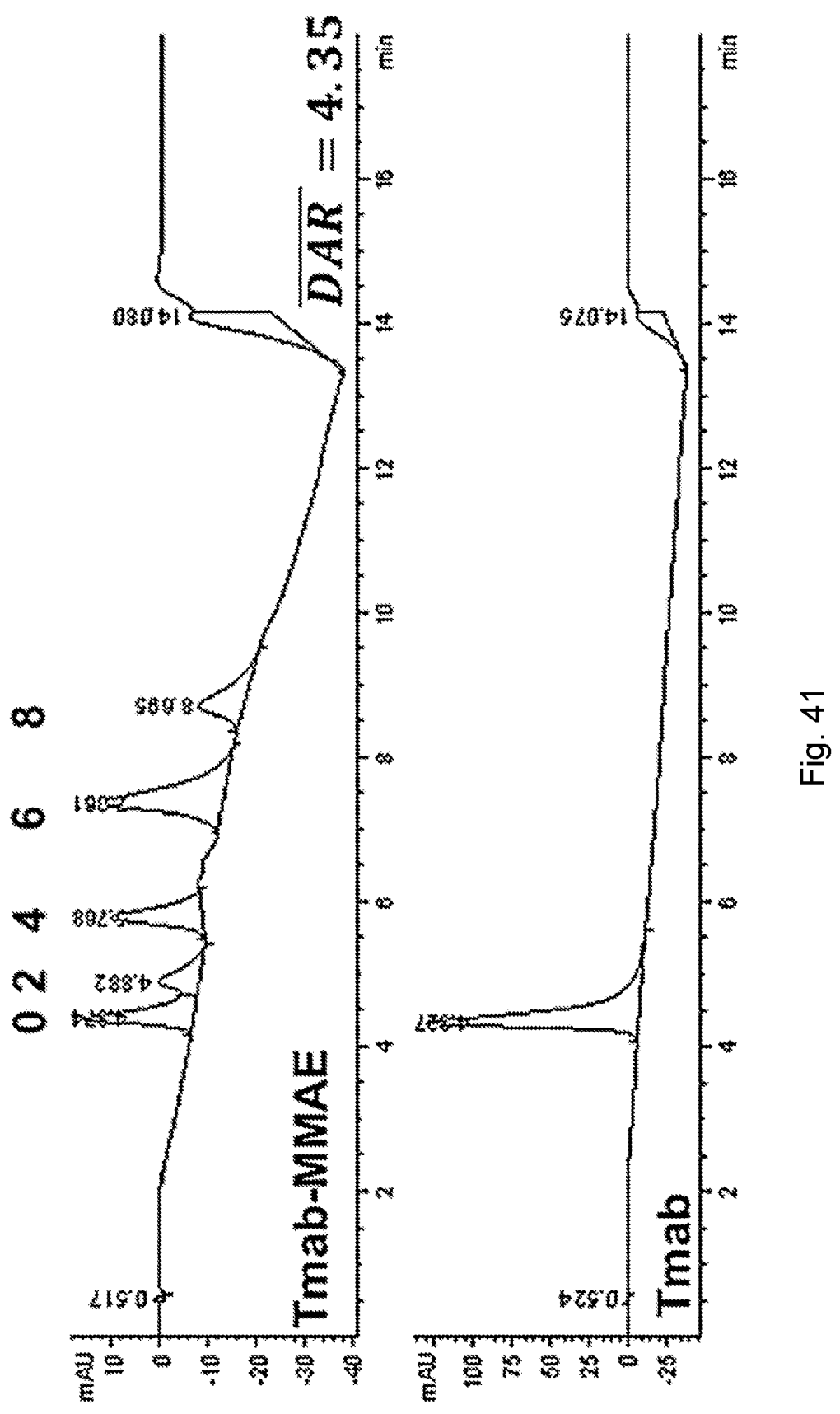
FIG. 41. Trastuzumab-MMAE construction and cell cytotoxicity evaluation with mouse and llama plasma co-incubation. A) Hydrophobic Interaction Chromatography (HIC) analysis of T-vc-MMAE and Tmab demonstrating an average DAR of 4.35 for T-vc-MMAE. B) Cytotoxicity of T-vc-MMAE in NCI-N87 cells with (squares) or without (black circles) llama plasma and Tmab only (upright triangles). T-vc-MMAE demonstrated the highest cytotoxicity at 0.1876±0.009747 nM. When incubated with llama, there was a slight shift in cytotoxicity of T-vc-MMAE to 0.2505±0.1011 nM (p=0.4289).
Figure 41:
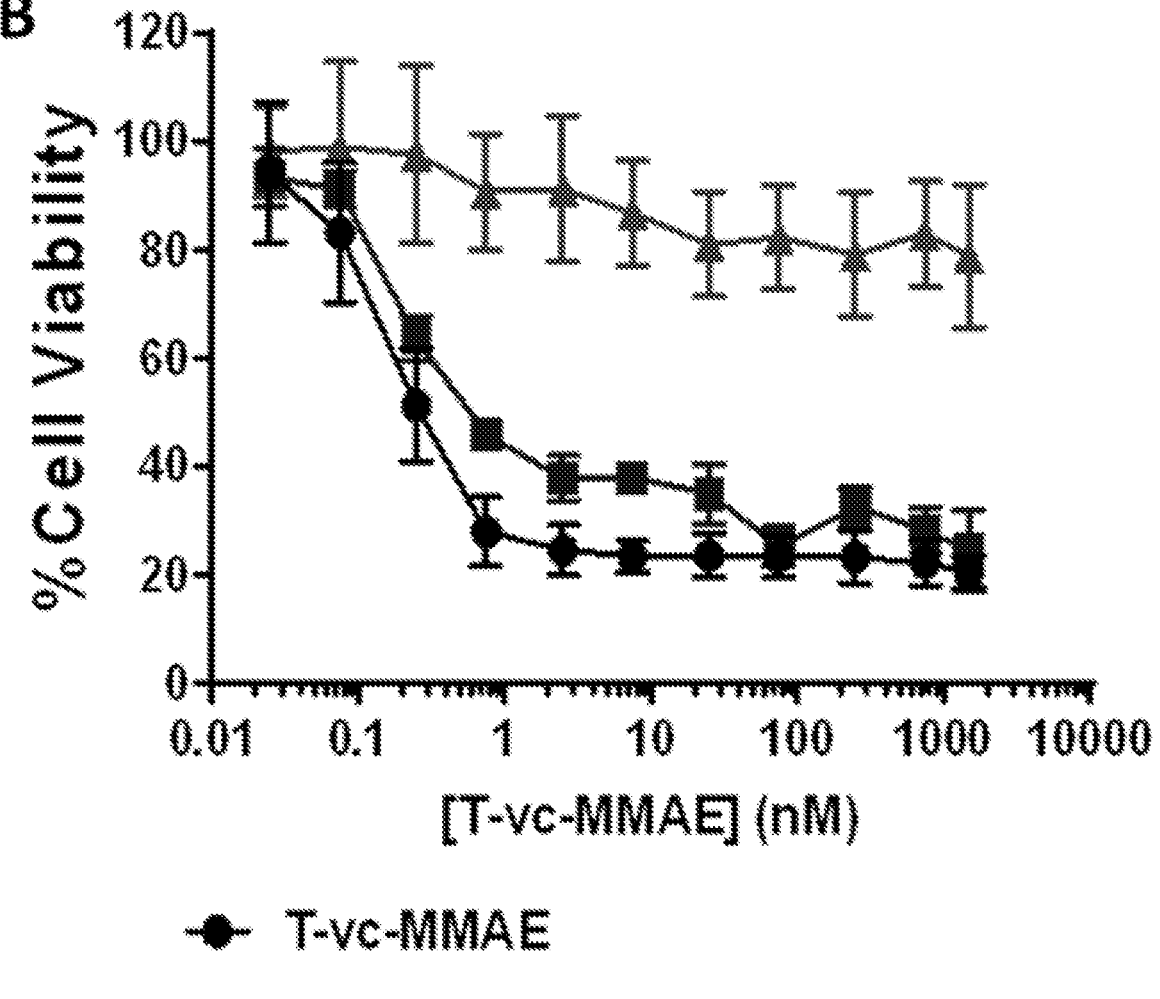

In tandem with generation of the sdAb library, cell cytotoxicity assays were conducted with mouse and llama plasma to observe the effect on MMAE and T-vc-MMAE exposed NCI-N87 cells. Incubation for 96 h with MMAE demonstrated high cytotoxicity, with an $IC_{50}$ value of 0.4962±0.03272 nM. When incubated with llama or mouse plasma, the cytotoxicity of MMAE was significantly reduced to 3.699±0.2973 nM and 3.393±0.3145 nM, respectively. Blank plasma did not significantly alter the cytotoxicity of MMAE (FIG. 40). T-vc-MMAE was synthesized in-house and DAR was determined by HIC (DAR=4.35) (FIG. 41A). The $IC_{50}$ of T-vc-MMAE for NCI-N87 was determined to be 0.1876±0.009747 nM. When incubated with llama plasma, there was a slight shift in cytotoxicity of T-vc-MMAE to 0.2505±0.1011 nM, but this was determined to be insignificant (p=0.4289) (FIG. 41B).

Figure 43:
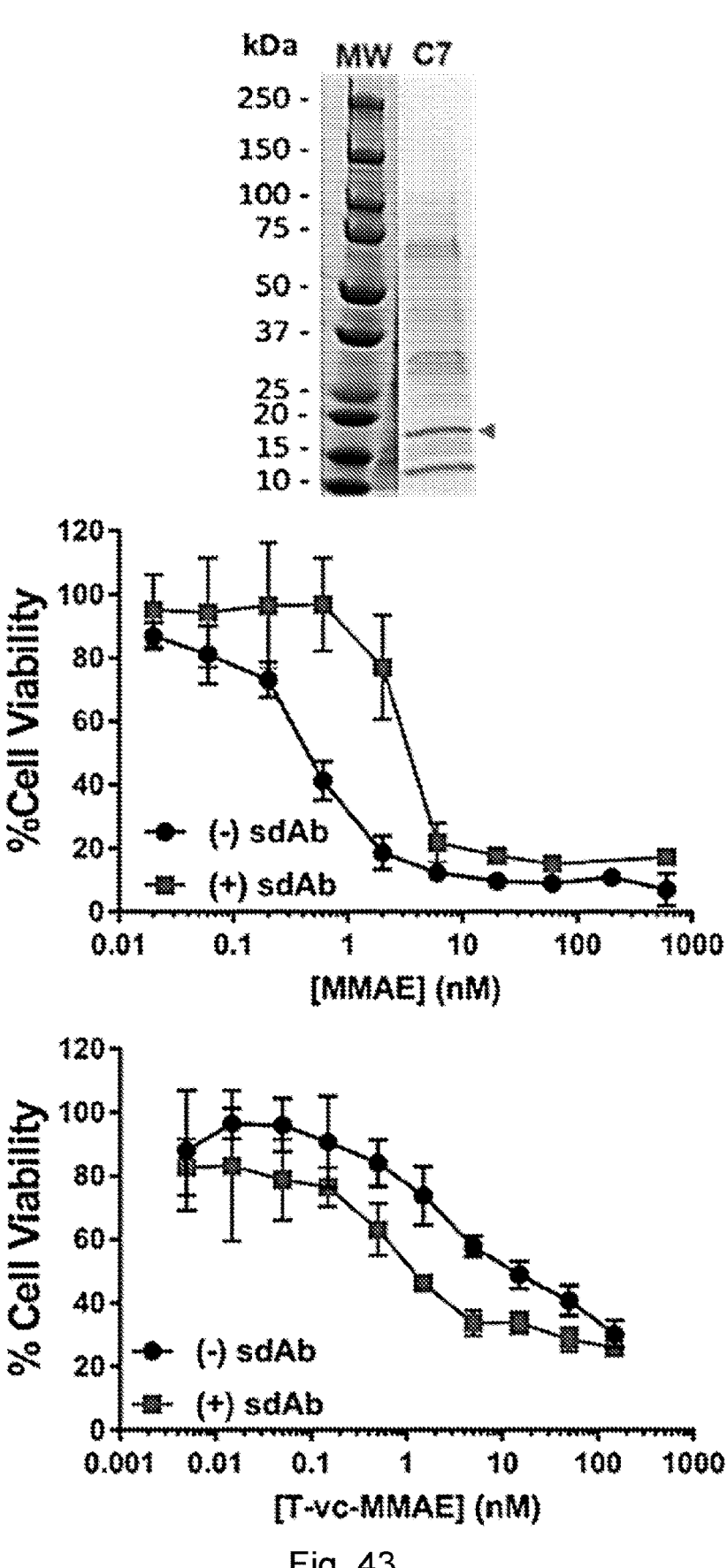
FIG. 43. Purification of C7 sdAb from BL21(DE3) transformed *E. coli* cells and inhibitory cell cytotoxicity assays. C7 sdAb was expressed to the periplasm using a pelB leader sequence and purified using IMAC Ni-NTA resin. SDS-PAGE analysis revealed a band at approximately 16 kDa (arrow), indicating expressed sdAb. Although the product was crude, it was employed in cell cytotoxicity assays. NCI-N87 cells were seeded at a density of 10,000 cells/well and pulse with treatment solutions for 2 h. After treatment removal and washing, cells were incubated for 96 h with sdAb prep, diluted 1:6.67 with fresh culture medium. Cell viability was measured using an MTT assay. sdAb prep inhibited the cytotoxicity of MMAE by 5.6-fold, but enhanced cytotoxicity of T-vc-MMAE by 5.2-fold.

From the single domain library, there were nine positive hits from three rounds of panning against BSA-MMAF/T-vc-MMAE. The screening of isolated colonies determined all were inhibited by incubation with free MMAE (FIG. 42), with three >10-fold inhibition. One colony, C7 was selected for infection of BL21(DE3) cells and protein expression. The C7 sdAb was purified using IMAC Ni²⁺-NTA resin and used for cell cytotoxicity with MMAE and T-vc-MMAE. NCI-N87 were pulsed with MMAE and T-vc-MMAE for 2 h and then incubated for 96 h in presence or absence of sdAb protein. Based on these experiments, sdAb prep inhibited the cytotoxicity of MMAE by 5.6-fold, but enhanced cytotoxicity of T-vc-MMAE by 5.2-fold (FIG. 43). The inhibition of free MMAE cytotoxicity and enhancement of trastuzumab-MMAE toxicity is consistent with results obtained for trastuzumab deruxtecan with 8C2 mAb.

```
Amino acid sequences
MA3
                                     (SEQ ID NO: 28)
QVQLVQSGGGLVQAGDSLTLSCVASGRPFRRYSIGWFRQAPGKEREFVAA
ISWSGSSTSYLDSLKGRFTISRDNAKNTVYLQMNSLKPEDTAVYYCNVRA
RATMFRSPSDYWGQGTQVTVSS MB2
                                     (SEQ ID NO: 29)
QVQLVQSGGGLVQPGGSLRLSCAASGRTLRSYAMGWFRQAPGKEREFVAA
ISWSGGSTYYADSVKGRFTISRDGVKNTVYLQMNSLKPEDTAVYYCSARV
LFRTSWGQGTQVTVSS MC7
                                     (SEQ ID NO: 30)
QVQLVQSGGGLVQAGGSLRLSCVASGRTFSMYRMGWFRQAPGKEREFVAS
IRWSGGSTYYTDSVKDRFTISRDNAKNTVYLQMNSLKPEDTAVYYCAADP
VWRLNSWYRGAVGYWGQGTQVTVSS
```

EXAMPLE 6

This examples describes PDB antagonists.
Evaluation of Pyrrolobenzodiazepine (PBD) Antagonists From the single domain library, there were five positive hits from three rounds of panning against BSA-PBD. The screening of isolated colonies determined all were inhibited by incubation with free PBD (FIG. 44A), with 2 colonies inhibited >2-fold. The colony, E9, demonstrated a 5.33-fold inhibition in binding with addition of free PBD. These colonies can be sequenced.

EXAMPLE 7

This example further describes affinity maturatin of some of the anti-maytansinoid sdAbs.

Materials and Methods

Mutagenesis

Random mutations were introduced into the original anti-maytansinoid sdAbs through error-prone PCR. In summary, optimized DNA of the anti-maytasinoid clones DF3A2, DF3A4, DF4B12, DF4D12, DF4B7, and DF4C7 were amplified through PCR under error-inducing conditions with the following reagents and volumes: 5 μL 10× Standard Taq buffer (100 mM Tris-HCl, 0.5 M KCl), 11 μL 25 mM MgCl₂, 2 μL 25 mM dCTP, 2 μL 25 mM dTTP, 2 μL 5 mM dATP, 2 μL 5 mM dGTP, 1 μL template DNA (1 ng/μL), 1 μL 25 mM MnCl₂, 0.5 μL Standard Taq Polymerase (5 U/μL), 0.5 μL 100 μM 5'-MutFor primer, 0.5 μL 100 μM 3'-MutRev primer, 22.5 μL DNAse/RNAse free H₂O. PCR primers were designed to facilitate the error-prone PCR products to be transferred from pET-22b expression vector for protein expression into pComb3XSS phagemid vector for library construction, and vice versa.

Bio-Panning

Bio-panning was performed to identify high affinity binders targeting DM4. In summary, stock StrepAvidin magnetic beads were blocked with 2% milk PBST for 1 hour at room temperature, then the blocked beads were incubated with 500 μL of biotin-DM4 for 30 minutes before phage binding step. Approximately 10¹² phages in PBST were incubated with the avidin-biotin-DM4 beads for another 1 hour, then washed and eluted via either with free-drug competition method or off-rate method. For the free-drug competition method, bound phages were incubated for 1 hour with 500 μL of 10 nM, 1 nM, and 0.1 nM DM4 in PBS in the first, second, and third round of panning, then the supernatant was collected and used for the subsequent round of panning or screening. For the off-rate method, bound phages were incubated with 1 mL of 1 μM DM4 in PBS overnight at 4° C., then on the next day, the supernatant was discarded, and the remaining bound phages were eluted with trypsin.

Competitive Screening

One hundred clones from the third round of each panning method were screened with phage media. Twenty positive clones from each screening that had highest binding signal to avidin-biotin-DM1/DM4 were rescreened via competitive assay with DM4. Briefly, phage media was diluted 4-fold in PB ST containing free DM4 at the final concentrations of 100 nM, 50 nM or 10 nM, and incubated for 1-hour before the antigen-binding step of ELISA.

Expression and Cytotoxicity Assay

Positive clone sdAbs' DNA in pComb3XSS plasmid was isolated and transferred into pET-22b expression vector in SHuffle cells for expression. SK-BR-3 cells were used to test the anti-DM4 sdAbs effect on DM4 cytotoxicity. Briefly, 2,500 cells/well were seeded into a 96-well plate and allowed to adhere for 24 h before cell culture media was aspirated and replaced with 100 μL of fresh media solution containing with or without 10 μM of anti-DM4 sdAb and a range of DM4 concentration for another 24 h exposure period. The cells were then washed 2 times before replacing with fresh media and allowed to grow for additional 72 h.

Assessment of Affinity via ELISA

To determine the binding affinity of the anti-DM4 sdAbs to DM4-conjugates and free DM4, indirect ELISA and competitive ELISA were employed. Briefly, ELISA plate were coated overnight with 100 μL of neutravidin at different concentration ranging from 1 μg/mL to 10 μg/mL. After blocking with 200 μL of 2% skimmed milk-PBST for 1 h, 100 μL of 1 μM biotin-DM4 solution was added into each well and incubated for 30 min, then 100 μL of purified anti-DM4 sdAb solution at concentration ranging from 0.1 nM to 1 μM was added and incubated for 1 h. Bound sdAbs were detected with HRP conjugated anti-His antibody and TMB substrate. After the linear range of binding was determined via the indirect ELISA, a concentration of anti-DM4 sdAb near the $IC_{50}$ of binding was selected to proceed with competitive ELISA. For the competitive ELISA, anti-DM4 sdAb concentration was held constant as determined from the indirect ELISA and incubated with increasing concentration of DM4 ranging from 0.1 nM to 1 μM.

Results

Bio-Panning and Initial Screening

Figure 45:
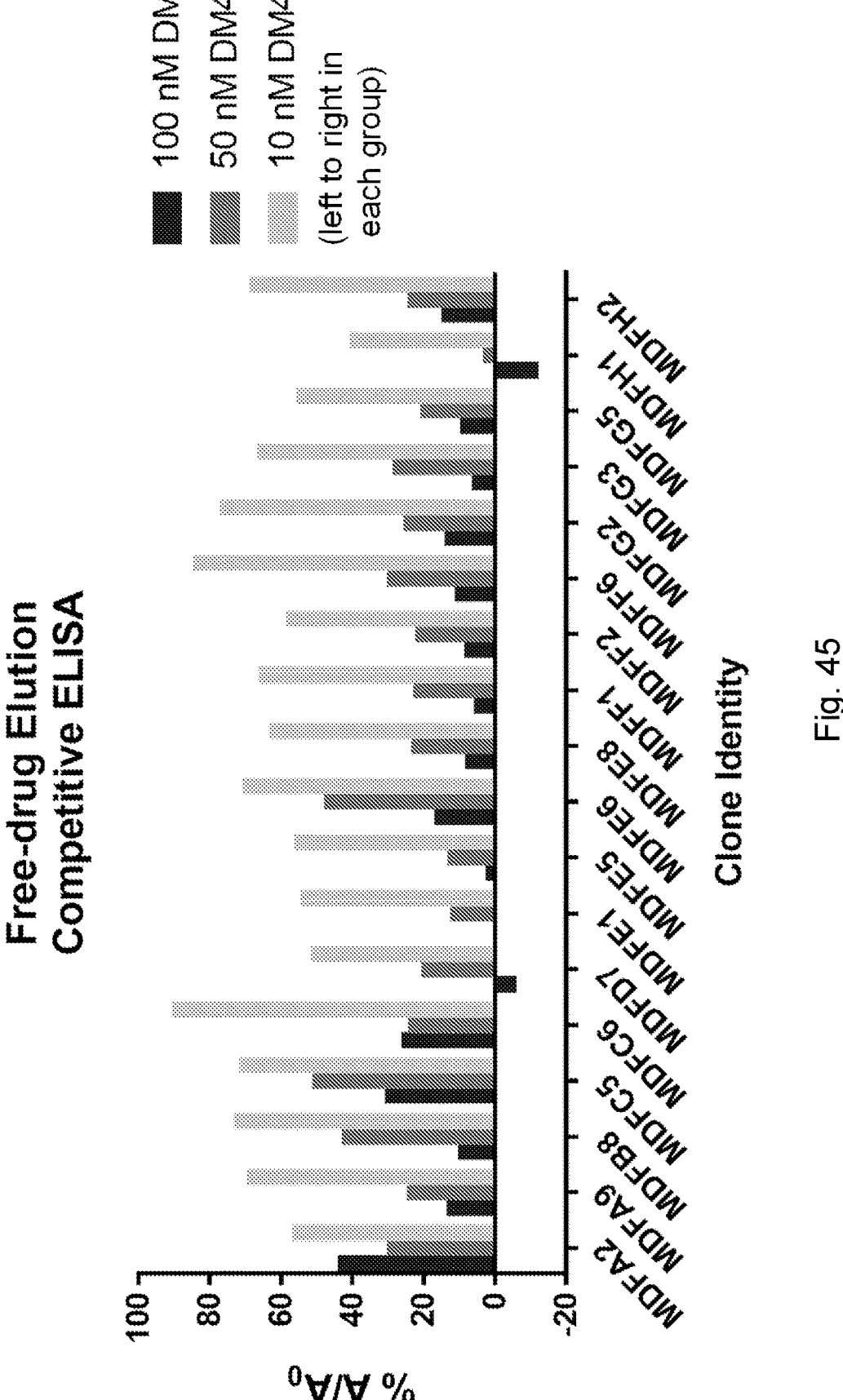
FIG. 45. Competitive binding of phage media with free DM4 from the derivative library. The binding signal of each clone were normalized to their absorbance values without co-incubation of free DM4.

Overall, while most of the original anti-DM1/DM4 sdAbs had their binding signals marginally inhibited when co-incubated with 1 uM of free DM1/DM4 (FIG. 29), all of the positive clones identified from the derivative library had their signals knocked down to the background by the same concentration of free DM4 (data not shown). Further analysis showed that the newly identified clones might have superior binding affinity to free DM4, as most of them had their binding inhibited more than 80% with 100 nM of DM4 co-incubation (FIG. 45). Notably, the two clone MDFH1 and MDOH9, one from each elution method, had more than 50% signal reduction when co-incubated with 10 nM of DM4.

Cytotoxicity Assay

Positive clones identified from screening with phage media were sequenced and expressed as sdAbs. Antagonism of the anti-DM4 sdAbs were evaluated in several cell lines. The $IC_{50}$ of DM4 on SK-BR-3 cells was around 0.3 to 0.4 nM in the absence of the anti-DM4 sdAbs; however, in presence of 10 μM of anti-DM4 sdAbs, DM4 toxicity was reduced up to 250-fold to an $IC_{50}$ around 100 nM (Table 1). The MTT assay result is in agreement with the initial screening results from phage media, in which DMOH9 and DMFH1 were identified as the better binders.

Assessment of Affinity

Affinity of the anti-DM4 sdAbs was determined by competitive ELISA with free DM4. Indirect ELISA was performed for each clone to titrate appropriate conditions including the amount of antigen coating and the concentration of sdAbs used in the competitive ELISA. All of the clones isolated from the mutated library have moderate to high affinity to free DM4 with $K_D$ ranging from 10 nM to 56 nM (Table 1). The estimated $K_D$ result is also in line with the initial screening and cytotoxicity assay, as DMFH1 and DMOH9 are the two clones with better affinity.

TABLE 1

Summarized results from competitive ELISA data and MTT cell cytotoxicity assay data of the characterized clones.

| Clone Identity | Cytotoxicity in SK-BR-3 Cell Line | | | Competitive ELISA |
| | Free DM4 IC50 (nM) | DM4 IC50 with sdAb (nM) | Fold shifted | Estimated KD (nM) |
| --- | --- | --- | --- | --- |
| DMOH9 | 0.2902 | 60.79 | 209.5 | 19.87 |
| DMOF8 | 0.4196 | 43.67 | 104.1 | 26.18 |
| DMFH2 | | 62.67 | 149.4 | 25.16 |
| DMFH1 | 0.3953 | 99.04 | 250.5 | 10.52 |
| DMFF2 | | 37.02 | 93.65 | 56.57 |
| DMFB8 | 0.3988 | 55.92 | 140.2 | N.D. |

Anti-DM1/DM4 sdAb DMFH1 Clone

Summary

Binding affinity was estimated with a Kd of 11 nM to free DM4 via competitive ELISA. Antagonism of DM4 and DM1 by DMFH1 sdAb in vitro was evaluated in SK-BR-3 breast cancer cell line. Over a 24-hour exposure period, with the presence of 10 μM DMFH1, the $IC_{50}$ of DM4 was shifted 254-fold from 0.39 nM to 99 nM, and the $IC_{50}$ of DM1 was shifted 85.6-fold from 4.43 nM to 380 nM. Co-incubation with DMFH1 did not alter the cytotoxicity of Trastuzumab Emtansine (Kadcyla). Antagonism of DM4 by DMFH1 sdAb in vitro was also evaluated in several acute myeloid leukemia (AML) cell lines including Kasumi-3, MV-4-11, MOLM-14, and KG-1. Over a 48-hour exposure period, with the presence of 10 μM DMFH1, the $IC_{50}$ of DM4 was shifted 60.7-fold, 57.2-fold, 38.3-fold, and 50.9-fold in MOLM-14, KG-1, Kasumi-3, and MV-4-11 cell line, respectively.

Experimental Data

DMFH1 Amino Acid Sequence
(SEQ ID NO: 31)
QVQLQESGGGLVQPGGSLRLSCAASGSIFGISYMGWYRQAPGKQREPVA
MITSGGSTYYADSVKGRVTISRDNAKKTVYLQMNSLRPEDASTYYCAAG
CYRSDSPNRYDYWGQGTQVTVSS Competitive binding assessment of DMFH1: Binding activity of DMFH1 against free DM4 was evaluated via competitive ELISA. Estimated binding affinity $IC_{50}$ of DMFH1 to free DM4 is 11 nM.

Figure 46:
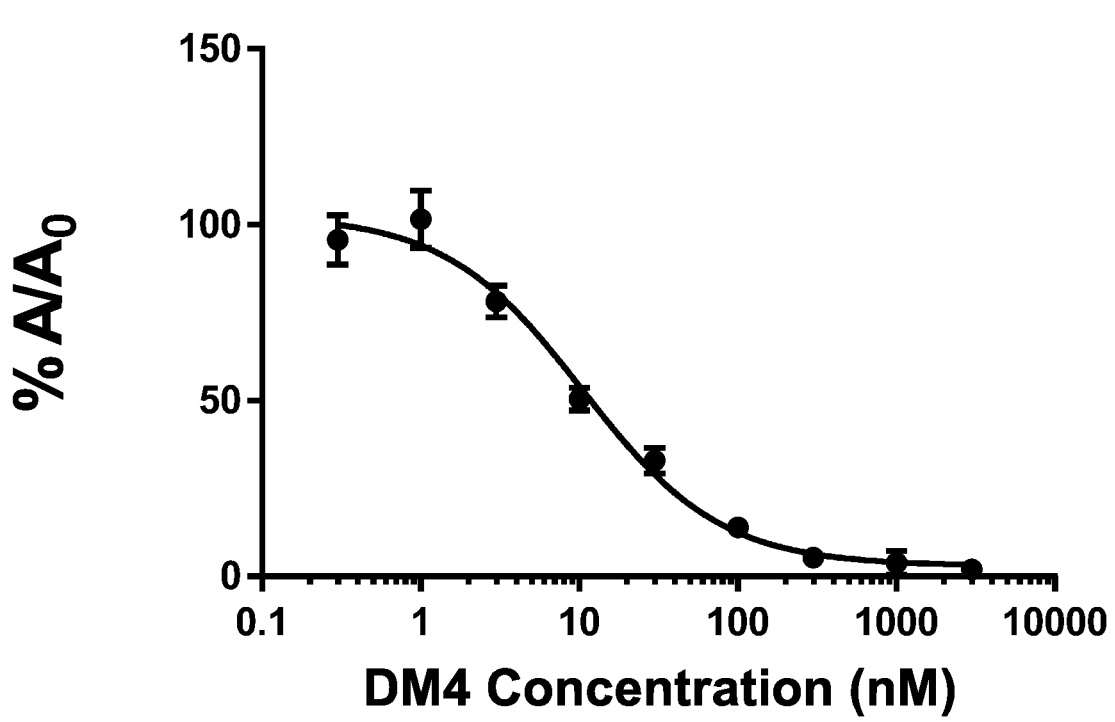
FIG. 46. DMFH1 Competitive ELISA. The binding signal for DMFH1 for immobilized maytansinoid was normalized to binding signal without co-incubation of free DM4. Inhibition of binding to immobilized maytansinoid reflects the binding and affinity of binding of DMFH1 to DM4.
Figure 47:
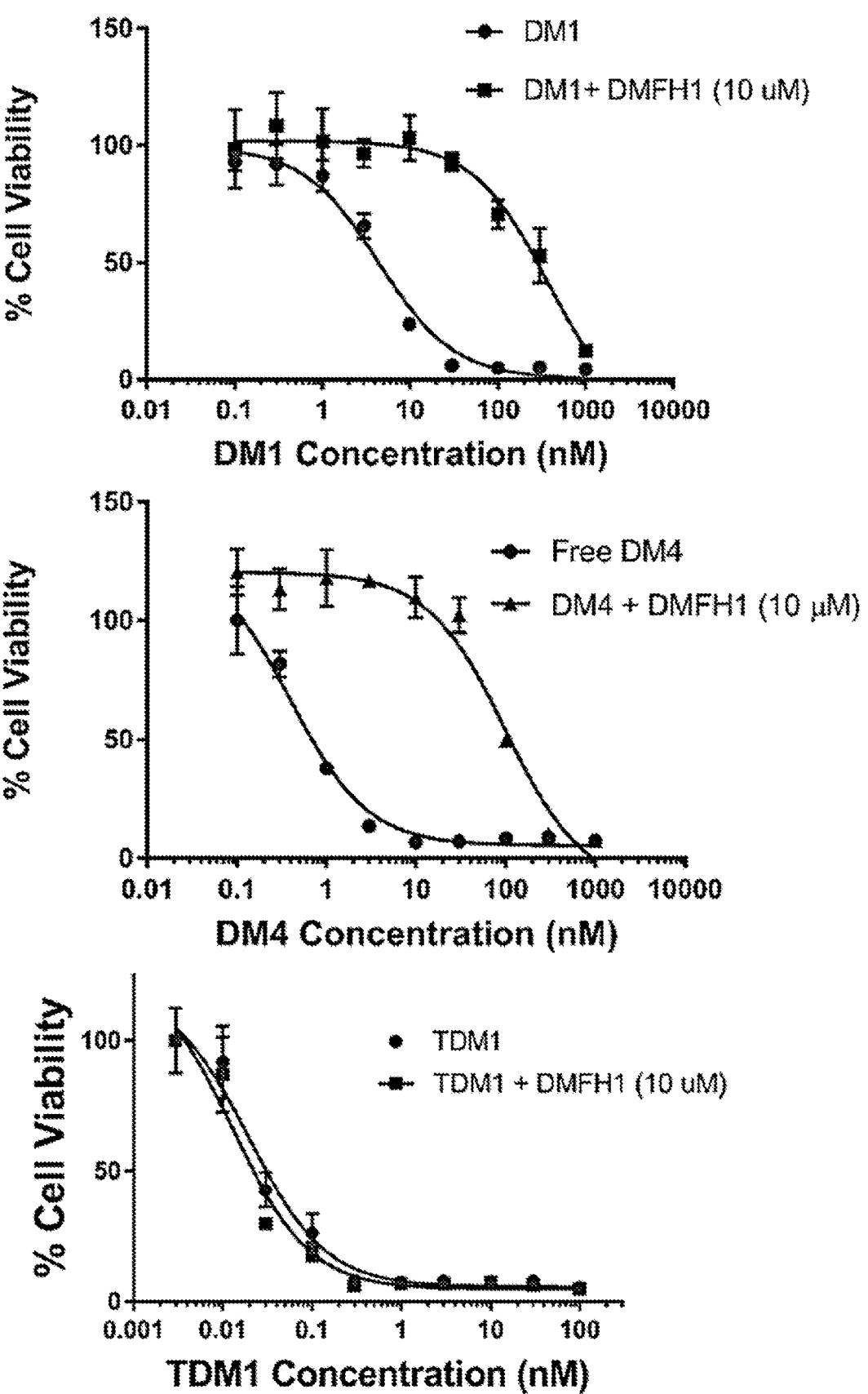
FIG. 47. MTT Cell based assay with DMFH1 in SK-BR-3 breast cancer cell line. Cell cytotoxicity of DM1, DM4, and T-DM1 (Trastuzumab Emtansine) on SK-BR-3 cells with and without 10 μM of DMFH1 sdAb over a 24 h exposure periods.

MTT Cell based assay with DMFH1 in SK-BR-3 breast cancer cell line. Cell cytotoxicity of DM1, DM4, and T-DM1 (Trastuzumab Emtansine) on SK-BR-3 cells with and without 10 μM of DMFH1 sdAb over a 24 h exposure periods. DM1 and DM4 exhibited $IC_{50}$ of 4.43 nM and 0.39 nM. DM1 and DM4 cytotoxicity was inhibited by DMFH1 to 380 nM and 99.0 nM, respectively. (FIG. 46). DMFH1 did not change T-DM1 cytotoxicity significantly, the $IC_{50}$ of T-DM1 with and without 10 μM of DMFH1 was 19.4 pM and 12.8 pM, respectively (FIG. 47).

Figure 48:
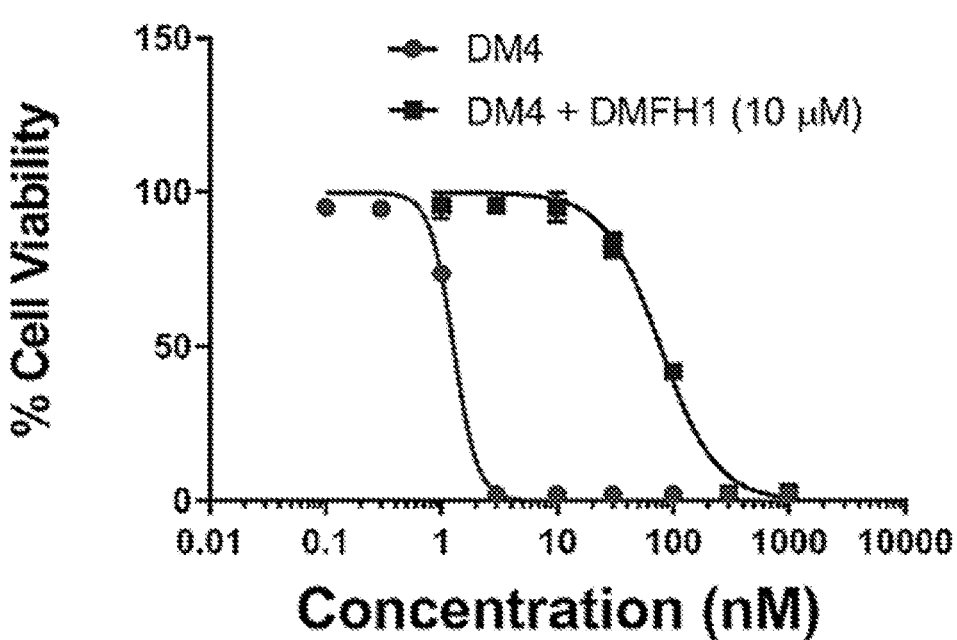
FIG. 48. MTT Cell based assay with DMFH1 in AML cell lines. Cell cytotoxicity of DM4 on MOLM-14, KG-1, Kasumi-3, MV-4-11 cells with and without 10 μM of DMFH1 sdAb over a 48-hour exposure periods.

MTT Cell based assay with DMFH1 in AML cell lines. Cell cytotoxicity of DM4 on MOLM-14, KG-1, Kasumi-3, MV-4-11 cells with and without 10 μM of DMFH1 sdAb over a 48-hour exposure periods. (FIG. 48). In MOLM-14, with and without DMFH1, DM4 exhibited $IC_{50}$ of 1.28 nM and 77.7 nM, respectively. In KG-1, with and without DMFH1, DM4 exhibited $IC_{50}$ of 3.18 nM and 182 nM, respectively. In Kasumi-3, with and without DMFH1, DM4 exhibited $IC_{50}$ of 6.04 nM and 231 nM, respectively. In MV-4-11, with and without DMFH1, DM4 exhibited $IC_{50}$ of 1.27 nM and 64.6 nM, respectively.

Anti-DM1/DM4 sdAb DMOH9 Clone

Summary

Binding affinity was estimated with a Kd of 20 nM to free DM4 via competitive ELISA. Antagonism of DM4 by DMOH9 sdAb in vitro was evaluated in SK-BR-3 cell line. Over a 24 h exposure period, with the presence of 10 μM DMOH9, the $IC_{50}$ of DM4 was shifted 210-fold from 0.29 nM to 61 nM.

Experimental Data

```
DMOH9 Amino Acid Sequence
                                    (SEQ ID NO: 32)
QVQLQESGGGLVQPGGSLRLSCAASGSIFGITYMGWYRQAPGKQREPVA
MITSGGSTYYADSVKGRVTISRDNAKKTVYLQMNSLRPEDTSTYYCAAG
YYRSDSPNRYDYWGQGTQVTVSS
```

Figure 49:
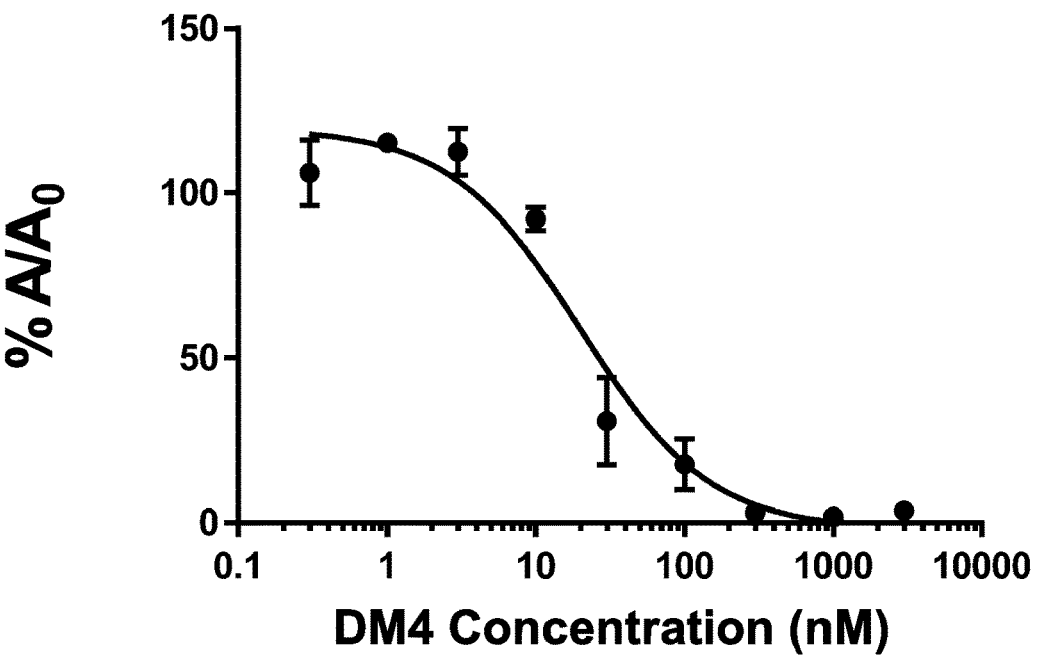
FIG. 49. Competitive binding assessment of DMOH9: Binding activity of DMOH9 against free DM4 was evaluated via competitive ELISA.

Competitive binding assessment of DMOH9: Binding activity of DMOH9 against free DM4 was evaluated via competitive ELISA. Estimated binding affinity $IC_{50}$ of DMOH9 to free DM4 is 20 nM (FIG. 49).

Figure 50:
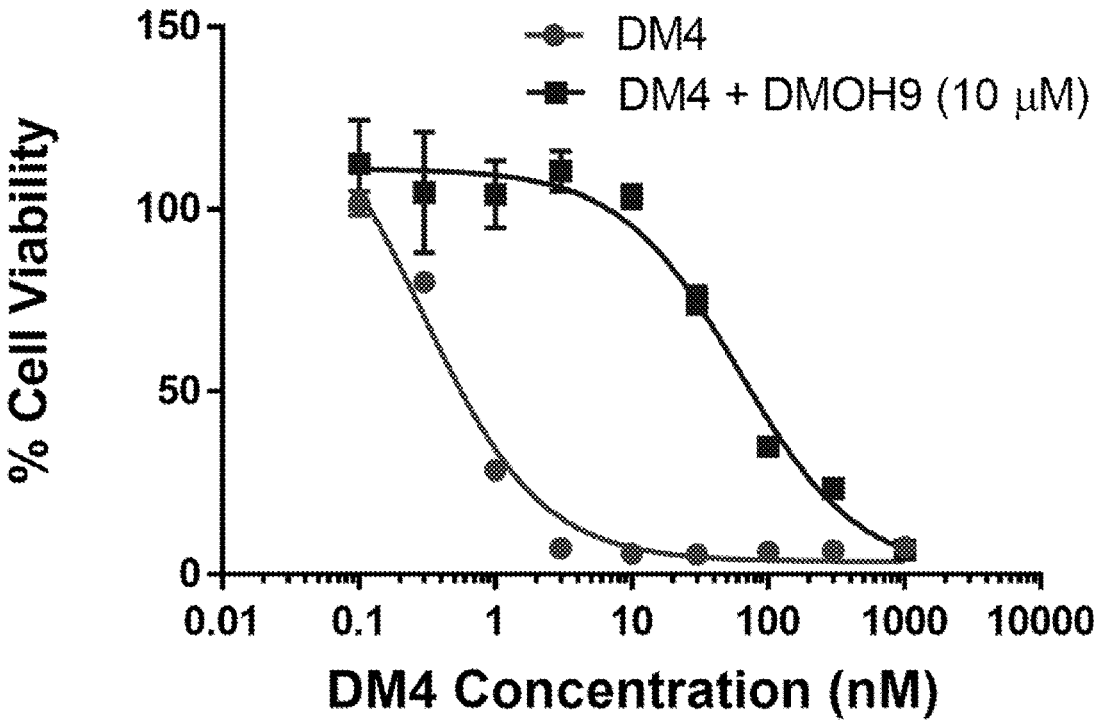
FIG. 50. MTT Cell based assay with DMOH9. Cell cytotoxicity of DM4 on SK-BR-3 cells with and without 10 μM of DMOH9 sdAb over a 24 h exposure periods.

MTT Cell based assay with DMOH9. Cell cytotoxicity of DM4 on SK-BR-3 cells with and without 10 μM of DMOH9 sdAb over a 24 h exposure periods (FIG. 50). Co-incubation with DMOH9 shifted $IC_{50}$ of DM4 in SK-BR-3 cells from 0.29 nM to 61 nM.

Anti-DM1/DM4 sdAb DMOF8 Clone

Summary

Binding affinity was estimated with a Kd of 26 nM to free DM4 via competitive ELISA. Antagonism of DM4 by DMOF8 sdAb in vitro was evaluated in SK-BR-3 cell line. Over a 24 h exposure period, with the presence of 10 μM DMOF8, the $IC_{50}$ of DM4 was shifted 104-fold from 0.42 nM to 44 nM.

Experimental Data

```
DMOF8 Amino Acid Sequence
                                    (SEQ ID NO: 33)
QVQLQESGGGLVQPGGSLRLSCAASGSIFGISYMGWYRQAPGKQREPVA
MITSSGSTYYADSVRGRVTISRANAKKTVYLQMNSLRPEDTSTYYCAAG
YYRSDSPNRYDYWGQGTQVTVSS.
```

Figure 51:
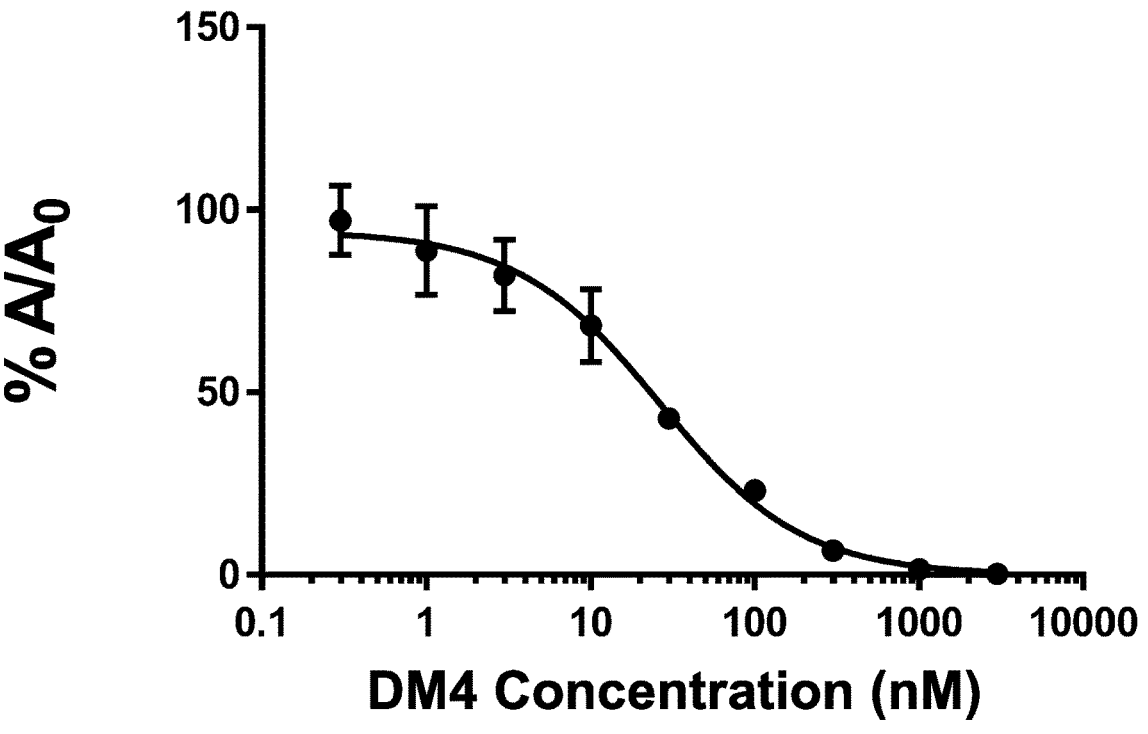
FIG. 51. Competitive binding assessment of DMOF8: Binding activity of DMOF8 against free DM4 was evaluated via competitive ELISA. Estimated binding affinity $IC_{50}$ of DMOF8 to free DM4 is 26 nM.

Competitive binding assessment of DMOF8: Binding activity of DMOF8 against free DM4 was evaluated via competitive ELISA. Estimated binding affinity $IC_{50}$ of DMOF8 to free DM4 is 26 nM (FIG. 51).

Figure 52:
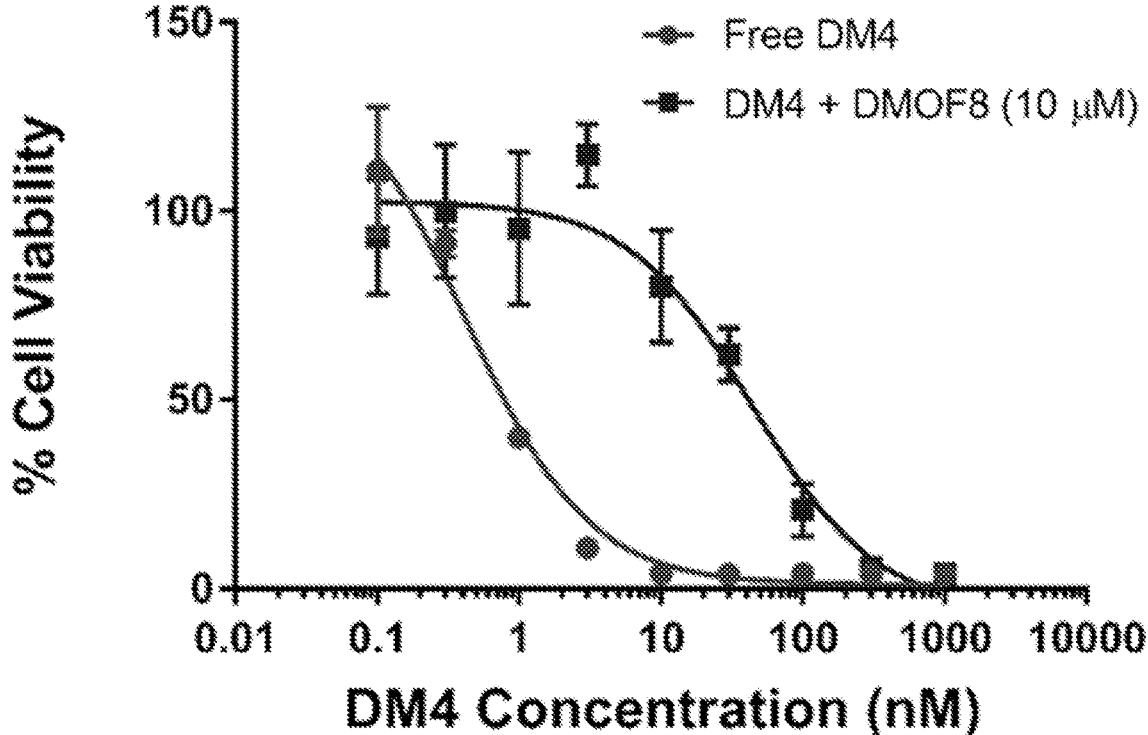
FIG. 52. MTT Cell based assay with DMOF8. Cell cytotoxicity of DM4 on SK-BR-3 cells with and without 10 μM of DMOH9 sdAb over a 24 h exposure periods.

MTT Cell based assay with DMOF8. Cell cytotoxicity of DM4 on SK-BR-3 cells with and without 10 μM of DMOH9 sdAb over a 24 h exposure periods. Co-incubation with DMOH9 shifted $IC_{50}$ of DM4 in SK-BR-3 cells from 0.42 nM to 44 nM (FIG. 52).

Anti-DM1/DM4 sdAb DMFH2 Clone

Summary

Binding affinity was estimated with a Kd of 25 nM to free DM4 via competitive ELISA. Antagonism of DM4 by DMFH2 sdAb in vitro was evaluated in SK-BR-3 cell line. Over a 24 h exposure period, with the presence of 10 μM DMFH2, the $IC_{50}$ of DM4 was shifted 150-fold from 0.42 nM to 63 nM.

Experimental Data

```
DMFH2 Amino Acid Sequence
                                    (SEQ ID NO: 34)
QVQLQESGGGLVQPGGSLRLSCAASGSTFGISYMGWYRQAPGKQREPVA
MITSGGSTYYVDSVKGRVTISRDNAKKTVYLQMNSLRPEDTSTYYCAAG
FYRSDSPNRYDYWGQGTQVTVSS.
```

Figure 53:
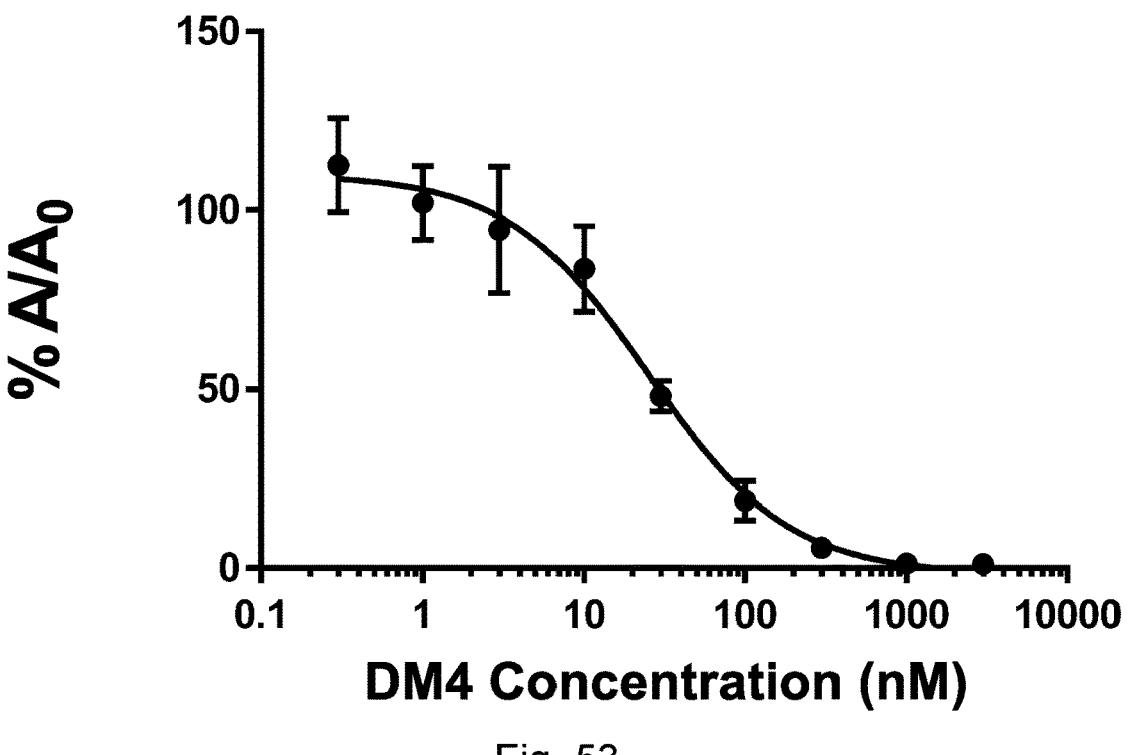
FIG. 53. Competitive binding assessment of DMFH2: Binding activity of DMFH2 against free DM4 was evaluated via competitive ELISA.

Competitive binding assessment of DMFH2: Binding activity of DMFH2 against free DM4 was evaluated via competitive ELISA. Estimated binding affinity $IC_{50}$ of DMFH2 to free DM4 is 25 nM (FIG. 53).

Figure 54:
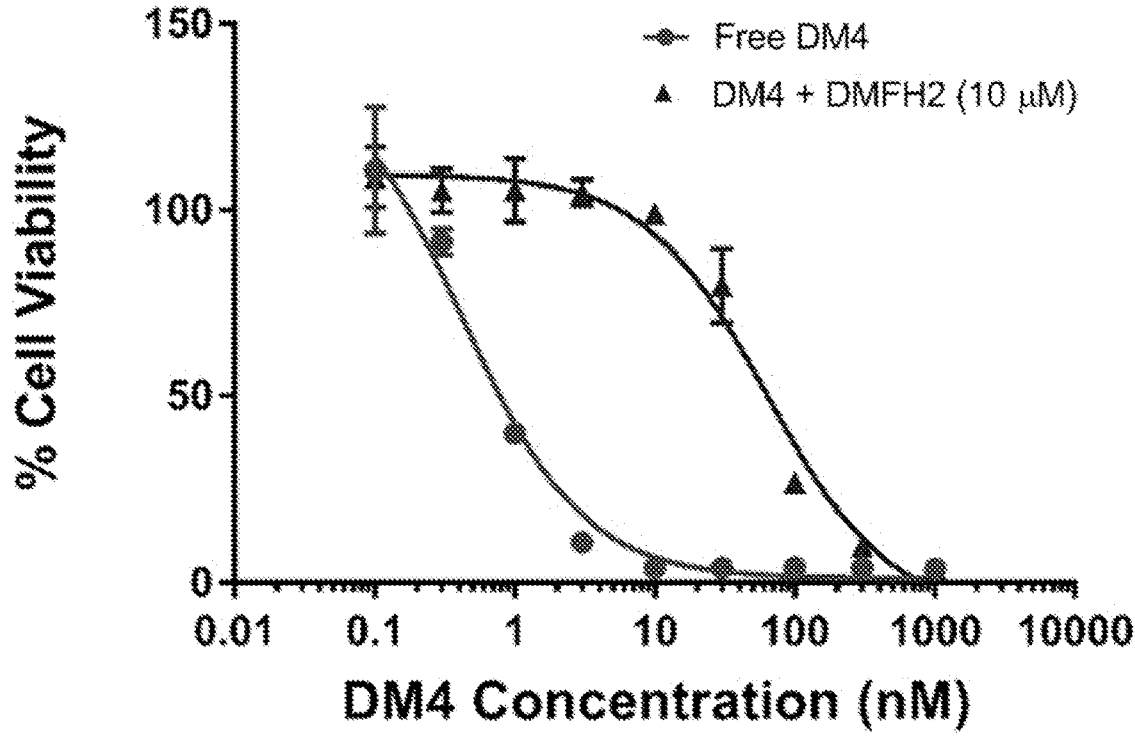
FIG. 54. MTT Cell based assay with DMFH2. Cell cytotoxicity of DM4 on SK-BR-3 cells with and without 10 μM of DMFH2 sdAb over a 24 h exposure periods.

MTT Cell based assay with DMFH2. Cell cytotoxicity of DM4 on SK-BR-3 cells with and without 10 μM of D1VIFH2 sdAb over a 24 h exposure periods. Co-incubation with DMFH2 shifted $IC_{50}$ of DM4 in SK-BR-3 cells from 0.42 nM to 63 nM (FIG. 54).

Anti-DM1/DM4 sdAb DMFF2 Clone

Summary

Binding affinity was estimated with a Kd of 57 nM to free DM4 via competitive ELISA. Antagonism of DM4 by DMFF2 sdAb in vitro was evaluated in SK-BR-3 cell line. Over a 24 h exposure period, with the presence of 10 μM DMFF2, the $IC_{50}$ of DM4 was shifted 95-fold from 0.39 nM to 37 nM.

Experimental Data

```
DMFF2 Amino Acid Sequence
                                    (SEQ ID NO: 35)
QVQLQESGGGLVQPGGSLRLSCAASGSIFGISYMGWYRQAPGKQREPVA
LITSGGSTYYVDSVKGRVTISRDNAKKTVYLQMNSLRPEDTSTYYCAAG
YYRSDSPNRYDYWGQGTQVTVSS.
```

Figure 55:
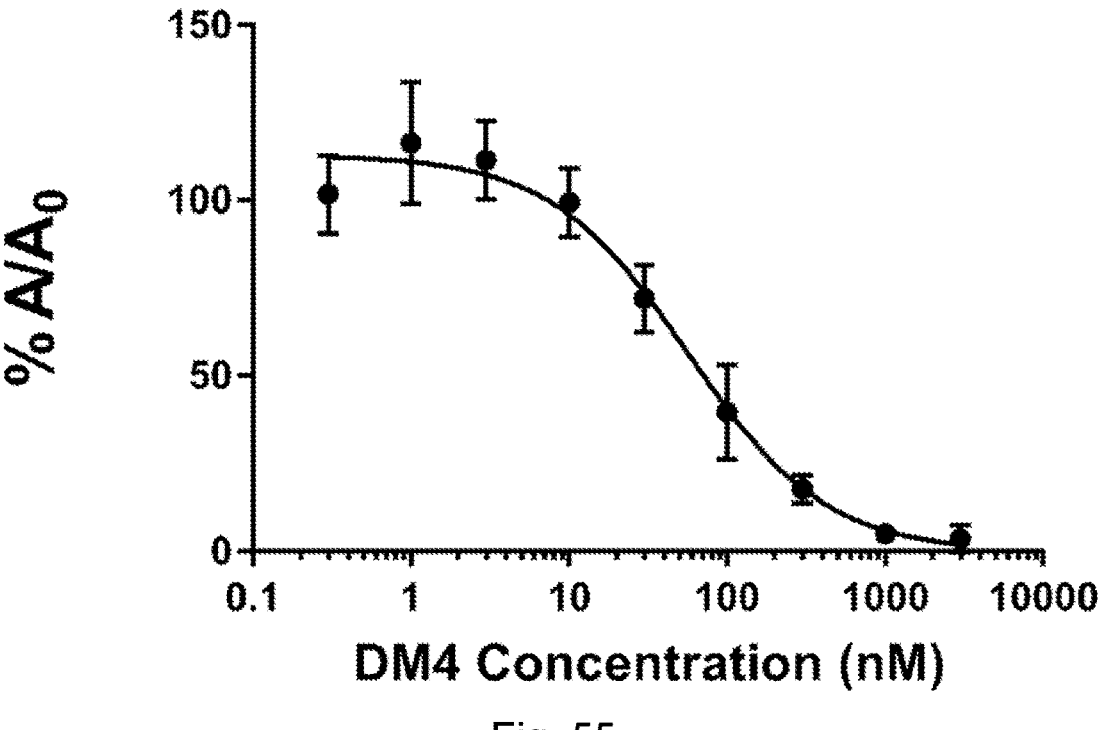
FIG. 55. Competitive binding assessment of DMFF2: Binding activity of DMFF2 against free DM4 was evaluated via competitive ELISA. Note: Incorrect plot for FIG. 55. The plot labeled as FIG. 55 is for DMFH2 (same as FIG. 53)

Competitive binding assessment of DMFF2: Binding activity of DMFF2 against free DM4 was evaluated via competitive ELISA. Estimated binding affinity $IC_{50}$ of DMFF2 to free DM4 is 57 nM (FIG. 55).

Figure 56:
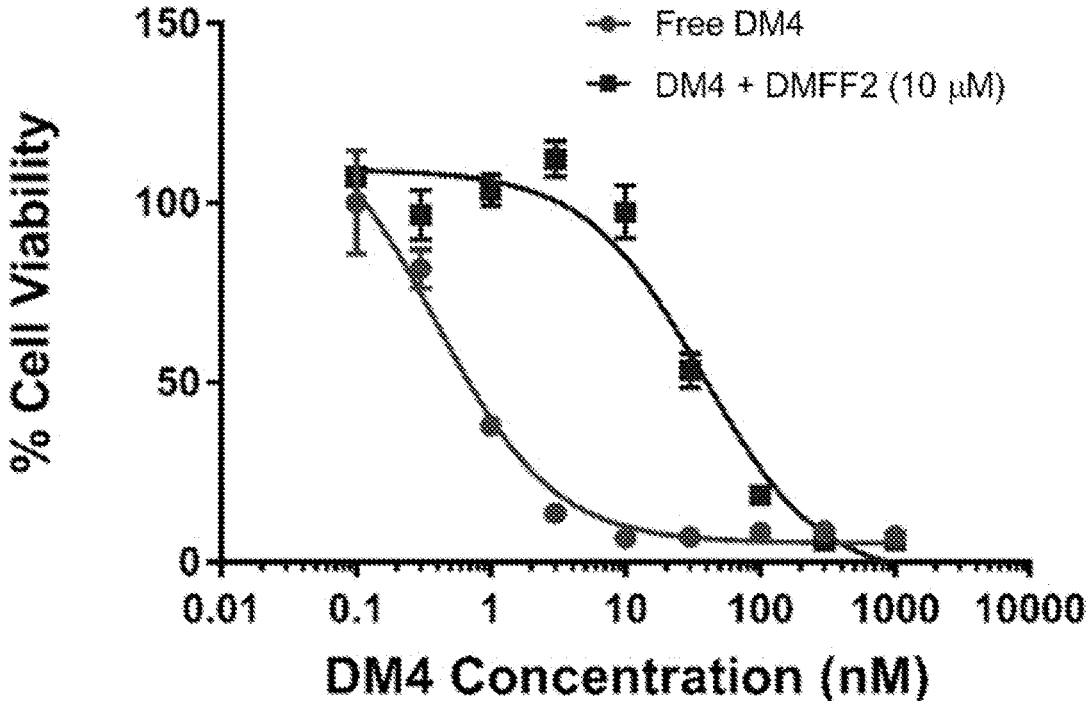
FIG. 56. MTT Cell based assay with DMFF2. Cell cytotoxicity of DM4 on SK-BR-3 cells with and without 10 μM of DMFF2 sdAb over a 24 h exposure periods.

MTT Cell based assay with DMFF2. Cell cytotoxicity of DM4 on SK-BR-3 cells with and without 10 μM of DMFF2 sdAb over a 24 h exposure periods. Co-incubation with DMFF2 shifted $IC_{50}$ of DM4 in SK-BR-3 cells from 0.39 nM to 37 nM (FIG. 56).

Anti-DM1/DM4 sdAb DMFB8 Clone

Summary

Antagonism of DM4 by DMFB8 sdAb in vitro was evaluated in SK-BR-3 cell line. Over a 24 h exposure period, with the presence of 10 μM DMFB8, the $IC_{50}$ of DM4 was shifted 140-fold from 0.40 nM to 56 nM.

Experimental Data

```
DMFB8 Amino Acid Sequence
                                    (SEQ ID NO: 36)
QVQLQESGGGLVQPGGSLRLSCAASGSIFGISYMGWYRQAPGKQREPVA
MITSGGSTYYADSVKGRVTISRDNAKKTVYLQMYSLRPEDTSTYYCAAG
YYRSDSPNRYDYWGQGTQVTVSS.
```

Figure 57:
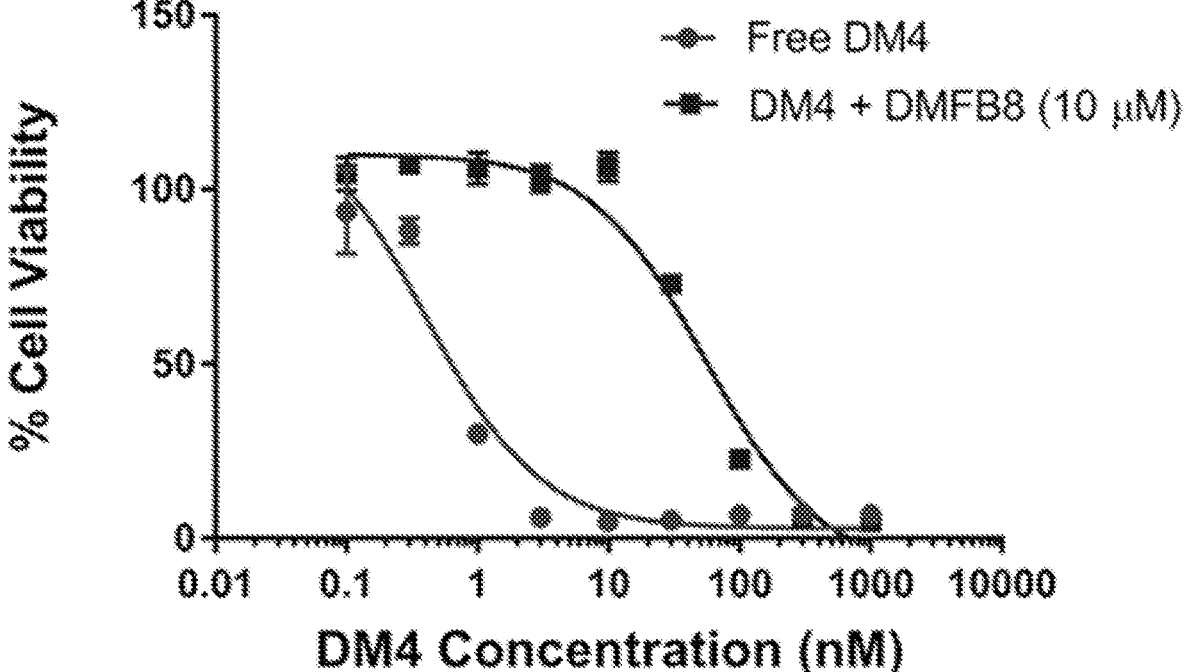
FIG. 57. MTT Cell based assay with DMFB8. Cell cytotoxicity of DM4 on SK-BR-3 cells with and without 10 μM of DMFB8 sdAb over a 24 h exposure periods.

MTT Cell based assay with DMFB8. Cell cytotoxicity of DM4 on SK-BR-3 cells with and without 10 μM of DMFB8 sdAb over a 24 h exposure periods. Co-incubation with DMFB8 shifted IC$_{50}$ of DM4 in SK-BR-3 cells from 0.40 nM to 56 nM (FIG. 57).

Additional Unique sdAb Clones with Positive ELISA Binding

DMFA2

(SEQ ID NO: 37)
QVQLQESGGGLVQPGGSLRLSCAASGSIFGISYMGWYRQAPGKQREPVA
LITSGGSTHYVDSVKGRVTISRDNAKKTVYLQMNSLRPEDTSTYYCAAG
SYRSDSPNRYDYWGQGTQVTVSS.

DMFA4

(SEQ ID NO: 38)
QVQLQESGGGLVQPGGSLRLSCAASGSMFGISYMGWYRQAPGKQREPVA
LITSGGSTYYADSAKGRVTISRDNAKKTVYLQMNSLRPEDTSTYYCAAG
YYRSDSPNRYDYWGQGTQVTVSS.

DMFA9

(SEQ ID NO: 39)
QVQLQESGGGLVQPGGSLRLSCAASGSIFGISYMGWYRQAPGNQREPVA
MITSGGSTYYADSVKGRVTISRDNAKKTVYLQMNSLRPEDTSTYYCAAG
YYRSDSPNRYDYWGQGTQVTVSS.

DMFC5

(SEQ ID NO: 40)
QVQLQESGGGQVQPGGSLRLSCAASGSIFGISYMGWYRQAPGKQREPVA
LITSGGSTYYVDSVKGRVTISRDNAKKTVYLQMNSLRPEDTSTYYCAAG
YYRSDSPNRYDYWGQGTQVTVSS.

DMFD3

(SEQ ID NO: 41)
QVQLQESGGGLVQPGGSLRLSCAASGSIFGISYMGWYRQAPGKQREPVA
MITSGGSTYYADSVKGRVTISRDNAEKTVYLQMNSLRPEDTSTYYCAAG
CYRSDSPNRYDYWGQGTQVTVSS.

DMFD7

(SEQ ID NO: 42)
QVQLQESGGGLVQPGGSLRLSCAASGSIFGISYMGWYRQAPGKQREPVA
MITSGGSTYYADSVKGRVTISRDNAKKTVYLQMNSLRPEDTSTYYCAAG
YYRSDSPNRYDYWGQGTQVTVSS.

DMFE1

(SEQ ID NO: 43)
QVQLQESGGGLVQPGGSLRLSCAASGSIFGISYMGWYRQAPGNQREPVA
MITSGGSTYYADSVKGRVTISRDNAKKTVYLQMNSLRPEDTSTYYCAAG
YYRSDSPNRYDYWGQGTQVTVSS.

DMFE5

(SEQ ID NO: 44)
QVQLQESGGGLVQPGGSLRLSCAASGSIFGISYMGWYRQAPGKQREPVA
MITSGGSTYYADSVKGRVTVSRDNAKKTVYLQMNSLRPEDTSTYYCAAG
YYRSDSPNRYDYWGQGTQVTVSS.

DMFE8

(SEQ ID NO: 45)
QVQLQESGGGLVQPGGSLRLSCAASGSIFGISYMGWYRQAPGKQREPVA
MITSGGSTYYADSVKGRVTISRDNAKKTIYLQMNSLRPEDTSTYYCAAG
FYRSDSPNRYDYWGRGTQVTVSS.

DMFF1

(SEQ ID NO: 46)
QVQLQESGGGLVQPGGSLRLSCAASGSIFGISYMGWYRQAPGKQREPVA
MITSGGSTYYADSVKGRVTISRDNAKKTIYLQMNSLRPEDTSTYYCAAG
FYRSDSPNRYDYWGRGTQVTVSS.

DMFF6

(SEQ ID NO: 47)
QVQLQESGGGLVQPGGSLRLSCAASGSIFGISYMGWYRQAPGKQREPVA
LITSGGSTYYVDSVKGRVTISRDNAKKTVYLQMNSLRPGDTSTYYCAAG
YYRSDSPNRYDYWGQGTQVTVSS.

DMFG2

(SEQ ID NO: 48)
QVQLQESGGGLVQPGGSLRLSCAASGSIFGISYMGWYRQAPGKQREPVA
MITSGGSTYYADSVKGRVTISRDNAKKTIYLQLISLRPEDTSTYYCAAG
FYRSDSPNRYDYWGQGTQVTVSS.

-continued

DMFG3

(SEQ ID NO: 49)
QVQLQESGGGLVQPGGSLRLSCAASGSIFGISYMGWYRLAPGNQREPVA
MITSGGSTYYADSVKGRVTISRDNAKKTVYLQMNSLRPEDTSTYYCAAG
YYRSDSPNRYDYWGQGTQVTVSS.

DMFG5

(SEQ ID NO: 50)
QVQLQESGGGLVQPGGSLRLSCAASGSIFGISYMGWYRQAPGKQREPVA
MITSGGSTYYADSVKGRVTISRDNAKKTVYLQMNSLRPEDTSTYYCAAG
YYRSDSPNRHDYWGQGTQVTVSS.

DMOA3

(SEQ ID NO: 51)
QVQLQERGGGLVQAGGSLRLSCAASGRTISGYAMGWFRQAPGKERDLVA
AISRSGTSTYYADSVKGRFTISRDNAKNTVYLQMNSLKPEDTAVYYCNA
PGGIWGQGTQVTVSS.

DMOA5

(SEQ ID NO: 52)
QVQLQESGGGLVQPGGSLRLSCAASGSIFGISYIGWYRQAPGKQREPVA
LITSGGSTYYVDSVKGRVTISRDNAKKTVYLQMNSLRPEDTSTYYCAAG
YYRSDSPNRYDYWGQGTQVTVSS.

DMOA11

(SEQ ID NO: 53)
QVQLQESGGGLVQPGGSLRLSCAASGSIFGISYMGWYRQAPGRQREPVA
LITSGGSTYYTDSVKGRVTISRDNAKKTVYLQMNSLRPEDTSTYYCAAG
YYRSDSPNRYDYWGQGTQVTVSS.

DMOB5

(SEQ ID NO: 54)
QVQLQESGGGLVQPGGSLRLSCAASGSIFGISYMGWYRQAPGKQREPVA
LITSGGSTYYVDSVNGRVTISRDNAKKTVYLQMNSLRPEDTSTYYCAAG
FYRSDSPNRYDYWGQGTQVTVSS.

DMOB7

(SEQ ID NO: 55)
QVQLQESGGGLVQPGGSLRLSCAASGSIFGISYMGWYRQAPGKQREPVA
MITSGGSTYYADSVKGRVTISRDNAKKTVYLQMNSLRPEDTSTYYCAAG
FYRSDSPNRYDYWGQGTQVTVSS.

DMOC10

(SEQ ID NO: 56)
QVQLQESGGGLVQPGGSLRLSCAASGSIFGISYMGWYRQAPGKQREPVA
LITSGGSTYYVDSVNGRVTISRDNAKKTVYLQMNSLRPEDTSTYYCAAG
FYRSDSPNRYDYWGQGTQVTVSS.

DMOD4

(SEQ ID NO: 57)
QVQLQESGGGLVQPGGSLRLSCAASGSIFGISYMGWYRQAPGKQREPVA
LITSGGSAYYVDSVKGRVTISRDNAKKTVYLQMNSLRPEDTSTYYCAAG
FYRSDSPNRYDYWGQGTQVTVSS.

DMOE7

(SEQ ID NO: 58)
QVQLQESGGGRVQPGGSLRLSCAASGSIFGISYMGWYRQAPGKQREPVA
LITSGGSTYYVDSVEGRVTISRDNAKKTVYLQMNSLRPEDTSTYYCAAG
YYRSDSPNRYDYWGQGTQVTVSS.

DMOF6

(SEQ ID NO: 59)
QVQLQESGGGLVQVGGSLRLSCAASGRTISGYAMGWFRQAPGKERDLVA
AISRSGTSTYYADSVKGRFTISRDNAKNTVYLQMSSLKPEDTAVYYCNA
PGGIWGQGTQATVSS.

DMOG1

(SEQ ID NO: 60)
QVQLQESGGGLVQPGGSLRLSCAASGSIFGISYMGWYRQAPGKQREPVA
LITSGGSTYYADSVNGRVTISRDNAKKTVYLQMNSLRPEDTSTYYCAAG
YYRSDSPNRYDYWGQGTQVTVSS.

DMOG4

(SEQ ID NO: 61)
QVQLQESGGGLVQPGGSLRLSCAASGSIFGISYMGWYRQAPGKQREPVA
MITSGGSTYYADSVKGRVTISRDNAKKTVHLQMNSLRPEDTSTYYCAAG
FYRSDSPNRYDYWGQGTQVTVSS.

-continued

DMOH12

(SEQ ID NO: 62)
QVQLQESGGGLVQPGGSLRLSCAASGSIFGISYMGWYRQAPGRQREPVA

MITSGGSTYYVDGVKGRVTISRDNAKKTVYLQMKSLRPEDTSTYYCAAG

FYRSDSPNRYDYWGQGTQVTVSS.

EXAMPLE 8

This example provides further characterization of antibodies or fragments against camptothecin derivatives.
Murine, Chimeric, Human 8C2 Fab
Expression and Purification:
DNA sequences encoding for murine, chimeric and human 8C2 Fab were synthesized by GeneArt. DNA sequences were ligated into the Pet22b vector between the XhoI and NdeI restriction enzyme sites. DNA was transformed into Shuffle T7 express *E. coli* cells and Fab expressed using standard recombinant expression techniques. Following expression Fab was purified using a nickel column and subsequently dialyzed in PBS. Following dialysis Fab was further purified using a protein L column using manufacturer recommendations and elution fractions containing Fab dialyzed into PBS.
SPR Binding Evaluation:
Exatecan was immobilized onto a CMS chip through amine coupling. 8C2 Fab fragments were injected over a range of concentrations and binding kinetics fit using a 1:1 Langmuir binding model. Competitive assays were completed with the addition of free Dxd, free SN38 and trastuzumab deruxtecan at various concentrations with a constant concentration of 5 nM Fab. Dilutions were incubated for one hour and subsequently injected over the exatecan immobilized chip. The observed maximum response data was fit to a 3 parameter inhibition equation in GraphPad Prism 7.
Competitive Cell Assays:
SKBR3 cells were diluted to 4000 cells/100 μL and 100 μL was added to individual wells of a 96 well culture plate. Cells were incubated overnight to allow cells to adhere to the plate. 8C2 Fab was diluted in complete McCoys 5a media at a concentration of 1 μM. Dxd and SN38 were diluted at the indicated concentrations and incubated for 90 minutes. Following incubation dilutions were added to individual wells in triplicate with fresh media dilutions added on day 1, 3 and 5 with cell viability evaluated on day 7 using an MTT assay.
8C2 VHH
The complementarily determining regions of the 8C2 heavy chain were placed into the stable human framework m0 that was reported by Dimitrov et al (PMID 18687338). DNA encoding for the 8C2 VHH was synthesized by GeneArt. DNA sequences were ligated into the Pet22b vector between the XhoI and NdeI restriction enzyme sites. DNA was transformed into Shuffle T7 express *E. coli* cells and expressed using standard recombinant expression. To evaluate binding activity, 8C2 VHH was incubated with SN38 immobilized onto magnetic beads and bound VHH detected with an anti-HIS tag HRP labeled reporter antibody. Intact 8C2 mAb was incubated alone and in-combination with 8C2 VHH and 8C2 mAb binding evaluated with an anti-mouse IgG HRP reporter antibody. The sequences of are shown in FIG. 58.
The amino acid sequence of the light chain of the murine antibody is:

(SEQ ID NO: 63)
DIQMTQSPASLSASVGETVTITCRASGNIHNSLAWYQQIKGRSPQLLVY

NAKTLADGVPSRFSGSGSGTQYSLKINSLHPEDFGSYYCQHFWSTPFTF

GSGTKLEIKRADAAPTVSIFPPSSEQLTSGGASVVCFLNNFYPKDINVK

WKIDGSERQNGVLNSWTDQDSKDSTYSMSSTLTLTKDEYERHNSYTCEA

THKTSTSPIVKSFNRNEC.

The amino acid sequence of the light chain of the chimeric antibody is:

(SEQ ID NO: 64)
DIQMTQSPASLSASVGETVTITCRASGNIHNSLAWYQQIKGRSPQLLVY

NAKTLADGVPSRFSGSGSGTQYSLKINSLHPEDFGSYYCQHFWSTPFTF

GSGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The amino acid sequence of the light chain of the human antibody is:

(SEQ ID: 65)
DIVLTQSPSSLSASVGETVTITCRASGNIHNSLAWYQQIKGKAPKLLIY

NAKTLADGVPSRFSGSGSGTDFSLTISSLEPEDFATYYCQHFWSTPFTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The amino acid sequence of heavy chain of murine antibody is:

(SEQ ID NO: 66)
EVQLQQSGAELVKPGASVKLSCTASGFNIKDTYIHWVKQRPEQGLEWIG

MIDLANDNTKYDPKFQGKATIITDTSSNKAYLQVSSLTSEDTAVYYCAT

WGAIITLGGWGQGTLVTVSAAKTTPPSVYPLAPGSAAQTNSMVTLGCLV

KGYFPEPVTVTWNSGSLSSGVHTFPAVLQSDLYTLSSSVTVPSSTWPSE

TVTCNVANPASSTKVDKKIVPRDC.

The amino acid sequence of the heavy chain of chimeric antibody is:

(SEQ ID NO: 67)
EVQLQQSGAELVKPGASVKLSCTASGFNIKDTYIHWVKQRPEQGLEWIG

MIDLANDNTKYDPKFQGKATIITDTSSNKAYLQVSSLTSEDTAVYYCAT

WGAIITLGGWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHL.

The amino acid sequence of the heavy chain of human antibody is:

(SEQ ID NO: 68)
EVQLQESGAELVKPGASVKLSCAASGFNIKDTYIHWVRQRPGQGLEWIG

-continued

```
MIDLANDNTKYDPKFQGRVTITVDTSTNKAYLQLSSLTSEDTAVYYCAT

WGAIITLGGWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHL.
```

The amino acid sequence of 8C2 VHH with the heavy chain CDRs of 8C2 placed into a stable human framework is:

(SEQ ID NO: 69)
```
QVQLVQSGGGLVQPGGSLRLSCAASGFNIKDTYIHWMSWVRQAPGKGLE
WVSPDLANDNTKYDPKYYADSVKGRFTISRDNSKNTLYLQMNTLRAEDT
AVYYCATWGAIITLGGWGQTMVTVSS.
```

Figure 59:
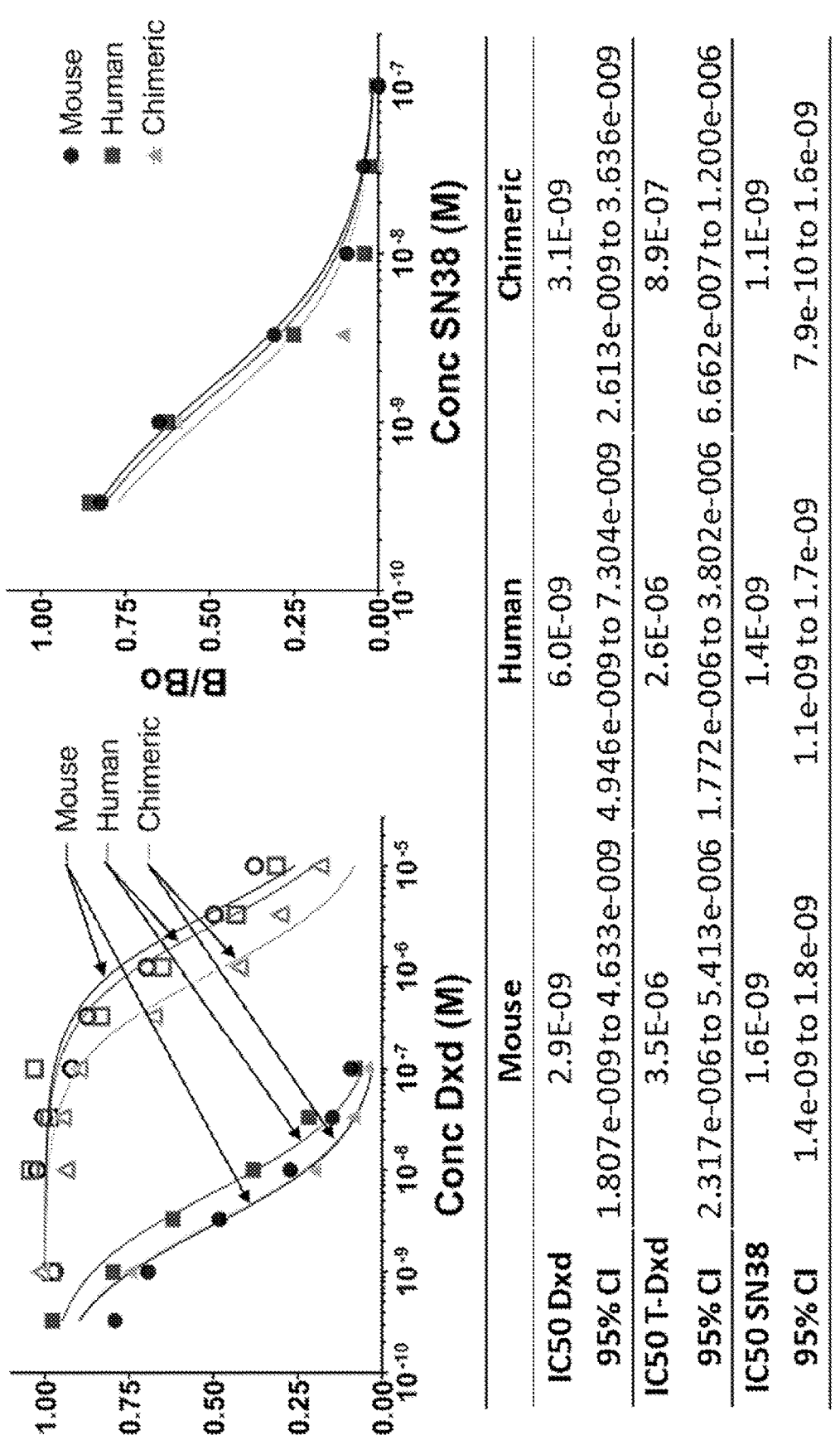
FIG. 59. Competitive SPR Assay. Solid symbols represent signal with free drug spiked open symbols are for samples with trastuzumab deruxtecan added. Best Fit IC50 values and the respective 95% confidence intervals are provided in the table within the figure.

Competitive SPR Assay: Fabs were diluted to 5 nM in PBST running buffer with Dxd, Trastuzumab Deruxtecan and SN38 spiked in at indicated concentrations and incubated for 1 hour. B/Bo is signal reached after a 3.5 minute injection with spiked in drugs divided by signal with Fab alone. (FIG. 59). Solid symbols represent signal with free drug spiked open symbols are for samples with trastuzumab deruxtecan added. Best Fit IC50 values and the respective 95% confidence intervals are provided in the table within the figure. Free SN38 and Free Dxd inhibited Fab binding with low-nanomolar IC50's whereas trastuzumab-deruxtecan inhibited binding at low micromolar concentrations indicating a ~1000× binding selectivity for free drug.

Competitive Cell Assay: Free drug was incubated with the 8C2 Fab constructs and added to SKBR3 cells. Fresh media was added on day 1, 3 and 5 and cell viability evaluated on day 7. The IC50 for Dxd alone is 0.7 nM whereas addition of 8C2 Fabs increased the IC50>100 nM. The observed IC50 for free SN38 is 1.4 nM with no cell toxicity observed with the addition of the Fab fragments (FIG. 60).

Competitive Cell Assay: Provided is a demonstration of the selectivity of 8C2 Fab for free drug in comparison to intact antibody drug conjugate. 8C2 Fab increases the IC50 of the free payload Dxd (Left) by >100-fold without impacting the cytotoxicity of the intact ADC trastuzumab deruxtecan (right) (FIG. 61).

Figure 62:
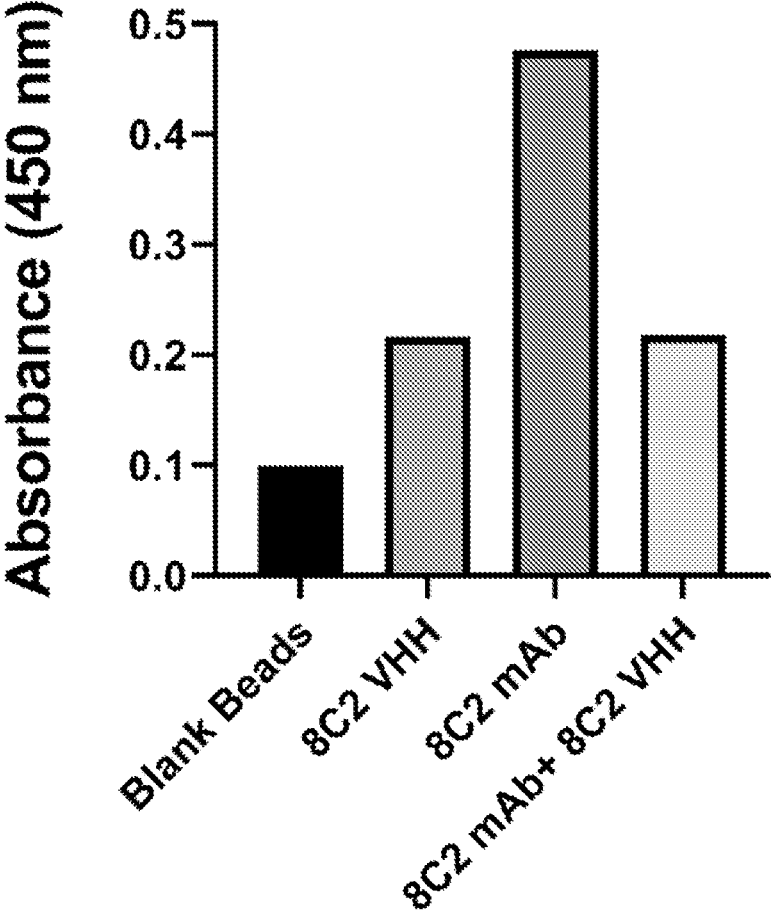
FIG. 62. Humanized 8C2 VHH Characterization: Humanized 8C2 VHH was incubated with SN38 immobilized on magnetic beads. Intact 8C2 antibody was incubated alone and with addition of humanized 8C2 VHH and intact 8C2 binding evaluated with a detection antibody that was specific for intact murine IgG.

8C2 VHH Characterization: 8C2 VHH was incubated with SN38 immobilized on magnetic beads. Addition of 8C2 VHH led to a 2× increase in binding signal in comparison to beads incubated with blank buffer. Intact 8C2 antibody was incubated alone and with addition of 8C2 VHH and intact 8C2 binding evaluated with a detection antibody that was specific for intact murine IgG. Addition of 8C2 VHH decreased 8C2 mAb binding by ~2-fold, indicating 8C2 VHH competes with intact 8C2 mAb for SN38 binding (FIG. 62.).

While the invention has been described through illustrative examples, routine modifications will be apparent to those skilled in the art, which modifications are intended to be within the scope of the present disclosure.

---

We claim:

1. A composition comprising an antigen binding antibody fragment and a pharmaceutical carrier, wherein the antigen binding fragment comprises the sequence of SEQ ID NO:3; or a heavy chain comprising the sequence of SEQ ID NO:4 and a light chain comprising the sequence of SEQ ID NO:5; or SEQ ID NO:6; or the sequence of SEQ ID NO:7; or the sequence of SEQ ID NO: 8; or the sequence of SEQ ID NO:9; or the sequence of SEQ ID NO:10; or the sequence of SEQ ID NO: 11; or the sequence of SEQ ID NO:69.

2. The composition of claim 1, wherein the antigen binding antibody fragment comprises the sequence of SEQ ID NO:3.

3. The composition of claim 1, wherein the antigen binding antibody fragment comprises the heavy chain comprising the sequence of SEQ ID NO:4 and a light chain comprising the sequence of SEQ ID NO:5.

4. The composition of claim 1, wherein the antigen binding antibody fragment comprises the sequence of SEQ ID NO:6.

5. The composition of claim 1, wherein the antigen binding antibody fragment comprises the sequence of SEQ ID NO:7.

6. The composition of claim 1, wherein the antigen binding antibody fragment comprises the sequence of SEQ ID NO:8.

7. The composition of claim 1, wherein the antigen binding antibody fragment comprises the sequence of SEQ ID NO:9.

8. The composition of claim 1, wherein the antigen binding antibody fragment comprises the sequence of SEQ ID NO:10.

9. The composition of claim 1, wherein the antigen binding antibody fragment comprises the sequence of SEQ ID NO: 11.

10. The composition of claim 1, wherein the antigen binding antibody fragment comprises the sequence of SEQ ID NO:69.

11. The composition of claim 1, further comprising an antibody drug conjugate (ADC) wherein the drug comprised by the ADC is a derivative of camptothecin.

* * * * *